US012485163B2

(12) United States Patent
Reed et al.

(10) Patent No.: US 12,485,163 B2
(45) Date of Patent: Dec. 2, 2025

(54) CANCER THERAPY COMPOSITIONS AND USES THEREOF

(71) Applicant: HDT Bio Corp, Seattle, WA (US)

(72) Inventors: Steven Gregory Reed, Bellevue, WA (US); Darrick Albert Carter, Seattle, WA (US); Malcolm Scott Duthie, Sammamish, WA (US); Lars Peter Aksel Berglund, Seattle, WA (US); Jesse Hong-Sae Erasmus, Port Orchard, WA (US); Jiho Kim, Seattle, WA (US)

(73) Assignee: HDT Bio Corp., Seattle, WA (US)

( * ) Notice: Subject to any disclaimer, the term of this patent is extended or adjusted under 35 U.S.C. 154(b) by 0 days.

(21) Appl. No.: 18/607,029

(22) Filed: Mar. 15, 2024

(65) Prior Publication Data

US 2024/0216493 A1 Jul. 4, 2024

Related U.S. Application Data

(63) Continuation of application No. PCT/US2022/076304, filed on Sep. 12, 2022.
(Continued)

(51) Int. Cl.
*A61K 39/00* (2006.01)
*A61K 9/127* (2025.01)
(Continued)

(52) U.S. Cl.
CPC .... *A61K 39/001193* (2018.08); *A61K 9/4858* (2013.01); *A61K 9/5015* (2013.01);
(Continued)

(58) Field of Classification Search
None
See application file for complete search history.

(56) References Cited

U.S. PATENT DOCUMENTS 7,045,335 B2 5/2006 Smith
7,425,337 B2 9/2008 Smith
(Continued)

FOREIGN PATENT DOCUMENTS

CN 107281161 B 2/2020
EP 3173092 B1 6/2019
(Continued)

OTHER PUBLICATIONS

Jesse H. Erasmus et al. "An Alphavirus-derived replicon RNA vaccine induces SARS-CoV-2 neutralizing antibody and T cell responses in mice and nonhuman primates." Science Translational Medicine, vol. 12, eabc9396 (2020) Aug. 5, 2020, pp. 1-11. (Year: 2020).*

(Continued)

*Primary Examiner* — Isaac Shomer
(74) *Attorney, Agent, or Firm* — Greenberg Traurig, LLP

(57) ABSTRACT

The disclosure provides compositions, methods of treatment, and methods of making and using compositions to deliver a nucleic acid to a subject. Compositions described herein include lipid carriers, optionally including an inorganic particle, capable of admixing with nucleic acids. Nucleic acids provided herein include those encoding for cancer antigens (full length proteins or fragments) as well as antibodies. Methods of using the compositions as a therapeutic vaccine for the treatment of a cancer are also provided.

26 Claims, 21 Drawing Sheets

Specification includes a Sequence Listing.

Related U.S. Application Data

(60) Provisional application No. 63/302,360, filed on Jan. 24, 2022, provisional application No. 63/247,167, filed on Sep. 22, 2021.

(51) Int. Cl.

| | |
|---|---|
| ***A61K 9/48*** | (2006.01) |
| ***A61K 9/50*** | (2006.01) |
| ***A61K 9/51*** | (2006.01) |
| ***C12N 15/86*** | (2006.01) |

(52) U.S. Cl.
CPC .......... *A61K 9/5115* (2013.01); *A61K 9/5123* (2013.01); *A61K 39/001156* (2018.08); *A61K 39/001186* (2018.08); *C12N 15/86* (2013.01); *A61K 9/127* (2013.01); *A61K 2039/53* (2013.01); *A61K 2039/55555* (2013.01); *A61K 2039/55566* (2013.01); *A61K 2039/6075* (2013.01); *C12N 2720/12143* (2013.01)

(56) References Cited

U.S. PATENT DOCUMENTS

| | | | | |
|---|---|---|---|---|
| 8,709,441 | B2 | 4/2014 | Rayner | |
| 8,734,832 | B2 | 5/2014 | O'Hagan et al. | |
| 8,853,179 | B2 | 10/2014 | Mauro | |
| 9,295,646 | B2 | 3/2016 | Brito et al. | |
| 9,555,136 | B2 | 1/2017 | Khandhar et al. | |
| 9,655,845 | B2 | 5/2017 | Brito | |
| 10,238,733 | B2 | 3/2019 | Brito | |
| 10,307,374 | B2 | 6/2019 | Brito | |
| 11,026,890 | B2 | 6/2021 | Brito | |
| 11,083,786 | B2 | 8/2021 | Kamrud | |
| 11,135,287 | B2 | 10/2021 | Brito | |
| 11,141,377 | B2 | 10/2021 | Fox | |
| 11,318,213 | B2 | 5/2022 | Khandhar | |
| 11,364,310 | B2 | 6/2022 | Kamrud | |
| 11,376,335 | B2 | 7/2022 | Khandhar | |
| 11,433,142 | B2 | 9/2022 | Khandhar | |
| 11,458,209 | B2 | 10/2022 | Khandhar | |
| 11,534,497 | B2 | 12/2022 | Khandhar | |
| 2006/0128011 | A1 | 6/2006 | Zhu | |
| 2009/0155301 | A1 | 6/2009 | Mason | |
| 2009/0252721 | A1 | 10/2009 | Buschmann | |
| 2012/0156251 | A1* | 6/2012 | Brito | A61P 37/04<br>424/193.1 |
| 2013/0177639 | A1* | 7/2013 | Geall | A61K 31/7088<br>424/274.1 |
| 2013/0195751 | A1 | 8/2013 | Hahn | |
| 2013/0202707 | A1 | 8/2013 | Ali | |
| 2016/0000886 | A1 | 1/2016 | Parker | |
| 2016/0201067 | A1 | 7/2016 | Ataullakhanov | |
| 2017/0189368 | A1 | 7/2017 | Troiano | |
| 2018/0008694 | A1 | 1/2018 | Ciaramella | |
| 2018/0104325 | A1 | 4/2018 | Gale, Jr. | |
| 2018/0147298 | A1* | 5/2018 | Besin | C08G 65/33306 |
| 2018/0153848 | A1 | 6/2018 | Chen | |
| 2018/0207295 | A1 | 7/2018 | Fotin-Mleczek | |
| 2018/0311336 | A1* | 11/2018 | Ciaramella | A61P 43/00 |
| 2018/0318409 | A1* | 11/2018 | Valiante | A61P 35/00 |
| 2019/0015501 | A1 | 1/2019 | Ciaramella | |
| 2019/0274968 | A1* | 9/2019 | Weissman | A61K 39/21 |
| 2019/0382450 | A1 | 12/2019 | Belov | |
| 2020/0006973 | A1 | 1/2020 | Petersen | |
| 2020/0069599 | A1 | 3/2020 | Smith | |
| 2020/0123573 | A1 | 4/2020 | Kamrud | |
| 2020/0157571 | A1 | 5/2020 | Nakanishi | |
| 2020/0224174 | A1 | 7/2020 | Irvine | |
| 2020/0230056 | A1* | 7/2020 | Fox | A61K 39/39 |
| 2020/0297834 | A1 | 9/2020 | Kehn-Hall | |
| 2020/0368344 | A1 | 11/2020 | Ciaramella | |
| 2020/0370052 | A1 | 11/2020 | Wilson | |
| 2021/0128583 | A1 | 5/2021 | Zhang | |
| 2021/0283242 | A1 | 9/2021 | Hutchins | |
| 2021/0290752 | A1 | 9/2021 | Sullivan | |
| 2021/0290756 | A1 | 9/2021 | Sullivan | |
| 2021/0330781 | A1 | 10/2021 | Kamrud | |

FOREIGN PATENT DOCUMENTS

| | | | |
|---|---|---|---|
| WO | 2001021810 | A1 | 3/2001 |
| WO | 2002080982 | A2 | 10/2002 |
| WO | 2005107760 | A1 | 11/2005 |
| WO | 2007024826 | A2 | 3/2007 |
| WO | 2008124647 | A2 | 10/2008 |
| WO | 2008153541 | A1 | 12/2008 |
| WO | WO2009049083 | | 4/2009 |
| WO | 2010042555 | A2 | 4/2010 |
| WO | 2010141861 | A1 | 12/2010 |
| WO | WO 2011/156761 | | 12/2011 |
| WO | 2014042780 | A1 | 3/2014 |
| WO | 2015103167 | A2 | 7/2015 |
| WO | 2017200852 | A1 | 11/2017 |
| WO | 2017200957 | A1 | 11/2017 |
| WO | 2017205225 | A2 | 11/2017 |
| WO | 2017210364 | A1 | 12/2017 |
| WO | 2017218704 | A1 | 12/2017 |
| WO | WO2018022957 | | 2/2018 |
| WO | 2018/044028 | | 3/2018 |
| WO | 2018053294 | A1 | 3/2018 |
| WO | WO 2018/147710 | | 8/2018 |
| WO | 2018232257 | | 12/2018 |
| WO | WO20182322257 | | 12/2018 |
| WO | 2019126524 | A1 | 6/2019 |
| WO | WO 2019/152884 | | 8/2019 |
| WO | 2020132279 | A1 | 6/2020 |
| WO | 2020/243115 | | 12/2020 |
| WO | 2020254804 | A1 | 12/2020 |
| WO | 2021021605 | A1 | 2/2021 |
| WO | 2021076630 | A1 | 4/2021 |
| WO | WO 2021/067480 | | 4/2021 |
| WO | WO 2021/072112 | | 4/2021 |
| WO | WO 2021/163536 | | 8/2021 |
| WO | 2021178886 | A1 | 9/2021 |
| WO | 2021183564 | A1 | 9/2021 |
| WO | 2021194672 | A1 | 9/2021 |
| WO | WO 2021/194672 | | 9/2021 |
| WO | 2021210686 | A1 | 10/2021 |
| WO | WO 2022/051022 | | 3/2022 |
| WO | 2022136952 | A1 | 6/2022 |
| WO | 2023286076 | A1 | 1/2023 |
| WO | 2023026301 | A1 | 3/2023 |
| WO | 2023049636 | A1 | 3/2023 |
| WO | 2023049636 | A2 | 3/2023 |
| WO | 2023056202 | A2 | 4/2023 |

OTHER PUBLICATIONS

Bert Hubert. "Reverse Engineering the Source Code of the BioNTech/Pfizer SARS-CoV-2 Vaccine." https://web.archive.org/web/20210223123219/https://berthub.eu/articles/posts/reverse-engineering-source-code-of-the-biontech-pfizer-vaccine/ published Feb. 23, 2021, pp. 1-15 and cover page. (Year: 2021).*

Takashi Nakamura, et al. "The Effect of Size and Charge of Lipid Nanoparticles Prepared by Microfluidic Mixing on Their Lymph Node Transitivity and Distribution." Molecular Pharmaceutics, vol. 17, 2020, pp. 944-953 and 4 supplemental pages. (Year: 2020).*

Mark Manzano et al. "Identification of Cis-Acting Elements in the 3'-Untranslated Region of the Dengue Virus Type 2 RNA That Modulate Translation and Replication." The Journal of Biological Chemistry, vol. 286, No. 25, Jun. 24, 2011, pp. 22521-22534. (Year: 2011).*

Elisa Pin et al. "Identification of a Novel Autoimmune Peptide Epitope of Prostein in Prostate Cancer." Journal of Proteome Research, vol. 16, 2017, pp. 204-216 and S-1 to S-14. (Year: 2017).*

International Search Report issued Jun. 13, 2024 in PCT/US2024/010326.

"Gennova's mRNA vaccine to come in powder form; will stay stable at 2-8 ° C." Business Standard. Sep. 13, 2021 02:56 IST.

(56) References Cited

OTHER PUBLICATIONS

Brinckerhoff, L. H., et al., "Melanoma vaccines" Current Opinion in Oncology: Mar. 2000—vol. 12—Issue 2—p. 163-173.
Brocato, R. L., et al., Protective efficacy of a SARS-CoV-2 DNA vaccine in wild-type and immunosuppressed Syrian hamsters. NPJ Vaccines 6, 16 (2021). https://doi.org/10.1038/s41541-020-00279-z.
Brown, C. M., et al. Outbreak of SARS-CoV-2 Infections, Including COVID-19 Vaccine Breakthrough Infections, Associated with Large Public Gatherings—Barnstable County, Massachusetts, Jul. 2021. MMWR Morb Mortal Wkly Rep 2021;70:1059-1062.
Corbett, K. S., et al., "Evaluation of the mRNA-1273 Vaccine against SARS-CoV-2 in Nonhuman Primates" N Engl J Med. Oct. 15, 2020;383(16):1544-1555. doi: 10.1056/NEJMoa2024671.
Corman, V. C., et al., Detection of 2019 novel coronavirus (2019-nCoV) by real-time RT-PCR. Euro Surveill. 2020;25 (3), https://doi.org/10.2807/1560-7917.ES.2020.25.3.2000045.
CustomBiotech Online Development Exchange (CODE), Beyond COVID: The Future of mRNA technology, Webinar held Thursday, Nov. 11, 2021, https://dianews.roche.com/CustomBiotech-Webinar-2021.html.
Edara, V., et al., Infection and Vaccine-Induced Neutralizing-Antibody Responses to the SARS-CoV-2 B. 1.617 Variants. N Engl J Med. Aug. 12, 2021;385(7):664-666. doi: 10.1056/NEJMc2107799. Epub Jul. 7, 2021. PMID: 34233096; PMCID: PMC8279090.
Erasmus, J. H., et al., "An Alphavirus-derived replicon RNA vaccine induces SARS-CoV-2 neutralizing antibody and T cell responses in mice and nonhuman primates" Science Translational Medicine, Aug. 5, 2020, vol. 12, Issue 555.
Erasmus, J.H., et al., Intramuscular Delivery of Replicon RNA Encoding ZIKV-117 Human Monoclonal Antibody Protects against Zika Virus Infection. Mol Ther—Methods Clin Dev. 2020; 18:402-414. PMID: 32695842.
File No. BIO/CT/20/000,182, CT No. CT-Feb. 2021 Government of India Directorate General of Health Services Central Drugs Standard Control Organization (Biological Division), Form CT-06 Permission to Conduct Clinical Trial of New Drug or Investigational New Drug, Jan. 25, 2021, 3 pages.
File No. BIO/CT/21/000,105, CT No. CT-28/2021 Government of India Directorate General of Health Services Central Drugs Standard Control Organization (Biological Division), Form CT-06 Permission to Conduct Clinical Trial of New Drug or Investigational New Drug, Aug. 22, 2021, 3 pages.
Fischer, Robert J., et al. "ChAdOx1 nCoV-19 (AZD1222) protects Syrian hamsters against SARS-CoV-2 B. 1.351 and B.1.1.7." bioRxiv : the preprint server for biology 2021.03.11.435000. Jun. 30, 2021, doi:10.1101/2021.03.11.435000. Preprint.
Geall, Andrew J., et al. "Nonviral delivery of self-amplifying RNA vaccines." PNAS. Vol 109. No 36, pp. 14604-14609 (2012).
Gilchuk, P., et al., "Integrated pipeline for the accelerated discovery of antiviral antibody therapeutics" Nat Biomed Eng. 2020;4(11):1030-1043. PMID: 32747832.
Hörner , C., et al., A highly immunogenic and effective measles virus-based Th1-biased COVID-19 vaccine, Proceedings of the National Academy of Sciences Dec. 2020, 117 (51) 32657-32666; DOI: 10.1073/pnas.2014468117.
Hou, X., et al., Lipid nanoparticles for mRNA delivery. Nat Rev Mater (2021). https://doi.org/10.1038/s41578-021-00358-0.
International Search Report and Written Opinion for PCT/US2021/019103 issued Sep. 30, 2021.
Jain, T.K., et al., Iron Oxide Nanoparticles for Sustained Delivery of Anticancer Agents, Molecular Pharmaceutics, American Chemical Society, 2 (3), 194-205, 2005.
Kalnin, K.V., et al., Immunogenicity and efficacy of mRNA COVID-19 vaccine MRT5500 in preclinical animal models. npj Vaccines 6, 61 (2021). https://doi.org/10.1038/s41541-021-00324-5.
Limbach, P A et al. "Summary: the modified nucleosides of RNA." Nucleic acids research vol. 22, 12 (1994): 2183-96. doi:10.1093/nar/22.12.2183.
Lopez Bernal, J, et al., Effectiveness of Covid-19 Vaccines against the B.1.617.2 (Delta) Variant. N Engl J Med. Aug. 12, 2021;385(7):585-594. doi: 10.1056/NEJMoa2108891. Epub Jul. 21, 2021. PMID: 34289274; PMCID: PMC8314739.
Machado, B.A.S., et al., The Importance of RNA-Based Vaccines in the Fight against COVID-19: An Overview. Vaccines (Basel). Nov. 17, 2021;9(11):1345. doi: 10.3390/vaccines9111345. PMID: 34835276; PMCID: PMC8623509.
Mckay, P. F., et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-17409-9. PMID: 32647131; PMCID: PMC7347890.
Mercado, N.B., et al., "Single-shot Ad26 vaccine protects against SARS-CoV-2 in rhesus macaques" Nature. Oct. 2020;586(7830):583-588. doi: 10.1038/s41586-020-2607-z. Epub Jul. 30, 2020. Erratum in: Nature. Feb. 2021;590(7844): E25. PMID: 32731257; PMCID: PMC7581548.
Meyer, B., et al., Characterising proteolysis during SARS-CoV-2 infection identifies viral cleavage sites and cellular targets with therapeutic potential. Nat Commun. Sep. 21, 2021;12(1):5553. doi: 10.1038/s41467-021-25796-w. PMID: 34548480; PMCID: PMC8455558.
Mohandas, S., et al., Immunogenicity and protective efficacy of BBV152, whole virion inactivated SARS-CoV-2 vaccine candidates in the Syrian hamster model. iScience. Feb. 19, 2021;24(2):102054. doi: 10.1016/j.isci.2021.102054. Epub Jan. 9, 2021. PMID: 33521604; PMCID: PMC7829205.
Planas, D., et al., Reduced sensitivity of SARS-CoV-2 variant Delta to antibody neutralization. Nature. Aug. 2021;596 (7871):276-280. doi: 10.1038/s41586-021-03777-9. Epub Jul. 8, 2021. PMID: 34237773.
Rauch, S, et al., mRNA-based SARS-CoV-2 vaccine candidate CVnCoV induces high levels of virus-neutralising antibodies and mediates protection in rodents. NPJ Vaccines. Apr. 16, 2021;6(1):57. doi: 10.1038/s41541-021-00311-w. PMID: 33863911; PMCID: PMC8052455.
Sheikh, A, et al., SARS-CoV-2 Delta VOC in Scotland: demographics, risk of hospital admission, and vaccine effectiveness. Lancet. Jun. 26, 2021;397(10293):2461-2462. doi: 10.1016/S0140-6736(21)01358-1. Epub Jun. 14, 2021. PMID: 34139198; PMCID: PMC8201647.
Shen, X, et al., SARS-CoV-2 variant B.1.1.7 is susceptible to neutralizing antibodies elicited by ancestral spike vaccines. Cell Host Microbe. Apr. 14, 2021;29(4):529-539.e3. doi: 10.1016/j.chom.2021.03.002. Epub Mar. 5, 2021. PMID: 33705729; PMCID: PMC7934674.
Szurgot, I., et al., DNA-launched RNA replicon vaccines induce potent anti-SARS-CoV-2 immune responses in mice. 2021 Scientific Reports. 11. 10.1038/s41598-021-82498-5.
Van Der Lubbe, J. E. M., et al., Ad26.COV2.S protects Syrian hamsters against G614 spike variant SARS-CoV-2 and does not enhance respiratory disease. NPJ Vaccines. Mar. 19, 2021;6(1):39. doi: 10.1038/s41541-021-00301-y. PMID: 33741993; PMCID: PMC7979827.
Van Doremalen, N., et al. Immunogenicity of low dose prime-boost vaccination of mRNA vaccine CV07050101 in non-human primates. bioRxiv [Preprint]. Jul. 7, 2021:2021.07.07.451505. doi: 10.1101/2021.07.07.451505. Update in: Viruses. Aug. 19, 2021;13(8): PMID: 34268507; PMCID: PMC8282095.
Van Doremalen, N., et al., ChAdOx1 nCoV-19 vaccine prevents SARS-CoV-2 pneumonia in rhesus macaques. Nature. Oct. 2020;586(7830):578-582. doi: 10.1038/s41586-020-2608-y. Epub Jul. 30, 2020. Erratum in: Nature. Feb. 2021;590(7844): E24. PMID: 32731258; PMCID: PMC8436420.
V'kovski, P, et al., "Coronavirus biology and replication: implications for SARS-CoV-2". Nature Reviews. (Mar. 2021). Microbiology. 19 (3): 155-170. doi: 10.1038/s41579-020-00468-6. PMC 7592455. PMID 33116300.
Wang, P., et al., Antibody resistance of SARS-CoV-2 variants B.1.351 and B.1.1.7. Nature. May 2021;593 (7857):130-135. doi: 10.1038/s41586-021-03398-2. Epub Mar. 8, 2021. PMID: 33684923.
Wang, Z., et al., Naturally enhanced neutralizing breadth against SARS-CoV-2 one year after infection. Nature. Jul. 2021; 595(7867):426-

(56) References Cited

OTHER PUBLICATIONS 431. doi: 10.1038/s41586-021-03696-9. Epub Jun. 14, 2021. PMID: 34126625; PMCID: PMC8277577.
Wu, C, et al. "Analysis of therapeutic targets for SARS-CoV-2 and discovery of potential drugs by computational methods," Acta Pharmaceutica Sinica (May 2020). B. 10 (5): 766-788. doi: 10.1016/j.apsb.2020.02.008. PMC 7102550. PMID 32292689, the contents of which are hereby incorporated by reference in their entirety.
Yinda, C. K., et al., Prior aerosol infection with lineage A SARS-CoV-2 variant protects hamsters from disease, but not reinfection with B.1.351 SARS-CoV-2 variant. Emerg Microbes Infect. Dec. 2021; 10(1):1284-1292. doi: 10.1080/22221751.2021.1943539. PMID: 34120579; PMCID: PMC8238069.
Yu, Jingyou et al. "DNA vaccine protection against SARS-COV-2 in rhesus macaques." Science (New York, N.Y.) vol. 369,6505 (2020): 806-811. doi:10.1126/science.abc6284.
Zhang, Y., et al., A second functional furin site in the SARS-CoV-2 spike protein. Emerg Microbes Infect. Dec. 3, 2021:1-35. doi: 10.1080/22221751.2021.2014284. Epub ahead of print. PMID: 34856891.
Zhou, D., et al., Evidence of escape of SARS-CoV-2 variant B.1.351 from natural and vaccine-induced sera. Cell. Apr. 29, 2021;184(9):2348-2361.e6. doi: 10.1016/j.cell.2021.02.037. Epub Feb. 23, 2021. PMID: 33730597; PMCID: PMC7901269.
Zost, S.J., et al., Rapid isolation and profiling of a diverse panel of human monoclonal antibodies targeting the SARS-CoV-2 spike protein. Nat Med. 2020;26(9):1422-1427. PMID: 32651581.
International Search Report issued Jun. 29, 2023 in PCT/US2022/076787.
International Search Report issued Jun. 7, 2023 in PCT/US2022/076304.
Kurup, Drishya, et al. "Inactivated rabies virus vectored SARS-CoV-2 vaccine prevents disease in a Syrian hamster model." PLOS Pathogens 17.3 (2021): e1009383.
Li, Qianwen, et al. "A review of the structure, preparation, and application of NLCs, PNPs, and PLNs." Nanomaterials 7.6 (2017): 122.
Erasmus, Jesse H., et al. "Single-dose replicating RNA vaccine induces neutralizing antibodies against SARS-CoV-2 in nonhuman primates." bioRxiv (2020): 2020-05.
Gerhardt, Alana, et al. "A thermostable, flexible RNA vaccine delivery platform for pandemic response." bioRxiv (2021): 2021-02.
Kulkarni, Jayesh A., et al. "Rapid synthesis of lipid nanoparticles containing hydrophobic inorganic nanoparticles." Nanoscale 9.36 (2017): 13600-13609.
Agnihothram, S., et al., "Development of a Broadly Accessible Venezuelan Equine Encephalitis Virus Replicon Particle Vaccine Platform" J Virol. May 14, 2018;92(11):e00027-18. doi: 10.1128/JVI.00027-18.
Anderluzzi, G., et al., "Investigating the Impact of Delivery System Design on the Efficacy of Self-Amplifying RNA Vaccines" Vaccines (Basel). May 8, 2020;8(2):212. doi: 10.3390/vaccines8020212.
Bazhan, S., et al., "Immunogenicity and Protective Efficacy of Influenza A DNA Vaccines Encoding Artificial Antigens Based on Conservative Hemagglutinin Stem Region and M2 Protein in Mice." Vaccines vol. 8,3 448. Aug. 9, 2020, doi: 10.3390/vaccines8030448.
Boettler, T., et al., "SARS-COV-2 vaccination can elicit a CD8 T-cell dominant hepatitis" J Hepatol. Sep. 2022;77 (3):653-659. doi: 10.1016/j.jhep.2022.03.040.
Brito, L.A., et al., "A Cationic Nanoemulsion for the Delivery of Next-Generation RNA Vaccines" Mol Ther. 2014;22 (12):2118-2129. doi:10.1038/mt.2014.133.
Chiu, C.Y.H., et al., "Association of antibodies to Plasmodium falciparum reticulocyte binding protein homolog 5 with protection from clinical malaria" Front Microbiol. Jun. 3, 20140;5:314. doi: 10.3389/fmicb.2014.00314.
Deo, S., et al. "Evaluation of self-amplifying mRNA platform for protein expression and genetic stability: Implication for mRNA therapies." Biochemical and Biophysical Research Communications 680 (2023): 108-118.
Dewey, E.C., et al., "Programming of RIG-I Signaling Through Co-Factor Interactions," The Journal of Immunology 96 (1 Suppl):203, May 2016, 4 pages.
Du, L., et al., "The Spike Protein of SARS-CoV—A Target for Vaccine and Therapeutic Development", Nat Rev Microbiol 7, 226-236 (2009). https://doi.org/10.1038/nrmicro2090.
Duerrwald, R., et al., "Influenza A virus (A/swine/Bueren/5439/2006(H3N2)) segment 4 hemagglutinin (HA) gene, complete cds". Genbank entry (online). National Center for Biotechnology Information. URL: Https://www.ncbi.nlm.nih.gov/nucleotide/MK362039.1J. Jan. 31, 2020; pp. 1-2.
Erasmus, J.A., et al., "A Nanostructured Lipid Carrier for Delivery of a Replicating Viral RNA Provides Single, Low-Dose Protection against Zika", Mol Ther. Oct. 3, 2018;26(10):2507-2522. doi: 10.1016/j.ymthe.2018.07.010. Epub Aug. 2, 2018. PMID: 30078765; PMCID: PMC6171036.
Felgner, Philip L., et al. "Lipofection: a highly efficient, lipid-mediated DNA-transfection procedure." Proceedings of the National Academy of Sciences 84.21 (1987): 7413-7417.
Fleeton, M. N., et al., "Self-Replicative RNA Vaccines Elicit Protection Against Influenza A Virus, Respiratory Syncytial Virus, and a Tickborne Encephalitis Virus", The Journal of Infectious Diseases, vol. 183, Issue 9, May 1, 2001, pp. 1395-1398, https://doi.org/10.1086/319857.
Fox, C.B., "Squalene emulsions for parenteral vaccine and drug delivery" Molecules. Sep. 1, 2009;14(9):3286-312. doi: 10.3390/molecules14093286.
Gao, Y., et al, "Structure of the RNA-dependent RNA polymerase from COVID-19 virus" Science. May 15, 2020;368 (6492):779-782. doi: 10.1126/science.abb7498.
Gehardt, Alana, et al., "A flexible, thermostable nanostructured lipid carrier platform for RNA vaccine delivery" Mol Ther Methods Clin Dev. Jun. 9, 2022;25:205-214. doi: 10.1016/j.omtm.2022.03.009.
Hartmann, G. "Chapter 4: Nucleic Acid Immunity," in F. Alt (ed.), "Advances in Immunology," 133:121-169, 2017.
Hatmal, M.M., et al., "Comprehensive Structural and Molecular Comparison of Spike Proteins of SARS-CoV-2, SARS-CoV and MERS-COV, and Their Interactions with ACE2" Cells Dec. 8, 2020;9(12):2638. doi: 10.3390/cells9122638.
Hawman, D. W. et al., "SARS-CoV2 variant-specific replicating RNA vaccines protect from disease and pathology and reduce viral shedding following challenge with heterologous SARS-CoV2 variants of concern" bioRxiv [Preprint]. Dec. 1, 20213:2021.12.10.472134. doi: 10.1101/2021.12.10.472134 bioRxiv 2021.12.10.472134; doi: https://doi.org/10.1101/2021.12.10.472134.
Heinz, F.X., and Stiasny, K., "Distinguishing features of current COVID-19 vaccines: knowns and unknowns of antigen presentation and modes of action" NPJ Vaccines. Aug. 16, 2021;6(1):104. doi: 10.1038/s41541-021-00369-6.
Huang, H.C., et al., "Formulation of novel lipid-coated magnetic nanoparticles as the probe for in vivo imaging" J Biomed Sci. Sep. 21, 2009;16(1):86. doi: 10.1186/1423-0127-16-86.
Huang, Y., et al., "Structural and functional properties of SARS-CoV-2 spike protein: potential antivirus drug development for COVID-19" Acta Pharmacol Sin 41, 1141-1149 (2020). https://doi.org/10.1038/s41401-020-0485-4.
International Search Report issued Jun. 6, 2022 in PCT/US2022/13513.
International Search Report issued Jun. 8, 22 in PCT/US2022/013516.
International Search Report issued Jun. 14, 2022 in PCT/US2022/13508.
International Search Report issued in PCT/US2023/060225 dated Jul. 28, 23.
International Search Report issued Jun. 6, 2022 in PCT/US2022/013513.
International Search Report issued Jun. 8, 2023 in PCT/US2022/076821.

(56) References Cited

OTHER PUBLICATIONS

Kautz, T. F., et al., "Low-fidelity Venezuelan equine encephalitis virus polymerase mutants to improve live-attenuated vaccine safety and efficacy" Virus Evol.:4(1); pp. 1-14, Mar. 6, 2018;. doi: 10.1093/ve/vey004.
Kimuira, T, et al., "A localizing nanocarrier formulation enables multi-target immune responses to multivalent replicating RNA with limited systemic inflammation", Molecular Therapy (2023), doi: https://doi.org/10.1016/j.ymthe.2023.06.017.
Kwon, S.M., et al., "In vivo time-dependent gene expression of cationic lipid-based emulsion as a stable and biocompatible non-viral gene carrier" J Control Release. May 22, 2008;128(1):89-97. doi: 10.1016/j.jconrel.2008.02.004. Epub Feb. 19, 2008. Erratum in: J Control Release. Nov. 16, 2009;140(1):74.
Li, X-Y., et al., "Tumor Suppressor Activity of RIG-I," Molecular and Cellular Oncology 1(4):e968016, Dec. 2014.
Marcus, M., et al., "Iron oxide nanoparticles for neuronal cell applications: uptake study and magnetic manipulations", J Nanobiotechnology, vol. 14, Issue 37, May 2016, https://doi.org/10.1186/s12951-016-0190-0.
Maruggi, G., et al., "A self-amplifying mRNA SARS-CoV-2 vaccine candidate induces safe and robust protective immunity in preclinical models" Mol Ther. Jan. 3, 2022:S1525-0016(22)00001-6. doi: 10.1016/j.ymthe.2022.01.001.
Min, J. W., et al., "Hemagglutinin (Influenza A virus (A/Aichi/2/1968(H3N2))]". Genbank entry (online). National Center for Biotechnology Information. Retrieved From The Internet. URL: https://www.ncbi.nlm.nih.gov/protein/AAA43239.1]. Jul. 13, 2006; p. 1.
Pardi, N., et al., "mRNA vaccines—a new era in vaccinology" Nat Rev Drug Discov. Apr. 2018;17(4):261-279. doi: 10.1038/nrd.2017.243. Epub Jan. 12, 2018. PMID: 29326426.
Roeffen, W., et al., "Transmission-blocking activity of antibodies to Plasmodium falciparum Glurp. 10C chimeric protein formulated in different adjuvants" Malar J 14, 443 (2015). https://doi.org/10.1186/s12936-015-0972-0.
Safety and Immunogenicity of HDT-301 Targeting a SARS-CoV-2 Variant Spike Protein, Sponsor: HDT Bio, posted 11/24/21ClinicalTrials.gov Identifier: NCT05132907 found at https://clinicaltrials.gov/ct2/show/record/NCT05132907?term=hdt+bio&draw=2&rank=1 11 pages.
Schoenmaker, L., et al. "mRNA-lipid nanoparticle COVID-19 vaccines: Structure and stability." International journal of pharmaceutics vol. 601 (2021): 120586. doi: 10.1016/j.ijpharm.2021.120586.
Shu, B., et al., "Structural basis of viral RNA-dependent RNA polymerase catalysis and translocation", Proc Natl Acad Sci USA; 113(28):E4005-14, Jun. 23, 2016 doi: 10.1073/pnas.1602591113.
Singh, K., et al., "Malaria vaccine candidate based on Duffy-binding protein elicits strain transcending functional antibodies in a Phase I trial" NPJ Vaccines. Sep. 28, 2018;3:48. doi: 10.1038/s41541-018-0083-3.
Starmans, L.W.E., et al., "Iron oxide nanoparticle-micelles (ION-micelles) for sensitive (molecular) magnetic particle imaging and magnetic resonance imaging" PLoS One. 2013;8(2):e57335. doi: 10.1371/journal.pone.0057335. Epub Feb. 20, 2013.
Stokes, A., et al., "Nonclinical safety assessment of repeated administration and biodistribution of a novel rabies self-amplifying mRNA vaccine in rats" Regul Toxicol Pharmacol. Jun. 2020; 113:104648. doi: 10.1016/j.yrtph.2020.104648.
Teixeira, T. et al., "Cationic nanoemulsions as nucleic acids delivery systems" Int J Pharm. Dec. 20, 2017;534 (1-2):356-367. doi: 10.1016/j.ijpharm.2017.10.030.
Tregoning, J. S., et al., "Formulation, inflammation, and RNA sensing impact the immunogenicity of self-amplifying RNA vaccines" Mol Ther Nucleic Acids. Dec. 5, 2022;31:29-42. doi: 10.1016/j.omtn.2022.11.024.
Tregoning, J.S.. "LION: Taming RNA vaccine inflammation" Mol Ther. Aug. 3, 2023:S1525-0016(23)00386-6. doi: 10.1016/j.ymthe.2023.07.006.
Valdivia, L, et al., Solid Lipid Particles for Lung Metastasis Treatment. Pharmaceutics. 2021; 13(1):93. Published Jan. 13, 2021. doi:10.3390/pharmaceutics13010093.
Voigt, E.A., et al., "A self-amplifying RNA vaccine against COVID-19 with long-term room-temperature stability" npj Vaccines 7, 136 (2022). https://doi.org/10.1038/s41541-022-00549-y.
Walton, T.E., et al., "Experimental infection of horses with an attenuated Venezuelan equine encephalomyelitis vaccine (strain TC-83)" Infect Immun. May 1972;5(5):750-6. doi: 10.1128/iai.5.5.750-756.1972.
Wu, F., et al., "Severe acute respiratory syndrome coronavirus 2 isolate Wuhan-Hu-1, complete genome" GenBank: MN908947.3, VRL Mar. 18, 2020, available at https://www.ncbi.nlm.nih.gov/nuccore/MN908947.
Vargas, Kevin M., and Young-Seok Shon. "Hybrid lipid-nanoparticle complexes for biomedical applications." Journal of Materials Chemistry B 7.5 (2019): 695-708.
Wang et al., Enterovirus D68 isolate DZH-ZJUC, complete genome, Pub. Med. Sequence submission on Sep. 17, 2019. Https://www.ncbi.nlm.nih.gov/nuccore/MK614087.1/ (printed Oct. 17, 2024).
Yates, M. in Microbiology of Waterborne Diseased, 2nd ed. In Enterovirus; Enterovirus—an overview, ScienceDirect Topics, 2014, 2 pages.
Ziegler, E., et al. "Foot-and-mouth disease virus Lb proteinase can stimulate rhinovirus and enterovirus IRES-driven translation and cleave several proteins of cellular and viral origin." Journal of Virology 69.6 (1995): 3465-3474.
Enterovirus D68 strain US/MO/14-18947, partial genome, 2014, www.ncbi.nlm.nih.gov/nuccore/KM851225, accessed Mar. 5, 2025. (Year: 2014).
Malhi, Harman, et al. "Immunization with a self-assembling nanoparticle vaccine displaying EBV gH/gL protects humanized mice against lethal viral challenge." Cell Reports Medicine 3.6 (2022).
Venezuelan equine encephalitis virus strain TC-83, complete genome, 2004, www.ncbi.nlm.nih.gov/nuccore/323714, accessed Mar. 5, 2025 (Year: 2004).
Xiong, Cheng, et al. "Sindbis virus: an efficient, broad host range vector for gene expression in animal cells." Science 243.4895 (1989): 1188-1191.
Yan, Qin, et al. "Vesicular stomatitis virus-based vaccines expressing EV71 virus-like particles elicit strong immune responses and protect newborn mice from lethal challenges." Vaccine 34.35 (2016): 4196-4204.
Zhang, Chao, et al. "Enterovirus D68 virus-like particles expressed in Pichia pastoris potently induce neutralizing antibody responses and confer protection against lethal viral infection in mice." Emerging Microbes & Infections 7.1 (2018): 1-22.

* cited by examiner

CANCER THERAPY COMPOSITIONS AND USES THEREOF

CROSS REFERENCE

This application is a continuation of International Application No. PCT/US2022/076304, filed Sep. 12, 2022, which claims the benefit of priority to U.S. Provisional Patent Application No. 63/247,167, filed Sep. 22, 2021, and U.S. Provisional Patent Application No. 63/302,360, filed Jan. 24, 2022, the contents of each of which are incorporated herein by reference in their entirety.

SEQUENCE LISTING

The instant application contains a Sequence Listing which has been submitted electronically in ST 0.26 xml format and is hereby incorporated by reference in its entirety. Said xml copy, created on Mar. 14, 2024, is named 201953-715301-SL.xml and is 199,986 bytes in size.

BACKGROUND

Cancer is one of the most challenging human diseases to treat or prevent. Cancer cells evade the immune system by suppressing immune cell signaling, avoid programmed cell death, are resistant and adaptive to chemotherapeutic agents. Cancer cells evade the immune system by presenting as "self" and generate tolerizing signals not recognized by the immune system. In addition, solid cancer cells form tight junctions within the affected organ that resist the delivery and impair the efficacy of chemotherapeutic agents and cell therapies. Thus, there is a need for improved compositions and methods for the prevention and treatment of a broad range of cancers.

BRIEF SUMMARY

Provided herein are compositions comprising: lipid nanoparticles, wherein the lipid nanoparticles comprise: surfactants, wherein the surfactants comprise: a cationic lipid; a hydrophilic surfactant; and a hydrophobic surfactant; and at least one nucleic acid, wherein the at least one nucleic acid comprises a sequence encoding for a cancer-associated protein region comprising a cell membrane-contacting domain or a functional fragment thereof. Further provided herein is a composition, wherein the cell membrane-contacting domain comprises a transmembrane-binding domain, an outer cell membrane-contacting domain, or an inner cell membrane-contacting domain. Further provided herein is a composition, wherein the cell membrane-contacting domain comprises a transmembrane-binding domain, an outer cell membrane-contacting domain, and an inner cell membrane-contacting domain. Further provided herein is a composition, wherein the cancer-associated protein is prostein. Further provided herein is a composition, wherein the at least one nucleic acid comprises a region encoding a sequence at least about 80%, 85%, 90%, 95%, 98%, or 99% identical to SEQ ID NO: 90. Further provided herein is a composition, wherein the at least one nucleic acid comprises a region encoding a sequence of SEQ ID NO: 90. Further provided herein is a composition, wherein the cancer-associated protein is a protein expressed by a solid cancer cell or a blood cancer cell. Further provided herein is a composition, wherein the blood cancer cell comprises a melanoma cancer cell, a prostate cancer cell, a colon cancer cell, an ovarian cancer cell, a breast cancer cell, or a pancreatic cancer cell. Further provided herein is a composition, wherein the at least one nucleic acid is in complex with the lipid nanoparticles to form nucleic acid-lipid nanoparticle complexes. Further provided herein is a composition, wherein the at least one nucleic acid further comprises sequence encoding for an RNA-dependent polymerase. Further provided herein is a composition, wherein the composition comprises a second nucleic acid that encodes for an RNA-dependent polymerase Further provided herein is a composition, wherein the RNA-dependent polymerase is a Venezuelan equine encephalitis virus (VEEV) RNA polymerase. Further provided herein is a composition, wherein is the sequence encoding the RNA-dependent polymerase comprises the nucleic acid sequence of SEQ ID NO: 71. Further provided herein is a composition, wherein the lipid nanoparticles comprise a hydrophobic core. Further provided herein is a composition, wherein lipids present in hydrophobic core are in liquid phase at 25 degrees Celsius. Further provided herein is a composition, wherein the lipid nanoparticles are characterized as having a z-average diameter particle size measurement of about 20 nm to about 80 nm when measured using dynamic light scattering. Further provided herein is a composition, wherein the hydrophobic core comprises liquid oil. Further provided herein is a composition, wherein the liquid oil is α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein is a composition, wherein the triglyceride is capric triglyceride, caprylic triglyceride, a caprylic and capric triglyceride, a triglyceride ester, or myristic acid triglycerin. Further provided herein is a composition, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP), dipalmitoyl(C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; 0-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl)

piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9"'"-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9"Z,9"'Z,12Z,12'Z,12"Z,12"'Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein is a composition, wherein the lipid nanoparticles comprise an inorganic particle. Further provided herein is a composition, wherein the inorganic particle is within the hydrophobic core. Further provided herein is a composition, wherein the inorganic particle comprises a metal. Further provided herein is a composition, wherein the metal comprises a metal salt, a metal oxide, a metal hydroxide, or a metal phosphate. Further provided herein is a composition, wherein the metal oxide comprises aluminum oxide, aluminum oxyhydroxide, iron oxide, titanium dioxide, or silicon dioxide. Further provided herein is a composition, wherein the hydrophobic surfactant is sorbitan monolaurate, sorbitan monopalmitate, sorbitan monostearate, sorbitan monooleate, or sorbitan trioleate. Further provided herein is a composition, wherein the hydrophilic surfactant is a polysorbate.

Provided herein are compositions lipid nanoparticles, wherein the lipid nanoparticles comprise: a surface comprising cationic lipids; and a hydrophobic core; and nucleic acids, wherein the nucleic acids comprise a sequence encoding for TRP-1 protein or a functional fragment thereof, and wherein the nucleic acids are complexed to the cationic lipids to form nucleic acid-lipid nanoparticle complexes. Further provided herein is a composition, wherein the nucleic acids comprise a sequence at least about 80%, 85%, 90%, 95%, 98%, or 99% identical to SEQ ID NO: 2. Further provided herein is a composition, wherein the nucleic acids comprise a sequence of SEQ ID NO: 2. Further provided herein is a composition, wherein the nucleic acids comprise a sequence at least about 80%, 85%, 90%, 95%, 98%, or 99% identical to SEQ ID NO: 76. Further provided herein is a composition, wherein the nucleic acids comprise a sequence of SEQ ID NO: 76. Further provided herein is a composition, wherein the nucleic acids encode an amino acid sequence that is at least about 80%, 85%, 90%, 95%, 98%, or 99% identical to SEQ ID NO: 78 or a functional fragment thereof. Further provided herein is a composition, wherein the nucleic acids encode an amino acid sequence that comprises SEQ ID NO: 78 or a functional fragment thereof. Further provided herein is a composition, further comprising a nucleic acid that encodes an RNA polymerase. Further provided herein is a composition, wherein the nucleic acids further comprise sequence encoding for an RNA polymerase. Further provided herein is a composition, wherein the RNA polymerase is a Venezuelan equine encephalitis virus (VEEV) RNA polymerase. Further provided herein is a composition, wherein the sequence encoding the RNA polymerase comprises the nucleic acid sequence of SEQ ID NO: 71. Further provided herein is a composition, wherein lipids present in hydrophobic core are in liquid phase at 25 degrees Celsius. Further provided herein is a composition, wherein the lipid nanoparticles are characterized as having a z-average diameter particle size measurement of about 20 nm to about 80 nm when measured using dynamic light scattering. Further provided herein is a composition, wherein the hydrophobic core comprises liquid oil. Further provided herein is a composition, wherein the liquid oil comprises α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein is a composition, wherein the triglyceride is capric triglyceride, caprylic triglyceride, a caprylic and capric triglyceride, a triglyceride ester, or myristic acid triglycerin. Further provided herein is a composition, wherein the cationic lipids comprise 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP), dipalmitoyl(C16:0)trimethyl ammonium propane (DPTAP), distearoyltrimethylammonium propane (DSTAP), N-[1-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3"'-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9"'"-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9"Z,9"'Z,12Z,12'Z,12"Z,12"'Z)-tetrakis (octadeca-9,12-dienoate); PEG2000-DMG, (R)-2,3-bis (myristoyloxy)propyl-1-(methoxy poly(ethylene glycol) 2000) carbamate; TT3; or N1,N3,N5-tris(3-(didodecylamino)propyl)benzene-1,3,5-tricarboxamide. Further provided herein is a composition, wherein the lipid nanoparticles comprise an inorganic particle. Further provided herein is a composition, wherein the inorganic particle is within the hydrophobic core. Further provided herein is a composition, wherein the inorganic particle comprises a metal. Further provided herein is a composition, wherein the metal comprises a metal salt, a metal oxide, a metal hydroxide, or a metal phosphate. Further provided herein is a composition, wherein the metal oxide comprises aluminum oxide, aluminum oxyhydroxide, iron oxide, titanium dioxide, or silicon dioxide. Further provided herein is a composition, further comprising a hydrophobic surfactant and a hydrophilic surfactant. Further provided herein is a composition, wherein the hydrophobic surfactant comprises sorbitan monolaurate, sorbitan monopalmitate, sorbitan monostearate, sorbitan monooleate, or sorbitan trioleate. Further provided herein is a composition, wherein the hydrophilic surfactant comprises polysorbate.

Provided here are compositions comprising a composition comprising: lipid nanoparticles, wherein the lipid nanoparticles comprise: a surface comprising cationic lipids; and a hydrophobic core; and nucleic acids, wherein the nucleic acids comprise a sequence encoding for MAGE-A1 protein or a functional fragment thereof, and wherein the nucleic acids are complexed to the cationic lipids to form nucleic acid-lipid nanoparticle complexes. Further provided herein is a composition, wherein the nucleic acids comprise a sequence at least about 80%, 85%, 90%, 95%, 98%, or 99% identical to SEQ ID NO: 1. Further provided herein is a composition, wherein the nucleic acids comprise a sequence of SEQ ID NO: 1. Further provided herein is a composition, wherein the nucleic acids comprise a sequence at least about 80%, 85%, 90%, 95%, 98%, or 99% identical to SEQ ID NO: 88. Further provided herein is a composition, wherein the nucleic acids comprise a sequence of SEQ ID NO: 88. Further provided herein is a composition, wherein the nucleic acids comprise a sequence at least about 80%, 85%, 90%, 95%, 98%, or 99% identical to SEQ ID NO: 75. Further provided herein is a composition, wherein the nucleic acids comprise a sequence of SEQ ID NO: 75. Further provided herein is a composition, wherein the nucleic acids comprise a sequence at least about 80%, 85%, 90%, 95%, 98%, or 99% identical to SEQ ID NO: 89. Further provided herein is a composition, wherein the nucleic acids comprise a sequence of SEQ ID NO: 89. Further provided herein is a composition, wherein the nucleic acids encode an amino acid sequence that is at least about 80%, 85%, 90%, 95%, 98%, or 99% identical to SEQ ID NO: 77 or a functional fragment thereof. Further provided herein is a composition, wherein the nucleic acids encode an amino acid sequence that comprises SEQ ID NO: 77 or a functional fragment thereof. Further provided herein is a composition, wherein the nucleic acids encode an amino acid sequence that is at least about 80%, 85%, 90%, 95%, 98%, or 99% identical to SEQ ID NO: 87 or a functional fragment thereof. Further provided herein is a composition, wherein the nucleic acids encode an amino acid sequence that comprises SEQ ID NO: 87 or a functional fragment thereof. Further provided herein is a composition, wherein comprising a nucleic acid that encodes an RNA polymerase. Further provided herein is a composition, wherein the nucleic acids further comprise sequence encoding for an RNA polymerase. Further provided herein is a composition, wherein the RNA polymerase is a Venezuelan equine encephalitis virus (VEEV) RNA polymerase. Further provided herein is a composition, wherein the sequence encoding the RNA polymerase comprises the nucleic acid sequence of SEQ ID NO: 71. Further provided herein is a composition, wherein lipids present in hydrophobic core are in liquid phase at 25 degrees Celsius. Further provided herein is a composition, wherein the lipid nanoparticles are characterized as having a z-average diameter particle size measurement of about 20 nm to about 80 nm when measured using dynamic light scattering. Further provided herein is a composition, wherein the hydrophobic core comprises liquid oil. Further provided herein is a composition, wherein the liquid oil comprises α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein is a composition, wherein the triglyceride is capric triglyceride, caprylic triglyceride, a caprylic and capric triglyceride, a triglyceride ester, or myristic acid triglycerin. Further provided herein is a composition, wherein the cationic lipids comprise 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP), dipalmitoyl(C16:0)trimethyl ammonium propane (DPTAP), distearoyltrimethylammonium propane (DSTAP), N-[1-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9'",9"",9'""-((((benzene-1,3,5-tricarbonyl)yris(azanediyl)) tris (propane-3,1-diyl)) tris(azanetriyl))hexanonanoate; Lipid H (SM-102), heptadecan- 9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9"Z,9'"Z,12Z,12'Z,12"Z,12'"Z)-tetrakis (octadeca-9,12-dienoate); PEG2000-DMG, (R)-2,3-bis (myristoyloxy)propyl-1-(methoxy poly(ethylene glycol) 2000) carbamate; TT3; or N1,N3,N5-tris(3-(didodecylamino)propyl)benzene-1,3,5-tricarboxamide. Further provided herein is a composition, wherein the lipid nanoparticles comprise an inorganic particle. Further provided herein is a composition, wherein the inorganic particle is within the hydrophobic core. Further provided herein is a composition, wherein the inorganic particle comprises a metal. Further provided herein is a composition, wherein the metal comprises a metal salt, a metal oxide, a metal hydroxide, or a metal phosphate. Further provided herein is a composition, wherein the metal oxide comprises aluminum oxide, aluminum oxyhydroxide, iron oxide, titanium dioxide, or silicon dioxide. Further provided herein is a composition, wherein comprising a hydrophobic surfactant and a hydrophilic surfactant. Further provided herein is a composition, wherein the hydrophobic surfactant comprises sorbitan monolaurate, sorbitan monopalmitate, sorbitan monostearate, sorbitan monooleate, or sorbitan trioleate. Further provided herein is a composition, wherein the hydrophilic surfactant comprises polysorbate.

Provided herein are compositions comprising a nucleic acid, wherein the nucleic acid comprises a sequence encoding for: a protein or a functional fragment thereof listed in Table 1; and an RNA polymerase complex region. Further provided herein is a composition, wherein the protein or functional fragment thereof is a cancer-associated protein. Further provided herein is a composition, wherein the protein or functional fragment thereof comprises an amino acid sequence referenced in Table 1. Further provided herein is a composition, wherein the protein or functional fragment thereof comprises an antibody or a functional fragment thereof. Further provided herein is a composition, wherein the antibody or the functional fragment thereof comprises an antibody listed in Table 2. Further provided herein is a composition, wherein the antibody comprises an immunoglobulin (Ig) molecule or a functional fragment thereof. Further provided herein is a composition, wherein the immunoglobulin molecule is an IgG, IgE, IgM, IgD, IgA, or an IgY isotype immunoglobulin molecule or a functional fragment thereof. Further provided herein is a composition, wherein the immunoglobulin molecule of the functional fragment comprises at least a fragment of an IgG1, an IgG2, an IgG3, an IgG4, an IgGA1, or an IgGA2 subclass immunoglobulin molecule. Further provided herein is a composition, wherein the antibody or functional fragment thereof specifically binds to a tumor antigen or a viral antigen. Further provided herein is a composition, wherein the antibody or functional fragment thereof is atezolizumab, avelumab, bevacizumab, cemiplimab, cetuximab, daratumumab, dinutuximab, durvalumab, elotuzumab, ipilimumab, isatuximab, mogamulizumab, necitumumab, nivolumab, obinutuzumab, ofatumumab, olaratumab, panitumumab, pembrolizumab, pertuzumab, ramucirumab, rituximab, or trastuzumab. Further provided herein is a composition, wherein the RNA polymerase complex region is downstream of a subgenomic promoter from an alphavirus. Further provided herein is a composition, wherein RNA polymerase complex region encodes for an RNA-dependent RNA polymerase. Further provided herein is a composition, wherein the RNA-dependent RNA polymerase is Venezuelan equine encephalitis virus (VEEV) RNA polymerase. Further provided herein is a composition, wherein the sequence encoding for the RNA polymerase complex region comprises SEQ ID NO: 71. Further provided herein is a composition, further comprising a lipid nanoparticle for complexation to the nucleic acid. Further provided herein is a composition, wherein the composition is lyophilized. Further provided herein is a composition, wherein the composition is in a liquid, semi-liquid, solution, propellant, or powder dosage form. Further provided herein is a composition, wherein the composition is formulated as a suspension.

Provided herein are pharmaceutical compositions comprising a composition described herein and a pharmaceutically acceptable excipient. In some embodiments, the pharmaceutically acceptable excipient comprises water. In some embodiments, the pharmaceutically acceptable excipient comprises a sugar. In some embodiments, the sugar comprises sucrose.

Provided herein are methods of generating an immune response in a subject, the method comprising: administering to a subject a composition described herein, or a pharmaceutical composition described herein, thereby generating an immune response to a cancer-associated protein. Further provided herein are methods, wherein the composition is administered to the subject over at least two doses. Further provided herein are methods, wherein the at least two doses are administered at least about 28 days apart. Further provided herein are methods, wherein up to 5 μg, 10 ug 25 ug, or more of nucleic acid is present in the composition administered to the subject. Further provided herein are methods, wherein the composition is administered via intramuscular injection, intranasal administration, oral administration, subcutaneous administration, intratumoral administration, intrathecal administration, or intravenous injection. Further provided herein are methods, wherein the subject is a domesticated animal or farmed animal. Further provided herein are methods, wherein the subject is a mammal. Further provided herein are methods, wherein the subject is a human. Further provided herein are methods, wherein the subject has, is at risk for, or is suspected of having a cancer. Further provided herein are methods, wherein the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has, is at risk for developing, or is suspected of having a skin cancer. Further provided herein are methods, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are methods, wherein the subject has, is at risk for developing, or is suspected of having a pancreatic cancer. Further provided herein are methods, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are methods, wherein the subject has, is at risk for developing, or is suspected of having a colon cancer, a prostate cancer, an ovarian cancer, or a breast cancer. Further provided herein are methods, wherein the cancer expresses a TRP-1 protein, a prostein protein, a MAGE-A1 protein, a MAGE-A3 protein, or a combination thereof.

Provided herein are methods treating a cancer in a subject, the method comprising: receiving a biomarker report that indicates that a subject has a cancer; classifying the cancer based on the biomarker report; and administering to the subject the composition or pharmaceutical composition described herein. Further provided herein are methods, wherein the composition is administered to the subject over at least two doses. Further provided herein are methods, wherein the at least two doses are administered at least about 28 days apart. Further provided herein are methods, wherein up to 5 μg, 10 ug 25 ug, or more of nucleic acid is present in the composition administered to the subject. Further provided herein are methods, wherein the composition is administered via intramuscular injection, intranasal administration, oral administration, subcutaneous administration, intratumoral administration, intrathecal administration, or intravenous injection. Further provided herein are methods, wherein the subject is a domesticated animal or farmed animal. Further provided herein are methods, wherein the subject is a mammal. Further provided herein are methods, wherein the subject is a human. Further provided herein are methods, wherein the cancer is a solid cancer or a blood cancer. Further provided herein are methods, wherein the cancer expresses a TRP-1 protein, a prostein protein, a MAGE-A1 protein, a MAGE-A3 protein, or a combination thereof.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for a cancer-associated protein.

Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for an antibody or a functional variant thereof.

Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for a cancer therapeutic antibody or a functional variant thereof.

Further provided herein are compositions, wherein the compositions comprise: a lipid carrier, wherein the lipid carrier comprises: liquid oil; an inorganic nanoparticle, wherein the inorganic nanoparticle comprises iron oxide present in an amount of about 0.2 mg/ml 12 nm iron oxide; and surfactants, wherein the surfactants comprise a cationic lipid; and at least one nucleic acid, wherein the nucleic acid comprises a sequence encoding for a cancer-associated protein sequence or functional variant thereof.

Further provided herein are compositions, wherein the compositions comprise: (a) a lipid carrier, wherein the lipid carrier is a nanoemulsion comprising: about 30 mg/mL DOTAP chloride; about 37.5 mg/ml squalene; about 37 mg/ml sorbitan monostearate; about 37 mg/ml polysorbate 80; about 10 mM sodium citrate; and about 0.2 mg Fe/ml 12 nm oleic acid-coated iron oxide nanoparticles; and (b) at least one nucleic acid, wherein the at least one nucleic acid comprises a sequence encoding for a cancer-associated protein sequence or functional variant thereof.

Further provided herein are compositions, wherein the compositions comprise: (a) a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; and oleic acid-coated iron oxide nanoparticles present in an amount of about 0.005 mg; and (b) at least one nucleic acid, wherein the at least one nucleic acid comprises a sequence encoding for a cancer-associated protein sequence or functional variant thereof.

Further provided herein are compositions, wherein the compositions comprise: a first nucleic acid comprising a sequence encoding for an RNA-dependent RNA polymerase; and a second nucleic acid comprising a sequence encoding for a cancer-associated protein sequence or functional variant thereof.

Further provided herein are compositions, wherein the compositions comprise: a first nucleic acid comprising a sequence encoding for an RNA-dependent RNA polymerase; and a second nucleic acid comprising a sequence encoding for a cancer-associated protein binding antibody or antibody fragment.

Further provided herein are compositions, wherein the compositions comprise: (a) a lipid carrier, wherein the lipid carrier is a nanoemulsion comprising a hydrophobic core, optionally one or more inorganic nanoparticles; and one or more lipids; and (b) at least one nucleic acid sequence, wherein the nucleic acid sequence comprises a sequence which encodes a sequence capable of expressing an antigen, wherein the antigen is a cancer-associated protein.

Further provided herein are vaccines, wherein the vaccines comprise: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein.

Further provided herein are methods of generating an immune response in a subject, wherein the methods comprise: administering to said subject a composition comprising a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein.

Further provided herein are compositions for immunoprotecting a subject, wherein the compositions comprise: a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein.

Further provided herein are dried compositions, wherein the dried compositions comprise: a composition provided herein; and at least one cryoprotectant.

Further provided herein are compositions for prophylaxis of a cancer, the compositions comprising: a sorbitan fatty acid ester, an ethoxylated sorbitan ester, a cationic lipid, an immune stimulant, and at least one RNA encoding an antigen sequence or functional fragment thereof.

Further provided herein are compositions for prophylaxis of a cancer, the compositions comprising: sorbitan monostearate (e.g., SPAN® 60), polysorbate 80 (e.g., TWEEN®

80), DOTAP, an immune stimulant, and at least one RNA encoding an antigen sequence or functional fragment thereof.

Further provided herein are pharmaceutical compositions, wherein the pharmaceutical compositions comprise: a composition provided herein; and a pharmaceutically acceptable excipient. Further provided herein are pharmaceutical compositions, wherein the pharmaceutical compositions comprise: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein.

Further provided herein are kits, wherein the kits comprise a composition provided herein.

Further provided herein are methods of generating an immune response in a subject, the methods comprise: administering to a subject a composition provided herein, thereby generating an immune response to a cancer-associated protein. Further provided herein are methods of generating an immune response in a subject, wherein the methods comprise: administering to a subject: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein.

Further provided herein are methods of prophylactically immunizing a subject for a cancer, the methods comprise: administering to a subject a composition provided herein, thereby immunizing the subject to a cancer expressing a cancer-associated protein.

Further provided herein are methods of reducing the severity of a cancer, wherein the methods comprise: administering a composition comprising a lipid carrier, wherein the lipid carrier is a nanoemulsion comprising a hydrophobic core, optionally one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein.

Further provided herein are methods of immunoprotecting a subject, wherein the methods comprise: administering to the subject a lipid carrier, wherein the lipid carrier is a nanoemulsion comprising a hydrophobic core, one or more inorganic nanoparticles and one or more lipids, at least one nucleic acid sequence, wherein the nucleic acid sequence comprises a sequence which encodes a sequence capable of expressing an antigen, wherein the antigen is a cancer-associated protein.

Further provided herein are methods for preparing a lyophilized composition, wherein the methods comprising: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, and lyophilizing the formulation to form a lyophilized composition.

Further provided herein are methods for preparing a spray-dried composition, wherein the methods comprise: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, and spray drying the formulation to form a spray-dried composition.

The present invention also relates to a method for reconstituting a lyophilized composition comprising obtaining a lipid carrier, wherein the lipid carrier is a nanoemulsion comprising a hydrophobic core, one or more inorganic nanoparticles, and one or more lipids, incorporating at least one nucleic acid into the said lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, lyophilizing the formulation to form a lyophilized composition, and reconstituting the lyophilized composition in a suitable diluent.

Further provided herein are methods for reconstituting a spray-dried composition, wherein the methods comprise: obtaining a lipid carrier, wherein the lipid carrier is a nanoemulsion comprising a hydrophobic core, one or more inorganic nanoparticles, and one or more lipids, incorporating at least one nucleic acid into the said lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, spray drying the formulation to form a spray-dried composition, and reconstituting the spray-dried composition in a suitable diluent.

Additional features of the present invention will be apparent to persons of ordinary skill in the art in view of the following disclosure, as well as the accompanying drawings and claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIG. 1A shows an oil-in-water emulsion. FIG. 1B shows a nanostructured lipid carrier (NLC). FIG. 1C shows a nanoparticle having an inorganic nanoparticle in liquid oil. FIG. 1D shows a nanoparticle having a cationic lipid membrane and a liquid oil core. FIG. 1E shows an oil-in-water emulsion with two or more RNA or DNA molecules. FIG. 1F shows a nanostructured lipid carrier (NLC) with two or more RNA or DNA molecules. FIG. 1G shows a nanoparticle having an inorganic nanoparticle in liquid oil two or more RNA or DNA molecules. FIG. 1H shows a nanoparticle having a cationic lipid membrane, a liquid oil core, and two or more RNA or DNA molecules. Drawings not to scale.

FIG. 2A shows the first assay. FIG. 2B shows the second assay.

FIG. 3A shows the first assay. FIG. 3B shows the second assay.

FIG. 4A shows the first assay. FIG. 4B shows the second assay.

FIG. 5A shows SEAP levels on day 4 post-injection. FIG. 5B shows SEAP levels on day 6 post-injection. FIG. 5C shows SEAP levels on day 8 post-injection. FIG. 5D shows SEAP levels on day 4 post-injection. FIG. 5E shows SEAP levels on day 6 post-injection. FIG. 5F shows SEAP levels on day 8 post-injection. X-axis: Condition, Y-axis: Relative light units (RLU).

FIG. 7A shows untreated B16 mouse tumor volume over time. X-axis: time, Y-axis: tumor volume ($mm^3$). FIG. 7B shows B16 mouse tumor volume over time for mice treated with lipid carrier+0.2 micrograms (μg) TRP-1 repRNA, at day 0 and day 14. X-axis: time, Y-axis: tumor volume ($mm^3$). FIG. 7C shows B16 mouse tumor volume over time for mice treated with lipid carrier+0.2 μg TRP-1 repRNA, at day 0 only. X-axis: time, Y-axis: tumor volume ($mm^3$). FIG. 7D shows B16 mouse tumor volume over time for mice treated with lipid carrier+1 μg TRP-1 repRNA, at day 0 and day 14. X-axis: time, Y-axis: tumor volume ($mm^3$). FIG. 7E shows B16 mouse tumor volume over time for mice treated with lipid carrier+1 μg TRP-1 repRNA, at day 0 only. X-axis: time, Y-axis: tumor volume ($mm^3$).

FIG. 7F shows animal survival rate over time. X axis: days after inoculation, Y-axis: percentage of animals alive.

FIG. 10A shows CD8 T cells expressing Tbet and IFNγ. FIG. 10B shows the % IFNγ positive CD8 T cells in MAGE treated animals. FIG. 10C shows CD4 T cells producing IFNγ. FIG. 10D shows CD4 T cells producing IL-2. Flow cytometry plots are representative, while plots show data obtained from individual animals as well as mean and SEM.

FIG. 11A shows mean tumor volume (Y-axis) as a function of days post-implantation of tumors (X-axis). FIG. 11B shows the probability of survival in animals treated with no RNA, TRP-1/MAGE RNAs pre-palpable, and TRP-1/MAGE post-palpable. X-axis: Probability of survival; Y-axis: Days post-transplantation of tumors.

Figure 1A:
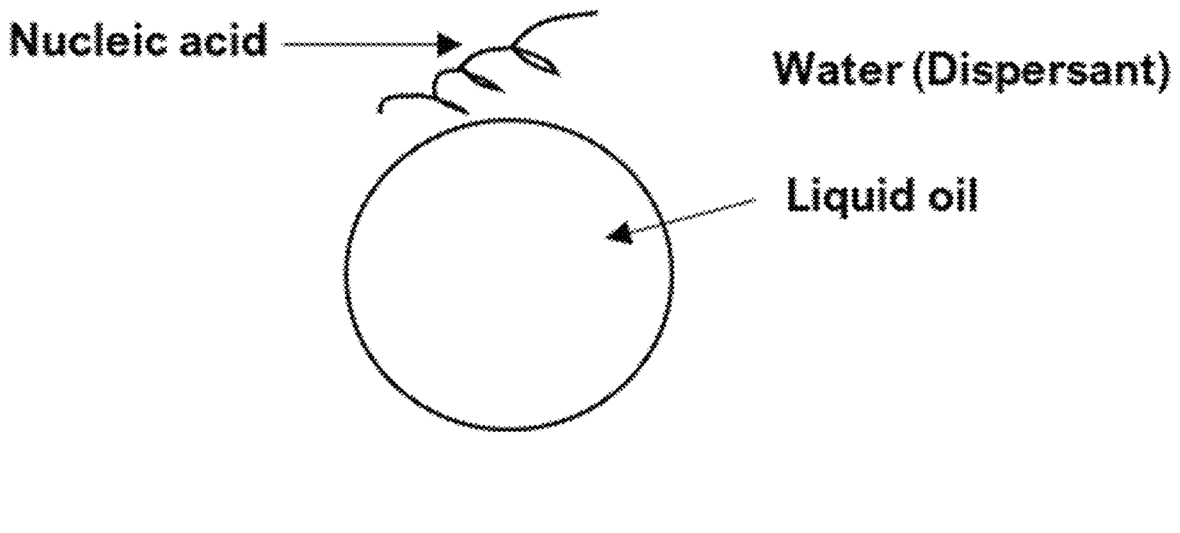
FIGS. 1A-1H show schematic representations of exemplary nanoparticle (NP) carriers.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION OF THE INVENTION

Provided herein are compositions, kits, methods, and uses thereof for inducing an immune response to a cancer cell or a tumor. Briefly, further described herein are (1) nucleic acids encoding for cancer-associated proteins, neoantigens, antibodies, and RNA polymerases; (2) nanoparticle carrier systems; (3) combination compositions; (4) thermally stable, dried, and lyophilized cancer vaccines; (5) pharmaceutical compositions; (6) dosing; (7) administration; (8) therapeutic applications; and (9) kits.

Definitions

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. All references disclosed herein, including patent references and non-patent references, are hereby incorporated by reference in their entirety as if each was incorporated individually. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as anon-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein, "optional" or "optionally" means that the subsequently described circumstance may or may not occur, so that the description includes instances where the circumstance occurs and instances where it does not.

Unless specifically stated or apparent from context, as used herein, the term "about" in reference to a number or range of numbers is understood to mean the stated number and numbers+/−20% thereof, or 20% below the lower listed limit and 20% above the higher listed limit for the values listed for a range.

The term "effective amount" or "therapeutically effective amount" refers to an amount that is sufficient to achieve or at least partially achieve the desired effect.

Nucleic Acids

Provided herein are compositions comprising nucleic acids. In some embodiments, compositions provided herein comprise one or more types of nucleic acid sequences. In some embodiments, compositions provided herein comprise two or more types of nucleic acid sequences. In some embodiments, compositions provided herein comprise at least one DNA molecule. In some embodiments, compositions provided herein comprise at least one RNA molecule. In some embodiments, compositions provided herein comprise at least one DNA molecule and at least one RNA molecule.

In some embodiments, a nucleic acid provided herein is in complex with a nanoparticle provided herein. In some embodiments, the nucleic acid is in complex with a surface of the nanoparticle. In some embodiments, the nucleic acid is in complex with a hydrophilic surface of the nanoparticle. In some embodiments, the nucleic acid is located within the nanoparticle. In some embodiments, the nucleic acid is located within the hydrophobic core of the nanoparticle. In some embodiments, the nanoparticle is a lipid carrier nanoparticle, and the surface may be referred to herein as a membrane.

In some embodiments, nucleic acids provided herein comprise a deoxyribonucleic acid (DNA), a ribonucleic acid (RNA), a peptide nucleic acid (PNA), or a combination thereof. A nucleic acid can be linear or include a secondary structure (e.g., a hair pin). In some embodiments, the nucleic acid is a polynucleotide comprising modified nucleotides or bases, and/or their analogs. A polynucleotide may comprise modified nucleotides, such as methylated nucleotides and their analogs. If present, modification to the nucleotide structure may be imparted before or after assembly of compositions provided herein. Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); hoSU (5-hydroxyuridine); moSU (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-0-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Any one or any combination of these modified nucleobases may be included in the self-replicating RNA of the invention. Many of these modified nucleobases and their corresponding ribonucleosides are available from commercial suppliers. If desired, the nucleic acid can contain phosphoramidate, phosphorothioate, and/or methylphosphonate linkages. The RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap structure can provide stability and translational efficacy to the RNA molecule. The 5' cap of the RNA molecule may be further modified by a 2'-O-Methyltransferase which results in the generation of a cap 1 structure (m7Gppp [m2'-O] N), which may further increase translation efficacy. A cap 1 structure may also increase in vivo potency.

In some embodiments, nucleic acids provided herein are present in an amount of about 5 ng to about 1 mg. In some embodiments, nucleic acids provided herein are present in an amount of up to about 25, 50, 75, 100, 150, 175 ng. In some embodiments, nucleic acids provided herein are present in an amount of up to about 1 mg. In some embodiments, nucleic acids provided herein are present in an amount of about 0.05 μg, 0.1 μg, 0.2 μg, 0.5 μg, 1 μg, 5 μg, 10 μg, 12.5 μg, 15 μg, 25 μg, 40 μg, 50 μg, 100 μg, 200 μg, 300 μg, 400 μg, 500 μg, 600 μg, 700 μg, 800 μg, 900 μg, 1 mg. In some embodiments, nucleic acids provided herein are present in an amount of 0.05 μg, 0.1 μg, 0.2 μg, 0.5 μg, 1 μg, 5 μg, 10 μg, 12.5 μg, 15 μg, 25 μg, 40 μg, 50 μg, 100 μg, 200 μg, 300 μg, 400 μg, 500 μg, 600 μg, 700 μg, 800 μg, 900 μg, 1 mg. In some embodiments, the nucleic acid is at least about 200, 250, 500, 750, 1000, 2000, 3000, 4000, 5000, 6000, 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is up to about 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is about 7500, 10,000, 15,000, or 20,000 nucleotides in length.

Nucleic Acids Encoding Cancer-Associated Proteins

Provided herein are compositions, wherein the compositions comprise: a lipid carrier provided herein; and one or more nucleic acids, wherein the one or more nucleic acids comprises a sequence encoding for an antigen. In some embodiments, the antigen is a cancer-associated protein (also referred to as a tumor protein antigen or tumor antigen). In some embodiments, nucleic acids provided herein encode for a cancer-associated protein. In some embodiments, the cancer-associated protein is a surface protein, a cytosolic protein, or a transmembrane protein. In some embodiments, the cancer-associated protein is a protein that is expressed by a cancer cell. In some embodiments, the cancer-associated protein is a protein that is expressed by a microbial organism that causes a cancer (e.g., viral proteins).

In some embodiments, nucleic acids provided herein encode for a protein expressed by a solid cancer cell or a blood cancer cell. In some embodiments, the solid cancer cell is a melanoma cell. In some embodiments, the protein expressed by the melanoma cell is not expressed by a non-cancer cell. In some embodiments, the protein expressed by a melanoma cell comprises a mutation in the amino acid sequence relative to a comparable amino acid sequence in a non-cancer cell. In some embodiments, nucleic acids provided herein encode for MAGE-A1 (SEQ ID NO: 1) or a functional fragment thereof. In some embodiments, nucleic acids provided herein encode for MAGE-A3 (SEQ ID NO: 87) or a functional fragment thereof. In some embodiments, nucleic acids provided herein encode for TRP-1 (SEQ ID NO: 2) or a functional fragment thereof. In some embodiments, nucleic acids provided herein encode for TRP-1 and MAGE-A1. In some embodiments, nucleic acids provided herein encode for TRP-1 and MAGE-A3. In some embodiments, nucleic acids provided herein encode for a tyrosinase. In some embodiments, nucleic acids provided herein comprise a sequence that is at least 80% identical to SEQ ID NOS: 1, 2, 75, 76, 88, or 89. In some embodiments, nucleic acids provided herein comprise a sequence that is at least 80% identical to SEQ ID NOS: 1, 2, 75, 76, 88, or 89. In some embodiments, nucleic acids provided herein encode for an amino acid sequence listed in Table 1. In some embodiments, nucleic acids provided herein encode for an amino acid sequence that is at least 80% identical to SEQ ID NO: 77 or SEQ ID NO: 78. In some embodiments, nucleic acids provided herein encode for an amino acid sequence that is at least 80% identical to SEQ ID NO: 87. In some embodiments, compositions provided herein comprise two or more, three or more, four or more, five or more, six or more, or up to seven or more nucleic acids coding different sequences listed in Table 1. In some embodiments, nucleic acids provided herein encoding for a protein sequence listed in Table 1 is used as part of a treatment or prevention of melanoma. In some embodiments, a nucleic acid provided herein encodes for a cancer-associated protein listed in Table 1. In some embodiments, compositions provided herein comprise two or more nucleic acids encoding for different sequences listed in Table 1. In some embodiments, nucleic acids provided herein encode for a cancer-associated protein sequence comprising at least 80%, 85%, 90%, 95%, 96%, 97%, 98%, or 99% sequence identity to a sequence listed in Table 1. In some embodiments, compositions provided herein comprise two or more nucleic acids encoding different sequences listed in Table 1. In some embodiments, the nucleic acid provided herein encodes for a cancer-associated protein or a functional fragment thereof comprising at least 80%, 85%, 90%, 95%, 96%, 97%, 98%, or 99% sequence similarity to a sequence listed Table 1. Percent (%) sequence identity for a given sequence relative to a reference sequence is defined as the percentage of identical residues identified after aligning the two sequences and introducing gaps if necessary, to achieve the maximum percent sequence identity. Percent identity can be calculated using alignment methods known in the art, for instance alignment of the sequences can be conducted using publicly available software such as BLAST, Align, ClustalW2. Those skilled in the art can determine the appropriate parameters for alignment, but the default parameters for BLAST are specifically contemplated.

TABLE 1

Exemplary Cancer-Associated Proteins on Melanoma Cells.

| SEQ ID NO: | Reference Protein | Amino Acid Sequence |
|---|---|---|
| SEQ ID NO: 3 | Tyrosinase | KCDICTDEY |
| SEQ ID NO: 4 | Tyrosinase | YMDGTMSQV |
| SEQ ID NO: 5 | Tyrosinase | MLLAYLYQL |
| SEQ ID NO: 6 | Tyrosinase | AFLPWHRLF, |
| SEQ ID NO: 7 | Tyrosinase | SEIWRDIDF |
| SEQ ID NO: 8 | gp100/pMEL17 | YLEPGPVTA |
| SEQ ID NO: 9 | gp100/pMEL17 | KTWGQUWQV |
| SEQ ID NO: 10 | gp100/pMEL17 | ITDQVPFSV |
| SEQ ID NO: 11 | gp100/pMEL17 | VLYRYGSFSV |
| SEQ ID NO: 12 | gp100/pMEL17 | LLDGTATLRL |
| SEQ ID NO: 13 | gp100/pMEL17 | ALLAVGATK |
| SEQ ID NO: 14 | gp100/pMEL17 | MLGTHTMEV |
| SEQ ID NO: 15 | gp100/pMEL17 | LIYRRRLMK |
| SEQ ID NO: 16 | gp100/pMEL17 | ALNFPGSQK |
| SEQ ID NO: 17 | MART-1/MelanA | AAGIGILTV[†] |
| SEQ ID NO: 18 | MART-1/MelanA | ILTVILGVL |
| SEQ ID NO: 19 | gp75/TRP-1 | MSLQRQFLR |
| SEQ ID NO: 20 | TRP-2 | SVYDFFVWL |
| SEQ ID NO: 21 | TRP-2 | LLGPGRPYR |
| SEQ ID NO: 22 | CEA | YLSGANLNL |
| SEQ ID NO: 23 | HER-2/neu | KIFGSLAFL |
| SEQ ID NO: 24 | HER-2/neu | VMAGVGSPYV |
| SEQ ID NO: 25 | HER-2/neu | IISAVVGIL |
| SEQ ID NO: 26 | PSMA | LLHETDSAV |
| SEQ ID NO: 27 | PSMA | ALFDIESKV |
| SEQ ID NO: 28 | MAGE-1 | EADPTGHSY |
| SEQ ID NO: 29 | MAGE-1 | SLFRAVITK |
| SEQ ID NO: 30 | MAGE-1 | SAYGEPRKL |
| SEQ ID NO: 31 | MAGE-2 | KMVELVHFL |
| SEQ ID NO: 32 | MAGE-2 | YLOLVFGIEV |
| SEQ ID NO: 33 | MAGE-3 | EVDPIGHLY |
| SEQ ID NO: 34 | MAGE-3 | FLWGPRALV |
| SEQ ID NO: 35 | MAGE-3 | MEVDPIGHLY |
| SEQ ID NO: 36 | BAGE | AARAVFLAL |
| SEQ ID NO: 37 | GAGE-1,2 | YRPRPRRY |
| SEQ ID NO: 38 | GnT-V | VLPDVFIRC |
| SEQ ID NO: 39 | NY-ESO-1 | QLSLLMWIT |
| SEQ ID NO: 40 | NY-ESO-1 | SLLMWITQC |
| SEQ ID NO: 41 | NY-ESO-1 | ASGPGGGAPR |
| SEQ ID NO: 42 | 43kD protein | QDLTMKYQIF |
| SEQ ID NO: 43 | p15 | (E)AYGLDFYIL |
| SEQ ID NO: 44 | Mutated beta-catenin | SYLDSGIHF[‡] |
| SEQ ID NO: 45 | Mutated elongation factor 2 | ETVSEQSNV[§] |
| SEQ ID NO: 46 | Mutated CASP-8 (FLICE/MACH) | FPSDSWCYF |
| SEQ ID NO: 47 | MUM-1 gene product mutated across intron/exon junction | EEKLIVVLF[¶] |
| SEQ ID NO: 77 | MAGE-A1 | See Sequences Section |
| SEQ ID NO: 78 | TRP-1 (also known as 5,6-dihydroxy-indole-2-carboxylic acid oxidase, DHICA oxidase, Melanoma antigen glycoprotein 75, Tyrosinase-related protein 1, and TRYP-1) | See Sequences Section |
| SEQ ID NO: 87 | MAGE-A3-melanoma-associated antigen 3 | See Sequences Section |
| SEQ ID NO: 90 | Prostein | See Sequences Section |

[†]AAGIGILTV (SEQ ID NO: 91) is also recognized by HLA B45-1-restricted cytotoxic T lymphocyte.
[‡]Phenylalanine (F) at position 9 is the result of mutation. The wild-type sequence is SYLDSGIHS (SEQ ID NO: 92).
[§]Glutamine (Q) at position 6 is the result of somatic mutation. The wild-type sequence is ETVSEESNV (SEQ ID NO: 93).
¶Isoleucine (I) at position 5 is the result of mutation. The wild-type sequence is EEKLSVVLF (SEQ ID NO: 94).

In some embodiments, a cancer-associated protein encoded by a nucleic acid provided herein comprises a cell membrane-contacting domain or functional fragment thereof. In some embodiments, the cell membrane-contacting domain comprises a transmembrane-binding domain, an outer cell membrane-contacting domain, or an inner cell membrane-contacting domain. In some embodiments, the cell membrane-contacting domain comprises a transmembrane-binding domain, an outer cell membrane-contacting domain, and an inner cell membrane-contacting domain. In some embodiments, the cancer-associated protein is a protein expressed by a melanoma cancer cell, a prostate cancer cell, a colon cancer cell, an ovarian cancer cell, a breast cancer cell, a pancreatic cancer cell, or a blood cell.

In some embodiments, a nucleic acid provided herein comprises a sequence encoding a dimer, trimer, or multimer of a cancer-associated protein provided herein. In some embodiments, nucleic acid provided herein comprises a sequence encoding an amino acid sequence that is at least about 500 amino acids in length or more. In some embodiments, nucleic acid provided herein comprises a sequence encoding an amino acid sequence that is at least about 200, 300, 400, 500, 750, 1000 or more amino acids in length or more. In some embodiments, nucleic acid provided herein comprises a sequence encoding one or more cancer-associated protein, wherein the one or more cancer-associated protein comprises a molecular weight of at least about 50 kiloDaltons (kDa) or more, at least about 100 kiloDaltons (kDa) or more, at least about 150 kiloDaltons (kDa) or more, at least about 200 kiloDaltons (kDa) or more, at least about 250 kiloDaltons (kDa) or more, at least about 300 kiloDaltons (kDa) or more, at least about 350 kiloDaltons (kDa) or more, at least about 400 kiloDaltons (kDa) or more, at least about 450 kiloDaltons (kDa) or more, at least about 500 kiloDaltons (kDa) or more, up to 1000 kDa or more. In some embodiments, nucleic acids provided herein comprise a sequence encoding one or more cancer-associated protein, wherein the one or more cancer-associated protein comprises a molecular weight of at least about 59 kDa or more.

In some embodiments, nucleic acids provided herein comprise a sequence encoding a cancer-associated protein associated with prostate cancer. In some embodiments, the cancer-associated protein with prostate cancer comprises prostein. In some embodiments, the cancer-associated protein is prostein. In some embodiments, the cancer-associated protein is at least about 50%, 60%, 70%, 80%, 90%, 95%, or 100% of full length prostein. In some embodiments, the prostein is human prostein. In some embodiments, the cancer-associated protein comprises an amino acid sequence that is at least about 80%, 85%, 90%, 95% or 100% identical to SEQ ID NO: 90.

Cancer Antigen Binding Molecules

Provided herein are compositions, wherein the composition comprises: a lipid carrier provided herein; and a nucleic acid encoding for an antibody or a functional fragment thereof. In some embodiments, nucleic acids provided herein encode for a monoclonal antibody. In some embodiments, nucleic acids provided herein encode for a murine antibody, a humanized antibody, or a fully human antibody. In some embodiments, the antibody is an immunoglobulin (Ig) molecule. In some embodiments, the immunoglobulin molecule is an IgG, IgE, IgM, IgD, IgA, or an IgY isotype immunoglobulin molecule. Further provided herein are compositions, wherein the immunoglobulin molecule is an IgG1, an IgG2, an IgG3, an IgG4, an IgGA1, or an IgGA2 subclass immunoglobulin molecule. In some embodiments, the antibody is a recombinant antibody, a chimeric antibody, or a multivalent antibody. In some embodiments, the multivalent antibody is a bispecific antibody, a trispecific antibody, or a multispecific antibody. In some embodiments, the antibody or functional fragment is an antigen-binding fragment (Fab), and Fab2 a F(ab'), a F(ab')2, an dAb, an Fe, a Fv, a disulfide linked Fv, a scFv, a tandem scFv, a free LC, a half antibody, a single domain antibody (dAb), a diabody, or a nanobody.

In some embodiments, the antibody or functional fragment thereof specifically binds to a cancer-associated protein. In some embodiments, the antibody or functional fragment thereof is a cancer therapeutic antibody. In some embodiments, the cancer therapeutic antibody is atezolizumab, avelumab, bevacizumab, cemiplimab, cetuximab, daratumumab, dinutuximab, durvalumab, elotuzumab, ipilimumab, isatuximab, mogamulizumab, necitumumab, nivolumab, obinutuzumab, ofatumumab, olaratumab, panitumumab, pembrolizumab, pertuzumab, ramucirumab, rituximab, or trastuzumab. Amino acid sequences for cancer therapeutic antibodies are provided below in Table 2.

In some embodiments, a nucleic acid provided herein encodes for a cancer-associated protein or an antibody amino acid sequence or a functional fragment thereof listed in Table 2. In some embodiments, compositions provided herein comprise two or more nucleic acids encoding for different sequences listed in Table 2. In some embodiments, nucleic acids provided herein encode for an antibody amino acid sequence comprising at least 80%, 85%, 90%, 95%, 96%, 97%, 98%, or 99% sequence identity to a sequence listed in Table 2. In some embodiments, compositions provided herein comprise two or more nucleic acids encoding different sequences listed in Table 2. In some embodiments, the nucleic acid provided herein encodes for an antibody or a functional fragment thereof comprising at least 80%, 85%, 90%, 95%, 96%, 97%, 98%, or 99% sequence similarity to a sequence listed Table 2.

TABLE 2

Cancer therapeutic antibodies.

| SEQ ID NO: | Antibody Name (Commercial Name) | Tumor Antigen | Heavy Chain Amino Acid Sequences |
|---|---|---|---|
| 48 | atezolizumab (TECENTRIQ ®) | CD274 (programmed cell death 1 ligand 1, B7H1, B7-H1, PDL1, PD-L1, PDCDIL1, B7 homolog 1, B7 homologue 1) [*Homo sapiens*] | EVQLVESGGGLVQPGGSLRLSCAASGFTFSDSWIHWVRQAPGK<br>GLEWVAWISPYGGSTYYADSVKGRFTISADTSKNTAYLQMNSL<br>RAEDTAVYYCARRHWPGGFDYWGQGTLVTVSSASTKGPSVEPL<br>APSSKSTSGGTAALGCLVKDYFPEPVTVSWNSGALTSGVHTEP<br>AVLQSSGLYSLSSVVTVPSSSLGTQTYICNVNHKPSNTKVDKK<br>VEPKSCDKTHTCPPCPAPELLGGPSVELFPPKPKDTLMISRTP<br>EVTCVVVDVSHEDPEVKENWYVDGVEVHNAKTKPREEQYASTY<br>RVVSVLTVLHQDWLNGKEYKCKVSNKALPAPIEKTISKAKGQP<br>REPQVYTLPPSREEMTKNQVSLTCLVKGFYPSDIAVEWESNGQ<br>PENNYKTTPPVLDSDGSFFLYSKLTVDKSRWQQGNVFSCSVMH<br>EALHNHYTQKSLSLSPGK |
| 49 | avelumab (BAVENCIO ®) | CD274 | EVQLLESGGGLVQPGGSLRLSCAASGFTFSSYIMMWVRQAPGK<br>GLEWVSSIYPSGGITFYADTVKGRFTISRDNSKNTLYLQMNSL<br>RAEDTAVYYCARIKLGTVTTVDYWGQGTLVTVSSASTKGPSVE<br>PLAPSSKSTSGGTAALGCLVKDYFPEPVTVSWNSGALTSGVHT<br>FPAVLQSSGLYSLSSVVTVPSSSLGTQTYICNVNHKPSNTKVD<br>KKVEPKSCDKTHTCPPCPAPELLGGPSVFLFPPKPKDTLMISR<br>TPEVTCVVVDVSHEDPEVKENWYVDGVEVHNAKTKPREEQYNS |

TABLE 2-continued

Cancer therapeutic antibodies.

| SEQ ID NO: | Antibody Name (Commercial Name) | Tumor Antigen | Heavy Chain Amino Acid Sequences |
|---|---|---|---|
| | | | TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 50 | bevacizumab (AVASTIN ®) | VEGFA (vascular endothelial growth factor A, VEGF-A, VEGF) [*Homo sapiens*] | EVQLVESGGGLVQPGGSLRLSCAASGYTFTNYGMNWVRQAPGK GLEWVGWINTYTGEPTYAADFKRRFTFSLDTSKSTAYLQMNSL RAEDTAVYYCAKYPHYYGSSHWYFDVWGQGTLVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNT KVDKKVEPKSCDKTHTCPPCPAPELLGGPSVFLFPPKPKDTLM ISRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| 51 | cemiplimab (LIBTAYO ®) | PDCD1 (programmed cell death 1, PD1, PD-1, CD279) [*Homo sapiens*] | EVQLLESGGVLVQPGGSLRLSCAASGFTFSNFGMTWVRQAPGK GLEWVSGISGGGRDTYFADSVKGRFTISRDNSKNTLYLQMNSL KGEDTAVYYCVKWGNIYFDYWGQGTLVTVSSASTKGPSVFPLA PCSRSTSESTAALGCLVKDYFPEPVTVSWNSGALTSGVHTFPA VLQSSGLYSLSSVVTVPSSSLGTKTYTCNVDHKPSNTKVDKRV ESKYGPPCPPCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSRLTVDKSRWQEGNVFSCSVMHEALH NHYTQKSLSLSLGK |
| 52 | cetuximab (ERBITUX ®) | EGFR (epidermal growth factor receptor, receptor tyrosine-protein kinase erbB-1, ERBB1, HER1, HER-1, ERBB) [*Homo sapiens*] | QVQLKQSGPGLVQPSQSLSITCTVSGFSLTNYGVHWVRQSPGK GLEWLGVIWSGGNTDYNTPFTSRLSINKDNSKSQVFFKMNSLQ SNDTAIYYCARALTYYDYEFAYWGQGTLVTVSAASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDK RVEPKSCDKTHTCPPCPAPELLGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| 53 | daratumumab (DARZALEX ™; DARZALEX; FASPRO ™) | CD38 (ADP-ribosyl cyclase 1, cyclic ADP-ribose hydrolase 1, cADPr hydrolase 1, T10) [*Homo sapiens*] | EVQLLESGGGLVQPGGSLRLSCAVSGFTFNSFAMSWVRQAPGK GLEWVSAISGSGGGTYYADSVKGRFTISRDNSKNTLYLQMNSL RAEDTAVYFCAKDKILWFGEPVFDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPELLGGPSVFLFPPKPKDTLMI SRTPEVTCVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| 54 | dinutuximab (UNITUXIN ™) | ganglioside GD2 (disialogang-lioside GD2) [*Homo sapiens*] | EVQLLQSGPELEKPGASVMISCKASGSSFTGYNMNWVRQNIGK SLEWIGAIDPYYGGTSYNQKFKGRATLTVDKSSSTAYMHLKSL TSEDSAVYYCVSGMEYWGQGTSVTVSSASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 55 | durvalumab (IMFINZI ™) | CD274 | EVQLVESGGGLVQPGGSLRLSCAASGFTFSRYWMSWVRQAPGK GLEWVANIKQDGSEKYYVDSVKGRFTISRDNAKNSLYLQMNSL RAEDTAVYYCAREGGWFGELAFDYWGQGTLVTVSSASTKGPSV FPLAPSSKSTSGGTAALGCLVKDYFPEPVTVSWNSGALTSGVH TFPAVLQSSGLYSLSSVVTVPSSSLGTQTYICNVNHKPSNTKV DKRVEPKSCDKTHTCPPCPAPEFEGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPASIEKTISKAK GQPREPQVYTLPPSREEMTKNQVSLTCLVKGFYPSDIAVEWES |

TABLE 2-continued

Cancer therapeutic antibodies.

| SEQ ID NO: | Antibody Name (Commercial Name) | Tumor Antigen | Heavy Chain Amino Acid Sequences |
|---|---|---|---|
| | | | NGQPENNYKTTPPVLDSDGSFFLYSKLTVDKSRWQQGNVESCSVMHEALHNHYTQKSLSLSPGK |
| 56 | elotuzumab (EMPLICITI ™) | SLAMF7 (SLAM family member 7, CD2 subset 1, CS1, CD2-like receptor-activating cytotoxic cells, CRACC, 19A24, CD319) [*Homo sapiens*] | EVQLVESGGGLVQPGGSLRLSCAASGEDESRYWMSWVRQAPGKGLEWIGEINPDSSTINYAPSLKDKFIISRDNAKNSLYLQMNSLRAEDTAVYYCARPDGNYWYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVELFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 57 | ipilimumab (YERVOY ®) | CTLA4 (cytotoxic T-lymphocyte-associated protein 4, CD152) [*Homo sapiens*] | QVQLVESGGGVVQPGRSLRLSCAASGFTESSYTMHWVRQAPGKGLEWVTFISYDGNNKYYADSVKGRFTISRDNSKNTLYLQMNSLRAEDTAIYYCARTGWLGPFDYWGQGTLVTVSSASTKGPSVFPLAPSSKSTSGGTAALGCLVKDYFPEPVTVSWNSGALTSGVHTEPAVLQSSGLYSLSSVVTVPSSSLGTQTYICNVNHKPSNTKVDKRVEPKSCDKTHTCPPCPAPELLGGPSVELFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 58 | isatuximab (SARCLISA ®) | CD38 (ADP-ribosyl cyclase 1, cyclic ADP-ribose hydrolase 1, cADPr hydrolase 1, T10) [*Homo sapiens*] | QVQLVQSGAEVAKPGTSVKLSCKASGYTFTDYWMQWVKQRPGQGLEWIGTIYPGDGDTGYAQKFQGKATLTADKSSKTVYMHLSSLASEDSAVYYCARGDYYGSNSLDYWGQGTSVTVSSASTKGPSVEPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVELFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVESCSVMHEALHNHYTQKSLSLSPGK |
| 59 | mogamulizumab (POTELIGEO ®) | CCR4 (chemokine (C—C motif) receptor 4, CC chemokine receptor 4, CCR-4, CKR4, k5-5, CD194) [*Homo sapiens*] | EVQLVESGGDLVQPGRSLRLSCAASGFIFSNYGMSWVRQAPGKGLEWVATISSASTYSYYPDSVKGRFTISRDNAKNSLYLQMNSLRVEDTALYYCGRHSDGNFAFGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 60 | necitumumab (PORTRAZZA ™) | EGFR (epidermal growth factor receptor, receptor tyrosine-protein kinase erbB-1, ERBB1, HER1, HER-1, ERBB) [*Homo sapiens*] | QVQLQESGPGLVKPSQTLSLTCTVSGGSISSGDYYWSWIRQPPGKGLEWIGYIYYSGSTDYNPSLKSRVTMSVDTSKNQFSLKVNSVTAADTAVYYCARVSIFGVGTEDYWGQGTLVTVSSASTKGPSVLPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVELFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVESCSVMHEALHNHYTQKSLSLSPGK |
| 61 | nivolumab (OPDIVO ®) | PDCD1 (programmed cell death 1, PD1, PD-1, CD279) [*Homo sapiens*] | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTEPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVESCSVMHEALHNHYTQKSLSLSLGK |

TABLE 2-continued

Cancer therapeutic antibodies.

| SEQ ID NO: | Antibody Name (Commercial Name) | Tumor Antigen | Heavy Chain Amino Acid Sequences |
|---|---|---|---|
| 62 | obinutuzumab (GAZYVA ®) | MS4A1 (membrane-spanning 4-domains subfamily A member 1, CD20) [*Homo sapiens*] | QVQLVQSGAEVKKPGSSVKVSCKASGYAFSYSWINWVRQAPGQ GLEWMGRIFPGDGDTDYNGKFKGRVTITADKSTSTAYMELSSL RSEDTAVYYCARNVFDGYWLVYWGQGTLVTVSSASTKGPSVFP LAPSSKSTSGGTAALGCLVKDYFPEPVTVSWNSGALTSGVHTE PAVLQSSGLYSLSSVVTVPSSSLGTQTYICNVNHKPSNTKVDK KVEPKSCDKTHTCPPCPAPELLGGPSVFLFPPKPKDTLMISRT PEVTCVVVDVSHEDPEVKENWYVDGVEVHNAKTKPREEQYNST YRVVSVLTVLHQDWLNGKEYKCKVSNKALPAPIEKTISKAKGQ PREPQVYTLPPSRDELTKNQVSLTCLVKGFYPSDIAVEWESNG QPENNYKTTPPVLDSDGSFFLYSKLTVDKSRWQQGNVESCSVM HEALHNHYTQKSLSLSPGK |
| 63 | ofatumumab (ARZERRA ® KESIMPTA ®) | MS4A1 (membrane-spanning 4-domains subfamily A member 1, CD20) [*Homo sapiens*] | EVQLVESGGGLVQPGRSLRLSCAASGFTENDYAMHWVRQAPGK GLEWVSTISWNSGSIGYADSVKGRFTISRDNAKKSLYLQMNSL RAEDTALYYCAKDIQYGNYYYGMDVWGQGTTVTVSSASTKGPS VFPLAPGSSKSTSGTAALGCLVKDYFPEPVTVSWNSGALTSGV HTFPAVLQSSGLYSLSSVVTVPSSSLGTQTYICNVNHKPSNTK VDKKVEP |
| 64 | olaratumab (LARTRUVO ™) | PDGFRA (platelet-derived growth factor receptor alpha subunit, PDGFR2, CD140a) [*Homo sapiens*] | QLQLQESGPGLVKPSETLSLTCTVSGGSINSSSYYWGWLRQSP GKGLEWIGSFFYTGSTYYNPSLRSRLTISVDTSKNQFSLMLSS VTAADTAVYYCARQSTYYYGSGNYYGWFDRWDQGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKRVEPKSCDKTHTCPPCPAPELLGGPSVELFPPKPK DTLMISRTPEVTCVVVDVSHEDPEVKENWYVDGVEVHNAKTKP REEQYNSTYRVVSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQQG NVFSCSVMHEALHNHYTQKSLSLSPG |
| 65 | panitumumab (VECTIBIX ®) | EGFR (epidermal growth factor receptor, receptor tyrosine-protein kinase erbB-1, ERBB1, HER1, HER-1, ERBB) [*Homo sapiens*] | QVQLQESGPGLVKPSETLSLTCTVSGGSVSSGDYYWTWIRQSP GKGLEWIGHIYYSGNTNYNPSLKSRLTISIDTSKTQFSLKLSS VTAADTAIYYCVRDRVTGAFDIWGQGTMVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERK |
| 66 | pembrolizumab (KEYTRUDA ®) | PDCD1 (programmed cell death 1, PD1, PD-1, CD279) [*Homo sapiens*] | VQLVQSGVEVKKPGASVKVSCKASGYTFTNYYMYWVRQAPGQG LEWMGGINPSNGGTNENEKFKNRVTLTTDSSTTTAYMELKSLQ FDDTAVYYCARRDYRFDMGFDYWGQGTTVTVSSASTKGPSVEP LAPCSRSTSESTAALGCLVKDYFPEPVTVSWNSGALTSGVHTF PAVLQSSGLYSLSSVVTVPSSSLGTKTYTCNVDHKPSNTKVDK RVESKYGPPCPPCPAPEFLGGPSVELFPPKPKDTLMISRTPEV TCVVVDVSQEDPEVQFNWYVDGVEVHNAKTKPREEQFNSTYRV VSVLTVLHQDWLNGKEYKCKVSNKGLPSSIEKTISKAKGQPRE PQVYTLPPSQEEMTKNQVSLTCLVKGFYPSDIAVEWESNGQPE NNYKTTPPVLDSDGSFFLYSRLTVDKSRWQEGNVESCSVMHEA LHNHYTQKSLSLSLGK |
| 67 | pertuzumab (PERJETA ®) | ERBB2 (epidermal growth factor receptor 2, receptor tyrosine-protein kinase erbB-2, EGFR2, HER2, HER-2, p185c-erbB2, NEU, CD340) [*Homo sapiens*] | EVQLVESGGGLVQPGGSLRLSCAASGFTFTDYTMDWVRQAPGK GLEWVADVNPNSGGSIYNQRFKGRFTLSVDRSKNTLYLQMNSL RAEDTAVYYCARNLGPSFYFDYWGQGTLVTVSSASTKGPSVEP LAPSSKSTSGGTAALGCLVKDYFPEPVTVSWNSGALTSGVHTF PAVLQSSGLYSLSSVVTVPSSSLGTQTYICNVNHKPSNTKVDK KVEPKSCDKTH |
| 68 | ramucirumab (CYRAMZATM) | KDR (kinase insert domain receptor, vascular | EVQLVQSGGGLVKPGGSLRLSCAASGFTFSSYSMNWVRQAPGK GLEWVSSISSSSSYIYYADSVKGRFTISRDNAKNSLYLQMNSL RAEDTAVYYCARVTDAFDIWGQGTMVTVSSASTKGPSVLPLAP SSKSTSGGTAALGCLVKDYFPEPVTVSWNSGALTSGVHTFPAV |

TABLE 2-continued

Cancer therapeutic antibodies.

| SEQ ID NO: | Antibody Name (Commercial Name) | Tumor Antigen | Heavy Chain Amino Acid Sequences |
|---|---|---|---|
| | | endothelial growth factor receptor 2, VEGFR2, VEGF-R2, FLK1, CD309) [*Homo sapiens*] | LQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 69 | rituximab (RITUXAN ®) | MS4A1 (membrane-spanning 4-domains subfamily A member 1, CD20) [*Homo sapiens*] | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVESCSVMHEALHNHYTQKSLSLSPGK |
| 70 | trastuzumab (HERCEPTIN ®) | ERBB2 (epidermal growth factor receptor 2, receptor tyrosine-protein kinase erbB-2, EGFR2, HER2, HER-2, p185c-erbB2, NEU, CD340) [*Homo sapiens*] | EVQLVESGGGLVQPGGSLRLSCAASGENIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |

*Sequences in Table 2 were determined by IMGT-monoclonal antibody database

As an alternative to, or in addition to the delivery of RNAs as antigens, combinations can be used, for example, RNA antigens combined with RNAs that stimulate innate immune responses, or RNAs that launch oncolytic viruses, or live-attenuated viruses, or agonists generally that stimulate immune responses including TLRs (toll-like receptors), RLR (RIG-I-like receptors), or NLRs (nod-like receptors). In certain embodiments, a composition provided herein comprises a combination of RNA-encoded antigens with another RNA that can stimulate innate immune responses or can launch oncolytic viruses or live-attenuated viruses. Alternatively, compositions provided herein that contain RNA-encoded antigens can be combined with a formulation that contains another RNA or other immune response agonist that can stimulate innate immune responses or can launch oncolytic viruses or live-attenuated viruses.

Self-Replicating Nucleic Acids

Provided herein are compositions comprising a self-replicating nucleic acid. The cancer-associated antigen or cancer therapeutic antibody provided herein or fragment thereof can be encoded as part of a self-replicating nucleic acid construct. In some embodiments, the self-replicating nucleic acid molecule comprises at least one or more genes selected from the group consisting of viral replicases, viral proteases, viral helicases and other nonstructural viral proteins, and also comprises 5'- and 3'-end cis-active replication sequences, and an antigenic sequence encoding for a cancer-associated antigen. A subgenomic promoter that directs expression of the heterologous sequence(s) can be included in the self-replicating nucleotide sequence. If desired, a heterologous sequence may be fused in frame to other coding regions in the self-replicating RNA and/or may be under the control of an internal ribosome entry site (IRES).

In some embodiments, the self-replicating nucleotide sequence is a self-replicating RNA molecule. Self-replicating RNA molecules are designed so that the self-replicating RNA molecule cannot induce production of infectious viral particles. This can be achieved, for example, by omitting one or more viral genes encoding for structural proteins that are necessary for the production of viral particles in the self-replicating RNA. For example, when the self-replicating RNA molecule is based on an alphavirus, such as Sindbis virus (SIN), Semliki forest virus and Venezuelan equine encephalitis virus (VEE), one or more genes encoding for viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to an animal cell even without any proteins, lead to the production of multiple daughter RNAs by transcription from itself (or from an antisense copy of itself). The self-replicating RNA can be directly translated after delivery to a cell, and this translation provides an RNA-dependent RNA polymerase which then produces transcripts from the delivered RNA. Thus, the delivered RNA leads to the production of multiple daughter RNAs. These transcripts are antisense relative to the delivered RNA and may be translated themselves to provide in situ expression of encoded cancer-associated antigen, or may be transcribed to provide further transcripts with the same sense as the delivered RNA which are translated to provide in situ expression of the encoded cancer-associated antigen(s).

The self-replicating RNA molecules provided herein can contain one or more modified nucleotides and therefore have improved stability and be resistant to degradation and clearance in vivo, and other advantages. In some embodiments, self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduce activation of the innate immune system and subsequent undesired consequences (e.g., inflammation at injection site, irritation at injection site, pain, and the like). RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of cancer-associated antigen spike proteins, as well as adjuvant effects.

In some embodiments, self-replicating RNA molecules provided herein contain at least one modified nucleotide. Modified nucleotides that are not part of the 5' cap (e.g., in addition to the modification that are part of the 5" cap) can be used. Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties. In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides. In other examples, between 0.001% and 99% or 100% of a particular unmodified nucleotide in a self-replicating RNA molecule is replaced with a modified nucleotide. For example, about 1% of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25%, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides. It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses. Suitable synthetic methods can be used alone, or in combination with one or more other methods (e.g., recombinant DNA or RNA technology), to produce a self-replicating RNA molecule that contain one or more modified nucleotides.

Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like.

In some embodiments, nucleic acids provided herein encode for an RNA polymerase. In some embodiments, nucleic acids provided herein encode for a viral RNA polymerase. In some embodiments, nucleic acids provided herein encode for: (1) a viral RNA polymerase; and (2) a cancer-associated protein or a functional fragment thereof. In some embodiments, compositions provided herein comprise a first nucleic acid encoding for a viral RNA polymerase; and a second nucleic acid encoding for a cancer-associated protein or a functional fragment thereof. In some embodiments, nucleic acids provided herein encode for: (1) a viral RNA polymerase; and (2) a cancer therapeutic antibody or a functional fragment thereof. In some embodiments, compositions provided herein comprise a first nucleic acid encoding for a viral RNA polymerase; and a second nucleic acid encoding for a cancer therapeutic antibody or a functional fragment thereof.

Provided herein are compositions comprising a self-replicating RNA. A self-replicating RNA (also called a replicon) includes any genetic element, for example, a plasmid, cosmid, bacmid, phage or virus that is capable of replication largely under its own control. Self-replication provides a system for self-amplification of nucleic acids provided herein in mammalian cells. In some embodiments, the self-replicating RNA is single stranded. In some embodiments, the self-replicating RNA is double stranded.

In some embodiments, a nucleic acid described herein comprises a sequence encoded for an infectious disease antigen described here and for an RNA-dependent RNA polymerase. In some embodiments, the RNA-dependent RNA polymerase is a VEEV RNA polymerase. In some embodiments, the two nucleic acid coding elements are present in separate nucleic acids. In some embodiments, the two nucleic acid coding elements are present on the same nucleic acid. An RNA polymerase provided herein can include but is not limited to: an alphavirus RNA polymerase, an Eastern equine encephalitis virus (EEEV) RNA polymerase, a Western equine encephalitis virus (WEEV), Venezuelan equine encephalitis virus (VEEV), Also, Chikungunya virus (CHIKV), Semliki Forest virus (SFV), or Sindbis virus (SINV). In some embodiments, the RNA polymerase is a VEEV RNA polymerase. In some embodiments, the nucleic acid encoding for the RNA polymerase comprises at least 85% identity to the nucleic acid sequence of SEQ ID NO: 71. In some embodiments, the nucleic acid encoding for the RNA polymerase comprises at least 90% identity to the nucleic acid sequence of SEQ ID NO: 71. In some embodiments, the nucleic acid encoding for the RNA polymerase comprises at least 95% identity to the nucleic acid sequence of SEQ ID NO: 71. In some embodiments, the nucleic acid encoding for the RNA polymerase comprises at least 99% identity to the nucleic acid sequence of SEQ ID NO: 71. In some embodiments, the nucleic acid encoding for the RNA polymerase is SEQ ID NO: 71.

In some embodiments, the amino acid sequence for VEEV RNA polymerase comprises at least 85% identity to RELPVLDSAAFNVECFKKYACNNEYWETFKENPIRLTEENVVNYITKLKGP (SEQ ID NO: 72), TQMRELPVLDSAAFNVECFKKYACNNEYWETFKENPIRLTE (SEQ ID NO: 73), or SEQ ID NO: 74. In some embodiments, the amino acid sequence for VEEV RNA polymerase comprises at least 90% identity to SEQ ID NO: 72, SEQ ID NO: 73, or SEQ ID NO: 74. In some embodiments, the amino acid sequence for VEEV RNA polymerase comprises at least 95% identity to SEQ ID NO: 72, SEQ ID NO: 73, or SEQ ID NO: 74. In some embodiments, the amino acid sequence for VEEV RNA polymerase comprises at least 99% identity SEQ ID NO: 72, SEQ ID NO: 73, or SEQ ID NO: 74. In some embodiments, the amino acid sequence for VEEV RNA polymerase is SEQ ID NO: 72, SEQ ID NO: 73, or SEQ ID NO: 74.

Provided herein are compositions and methods comprising replicon RNA (repRNA) encoding for one or more structural proteins from a non-enveloped virus. In some embodiments, the repRNA encodes a protease. In some embodiments, the repRNA encodes the 3CD protease. In some embodiments, the structural protein and the protease are co-expressed. In further embodiments, the repRNA comprises one or more open reading frames. In some embodiments, the open reading frames are separated by an internal ribosomal entry site (IRES). In some embodiments, the open reading frames are separated by a ribosomal skipping peptide sequence. In some embodiments the ribosomal skipping peptide sequence is from Thosea asigna virus (T2A).

Nanoparticles

Provided herein are various compositions comprising a nanoparticle. In some embodiments, the nanoparticle comprises a lipid carrier. Nanoparticles are abbreviated as NPs herein. Nanoparticles provided herein may be an organic, inorganic, or a combination of inorganic and organic materials that are less than about 1 micrometer (μm) in diameter. In some embodiments, nanoparticles provided herein are used as a delivery system for a bioactive agent provided herein (e.g., a nucleic acid encoding a cancer-associated protein, or a cancer therapeutic antibody). Further provided herein are various compositions comprising lipid carrier complexes or nanoparticle-complexes, wherein a plurality of lipid carriers or a plurality of nanoparticles interact physically, chemically, and/or covalently. The specific type of interaction between lipid carriers or between nanoparticles will depend upon the characteristic shapes, sizes, chemical compositions, physical properties, and physiologic properties. Nanoparticles provided herein can include but are not limited to: oil in water emulsions, nanostructured lipid carriers (NLCs), cationic nanoemulsions (CNEs), vesicular phospholipid gels (VPG), polymeric nanoparticles, cationic lipid nanoparticles, liposomes, gold nanoparticles, solid lipid nanoparticles (LNPs or SLNs), mixed phase core NLCs, ionizable lipid carriers, magnetic carriers, polyethylene glycol (PEG)-functionalized carriers, cholesterol-functionalized carriers, polylactic acid (PLA)-functionalized carriers, and polylactic-co-glycolic acid (PLGA)-functionalized lipid carriers.

Figure 1B:
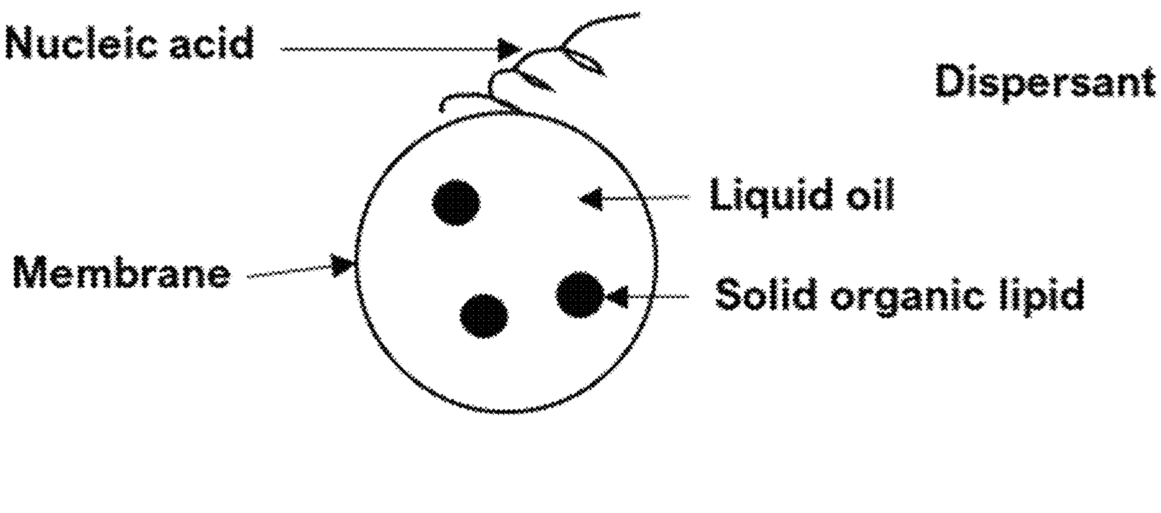
Figure 1C:
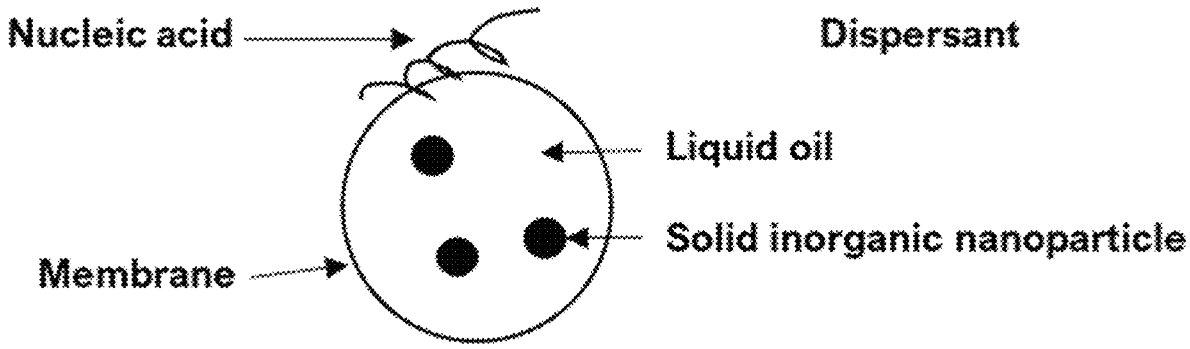
Figure 1D:
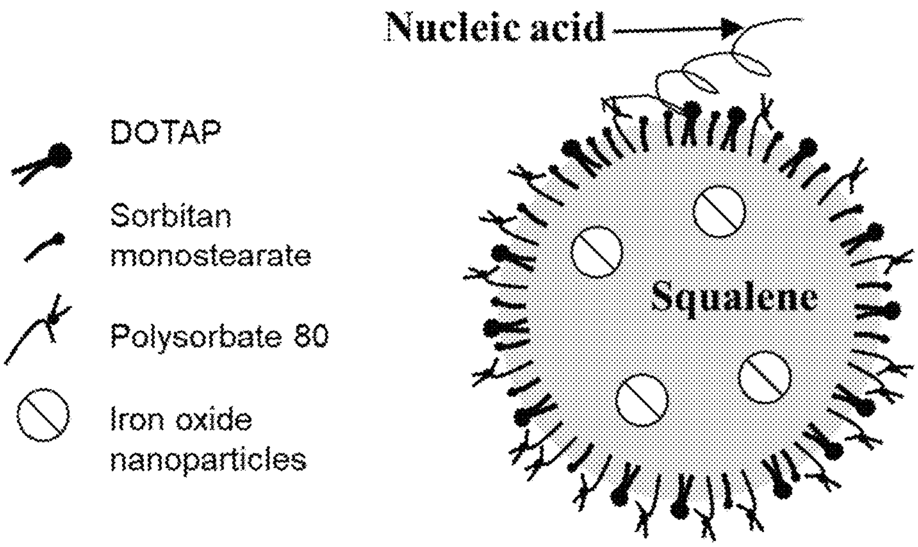
Figure 1E:
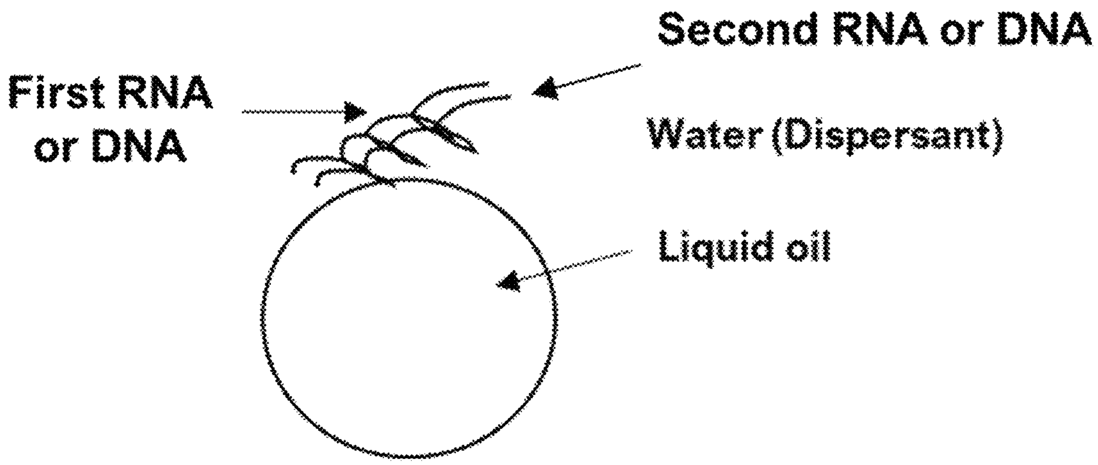
Figure 1F:
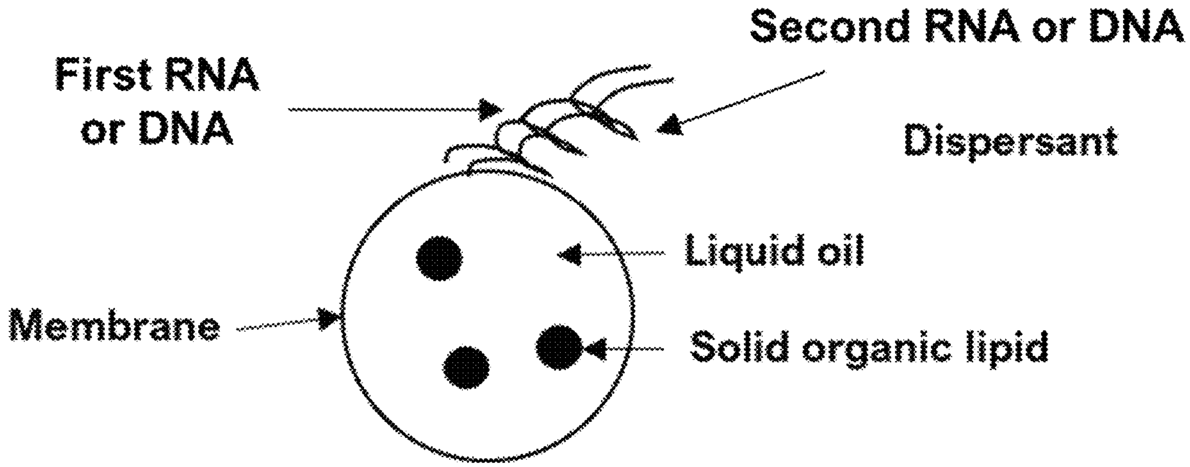
Figure 1G:
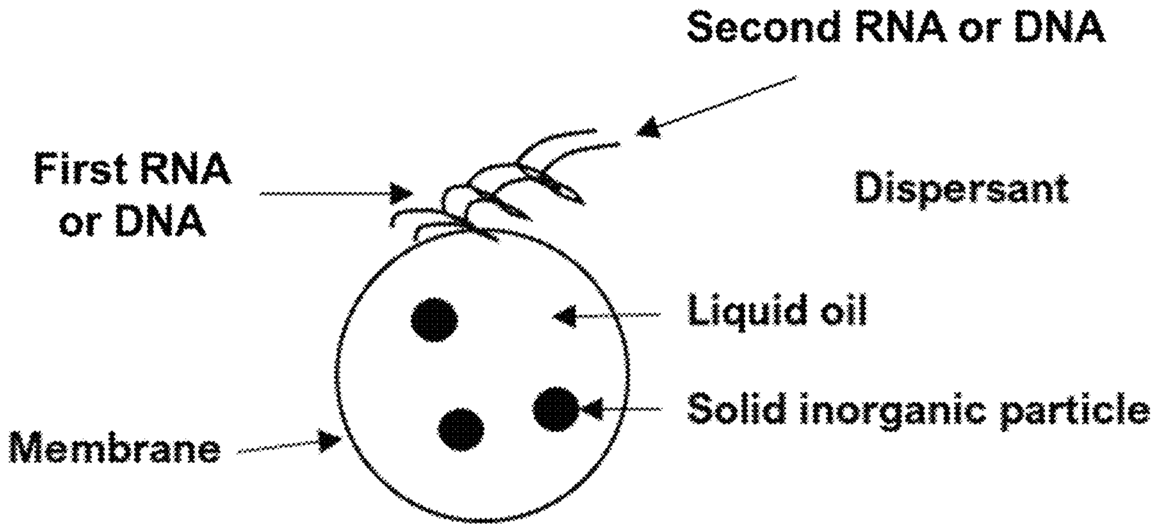
Figure 1H:
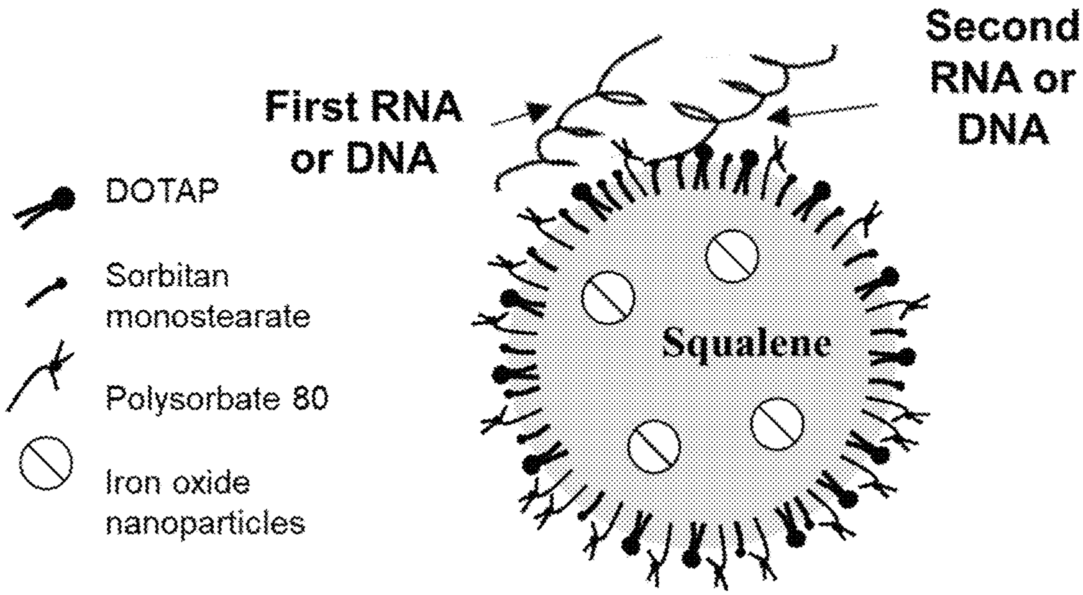

Various nanoparticles and formulations of nanoparticles (i.e., nanoemulsions) are employed. Exemplary nanoparticles are illustrated in FIGS. 1A-1H. Oil in water emulsions, as illustrated in FIG. 1A (not to scale), are stable, immiscible fluids containing an oil droplet dispersed in water or aqueous phase. FIG. 1B (not to scale) illustrates a nanostructured lipid carrier (NLCs) which can comprise a blend of solid organic lipids (e.g., trimyristin) and liquid oil (e.g., squalene). In NLCs, the solid lipid is dispersed in the liquid oil. The entire nanodroplet is dispersed in the aqueous (water) phase. In some embodiments, the nanoparticle comprises inorganic nanoparticles, as illustrated in FIG. 1C (not to scale), as solid inorganic nanoparticles (e.g., iron oxide nanoparticles) dispersed in liquid oil. FIG. 1D (not to scale) illustrates a nanoparticle comprising a cationic lipid membrane and a liquid oil without an inorganic particle. Nucleic acids provided herein can be complexed with a nanoparticle in Table 3 in cis (FIGS. 1A-1D) or in trans (FIGS. 1E-1H). For example, a first RNA or DNA molecule can comprise a plurality of cancer-associated proteins and a second RNA or DNA molecule can comprise an RNA polymerase complex. As another example, a first RNA or DNA molecule can comprise one or more cancer-associated proteins and a RNA polymerase on the same nucleic acid; and a second RNA or DNA molecule can comprise an additional cancer-associated protein and/or an RNA polymerase.

Provided herein are nanoemulsions and nanodroplets comprising a plurality of lipid carriers or nanoparticles, wherein each lipid carrier or nanoparticle comprises a cationic lipid. In some embodiments, nanoemulsions comprises a plurality of cationic lipid carriers. In some embodiments, a composition provided herein comprises a cationic nanoemulsion. In some embodiments, cationic nanoemulsions described herein comprise a lipid (or other surfactant) molecules surrounding an oil particle that is dispersed in water and give the oil particle a cationic (positively charged) surface to which negatively-charged RNA molecules can adhere.

The entire nanodroplet can be dispersed as a colloid in the aqueous (water) phase or in a suspension. In some embodiments, nanoparticles provided herein are dispersed in an aqueous solution. Non-limiting examples of aqueous solutions include water (e.g., sterilized, distilled, deionized, ultra-pure, RNAse-free, etc.), saline solutions (e.g., Kreb's, *Ascaris*, Dent's, Tet's saline), or 1% (w/v) dimethyl sulfoxide (DMSO) in water.

In some embodiments, nanoparticles provided herein comprise a hydrophilic surface. In some embodiments, the hydrophilic surface comprises a cationic lipid. In some embodiments, the hydrophilic surface comprises an ionizable lipid. In some embodiments, the nanoparticle comprises a membrane. In some embodiments, the membrane comprises a cationic lipid. In some embodiments, the nanoparticles provided herein comprise a cationic lipid. Exemplary cationic lipids for inclusion in the hydrophilic surface include, without limitation: 1,2-dioleoyloxy-3 (trimethylammonium)propane (DOTAP), 30-[N—(N',N'-dimethylamino-ethane) carbamoyl]cholesterol (DC Cholesterol), dimethyldioctadecylammonium (DDA); 1,2-dimyristoyl 3-trimethylammoniumpropane(DMTAP), dipalmitoyl(C16:0)trimethyl ammonium propane (DPTAP), distearoyltrimethylammonium propane (DSTAP), N-[1-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1, 1'-((2-(4-(2-((2-(bis(2-hydroxy-dodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N, N-ditetradecylacetamide; 0-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9'",9"",9'""-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2, 1-diyl) (9Z,9'Z,9"Z,9'"Z,12Z,12'Z,12"Z,12'"Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Other examples for suitable classes of lipids include, but are not limited to, the phosphatidylcholines (PCs), phosphatidylethanolamines (PEs), phosphatidylglycerol (PGs); and PEGylated lipids including PEGylated version of any of the above lipids (e.g., DSPE-PEGs). In some embodiments, the nanoparticle provided herein comprises DOTAP.

In some embodiments, the nanoparticle provided herein comprises a hydrophobic lipid core. In some embodiments, the hydrophobic lipid core is in liquid phase at 25 degrees C. Non-limiting examples of hydrophobic lipid core components that can be used include α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, solanesol, soy lecithin, soybean oil, sunflower oil, a triglyceride, or vitamin E. In some embodiments, the nanoparticle provided herein comprises a triglyceride. Exemplary triglycerides include but are not limited to: capric triglycerides, caprylic triglycerides, a caprylic and capric triglycerides, triglyceride esters, and myristic acid triglycerins. In some embodiments, the hydrophobic lipid is in solid phase. In some embodiments, the hydrophobic lipid is in liquid phase, also referred to as an oil. In some embodiments, the hydrophobic lipid comprises squalene. In some embodiments, the hydrophobic lipid comprises solanesol.

In some embodiments, the nanoparticles provided herein comprise a liquid organic material and a solid inorganic material. In some embodiments, the nanoparticle provided herein comprises an inorganic particle. In some embodiments, the inorganic particle is a solid inorganic particle. In some embodiments, the nanoparticle provided herein comprises the inorganic particle within the hydrophobic core. In some embodiments, the nanoparticle provided herein comprises a metal. In some embodiments, the nanoparticle provided herein comprises a metal within the hydrophobic core. The metal can be without limitation, a metal salt such as a transition metal salt, a metal oxide such as a transition metal oxide, a metal hydroxide such as a transition metal hydroxide, a metal phosphate such as a transition metal phosphate, or a metalloid (e.g., silicon and silicon-based compounds or alloys). In some embodiments, the nanoparticle provided herein comprises aluminum oxide ($Al_2O_3$), aluminum oxyhydroxide, iron oxide ($Fe_3O_4$, $Fe_2O_3$, FeO, or combinations thereof), titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. The inorganic particles may be formed from one or more same or different metals (any metals including transition metal). In some embodiments, the inorganic particle is a transition metal oxide. In some embodiments, the transition metal is magnetite ($Fe_3O_4$), maghemite (y-$Fe_2O_3$), wüstite (FeO), or hematite (alpha (α)-$Fe_2O_3$). In some embodiments, the metal is aluminum hydroxide or aluminum oxyhydroxide, and a phosphate-terminated lipid or a surfactant, such as oleic acid, oleylamine, SDS, TOPO or DSPA is used to coat the inorganic solid nanoparticle, before it is mixed with the liquid oil to form the hydrophobic core. In some embodiments, the metal can comprise a paramagnetic, a superparamagnetic, a ferrimagnetic or a ferromagnetic compound. In some embodiments, the metal is a superparamagnetic iron oxide ($Fe_3O_4$).

In some embodiments, nanoparticles provided herein comprise a cationic lipid, an oil, and an inorganic particle. In some embodiments, the nanoparticle provided herein comprises DOTAP; squalene and/or glyceryl trimyristate-dynasan; and iron oxide. In some embodiments, the nanoparticle provided herein further comprises a surfactant.

In some embodiments, nanoparticles provided herein comprise a cationic lipid, an oil, an inorganic particle, and a surfactant.

Surfactants are compounds that lower the surface tension between two liquids or between a liquid and a solid component of the nanoparticles provided herein. Surfactants can be hydrophobic, hydrophilic, or amphiphilic. In some embodiments, the nanoparticle provided herein comprises a hydrophobic surfactant. Exemplary hydrophobic surfactants that can be employed include but are not limited to: sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85).

Suitable hydrophobic surfactants include those having a hydrophilic-lipophilic balance (HLB) value of 10 or less, for instance, 5 or less, from 1 to 5, or from 4 to 5. For instance, the hydrophobic surfactant can be a sorbitan ester having an HLB value from 1 to 5, or from 4 to 5. In some embodiments, nanoparticles provided herein comprise a ratio of the esters that yields a hydrophilic-lipophilic balance between 8 and 11. HLB is used to categorize surfactants as hydrophilic or lipophilic. The HLB scale provides for the classification of surfactant function calculated e.g., by Griffin's method:

$$HLB = \frac{20M_h}{M},$$

where $M_h$ is the molecular mass of the hydrophilic portion of the lipid carrier and M is the molecular mass of the lipid carrier. The HLB scale is provided below:

HLB=0: fully lipophilic/hydrophobic carrier;

HLB between 0 and 6 is an oil soluble carrier;

HLB between 6 and 9 is a water dispersible carrier;

HLB between 9 and 20 is a hydrophilic, water soluble carrier;

HLB=20: fully hydrophilic/lipophobic carrier.

In some embodiments, a nanoparticle or a lipid carrier provided herein comprises a hydrophilic surfactant, also called an emulsifier. In some embodiments, a nanoparticle or a lipid carrier provided herein comprises polysorbate. Polysorbates are oily liquids derived from ethoxylated sorbitan (a derivative of sorbitol) esterified with fatty acids. Exemplary hydrophilic surfactants that can be employed include but are not limited to: polysorbates such as TWEEN®, Kolliphor, Scattics, Alkest, or Canarcel; polyoxyethylene sorbitan ester (polysorbate); polysorbate 80 (polyoxyethylene sorbitan monooleate, or TWEEN® 80); polysorbate 60 (polyoxyethylene sorbitan monostearate, or TWEEN® 60); polysorbate 40 (polyoxyethylene sorbitan monopalmitate, or TWEEN® 40); and polysorbate 20 (polyoxyethylene sorbitan monolaurate, or TWEEN® 20). In one embodiment, the hydrophilic surfactant is polysorbate 80.

In some embodiments, nanoparticles and lipid carriers provided herein comprise a hydrophobic core surrounded by a lipid membrane (e.g., a cationic lipid such as DOTAP). In some embodiments, the hydrophobic core comprises: one or more inorganic particles; a phosphate-terminated lipid; and a surfactant.

Inorganic solid nanoparticles described herein can be surface modified before mixing with the liquid oil. For instance, if the surface of the inorganic solid nanoparticle is hydrophilic, the inorganic solid nanoparticle may be coated with hydrophobic molecules (or surfactants) to facilitate the miscibility of the inorganic solid nanoparticle with the liquid oil in the "oil" phase of the nanoemulsion particle. In some embodiments, the inorganic particle is coated with a capping ligand, the phosphate-terminated lipid, and/or the surfactant. In some embodiments the hydrophobic core comprises a phosphate-terminated lipid. Exemplary phosphate-terminated lipids that can be employed include but are not limited to: trioctylphosphine oxide (TOPO) or distearyl phosphatidic acid (DSPA). In some embodiments, the hydrophobic core comprises a surfactant such as a phosphorous-terminated surfactant, a carboxylate-terminated surfactant, a sulfate-terminated surfactant, or an amine-terminated surfactant. Exemplary carboxylate-terminated surfactants include oleic acid. Typical amine terminated surfactants include oleylamine. In some embodiments, the surfactant is distearyl phosphatidic acid (DSPA), oleic acid, oleylamine or sodium dodecyl sulfate (SDS). In some embodiments, the inorganic solid nanoparticle is a metal oxide such as an iron oxide, and a surfactant, such as oleic acid, oleylamine, SDS, DSPA, or TOPO, is used to coat the inorganic solid nanoparticle, before it is mixed with the liquid oil to form the hydrophobic core.

In some embodiments, the hydrophobic core comprises: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate.

In some embodiments, the hydrophobic core comprises: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80.

In some embodiments, the hydrophobic core consists of: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate.

In some embodiments, the hydrophobic core consists of: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80. In some embodiments, the nanoparticle provided herein can comprise from about 0.2% to about 40% w/v squalene, from about 0.001% to about 10% w/v iron oxide nanoparticles, from about 0.2% to about 10% w/v DOTAP, from about 0.25% to about 5% w/v sorbitan monostearate, and from about 0.5% to about 10% w/v polysorbate 80. In some embodiments the nanoparticle provided herein from about 2% to about 6% w/v squalene, from about 0.01% to about 1% w/v iron oxide nanoparticles, from about 0.2% to about 1% w/v DOTAP, from about 0.25% to about 1% w/v sorbitan monostearate, and from about 0.5%) to about 5% w/v polysorbate 80. In some embodiments, the nanoparticle provided herein can comprise from about 0.2% to about 40% w/v squalene, from about 0.001% to about 10% w/v aluminum hydroxide or aluminum oxyhydroxide nanoparticles, from about 0.2% to about 10% w/v DOTAP, from about 0.25% to about 5% w/v sorbitan monostearate, and from about 0.5% to about 10% w/v polysorbate 80. In some embodiments, the nanoparticle provided herein can comprise from about 2% to about 6% w/v squalene, from about 0.01% to about 1% w/v aluminum hydroxide or aluminum oxyhydroxide nanoparticles, from about 0.2% to about 1% w/v DOTAP, from about 0.25% to about 1% w/v sorbitan monostearate, and from about 0.5%) to about 5% w/v polysorbate 80.

In some embodiments, a composition described herein comprises at least one nanoparticle formulation as described in Table 3. In some embodiments, a composition described herein comprises any one of NP-1 to NP-30. In some embodiments, a composition described herein comprises any one of NP-1 to NP-34. In some embodiments, the nanoparticles provided herein are admixed with a nucleic acid provided herein. In some embodiments, nanoparticles provided herein are made by homogenization and ultrasonication techniques.

TABLE 3

Nanoparticle Formulations.

| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
|---|---|---|---|---|
| NP-1 | 30 mg/ml 1,2- dioleoyl-3-trimethylammonium- propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$ Polysorbate 80 (TWEEN ® 80) | 0.2 mg Fe/ml 12 nm oleic acid-coated iron oxide nanoparticles 10 mM sodium citrate dihydrate. |
| NP-2 | 30 mg/ml 1,2- dioleoyl-3-trimethylammonium- propane (DOTAP) chloride | 37.5 mg/ml squalene | 37 mg/ml sorbitan monostearate (2R)-2-[(2R,3R,4S)-3,4-Dihydroxyoxolan-2-y1]-2-hydroxyethyl octadecenoate $C_{24}H_{46}O_6$ (SPAN ® 60) 37 mg/ml polyoxyethylene (20) sorbitan monooleate, $C_{64}H_{124}O_{26}$, Polysorbate 80 (TWEEN ® 80) | 1 mg Fe/ml 15 nm oleic acid-coated iron oxide nanoparticles 10 mM sodium citrate dihydrate |
| NP-3 | 30 mg/ml 1,2- dioleoy1-3-trimethylammonium- propane (DOTAP) chloride | 37.5 mg/ml | 37 mg/ml sorbitan monostearate, (2R)-2-[(2R,3R,4S)-3,4-Dihydroxyoxolan-2-yl]-2-hydroxyethyl octadecenoate $C_{24}H_{46}O_6$ SPAN ® 60) 37 mg/ml polyoxyethylene (20) sorbitan monooleate, $C_{64}H_{124}O_{26}$ Polysorbate 80 (TWEEN ® 80) | 0.2 mg Fe/ml 15 nm oleic acid-coated iron oxide nanoparticles 10 mM sodium citrate dihydrate |
| NP-4 | 30 mg/ml 1,2- dioleoy1-3-trimethylammonium- propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN ® 80) | 1 mg Fe/ml 15 nm oleic acid-coated iron oxide nanoparticles 10 mM sodium citrate dihydrate. |

TABLE 3-continued

| Nanoparticle Formulations. | | | | |
|---|---|---|---|---|
| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
| NP-5 | 30 mg/ml DOTAP chloride | 37.5 mg/ml squalene | 37 mg/ml sorbitan monostearate (SPAN ® 60) 37 mg/ml polysorbate 80 (TWEEN ® 80) | 1 mg/ml trioctylphosphine oxide (TOPO)-coated aluminum hydroxide (Alhydrogel ® 2%) particles 10 mM sodium citrate dihydrate |
| NP-6 | 30 mg/ml DOTAP chloride | 37.5 mg/ml Solanesol (Cayman chemicals) | 37 mg/ml sorbitan monostearate (SPAN ® 60) 37 mg/ml polysorbate 80 (TWEEN ® 80) | 0.2 mg Fe/ml oleic acid-coated iron oxide nanoparticles 10 mM sodium citrate |
| NP-7 | 30 mg/ml DOTAP chloride | 37.5 mg/ml squalene 2.4 mg/ml Dynasan 114 | 37 mg/ml sorbitan monostearate (SPAN ® 60) 37 mg/ml polysorbate 80 (TWEEN ® 80) | 10 mM sodium citrate |
| NP-8 | 4 mg/ml DOTAP chloride | 43 mg/ml squalene | 5 mg/ml sorbitan trioleate (SPAN ® 85) 5 mg/ml polysorbate 80 (TWEEN ® 80) | 10 mM sodium citrate |
| NP-9 | 7.5 mg/ml 1,2- dioleoy1-3-trimethylammonium- propane (DOTAP) chloride | 9.4 mg/ml squalene ((6E,10E,14E,18E)-2,6,10,15,19,23-Hexamethyltetracosa-2,6,10,14,18,22-hexaene, $C_{30}H_{50}$) 0.63 mg/ml glyceryl trimyristate-dynasan (DYNASAN 114 ®) | 9.3 mg/ml sorbitan monostearate (2R)-2-[(2R,3R,4S)-3,4-Dihydroxyoxolan-2-yl]-2-hydroxyethyl octadecenoate, $C_{24}H_{46}O_6$) (SPAN ® 60) 9.3 mg/ml polyoxyethylene (20) sorbitan monooleate, $C_{64}H_{124}O_{26}$, Polysorbate 80 (TWEEN ® 80) | 0.05 mg/ml 15 nanometer superparamagnetic iron oxide ($Fe_3O_4$) 10 mM sodium citrate dihydrate |
| NP-10 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN ® 80) | |
| NP-11 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN ® 80) | |
| NP-12 | 0.4% DOTAP | 4.3% Squalene | 0.5% sorbitan trioleate (SPAN ® 85) 0.5% polysorbate 80 (TWEEN ® 80) | |
| NP-13 | 0.4% DOTAP | 0.25% glyceryl trimyristate-dynasan (DYNASAN 114 ®) 4.08% squalene | 2.0% polysorbate 80 (TWEEN ® 80) | |
| NP-14 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80) | |
| NP-15 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80) | |
| NP-16 | 0.4% DOTAP | 5% squalene | 0.5% sorbitan trioleate (SPAN ® 85) 2.0% polysorbate 80 (TWEEN ® 80) | |

TABLE 3-continued

| Nanoparticle Formulations. | | | | |
|---|---|---|---|---|
| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
| NP-17 | 0.4% DOTAP | 5% squalene | 0.5% sorbitan monostearate (SPAN ® 60) 2% polysorbate 80 (TWEEN ® 80) | |
| NP-18 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | |
| NP-19 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN ® 80) | 1% aluminum hydroxide |
| NP-20 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN ® 80) | 1% aluminum hydroxide |
| NP-21 | 0.4% DOTAP | 4.3% Squalene | 0.5% sorbitan trioleate (SPAN ® 85) 0.5% polysorbate 80 (TWEEN ® 80 | 1% aluminum hydroxide |
| NP-22 | 0.4% DOTAP | 0.25% glyceryl trimyristate-dynasan (DYNASAN 114 ®) 4.08% squalene | 2.0% polysorbate 80 (TWEEN ® 80) | 1% aluminum hydroxide |
| NP-23 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80 | 1% aluminum hydroxide |
| NP-24 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80) | 1% aluminum hydroxide |
| NP-25 | 0.4% DOTAP | 5% squalene | 0.5% sorbitan trioleate (SPAN ® 85) 2.0% polysorbate 80 (TWEEN ® 80) | 1% aluminum hydroxide |
| NP-26 | 0.4% DOTAP | 5% squalene | 0.5% sorbitan monostearate (SPAN ® 60) 2% polysorbate 80 (TWEEN ® 80) | 1% aluminum hydroxide |
| NP-27 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | 1% aluminum hydroxide |
| NP-28 | 0.5-5.0 mg/ml DOTAP | 0.2-10% (v/v) squalene | 0.01-2.5% (v/v) polysorbate 80 (TWEEN ® 80) | |
| NP-29 | 0.4% (w/w) DOTAP | 4.3% (w/w) squalene | 0.5% (w/w) sorbitan trioleate (SPAN ® 85) 0.5% (w/w) polysorbate 80 (TWEEN ® 80) | |
| NP-30 | 30 mg/ml DOTAP chloride | 37.5 mg/ml squalene | 37 mg/ml sorbitan monostearate (SPAN ® 60) 37 mg/ml polysorbate 80 (TWEEN ® 80) | 10 mM sodium citrate |
| NP-31 | 30 mg/ml DOTAP chloride | 37.5 mg/ml squalene | 37 mg/ml sorbitan monostearate (SPAN ® 60) 37 mg/ml polysorbate 80 (TWEEN ® 80) | 0.4 mg Fe/ml 5 nm oleic acid-coated iron oxide nanoparticles 10 mM sodium citrate dihydrate |

TABLE 3-continued

Nanoparticle Formulations.

| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
|---|---|---|---|---|
| NP-32 | 0.8-1.6 mg/ml DOTAP chloride | 4.5% squalene | 0.5% (w/w) sorbitan trioleate (SPAN 85®) 0.5% (w/w) polysorbate 80 (TWEEN® 80) | 10 mM sodium citrate |
| NP-33 | 45-55 mol % ionizable cationic lipid 8-12 mol % distearoylphosphatidylcholine (DSPC) | 35-42 mol % cholesterol | 1.25-1.75 mol % PEG2000-DMG | |
| NP-34 | 50 mol % D-Lin-MC3-DMA (MC3) 10 mol % distearoylphosphatidylcholine (DSPC) | 38.5% cholesterol | 1.5% PEG-lipid | |

In some embodiments, nanoparticles provided herein comprise: sorbitan monostearate (e.g., SPAN® 60), polysorbate 80 (e.g., TWEEN® 80), DOTAP, squalene, and no solid particles. In some embodiments, nanoparticles provided herein comprise: sorbitan monostearate (e.g., SPAN® 60), polysorbate 80 (e.g., TWEEN® 80), DOTAP, squalene, and iron oxide particles. In some embodiments, nanoparticles provided herein comprise an immune stimulant. In some embodiments, the immune stimulant is squalene. In some embodiments, the immune stimulant is Miglyol 810 or Miglyol 812. Miglyol 810 is a triglyceride ester of saturated caprylic and capric fatty acids and glycerol. Miglyol 812 is a triglyceride ester of saturated coconut/palmkernel oil derived caprylic and capric fatty acids and plant derived glycerol. In some embodiments, the immune stimulant can decrease the total amount of protein produced, but can increase the immune response to a composition provided herein (e.g., when delivered as a vaccine). In some embodiments, the immune stimulant can increase the total amount of protein produced, but can decrease the immune response to a composition provided herein.

Nanoparticles provided herein can be of various average diameters in size. In some embodiments, nanoparticles provided herein have an average diameter (z-average hydrodynamic diameter, measured by dynamic light scattering) ranging from about 20 nanometers (nm) to about 200 nm. In some embodiments, the z-average diameter of the nanoparticle ranges from about 20 nm to about 150 nm, from about 20 nm to about 100 nm, from about 20 nm to about 80 nm, from about 20 nm to about 60 nm. In some embodiments, the z-average diameter of the nanoparticle) ranges from about 40 nm to about 200 nm, from about 40 nm to about 150 nm, from about 40 nm to about 100 nm, from about 40 nm to about 90 nm, from about 40 nm to about 80 nm, or from about 40 nm to about 60 nm. In one embodiment, the z-average diameter of the nanoparticle is from about 40 nm to about 80 nm. In some embodiments, the z-average diameter of the nanoparticle is from about 40 nm to about 60 nm. In some embodiments, the nanoparticle is up to 100 nm in diameter. In some embodiments, the nanoparticle is 50 to 70 nm in diameter. In some embodiments, the nanoparticle is 40 to 80 nm in diameter. In some embodiments, the inorganic particle (e.g., iron oxide) within the hydrophobic core of the nanoparticle can be an average diameter (number weighted average diameter) ranging from about 3 nm to about 50 nm. For instance, the inorganic particle can have an average diameter of about 5 nm, about 10 nm, about 15 nm, about 20 nm, about 25 nm, about 30 nm, about 35 nm, about 40 nm, about 45 nm, or about 50 nm. In some embodiments, the ratio of esters and lipids yield a particle size between 30 nm and 200 nm. In some embodiments, the ratio of esters and lipids yield a particle size between 40 nm and 70 nm.

Nanoparticles provided herein may be characterized by the polydispersity index (PDI), which is an indication of their quality with respect to size distribution. In some embodiments, average polydispersity index (PDI) of the nanoparticles provided herein ranges from about 0.1 to about 0.5. In some embodiments, the average PDI of the nanoparticles can range from about 0.2 to about 0.5, from about 0.1 to about 0.4, from about 0.2 to about 0.4, from about 0.2 to about 0.3, or from about 0.1 to about 0.3.

In some embodiments, nanoparticles provided herein comprise an oil-to-surfactant molar ratio ranging from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, nanoparticles provided herein comprise a hydrophilic surfactant-to-lipid ratio ranging from about 0.1:1 to about 2:1, from about 0.2:1 to about 1.5:1, from about 0.3:1 to about 1:1, from about 0.5:1 to about 1:1, or from about 0.6:1 to about 1:1. In some embodiments, the nanoparticles provided herein comprise a hydrophobic surfactant-to-lipid ratio ranging from about 0.1:1 to about 5:1, from about 0.2:1 to about 3:1, from about 0.3:1 to about 2:1, from about 0.5:1 to about 2:1, or from about 1:1 to about 2:1.

In some embodiments, nanoparticles provided herein comprise from about 0.2% to about 40% w/v liquid oil, from about 0.0010% to about 10% w/v inorganic solid nanoparticle, from about 0.2% to about 10% w/v lipid, from about 0.25% to about 5% w/v hydrophobic surfactant, and from about 0.5% to about 10% w/v hydrophilic surfactant. In some embodiments, the lipid comprises a cationic lipid, and the oil comprises squalene, and/or the hydrophobic surfactant comprises sorbitan ester.

Combination Compositions

Provided herein are compositions comprising a nanoparticle described herein and a nucleic acid encoding for a cancer-associated protein, or cancer-associated protein binding protein. In some embodiments, nucleic acids provided herein are incorporated, associated with, or complexed a lipid carrier provided herein to form a lipid carrier-nucleic acid complex. The lipid carrier-nucleic acid complex is formed via non-covalent interactions or via reversible covalent interactions.

Further provided herein is a nanoemulsion comprising a plurality of nanoparticles provided herein. In some embodiments, the nucleic acid further encodes for an RNA-dependent polymerase. In some embodiments, the RNA-dependent polymerase is a viral RNA polymerase. In some embodiments, the nucleic acid encoding for the RNA polymerase is on the same nucleic acid strand as the nucleic acid sequence encoding for the protein (e.g., cis). In some embodiments, the nucleic acid encoding for the RNA polymerase is on a different nucleic acid strand as the nucleic acid sequence encoding for the protein (e.g., trans). In some embodiments, the nucleic acid encoding for the RNA polymerase is a DNA molecule. In some embodiments, nucleic acid sequences encoding for a cancer-associated protein, a tumor antigen, a neoantigen, a cancer therapeutic antibody, or a functional fragment thereof are DNA or RNA molecules. In some embodiments, cancer-associated proteins and cancer therapeutic antibodies provided herein are encoded by DNA. Nanoparticles for inclusion include, without limitation, any one of NP-1 to NP-31, or any one of NP-1 to NP-34. Nucleic acids for inclusion include, without limitation, comprise a region comprising any one of, or a plurality of, SEQ ID NOS: 1, 2, 75, 76, 88, 89 and/or encodes for an amino acid sequence set forth in any one of SEQ ID NOS: 3 to 70, 77, 78, 87. In some instances, the nucleic acids further comprise a region encoding for an RNA polymerase, e.g., a region comprising a sequence of SEQ ID NO: 71.

Compositions provided herein can be characterized by an nitrogen:phosphate (N:P) molar ratio. The N:P ratio is determined by the amount of cationic lipid in the nanoparticle which contain nitrogen and the amount of nucleic acid used in the composition which contain negatively charged phosphates. A molar ratio of the lipid carrier to the nucleic acid can be chosen to increase the delivery efficiency of the nucleic acid, increase the ability of the nucleic acid-carrying nanoemulsion composition to elicit an immune response to the antigen, increase the ability of the nucleic acid-carrying nanoemulsion composition to elicit the production of antibody titers to the antigen in a subject. In some embodiments, compositions provided herein have a molar ratio of the lipid carrier to the nucleic acid can be characterized by the nitrogen-to-phosphate molar ratio, which can range from about 0.01:1 to about 1000:1, for instance, from about 0.2:1 to about 500:1, from about 0.5:1 to about 150:1, from about 1:1 to about 150:1, from about 1:1 to about 125:1, from about 1:1 to about 100:1, from about 1:1 to about 50:1, from about 1:1 to about 50:1, from about 5:1 to about 50:1, from about 5:1 to about 25:1, or from about 10:1 to about 20:1. In certain embodiments, the molar ratio of the lipid carrier to the nucleic acid, characterized by the nitrogen-to-phosphate (N:P) molar ratio, ranges from about 1:1 to about 150:1, from about 5:1 to about 25:1, or from about 10:1 to about 20:1. In one embodiment, the N:P molar ratio of the nanoemulsion composition is about 15:1. In some embodiments, the nanoparticle comprises a nucleic acid provided herein covalently attached to the membrane.

Compositions provided herein can be characterized by an oil-to-surfactant molar ratio. In some embodiments, the oil-to-surfactant ratio is the molar ratio of squalene: DOTAP, hydrophobic surfactant, and hydrophilic surfactant. In some embodiments, the oil-to-surfactant ratio is the molar ratio of squalene: DOTAP, sorbitan monostearate, and polysorbate 80. In some embodiments, the oil-to surfactant molar ratio ranges from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the oil-to-surfactant molar ratio is at least about 0.1:1, at least about 0.2:1, at least about 0.3:1, at least about 0.4:1, at least about 0.5:1, at least about 0.6:1, at least about 0.7:1. In some embodiments, the oil-to surfactant molar ratio is at least about 0.4:1 up to 1:1.

Compositions provided herein can be characterized by hydrophilic surfactant-to-lipid (e.g., cationic lipid) ratio. In some embodiments, the hydrophilic surfactant-to-lipid ratio ranges from about 0.1:1 to about 2:1, from about 0.2:1 to about 1.5:1, from about 0.3:1 to about 1:1, from about 0.5:1 to about 1:1, or from about 0.6:1 to about 1:1. Compositions provided herein can be characterized by hydrophobic surfactant-to-lipid (e.g., cationic lipid) ratio ranging. In some embodiments, the hydrophobic surfactant-to-lipid ratio ranges from about 0.1:1 to about 5:1, from about 0.2:1 to about 3:1, from about 0.3:1 to about 2:1, from about 0.5:1 to about 2:1, or from about 1:1 to about 2:1.

Provided herein is a dried composition comprising a sorbitan fatty acid ester, an ethoxylated sorbitan ester, a cationic lipid, an immune stimulant, and an RNA. Further provided herein are dried compositions, wherein the dried composition comprises sorbitan monostearate (e.g., SPAN® 60), polysorbate 80 (e.g., TWEEN® 80), DOTAP, an immune stimulant, and an RNA.

Thermally Stable, Dried, and Lyophilized Cancer Vaccines

Provided herein are dried or lyophilized compositions and vaccines. Further provided herein are pharmaceutical compositions comprising a dried or lyophilized composition provided herein that is reconstituted in a suitable diluent and a pharmaceutically acceptable carrier. In some embodiments, the diluent is aqueous. In some embodiments, the diluent is water.

A lyophilized composition is generated by a low temperature dehydration process involving the freezing of the composition, followed by a lowering of pressure, and removal of ice by sublimation. In certain cases, lyophilization also involves the removal of bound water molecules through a desorption process. In some embodiments, compositions and vaccine compositions provided herein are spray-dried. Spray drying is a process by which a solution is fed through an atomizer to create a spray, which is thereafter exposed to a heated gas stream to promote rapid evaporation. When sufficient liquid mass has evaporated, the remaining solid material in the droplet forms particles which are then separated from the gas stream (e.g., using a filter or a cyclone). Drying aids in the storage of the compositions and vaccine compositions provided herein at higher temperatures (e.g., greater than 4° C.) as compared to the sub-zero temperatures needed for the storage of existing mRNA vaccines. In some embodiments, dried compositions and lyophilized compositions provided herein comprise (a) a lipid carrier, wherein the lipid carrier is a nanoemulsion comprising: (i) a hydrophobic core; (ii) one or more inorganic nanoparticles; (iii) and one or more lipids; (b) one or more nucleic acids; and (c) at least one cryoprotectant. In some embodiments, the cryoprotectant is selected from the group consisting of: sucrose, maltose, trehalose, mannitol, glucose, and any combinations thereof. Additional examples of cryoprotectants include but are not limited to: dimethyl sulfoxide (DMSO), glycerol, propylene glycol, ethylene glycol, 3-O-methyl-D-glucopyranose (3-OMG), olyethylene glycol (PEG), 1,2-propanediol, acetamide, trehalose, formamide, sugars, proteins, and carbohydrates.

In some embodiments, compositions and methods provided herein comprise at least one cryoprotectant. Exemplary cryoprotectants for inclusion are, but not limited to, sucrose, maltose, trehalose, mannitol, or glucose, and any combinations thereof. In some embodiments, additional or alternative cryoprotectant for inclusion is sorbitol, ribitol, erthritol, threitol, ethylene glycol, or fructose. In some embodiments, additional or alternative cryoprotectant for inclusion is dimethyl sulfoxide (DMSO), glycerol, propylene glycol, ethylene glycol, 3-O-methyl-D-glucopyranose (3-OMG), polyethylene glycol (PEG), 1,2-propanediol, acetamide, trehalose, formamide, sugars, proteins, and carbohydrates. In some embodiments, the cryoprotectant is present at about 1% w/v to at about 20% w/v, preferably about 10% w/v to at about 20% w/v, and more preferably at about 10% w/v. In certain aspects of the disclosure, the cryoprotectant is sucrose. In some aspects of the disclosure, the cryoprotectant is maltose. In some aspects of the disclosure, the cryoprotectant is trehalose. In some aspects of the disclosure, the cryoprotectant is mannitol. In some aspects of the disclosure, the cryoprotectant is glucose. In some embodiments, the cryoprotectant is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the cryoprotectant is present in an amount of about 50 to about 500 mg. In some embodiments, the cryoprotectant is present in an amount of about 200 to about 300 mg. In some embodiments, the cryoprotectant is present in an amount of about 250 mg. In some embodiments, the cryoprotectant is present in amount of a lyophilized composition by weight of at least about 50, 55, 60, 65, 70, 75, 80, 85, 90, 95 or more percent. In some embodiments, the cryoprotectant is present in amount of a lyophilized composition by weight of about 95%. In some embodiments, the cryoprotectant is present in amount of a lyophilized composition by weight of 80 to 98%, 85 to 98%, 90 to 98%, or 94 to 96%. In some embodiments, the cryoprotectant is a sugar. In some embodiments, the sugar is sucrose, maltose, trehalose, mannitol, or glucose. In some embodiments, the sugar is sucrose. In some embodiments, the sucrose is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the sucrose is present in an amount of about 50 to about 500 mg. In some embodiments, the sucrose is present in an amount of about 200 to about 300 mg. In some embodiments, the sucrose is present in an amount of about 250 mg. In some embodiments, the sucrose is present in amount of a lyophilized composition by weight of at least about 50, 55, 60, 65, 70, 75, 80, 85, 90, 95 or more percent. In some embodiments, the sucrose is present in amount of a lyophilized composition by weight of about 95%. In some embodiments, the sucrose is present in amount of a lyophilized composition by weight of 80 to 98%, 85 to 98%, 90 to 98%, or 94 to 96%.

In some embodiments, the cryoprotectant is sucrose. In some embodiments, the cryoprotectant is at a concentration of at least about 0.1% w/v. In some embodiments, the cryoprotectant is at a concentration of about 1% w/v to at about 20% w/v. In some embodiments, the cryoprotectant is at a concentration of about 10% w/v to at about 20% w/v. In some embodiments, the cryoprotectant is at a concentration of about 10% w/v.

In some embodiments, compositions and vaccine compositions provided herein are thermally stable. A composition is considered thermally stable when the composition resists the action of heat or cold and maintains its properties, such as the ability to protect a nucleic acid molecule from degradation at given temperature. In some embodiments, compositions and vaccine compositions provided herein are thermally stable at about 25 degrees Celsius (° C.) or standard room temperature. In some embodiments, compositions and vaccine compositions provided herein are thermally stable at about 45° C. In some embodiments, compositions and vaccine compositions provided herein are thermally stable at about −20° C. In some embodiments, compositions and vaccine compositions provided herein are thermally stable at about 2° C. to about 8° C. In some embodiments, compositions and vaccine compositions provided herein are thermally stable at a temperature of at least about −80° C., at least about −20° C., at least about 0° C., at least about 2° C., at least about 4° C., at least about 6° C., at least about 8° C., at least about 10° C., at least about 20° C., at least about 25° C., at least about 30° C., at least about 37° C., up to 45° C. In some embodiments, compositions and vaccine compositions provided herein are thermally stable for at least about 5 day, at least about 1 week, at least about 2 weeks, at least about 1 month, up to 3 months. In some embodiments, compositions and vaccine compositions provided herein are stored at a temperature of at least about 4° C. up to 37° C. for at least about 5 day, at least about 1 week, at least about 2 weeks, at least about 1 month, up to 3 months. In some embodiments, compositions and vaccine compositions provided herein are stored at a temperature of at least about 20° C. up to 25° C. for at least about 5 day, at least about 1 week, at least about 2 weeks, at least about 1 month, up to 3 months.

Also provided herein are methods for preparing a lyophilized composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and lyophilizing the formulation to form a lyophilized composition.

Further provided herein are methods for preparing a spray-dried composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and spray drying the formulation to form a spray-dried composition.

Further provided herein are methods for reconstituting a lyophilized composition comprising: obtaining a lipid carrier, wherein the lipid carrier is a nanoemulsion comprising a hydrophobic core, one or more inorganic nanoparticles, and one or more lipids; incorporating one or more nucleic acid into the said lipid carrier to form a lipid carrier-nucleic acid complex; adding at least one cryoprotectant to the lipid carrier-nucleic acid complex to form a formulation; lyophilizing the formulation to form a lyophilized composition; and reconstituting the lyophilized composition in a suitable diluent.

Further provided herein are methods for reconstituting a spray-dried composition comprising: obtaining a lipid carrier, wherein the lipid carrier is a nanoemulsion comprising a hydrophobic core, one or more inorganic nanoparticles, and one or more lipids, incorporating one or more nucleic acid into the said lipid carrier to form a lipid carrier-nucleic acid complex; adding at least one cryoprotectant to the lipid carrier-nucleic acid complex to form a formulation; spray drying the formulation to form a spray-dried composition; and reconstituting the spray-dried composition in a suitable diluent.

Pharmaceutical Compositions

Provided herein is a suspension comprising a composition provided herein. In some embodiments, suspensions provided herein comprise a plurality of nanoparticles or compositions provided herein. In some embodiments, compositions provided herein are in a suspension, optionally a homogeneous suspension. In some embodiments, compositions provided herein are in an emulsion form.

Also provided herein is a pharmaceutical composition comprising a composition provided herein. In some embodiments, compositions provided herein are combined with pharmaceutically acceptable salts, excipients, and/or carriers to form a pharmaceutical composition. Pharmaceutical salts, excipients, and carriers may be chosen based on the route of administration, the location of the target issue, and the time course of delivery of the drug. A pharmaceutically acceptable carrier or excipient may include solvents, dispersion media, coatings, antibacterial and antifungal agents, isotonic and absorption delaying agents, etc., compatible with pharmaceutical administration.

In some embodiments, the pharmaceutical composition is in the form of a solid, semi-solid, liquid or gas (aerosol). Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent. Among the acceptable vehicles and solvents that may be employed are water, Ringer's solution, U.S.P., and isotonic sodium chloride solution. In addition, sterile, fixed oils are employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Dosing

Compositions provided herein may be formulated in dosage unit form for ease of administration and uniformity of dosage. A dosage unit form is a physically discrete unit of a composition provided herein appropriate for a subject to be treated. It will be understood, however, that the total usage of compositions provided herein will be decided by the attending physician within the scope of sound medical judgment. For any composition provided herein the therapeutically effective dose can be estimated initially either in cell culture assays or in animal models, such as mice, rabbits, dogs, pigs, or non-human primates. Subjects include, without limitation, domesticate or farmed animals (including without limitation pigs, cows, horses, buffalo, pigs, ducks, geese, chicken, turkey, fish) as well as humans. Dosing may be for veterinary or human therapeutic uses. The animal model is also used to achieve a desirable concentration range and route of administration. Such information can then be used to determine useful doses and routes for administration in humans. Therapeutic efficacy and toxicity of compositions provided herein can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies may be used in formulating a range of dosage for human use.

Administration

Provided herein are compositions and pharmaceutical compositions for administering to a subject in need thereof. In some embodiments, pharmaceutical compositions provided here are in a form which allows for compositions provided herein to be administered to a subject.

In some embodiments, the administering is local administration or systemic administration. In some embodiments, a composition described herein is formulated for administration/for use in administration via a subcutaneous, intradermal, intramuscular, inhalation, intravenous, intraperitoneal, intracranial, or intrathecal route. In some embodiments, the administering is every 1, 2, 4, 6, 8, 12, 24, 36, or 48 hours. In some embodiments, the administering is daily, weekly, or monthly. In some embodiments, the administering is repeated at least about every 28 days or 56 days.

In some embodiments, a single dose of a composition provided herein is administered to a subject. In some embodiments, a composition or pharmaceutical composition provided herein is administered to the subject by two doses. In some embodiments, a second dose of a composition or pharmaceutical composition provided herein is administered about 28 days or 56 days after the first dose. In some embodiments, a first dose is administered, and a second dose is administered about 14 days later, or about 21 days later, or about 28 days later, or about 35 days later, or about 42 days later, or about 49 days later, or about 56 days later, or about 63 days later, or about 70 days later, or about 77 days later, or about 84 days later. In some embodiments, the second dose is administered about 10-90 days following administration of the first dose, or about 15-85 days following administration of the first dose, or about 20-80 days following administration of the first dose, or about 25-75 days following administration of the first dose, or about 30-70 days following administration of the first dose, or about 35-65 days following administration of the first dose, or about 40-60 days following administration of the first dose.

In some embodiments, an additional, for example third or more, dose of a composition or pharmaceutical composition provided herein is administered to a subject. In some embodiments, the additional dose is administered about 1 month following administration of the second dose, about 2 months following administration of the second dose, about 3 months following administration of the second dose, about 4 months following administration of the second dose, about 5 months following administration of the second dose, about 6 months following administration of the second dose, about 7 months following administration of the second dose, about 8 months following administration of the second dose, about 9 months following administration of the second dose, about 10 months following administration of the second dose, about 11 months following administration of the second dose, about 12 months following administration of the second dose, about 13 months following administration of the second dose, about 14 months following administration of the second dose, about 15 months following administration of the second dose, about 16 months following administration of the second dose, about 17 months following administration of the second dose, or about 18 months following administration of the second dose.

Methods

Provided herein are methods of treating or preventing a disease in a subject. In some embodiments, compositions described herein are used for the treatment of cancer. In some embodiments, the cancer is a solid cancer or a blood cancer. In some embodiments, the solid cancer is a carcinoma, a melanoma, or a sarcoma. In some embodiments, the blood cancer is lymphoma or leukemia. In some embodiments, the cancer is a metastatic cancer. In some embodiments, the cancer is a skin cancer. In some embodiments, the skin cancer is a basal cell cancer, a melanoma, a Merkel cell cancer, a squamous cell carcinoma, a cutaneous lymphoma, a Kaposi sarcoma, or a skin adnexal cancer. In some embodiments, the subject has lung cancer. In some embodiments, the lung cancer is a non-small cell lung cancer (NSCLC) or a small cell lung cancer (SCLC). In some embodiments, the NSCLC is an adenocarcinoma, a squamous cell carcinoma, a large cell carcinoma, an adenosquamous carcinoma, or a sarcomatoid carcinoma. In some embodiments, the cancer is a pancreatic cancer. In some embodiments, the pancreatic cancer is a pancreatic adenocarcinoma or a pancreatic exocrine cancer. In some embodiments, the pancreatic cancer is a pancreatic neuroendocrine cancer, an islet cell cancer, or a pancreatic endocrine cancer. In some embodiments, the cancer is a prostate cancer.

Provided herein are personalized treatments for the treatment of a cancer in a subject. The personalized treatment provided herein can be tailored to the expression of a cancer-associated protein provided herein and/or a particular genotype of the subject identified as having a cancer. For example, the subject can be tested for a specific mutation in an oncogenic driver gene (e.g., KRAS G12C or G12D) that is known to cause a specific subtype of cancer (e.g., a NSCLC lung cancer). Oncogenic driver mutations are genetic mutations that are responsible for both the initiation and maintenance of the cancer. In some embodiments, the subject is identified as having a mutation in an oncogenic driver gene or biomarker. Non-limiting examples of oncogenic driver genes/biomarkers and their associated cancer type include: breast cancer: BRCA1, BRCA2, TP53, TTN, FLG, OBSCN, ERBB2, GATA3, FGFR1, CCND1, PIK3CA, CACNA1C, ARHGAP35, ARID5B, BIRC6, CDH1, CTCF, DSPP, HDAC9, KDM5B, MAST1, MEF2A, NCOR2, SETD1A, SXL2, RID1A, CTNND1, NUP107, CHD8, FANCI, CHD9, CTCF, KEAP1, PCDH18, LAMA2, HDAC9, ARFGEF1, MLLT4, NRK, FOXO3, CDKN2A, MAP3K1, GPS2, ROCK2, RYR2, PGR, STAT6, PIK3CD, CTCF, CDH1, GATA3, AKT1; gastric cancers: ADCY3, BCL6B, CACNA1C, FRMD4A, NID1, ROCK2; pancreatic cancer: ARHGAP35, CACNA1C, GRIA3, PDAC, PALB2, KRAS, CDKN2A, TP53, and SMAD4; lung cancer: EGFR, MET, KRAS, ALK, ALK L1196M, ALK C1156Y, EML4-ALK, ERBB3, ERBB4, VEGFR, NBPF12, NTRK, ROCK2, RYR2, SCAF11, SDK2, STAT6; prostate cancer: SLC45A3, DNAH12, DSPP, KRAS, PCDH11X; ovarian cancer: DNAH14, PGR, PIK3CD, TTN; colon cancer: LAMA, PIK3CD, TTN; bladder: RYR2; skin: BRAF V600, NRAS, NRAS Q61L/R, GNAQ, GNA11, AC1, PPP6C, RAC1, PPP6C, STK19.

In some embodiments, methods provided herein comprise modulating an immune response in a subject. In some embodiments, the immune response in the subject is modulated by a method comprising: (a) administering to a subject having a cancer, a composition, wherein the composition comprises: at least one nucleic acid, wherein the at least one nucleic acid comprises a sequence encoding for a plurality of cancer-associated proteins, wherein, prior to the administering, the plurality of cancer-associated proteins are increased in presence compared to non-cancer cells of the subject; or comprise a sequence modification compared to non-cancer cells of the subject; and a plurality of nanoparticles, wherein each nanoparticle comprises a cationic surface, and wherein the at least one nucleic acid is complexed to the cationic surface. Methods provided herein may further comprise obtaining nucleic acid sequence information or amino acid sequence information from a sample comprising cancer cells obtained from the subject. Cancer cells and non-cancer cells can be obtained from the subject by any method, including for example, surgery, biopsy, blood draw, nasal swab, pap test, colonoscopy, urinalysis, and the like. In some embodiments, the cancer cells are circulating cancer cells. Nucleic acid sequence information can be obtained from a sample comprising non-cancer cells from the same subject to serve as a control. The sequence information can be compared between the cancer cell sample and the non-cancer-cell sample to identify somatic mutations present in the cancer cell sequence information, thereby identifying one or more cancer-associated proteins or cancer cell markers in the subject. Sequence information can be obtained from the sample by any method, including but not limited to, e.g., sequencing, PCR, reverse-transcriptase PCR (RT-PCR), proteomics, immunosorbent assays, and RNA-seq. The sequence information can be used to classify immunogenic epitopes with one or more of the following properties: (i) the epitope occurs in a transcript; (ii) the epitope occurs in a protein-coding region; (iii) the epitope introduces a change in an amino acid sequence; and (iv) the epitope is predicted to exhibit MHC binding. These properties are useful for identifying cancer-associated proteins and cancer cell markers to be used in the personalized vaccine composition for administration to the subject. Following the identification of cancer-associated protein epitopes in the cancer cells of the subject, the methods provided herein comprise producing the at least one nucleic acid encoding for a plurality of cancer-associated proteins provided herein; and/ or a nucleic acid encoding for an antibody that binds to a cancer-associated protein provided herein.

Provided herein are methods for the personalized treatment of cancer in a subject, the methods comprising: (a) receiving the results of an assay that indicates that the subject has a tumor, wherein the tumor comprises a cancer-associated protein; and (b) administering to the subject a composition, wherein the composition comprises at least one nucleic acid encoding for the cancer-associated protein in (a), thereby treating the cancer in the subject. Further provided herein are method for the personalized treatment of cancer in a subject, the method comprising: (a) receiving the results of an assay that indicates that the subject has a tumor, wherein the tumor comprises a cancer-associated protein; and (b) administering to the subject a composition, wherein the composition comprises at least one nucleic acid encoding for an antibody that specifically binds to the cancer-associated protein in (a), thereby treating the cancer in the subject. In some embodiments, the composition further comprises a nanoparticle described herein. In some embodiments, the nucleic acid further comprises a replicon sequence described herein. In some embodiments, the method provides for reduction in severity, tumor size, tumor volume, or incidence of tumor occurrence in a subject.

In some embodiments, the subject has a tumor comprising a cancer-associated protein selected from the group consisting of: (i) epidermal growth factor receptor (EGFR); (ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCNDT); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (a) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (1) Melanoma-associated antigen recognized by T cells 1 (MART-1); and functional fragments thereof. In some embodiments, the subject has a tumor comprising a cancer-associated protein selected from Table 1.

Further provided herein are methods of modulating an immune response in a subject, the methods comprising: administering to a subject having cancer the composition provided herein, or a pharmaceutical composition provided herein. Compositions provided herein can also be administered prophylactically to immunize a subject for a cancer. In some embodiments, compositions described herein are used for prophylactically immunizing a subject for a skin cancer or a lung cancer. In some embodiments, the subject is at risk of developing a cancer described herein. In some embodiments, the administration provides for a reduction in tumor occurrence, size, volume, and/or frequency in a subject compared to a subject having the tumor without the administration.

Kits

Provided herein is a kit comprising a composition provided herein, a pharmaceutical composition provided herein; and optionally, a delivery system for administration to a subject. Kits described herein may comprise lyophilized reagents and, optionally, a reagent for hydration. Kits described herein may also comprise non-lyophilized reagents. In some embodiments, the kit comprises two or more separate units comprising the lipid carrier and the nucleic acid, respectively.

In some embodiments, the kit comprises a unit that comprises the lipid carrier and the nucleic acid. In some embodiments, the kit further comprises a unit comprising a reagent for hydration of the dried composition. In some embodiments, the reagent for hydration comprises water.

In some embodiments, the kit further comprises one or more surfactants. In some embodiments, a formulation of a composition described herein is prepared in a single container for administration. In some embodiments, a formulation of a composition described herein is prepared two containers for administration, separating the nucleic acid from the nanoparticle carrier. As used herein, "container" includes vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Examples of such containers include glass and/or plastic sealed or re-sealable tubes and ampules, including those having a rubber septum or other sealing means that is compatible with withdrawal of the contents using a needle and syringe. In some implementations, the containers are RNase free.

In some embodiments, the kit comprises: (a) a lipid carrier, wherein the lipid carrier is a nanoemulsion comprising a hydrophobic core, one or more lipids, and one or more surfactants; and (b) at least one nucleic acid sequence, which comprises a sequence which encodes a sequence capable of expressing an antigen, wherein the antigen is a cancer-associated protein.

Exemplary Embodiments

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for a cancer-associated protein. Further provided herein are compositions, wherein the cancer-associated protein is a protein expressed by a melanoma cell. Further provided herein are compositions, wherein the nucleic acid comprises a sequence region that is at least 85% identical to one of SEQ ID NOS: 1-2, 75, 76, 88, or 89. Further provided herein are compositions, wherein the cancer-associated protein sequence or functional variant thereof has an amino acid sequence as set forth in one of SEQ ID NOS: 3-47, 77, 78, 87, 90. Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid coding the RNA polymerase comprises the nucleic acid sequence of SEQ ID NO: 71. Further provided herein are compositions, wherein the liquid oil is α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl (C16:0)trimethyl ammonium propane (DPTAP), distearoyltrimethylammonium propane (DSTAP), N-[1-(2, 3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis (2-hydroxydodecyl)amino)ethyl)(2-hydroxydodecyl)amino) ethyl)piperazin-1-yl)ethyl)azanediyl)bis(dodecan-2-ol) (C12-200), 306Oi10, tetrakis(8-methylnonyl) 3,3',3'',3'''-(((methylazanediyl)bis(propane-3,1 diyl))bis (azanetriyl)) tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9'',9''', 9'''',9'''''-((((benzene-1, 3,5-tricarbonyl)yris(azanediyl)) tris (propane-3,1-diyl)) tris (azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9''Z,9'''Z,12Z,12'Z,12''Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein the lipid carrier comprises a hydrophobic core. Further provided herein are compositions, wherein the lipid carrier comprises an inorganic particle. Further provided herein are compositions, wherein the inorganic particle is within the hydrophobic core. Further provided herein are compositions, wherein the inorganic particle comprises a metal. Further provided herein are compositions, wherein the metal comprises a metal salt, a metal oxide, a metal hydroxide, or a metal phosphate. Further provided herein are compositions, wherein the metal oxide comprises aluminum oxide, aluminum oxyhydroxide, iron oxide, titanium dioxide, or silicon dioxide. Further provided herein are compositions, wherein the hydrophobic surfactant is sorbitan monolaurate, sorbitan monopalmitate, sorbitan monostearate, sorbitan monooleate, or sorbitan trioleate. Further provided herein are compositions, wherein the hydrophilic surfactant is a polysorbate. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for an antibody or a functional variant thereof. Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence encoding for a cancer therapeutic antibody or a functional variant thereof. Further provided herein are compositions, wherein the antibody is a cancer therapeutic antibody or a functional variant thereof. Further provided herein are compositions, wherein the cancer therapeutic antibody is an antibody listed in Table 2. Further provided herein are compositions, wherein the cancer therapeutic antibody is antibody is atezolizumab, avelumab, bevacizumab, cemiplimab, cetuximab, daratumumab, dinutuximab, durvalumab, elotuzumab, ipilimumab, isatuximab, mogamulizumab, necitumumab, nivolumab, obinutuzumab, ofatumumab, olaratumab, panitumumab, pembrolizumab, pertuzumab, ramucirumab, rituximab, or trastuzumab. Further provided herein are compositions, wherein the cancer therapeutic antibody has an amino acid sequence as set forth in any one of SEQ ID NOS: 48-70. Further provided herein are compositions, wherein the nucleic acid is in complex with the lipid carrier. Further provided herein are compositions, wherein the nucleic acid further encodes for an RNA-dependent polymerase. Further provided herein are compositions, wherein the RNA-dependent polymerase is a Venezuelan equine encephalitis virus (VEEV) RNA polymerase. Further provided herein are compositions, wherein the nucleic acid encoding for the RNA-dependent polymerase comprises the nucleic acid sequence of SEQ ID NO: 71. Further provided herein are compositions, wherein the liquid oil is α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16:0)trimethyl ammonium propane (DPTAP), distearoyltrimethylammonium propane (DSTAP), N-[1-(2, 3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis (2-hydroxydodecyl)amino)ethyl)(2-hydroxydodecyl)amino) ethyl)piperazin-1-yl)ethyl)azanediyl)bis(dodecan-2-ol) (C12-200), 306Oi10, tetrakis(8-methylnonyl) 3,3',3'',3'''-(((methylazanediyl)bis(propane-3,1 diyl))bis (azanetriyl)) tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9'',9''',9'''',9'''''-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9''Z,9'''Z,12Z,12'Z,12''Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein the lipid carrier comprises a hydrophobic core. Further provided herein are compositions, wherein the lipid carrier comprises an inorganic particle. Further provided herein are compositions, wherein the inorganic particle is within the hydrophobic core. Further provided herein are compositions, wherein the inorganic particle comprises a metal. Further provided herein are compositions, wherein the metal comprises a metal salt, a metal oxide, a metal hydroxide, or a metal phosphate. Further provided herein are compositions, wherein the metal oxide comprises aluminum oxide, aluminum oxyhydroxide, iron oxide, titanium dioxide, or silicon dioxide. Further provided herein are compositions, wherein the hydrophobic surfactant is sorbitan monolaurate, sorbitan monopalmitate, sorbitan monostearate, sorbitan monooleate, or sorbitan trioleate. Further provided herein are compositions, wherein the hydrophilic surfactant is a polysorbate. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are compositions, wherein the compositions comprise: a lipid carrier, wherein the lipid carrier comprises: liquid oil; an inorganic nanoparticle, wherein the inorganic nanoparticle comprises iron oxide present in an amount of about 0.2 mg/ml 12 nm iron oxide; and surfactants, wherein the surfactants comprise a cationic lipid; and at least one nucleic acid, wherein the nucleic acid comprises a sequence encoding for a cancer-associated protein sequence or functional variant thereof. Further provided herein are compositions, wherein the lipid carrier further comprises: about 30 mg/mL DOTAP chloride; about 37.5 mg/mL squalene; about 37 mg/ml sorbitan monostearate; about 37 mg/ml polysorbate 80; and about 10 mM sodium citrate. Further provided herein are compositions, wherein the lipid carrier comprises a hydrophobic core. Further provided herein are compositions, wherein the iron oxide comprises oleic acid-coated iron oxide. Further provided herein are compositions, wherein the oleic acid-coated iron oxide nanoparticles are within the hydrophobic core. Further provided herein are compositions, wherein the liquid oil is α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16:0)trimethyl ammonium propane (DPTAP), distearoyltrimethylammonium propane (DSTAP), N-[1-(2, 3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis (2-hydroxydodecyl)amino)ethyl)(2-hydroxydodecyl)amino) ethyl)piperazin-1-yl)ethyl)azanediyl)bis(dodecan-2-ol) (C12-200), 306Oi10, tetrakis(8-methylnonyl) 3,3',3",3'"-(((methylazanediyl)bis(propane-3,1 diyl))bis (azanetriyl)) tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9'", 9"",9'""-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9"Z,9'"Z,12Z,12'Z,12"Z,12'"Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein the nucleic acid is in complex with the lipid carrier. Further provided herein are compositions, wherein the nucleic acid comprises a sequence as set forth in one of SEQ ID NOS: 1-2, 75, 76, 88, or 89. Further provided herein are compositions, wherein the cancer-associated protein sequence or functional variant thereof has an amino acid sequence as set forth in one of SEQ ID NOS: 3-47, 77, 78, 88, 89. Further provided herein are compositions, wherein the nucleic acid further encodes for an RNA-dependent polymerase. Further provided herein are compositions, wherein the RNA-dependent polymerase is a Venezuelan equine encephalitis virus (VEEV) RNA polymerase. Further provided herein are compositions, wherein the nucleic acid coding the RNA-dependent polymerase comprises the nucleic acid sequence of SEQ ID NO: 71. Further provided herein are compositions, wherein the hydrophilic surfactant is a polysorbate. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are compositions, wherein the compositions comprise: (a) a lipid carrier, wherein the lipid carrier is a nanoemulsion comprising: about 30 mg/mL DOTAP chloride; about 37.5 mg/ml squalene; about 37 mg/ml sorbitan monostearate; about 37 mg/ml polysorbate 80; about 10 mM sodium citrate; and about 0.2 mg Fe/ml 12 nm oleic acid-coated iron oxide nanoparticles; and (b) at least one nucleic acid, wherein the at least one nucleic acid comprises a sequence encoding for a cancer-associated protein sequence or functional variant thereof. Further provided herein are compositions, wherein the compositions further comprise: sucrose, optionally, wherein the sucrose is present in an about of about 50 mg. Further provided herein are compositions, wherein the nucleic acid is in complex with the lipid carrier. Further provided herein are compositions, wherein the nucleic acid comprises a sequence as set forth in one of SEQ ID NOS: 1-2, 75, 76, 88, or 89. Further provided herein are compositions, wherein the cancer-associated protein sequence or functional variant thereof has an amino acid sequence as set forth in one of SEQ ID NOS: 3-47, 77, 78, 87, or 90. Further provided herein are compositions, wherein the nucleic acid further encodes for an RNA-dependent polymerase. Further provided herein are compositions, wherein the RNA-dependent polymerase is a Venezuelan equine encephalitis virus (VEEV) RNA polymerase. Further provided herein are compositions, wherein the nucleic acid encoding for the RNA-dependent polymerase comprises the nucleic acid sequence of SEQ ID NO: 71. Further provided herein are compositions, wherein the lipid carrier comprises a hydrophobic core. Further provided herein are compositions, wherein the oleic acid-coated iron oxide nanoparticles are within the hydrophobic core. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the composition is lyophilized.

Provided herein are compositions, wherein the compositions comprise: (a) a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; and oleic acid-coated iron oxide nanoparticles present in an amount of about 0.005 mg; and (b) at least one nucleic acid, wherein the at least one nucleic acid comprises a sequence encoding for a cancer-associated protein sequence or functional variant thereof. Further provided herein are compositions, wherein the nucleic acid is in complex with the lipid carrier. Further provided herein are compositions, wherein the nucleic acid comprises a sequence as set forth in any one of SEQ ID NOS: 1-2, 75, 76, 88, or 89. Further provided herein are compositions, wherein the cancer-associated protein sequence or functional variant thereof has an amino acid sequence as set forth in one of SEQ ID NOS: 3-47, 77, 78, 87, or 90. Further provided herein are compositions, wherein the nucleic acid further encodes for an RNA-dependent polymerase. Further provided herein are compositions, wherein the RNA-dependent polymerase is a Venezuelan equine encephalitis virus (VEEV) RNA polymerase. Further provided herein are compositions, wherein the nucleic acid encoding for the RNA-dependent polymerase comprises the nucleic acid sequence of SEQ ID NO: 71. Further provided herein are compositions, wherein the lipid carrier comprises a hydrophobic core. Further provided herein are compositions, wherein the oleic acid-coated iron oxide nanoparticles are within the hydrophobic core. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are compositions, wherein the compositions comprise: a first nucleic acid comprising a sequence encoding for an RNA-dependent RNA polymerase; and a second nucleic acid comprising a sequence encoding for a cancer-associated protein sequence or functional variant thereof wherein the cancer-associated protein sequence is least 85% identical to one of SEQ ID NOS: 1-2, 75, 76, 88, or 89. Further provided herein are compositions, wherein the cancer-associated protein sequence comprises a sequence listed in Table 1. Further provided herein are compositions, wherein the cancer-associated protein sequence comprises a TRP-1 tumor associated antigen sequence. Further provided herein are compositions, wherein the first nucleic acid and the second nucleic acid are present on a shared nucleic acid. Further provided herein are compositions, wherein the first nucleic acid and the second nucleic acid are present on separate nucleic acids. Further provided herein are compositions, wherein the RNA-dependent RNA polymerase comprises a VEEV RNA polymerase. Further provided herein are compositions, wherein the compositions further comprise a nanoparticle carrier system. Further provided herein are compositions, wherein the nanoparticle carrier system comprises a cationic lipid and a hydrophobic core. Further provided herein are compositions, wherein the hydrophobic core comprises an inorganic nanoparticle. Further provided herein are compositions, wherein the first nucleic acid and/or the second nucleic acid comprises RNA. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are compositions, wherein the compositions comprise: a first nucleic acid comprising a sequence encoding for an RNA-dependent RNA polymerase; and a second nucleic acid comprising a sequence encoding for a cancer-associated protein binding antibody or antibody fragment. Further provided herein are compositions, wherein the cancer-associated protein sequence is least 85% identical to a sequence listed in Table 2. Further provided herein are compositions, wherein the first nucleic acid and the second nucleic acid are present on a shared nucleic acid. Further provided herein are compositions, wherein the first nucleic acid and the second nucleic acid are present on separate nucleic acids. Further provided herein are compositions, wherein the RNA-dependent RNA polymerase comprises a VEEV RNA polymerase. Further provided herein are compositions, wherein the compositions further comprise a nanoparticle carrier system. Further provided herein are compositions, wherein the nanoparticle carrier system comprises a cationic lipid and a hydrophobic core. Further provided herein are compositions, wherein the hydrophobic core comprises an inorganic nanoparticle. Further provided herein are compositions, wherein the first nucleic acid and/or the second nucleic acid comprises RNA. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are compositions, wherein the compositions comprise: (a) a lipid carrier, wherein the lipid carrier is a nanoemulsion comprising a hydrophobic core, optionally one or more inorganic nanoparticles; and one or more lipids; and (b) at least one nucleic acid sequence, wherein the nucleic acid sequence comprises a sequence which encodes a sequence capable of expressing an antigen, wherein the antigen is a cancer-associated protein. Further provided herein are compositions, wherein the nucleic acid is RNA. Further provided herein are compositions, wherein the compositions further comprise a nucleic acid polymerase or a further nucleic acid comprising a sequence which encodes a sequence capable of expressing a nucleic acid polymerase. Further provided herein are compositions, wherein the compositions further comprise an RNA polymerase or a further nucleic acid comprising a sequence which encodes a sequence capable of expressing an RNA polymerase. Further provided herein are compositions, wherein the cancer-associated protein is associated with melanoma. Further provided herein are compositions, wherein the cancer-associated protein sequence comprises a sequence listed in Table 1. Further provided herein are compositions, wherein the cancer-associated protein is MAGE-A1. Further provided herein are compositions, wherein the cancer-associated protein is MAGE-A3. Further provided herein are compositions, wherein the cancer-associated protein is TYRP-1 or TRP-1. Further provided herein are compositions, wherein the hydrophobic core comprises an oil. Further provided herein are compositions, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, and vitamin E, and a medium chain triglyceride. Further provided herein are compositions, wherein the one or more inorganic nanoparticles is selected from the group consisting of a metal salt, metal oxide, metal hydroxide, metal phosphate, and any combinations thereof. Further provided herein are compositions, wherein the one or more lipids is selected from the group consisting of cationic lipids, anionic lipids, neutral lipids, and any combinations thereof. Further provided herein are compositions, wherein the one or more lipids is a cationic lipid. Further provided herein are compositions, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), and any combinations thereof. Further provided herein are compositions, wherein the lipid carrier optionally comprises one or more surfactants. Further provided herein are compositions, wherein the one or more surfactants is selected from the group consisting of hydrophobic surfactant, hydrophilic surfactant, and any combinations thereof. Further provided herein are compositions, wherein the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein are compositions, wherein the lipid carrier have a z-average hydrodynamic diameter ranging from about 40 nm to about 150 nm, with an average polydispersity index ranging from about 0.1 to about 0.4. Further provided herein are compositions, wherein the one or more nucleic acids is incorporated or complexed with the lipid carrier to form a lipid carrier-nucleic acid complex. Further provided herein are compositions, wherein the lipid carrier-RNA complex is formed via non-covalent interactions or via reversible covalent interactions. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the compositions are stable at 2 to 8 degrees Celsius. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the compositions are lyophilized.

Provided herein are vaccines, wherein the vaccines comprise: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein. Further provided herein are vaccines, wherein the nucleic acid is RNA. Further provided herein are vaccines, wherein the vaccines further comprise a nucleic acid polymerase or a further nucleic acid comprising a sequence which encodes a sequence capable of expressing a nucleic acid polymerase. Further provided herein are vaccines, wherein the vaccines further comprise an RNA polymerase or a further nucleic acid comprising a sequence which encodes a sequence capable of expressing an RNA polymerase. Further provided herein are vaccines, wherein the cancer-associated protein is associated with melanoma. Further provided herein are compositions, wherein the cancer-associated protein sequence comprises a sequence listed in Table 1. Further provided herein are vaccines, wherein the cancer-associated protein is MAGE-A1. Further provided herein are vaccines, wherein the cancer-associated protein is MAGE-A3. Further provided herein are vaccines, wherein the cancer-associated protein is TYRP-1 or TRP-1. Further provided herein are vaccines, wherein the hydrophobic core comprises an oil. Further provided herein are vaccines, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, and vitamin E, and a medium chain triglyceride. Further provided herein are vaccines, wherein the one or more inorganic nanoparticles is selected from the group consisting of a metal salt, metal oxide, metal hydroxide, metal phosphate, and any combinations thereof. Further provided herein are vaccines, wherein the one or more lipids is selected from the group consisting of cationic lipids, anionic lipids, neutral lipids, and any combinations thereof. Further provided herein are vaccines, wherein the one or more lipids is a cationic lipid. Further provided herein are vaccines, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), and any combinations thereof. Further provided herein are vaccines, wherein the lipid carrier optionally comprises one or more surfactants. Further provided herein are vaccines, wherein the one or more surfactants is selected from the group consisting of hydrophobic surfactant, hydrophilic surfactant, and any combinations thereof. Further provided herein are vaccines, wherein the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein are vaccines, wherein the lipid carrier have a z-average hydrodynamic diameter ranging from about 40 nm to about 150 nm, with an average polydispersity index ranging from about 0.1 to about 0.4. Further provided herein are vaccines, wherein the one or more nucleic acids is incorporated or complexed with the lipid carrier to form a lipid carrier-nucleic acid complex. Further provided herein are vaccines, wherein the lipid carrier-RNA complex is formed via non-covalent interactions or via reversible covalent interactions. Further provided herein are vaccines, wherein the molar ratio of the lipid carrier to the one or more nucleic acids, characterized by the nitrogen-to-phosphate (N:P) molar ratio, ranges from about 1:1 to about 150:1. Further provided herein are vaccines, wherein the compositions are stable at 2 to 8 degrees Celsius. Further provided herein are vaccines, wherein the at least one nucleic acid sequence is present in an amount of up to about 100 micrograms (μg). Further provided herein are vaccines, wherein the at least one nucleic acid sequence is present in an amount of up to about 5, about 10, about 25, about 50, or about 100 micrograms (μg). Further provided herein are vaccines, wherein the at least one nucleic acid sequence is present in an amount of up to about 25 μg. Further provided herein are vaccines, wherein the vaccines are in the form of a suspension. Further provided herein are vaccines, wherein the vaccines are lyophilized.

Provided herein are compositions for immunoprotecting a subject, wherein the compositions comprise: a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein. Further provided herein are compositions, wherein the cancer-associated protein sequence comprises a sequence listed in Table 1. Further provided herein are vaccines, wherein the hydrophobic core comprises an oil. Further provided herein are vaccines, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, and vitamin E, and a medium chain triglyceride. Further provided herein are vaccines, wherein the one or more inorganic nanoparticles is selected from the group consisting of a metal salt, metal oxide, metal hydroxide, metal phosphate, and any combinations thereof. Further provided herein are vaccines, wherein the one or more lipids is selected from the group consisting of cationic lipids, anionic lipids, neutral lipids, and any combinations thereof. Further provided herein are vaccines, wherein the one or more lipids is a cationic lipid. Further provided herein are vaccines, wherein the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), and any combinations thereof. Further provided herein are vaccines, wherein the lipid carrier optionally comprises one or more surfactants. Further provided herein are vaccines, wherein the one or more surfactants is selected from the group consisting of hydrophobic surfactant, hydrophilic surfactant, and any combinations thereof. Further provided herein are vaccines, wherein the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the composition is lyophilized.

Provided herein are dried compositions, wherein the dried compositions comprise: a composition provided herein; and at least one cryoprotectant. Further provided herein are dried compositions, wherein the compositions are lyophilized. Further provided herein are dried compositions, wherein the compositions are spray-dried. Further provided herein are dried compositions, wherein the compositions are thermally stable. Further provided herein are dried compositions, wherein the compositions are thermally stable at about 25° C. Further provided herein are dried compositions, wherein the compositions are thermally stable at about 45° C. Further provided herein are dried compositions, wherein the compositions are thermally stable at about −20° C. Further provided herein are dried compositions, wherein the compositions are thermally stable at about 2° C. to about 8° C. Further provided herein are dried compositions, wherein the compositions are thermally stable for at least 1 week, at least 2 weeks, and/or at least 1 month. Further provided herein are dried compositions, wherein the hydrophobic core comprises an oil. Further provided herein are dried compositions, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, and vitamin E, and a medium chain triglyceride. Further provided herein are dried compositions, wherein the one or more inorganic nanoparticles is selected from the group consisting of a metal salt, metal oxide, metal hydroxide, metal phosphate, and any combinations thereof. Further provided herein are dried compositions, wherein the one or more lipids is selected from the group consisting of cationic lipids, anionic lipids, neutral lipids, and any combinations thereof. Further provided herein are dried compositions, wherein the one or more lipids is a cationic lipid. Further provided herein are vaccines, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), and any combinations thereof. Further provided herein are dried compositions, wherein the lipid carrier optionally comprises one or more surfactants. Further provided herein are dried compositions, wherein the one or more surfactants is selected from the group consisting of hydrophobic surfactant, hydrophilic surfactant, and any combinations thereof. Further provided herein are dried compositions, wherein the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein are dried compositions, wherein the molar ratio of the lipid carrier to the one or more nucleic acids, characterized by the nitrogen-to-phosphate (N:P) molar ratio, ranges from about 1:1 to about 150:1. Further provided herein are dried compositions, wherein the lipid carrier comprises a z-average hydrodynamic diameter ranging from about 40 nm to about 150 nm, with an average polydispersity index ranging from about 0.1 to 0.4. Further provided herein are dried compositions, wherein the at least one nucleic acid sequence is present in an amount of up to about 100 micrograms (μg). Further provided herein are dried compositions, wherein the at least one nucleic acid sequence is present in an amount of up to about 5, about 10, about 25, about 50, or about 100 micrograms (μg). Further provided herein are dried compositions, wherein the at least one nucleic acid sequence is present in an amount of up to about 25 μg.

Provided herein are compositions for prophylaxis of a cancer, the compositions comprising: a sorbitan fatty acid ester, an ethoxylated sorbitan ester, a cationic lipid, an immune stimulant, and at least one RNA encoding an antigen sequence or functional fragment thereof the sorbitan fatty acid ester is sorbitan monostearate. Further provided herein are compositions, wherein the ethoxylated sorbitan ester is polysorbate 80. Further provided herein are compositions, wherein the cationic lipid is DOTAP. Further provided herein are compositions, wherein the immune stimulant is squalene. Further provided herein are compositions, wherein the RNA encodes a cancer-associated protein. Further provided herein are compositions, wherein the immune stimulant decreases the total amount of protein produced, but increases the immune response to the vaccine. Further provided herein are compositions, wherein n the immune stimulant increases the total amount of protein, produced, but decreases the immune response to the vaccine. Further provided herein are compositions, wherein the immune stimulant is Miglyol 810 or Miglyol 812. Further provided herein are compositions, wherein the composition comprises squalene and no solid particles. Further provided herein are compositions, wherein the ratio of the esters yields a Hydrophilic-Lipophilic Balance between 8 and 11. Further provided herein are compositions, wherein the particle size is between 30 and 200 nanometers. Further provided herein are compositions, wherein the N to P ratio is between 5 and 35. Further provided herein are compositions, wherein the antigen sequence comprises a sequence listed in Table 1. Further provided herein are compositions, wherein the compositions are in the form of a suspension. Further provided herein are compositions, wherein the composition is lyophilized.

Provided herein are compositions for prophylaxis of a cancer, the compositions comprising: sorbitan monostearate (e.g., SPAN® 60), polysorbate 80 (e.g., TWEEN® 80), DOTAP, an immune stimulant, and at least one RNA encoding an antigen sequence or functional fragment thereof. Further provided herein are compositions, wherein the immune stimulant decreases the total amount of protein produced, but increases the immune response to the vaccine. Further provided herein are compositions, wherein n the immune stimulant increases the total amount of protein, produced, but decreases the immune response to the vaccine. Further provided herein are compositions, wherein the immune stimulant is Miglyol 810 or Miglyol 812. Further provided herein are compositions, wherein the composition comprises squalene and no solid particles. Further provided herein are compositions, wherein the ratio of the esters yields a Hydrophilic-Lipophilic Balance between 8 and 11. Further provided herein are compositions, wherein the particle size is between 30 and 200 nanometers. Further provided herein are compositions, wherein the N to P ratio is between 5 and 35. Further provided herein are compositions, wherein the antigen sequence comprises a sequence listed in Table 1. Further provided herein are compositions, wherein the compositions are in the form of a suspension. Further provided herein are compositions, wherein the composition is lyophilized. Further provided herein are pharmaceutical compositions, wherein the pharmaceutical compositions comprise: a composition provided herein; and a pharmaceutically acceptable excipient. Further provided herein are pharmaceutical compositions, wherein the pharmaceutical compositions comprise: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein.

Provided herein are kits, wherein the kits comprise a composition provided herein.

Provided herein are methods of generating an immune response in a subject, the methods comprise: administering to a subject a composition provided herein, thereby generating an immune response to a cancer-associated protein. Further provided herein are methods of generating an immune response in a subject, wherein the methods comprise: administering to a subject: (a) a lipid carrier, wherein the lipid carrier is a nanoemulsion comprising a hydrophobic core, optionally one or more inorganic nanoparticles and one or more lipids; and (b) at least one nucleic acid sequence, wherein the nucleic acid sequence comprises a sequence which encodes a sequence capable of expressing an antigen, wherein the antigen is a cancer-associated protein. Further provided herein are methods, wherein the composition is administered to the subject by two doses. Further provided herein are methods, wherein the second dose is administered at about 28 days after the first dose. Further provided herein are methods, wherein the methods further comprise: administering a third dose of the composition to said subject. Further provided herein are methods, wherein 5 μg of the composition is administered to the subject. Further provided herein are methods, wherein 10 μg of the composition is administered to said subject. Further provided herein are methods, wherein 25 μg of the composition is administered to said subject. Further provided herein are methods, wherein the composition is administered via intramuscular injection, intranasal administration, oral administration, subcutaneous administration, intratumoral administration, intrathecal administration, or intravenous injection. Further provided herein are methods, wherein the subject is a human. Further provided herein are methods, wherein the subject has, is at risk for, or is suspected of having a cancer. Further provided herein are methods, wherein the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has, is at risk for, or is suspected of having a skin cancer. Further provided herein are methods, wherein the skin cancer is a basal cell cancer, a melanoma, a Merkel cell cancer, a squamous cell carcinoma, a cutaneous lymphoma, a Kaposi sarcoma, or a skin adnexal cancer.

Further provided herein are methods of prophylactically immunizing a subject for a cancer, the methods comprise: administering to a subject a composition provided herein, thereby immunizing the subject to a cancer expressing a cancer-associated protein. Further provided herein are methods, wherein the subject is at risk for developing a skin cancer. Further provided herein are methods, wherein 5 μg of the composition is administered to the subject. Further provided herein are methods, wherein 10 μg of the composition is administered to said subject. Further provided herein are methods, wherein 25 μg of the composition is administered to said subject. Further provided herein are methods, wherein the composition is administered via intramuscular injection, intranasal administration, oral administration, subcutaneous administration, intratumoral administration, intrathecal administration, or intravenous injection. Further provided herein are methods, wherein the subject is a human. Further provided herein are methods, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are methods, wherein the cancer expresses a cancer-associated protein, wherein the cancer-associated protein is a TRP-1 protein.

Further provided herein are methods of reducing the severity of a cancer, wherein the methods comprise: administering a composition comprising a lipid carrier, wherein the lipid carrier is a nanoemulsion comprising a hydrophobic core, optionally one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein.

Further provided herein are methods of immunoprotecting a subject, wherein the methods comprise: administering to the subject a lipid carrier, wherein the lipid carrier is a nanoemulsion comprising a hydrophobic core, one or more inorganic nanoparticles and one or more lipids, at least one nucleic acid sequence, wherein the nucleic acid sequence comprises a sequence which encodes a sequence capable of expressing an antigen, wherein the antigen is a cancer-associated protein.

Provided herein are methods of generating an immune response in a subject, wherein the methods comprise: administering to said subject a composition comprising a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes a sequence capable of expressing an antigen, wherein the antigen is a cancer-associated protein. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the lipid carrier comprises a z-average hydrodynamic diameter ranging from about 40 nm to about 150 nm, with an average polydispersity index ranging from about 0.1 to 0.4. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are in the form of a suspension. Further provided herein are compositions, wherein the composition is lyophilized.

Further provided herein are methods for preparing a lyophilized composition, wherein the methods comprising: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, and lyophilizing the formulation to form a lyophilized composition.

Further provided herein are methods for preparing a spray-dried composition, wherein the methods comprise: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, wherein the nucleic acid has a sequence comprising an antigen sequence as set forth in one of SEQ ID NOS: 1-2, 75, 76, 88, or 89; adding at least one cryoprotectant to the lipid carrier-nucleic acid complex to form a formulation, and spray drying the formulation to form a spray-dried composition.

The present invention also relates to a method for reconstituting a lyophilized composition comprising obtaining a lipid carrier, wherein the lipid carrier is a nanoemulsion comprising a hydrophobic core, one or more inorganic nanoparticles, and one or more lipids, incorporating at least one nucleic acid into the said lipid carrier to form a lipid carrier-nucleic acid complex, wherein the nucleic acid has a sequence comprising an antigen sequence as set forth in one of SEQ ID NOS: 1-2, 75 or 76; adding at least one cryoprotectant to the lipid carrier-nucleic acid complex to form a formulation, lyophilizing the formulation to form a lyophilized composition, and reconstituting the lyophilized composition in a suitable diluent. Further provided herein are methods, wherein the diluent is aqueous. Further provided herein are methods, wherein the diluent is water. Further provided herein are methods, wherein the lyophilized compositions are thermally stable. Further provided herein are methods, wherein the lyophilized compositions are thermally stable at temperatures up to about 25° C. Further provided herein are methods, wherein the lyophilized compositions are thermally stable at temperatures up to about 45° C. Further provided herein are methods, wherein the lyophilized compositions are thermally stable at temperatures down to about −20° C. Further provided herein are methods, wherein the lyophilized compositions are thermally stable at temperatures ranging from about 2° C. to about 8° C. Further provided herein are methods, wherein the lyophilized compositions are thermally stable for at least 1 week, at least 2 weeks, and/or at least 1 month. Further provided herein are methods, wherein the hydrophobic core comprises an oil. Further provided herein are methods, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, medium chain triglyceride, dihydroisosqualene (DHIS), famesene and squalane. Further provided herein are methods, wherein the one or more inorganic nanoparticles is selected from the group consisting of metal salts, metal oxides, metal hydroxides, metal phosphates, metalloids and any combinations thereof. Further provided herein are methods, wherein the one or more lipids is selected from the group consisting of cationic lipids, anionic lipids, neutral lipids, and any combinations thereof. Further provided herein are methods, wherein the one or more lipids is a cationic lipid. Further provided herein are methods, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[1-(2, 3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis (2-hydroxydodecyl)amino)ethyl) (2-hydroxydodecyl) amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are methods, wherein the lipid carrier optionally comprises one or more surfactant. Further provided herein are methods, wherein the one or more surfactant is selected from the group consisting of hydrophobic surfactant, hydrophilic surfactant, and any combinations thereof. Further provided herein are methods, wherein the hydrophobic surfactant comprises a sorbitan ester selected from the group consisting of SPAN® 20, SPAN® 40, SPAN® 60, SPAN® 65, SPAN®80 and SPAN® 85; and the hydrophilic surfactant comprises a polysorbate. Further provided herein are methods, wherein the lipid carrier has a z-average hydrodynamic diameter ranging from about 40 nm to about 150 nm, with an average polydispersity index ranging from about 0.1 to about 0.4. Further provided herein are methods, wherein the one or more nucleic acid is an RNA. Further provided herein are methods, wherein the RNA is a self-replicating RNA. Further provided herein are methods, wherein the one or more nucleic acid comprises a sequence which encodes an antigen, wherein the antigen is derived from a virus. Further provided herein are methods, wherein the virus is an oncovirus. Further provided herein are methods, wherein the RNA encodes an amino acid sequence which is at least 80% identical to the amino acid sequence of MAGE-A1 or MAGE-A3. Further provided herein are methods, wherein the RNA encodes an amino acid sequence which is at least 80% identical to the amino acid sequence of TRYP-1 or TRP-1. Further provided herein are methods, wherein the one or more nucleic acid is incorporated or complexed with the lipid carrier to form a lipid carrier-nucleic acid complex. Further provided herein are methods, wherein the lipid carrier-nucleic acid complex is formed via non-covalent interactions or via reversible covalent interactions. Further provided herein are methods, wherein the at least one cryoprotectant is selected from the group consisting of sucrose, maltose, trehalose, mannitol, glucose, and any combinations thereof. Further provided herein are methods, wherein the at least one cryoprotectant is sucrose. Further provided herein are methods, wherein the at least one cryoprotectant is at about 1% w/v to at about 20% w/v. Further provided herein are methods, wherein the at least one cryoprotectant is at about 10% w/v to at about 20% w/v. Further provided herein are methods, wherein the at least one cryoprotectant is at about 10% w/v.

Further provided herein are methods for reconstituting a spray-dried composition, wherein the methods comprise: obtaining a lipid carrier, wherein the lipid carrier is a nanoemulsion comprising a hydrophobic core, one or more inorganic nanoparticles, and one or more lipids, incorporating at least one nucleic acid into the said lipid carrier to form a lipid carrier-nucleic acid complex, wherein the nucleic acid has a sequence comprising an antigen sequence as set forth in one of SEQ ID NOS: 1-2, 75 or 76; adding at least one cryoprotectant to the lipid carrier-nucleic acid complex to form a formulation, spray drying the formulation to form a spray-dried composition, and reconstituting the spray-dried composition in a suitable diluent. Further provided herein are methods, wherein the diluent is aqueous. Further provided herein are methods, wherein the diluent is water. Further provided herein are methods, wherein the spray-dried compositions are thermally stable. Further provided herein are methods, wherein the spray-dried compositions are thermally stable at temperatures up to about 25° C. Further provided herein are methods, wherein the spray-dried compositions are thermally stable at temperatures up to about 45° C. Further provided herein are methods, wherein the spray-dried compositions are thermally stable at temperatures down to about −20° C. Further provided herein are methods, wherein the spray-dried compositions are thermally stable at temperatures ranging from about 2° C. to about 8° C. Further provided herein are methods, wherein the spray-dried compositions are thermally stable for at least 1 week, at least 2 weeks, and/or at least 1 month. Further provided herein are methods, wherein the hydrophobic core comprises an oil. Further provided herein are methods, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, medium chain triglyceride, dihydroisosqualene (DHIS), farnesene and squalane. Further provided herein are methods, wherein the one or more inorganic nanoparticles is selected from the group consisting of metal salts, metal oxides, metal hydroxides, metal phosphates, metalloids and any combinations thereof. Further provided herein are methods, wherein the one or more lipids is selected from the group consisting of cationic lipids, anionic lipids, neutral lipids, and any combinations thereof. Further provided herein are methods, wherein the one or more lipids is a cationic lipid. Further provided herein are methods, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[1-(2, 3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis (2-hydroxydodecyl)amino)ethyl) (2-hydroxydodecyl) amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are methods, wherein the lipid carrier optionally comprises one or more surfactant. Further provided herein are methods, wherein the one or more surfactant is selected from the group consisting of hydrophobic surfactant, hydrophilic surfactant, and any combinations thereof. Further provided herein are methods, wherein the hydrophobic surfactant comprises a sorbitan ester selected from the group consisting of SPAN® 20, SPAN® 40, SPAN® 60, SPAN® 65, SPAN® 80 and SPAN® 85; and the hydrophilic surfactant comprises a polysorbate. Further provided herein are methods, wherein the lipid carrier has a z-average hydrodynamic diameter ranging from about 40 nm to about 150 nm, with an average polydispersity index ranging from about 0.1 to about 0.4. Further provided herein are methods, wherein the one or more nucleic acid is an RNA. Further provided herein are methods, wherein the RNA is a self-replicating RNA. Further provided herein are methods, wherein the one or more nucleic acid comprises a sequence which encodes an antigen, wherein the antigen is derived from a virus. Further provided herein are methods, wherein the virus is an oncovirus. Further provided herein are methods, wherein the RNA encodes an amino acid sequence which is at least 80% identical to the amino acid sequence of MAGE-A1 or MAGE-A3. Further provided herein are methods, wherein the RNA encodes an amino acid sequence which is at least 80% identical to the amino acid sequence of TRYP-1 or TRP-1. Further provided herein are methods, wherein the one or more nucleic acid is incorporated or complexed with the lipid carrier to form a lipid carrier-nucleic acid complex. Further provided herein are methods, wherein the lipid carrier-nucleic acid complex is formed via non-covalent interactions or via reversible covalent interactions. Further provided herein are methods, wherein the at least one cryoprotectant is selected from the group consisting of sucrose, maltose, trehalose, mannitol, glucose, and any combinations thereof. Further provided herein are methods, wherein the at least one cryoprotectant is sucrose. Further provided herein are methods, wherein the at least one cryoprotectant is at about 1% w/v to at about 20% w/v. Further provided herein are methods, wherein the at least one cryoprotectant is at about 10% w/v to at about 20% w/v. Further provided herein are methods, wherein the at least one cryoprotectant is at about 10% w/v.

Provided herein are compositions, wherein the compositions comprise: at least one nucleic acid, wherein the at least one nucleic acid comprises a sequence encoding for: a plurality of cancer-associated proteins or functional fragments thereof; and an RNA polymerase complex region; and a plurality of nanoparticles, wherein each nanoparticle comprises a cationic surface, and wherein the at least one nucleic acid is complexed to the cationic surface. Further provided herein are compositions, wherein the at least one nucleic acid is RNA or DNA. Further provided herein are compositions, wherein the plurality of cancer-associated proteins are expressed by one or more cancer cells of a subject. Further provided herein are compositions, wherein the subject has a solid tumor or a blood cancer. Further provided herein are compositions, wherein the solid tumor is a carcinoma, a melanoma, or a sarcoma. Further provided herein are compositions, wherein the blood cancer is lymphoma or leukemia. Further provided herein are compositions, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are compositions, wherein the subject has a lung cancer. Further provided herein are compositions, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are compositions, the subject has a pancreatic cancer. Further provided herein are compositions, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are compositions, wherein the subject has a metastatic cancer. Further provided herein are compositions, wherein the at least one nucleic acid encodes for two or more cancer-associated proteins, wherein the two or more cancer-associated proteins are selected from: (i) epidermal growth factor receptor (EGFR); (ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCND1); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (a) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (1) Melanoma-associated antigen recognized by T cells 1 (MART-1); and functional fragments thereof. Further provided herein are compositions, wherein the MAGE is MAGE-A1, MAGE-A3, MART-1/Melan-A, MAGE-A, MAGE-B, MAGE-C, MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Further provided herein are compositions, the cluster of differentiation family protein is CD5, CD19, CD20, CD22, CD23, CD25, CD27, CD30, CD33, CD36, CD46, CD52, CD79a, CD79b, CD123, or CD317. Further provided herein are compositions, the RNA polymerase complex region is downstream of a subgenomic promoter from an alphavirus. Further provided herein are compositions, wherein RNA polymerase complex region encodes for an RNA-dependent RNA polymerase. Further provided herein are compositions, the RNA-dependent RNA polymerase is Venezuelan equine encephalitis virus (VEEV) RNA polymerase. Further provided herein are compositions, wherein the cationic surface comprises a cationic lipid. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), 306Oi10, tetrakis(8-methylnonyl) 3,3',3",3"'-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl)dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl)piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"', 9"",9""'-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl)amino) octanoate; OF-Deg-Lin, (((3,6-dioxopiperazine-2,5-diyl)bis(butane-4, 1-diyl))bis(azanetriyl))tetrakis(ethane-2,1-diyl) (9Z,9'Z,9"Z,9"'Z,12Z,12'Z,12"Z,12"'Z)-tetrakis(octadeca-9,12-dienoate); PEG2000-DMG, (R)-2,3-bis(myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein each nanoparticle further comprises a hydrophobic core. Further provided herein are compositions, wherein the hydrophobic core comprises an oil. Further provided herein are compositions, wherein the oil is in liquid phase. Further provided herein are compositions, wherein the oil comprises α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein each nanoparticle comprises a cationic lipid and an oil. Further provided herein are compositions, wherein each nanoparticle further comprises a surfactant. Further provided herein are compositions, wherein the surfactant is polysorbate, a phosphorous-terminated surfactant, a carboxylate-terminated surfactant, a sulfate-terminated surfactant, an amine-terminated surfactant, trioctylphosphine oxide (TOPO), or distearyl phosphatidic acid (DSPA). Further provided herein are compositions, wherein the composition is lyophilized. Further provided herein are compositions, wherein the composition is in a liquid, semi-liquid, solution, propellant, or powder dosage form. Further provided herein are compositions, wherein the composition is formulated as a suspension.

Provided herein are compositions, wherein the compositions comprise: a plurality of nucleic acids, wherein the plurality of nucleic acids comprises sequence encoding separately for: a plurality of cancer-associated proteins; and an RNA polymerase complex region; and a plurality of nanoparticles, wherein each nanoparticle comprises a cationic surface, and wherein the at least one nucleic acid is complexed to the cationic surface. Further provided herein are compositions, wherein the at least one nucleic acid is RNA or DNA. Further provided herein are compositions, wherein the plurality of cancer-associated proteins are expressed by one or more cancer cells of a subject. Further provided herein are compositions, wherein the subject has a solid tumor or a blood cancer. Further provided herein are compositions, wherein the solid tumor is a carcinoma, a melanoma, or a sarcoma. Further provided herein are compositions, wherein the blood cancer is lymphoma or leukemia. Further provided herein are compositions, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are compositions, wherein the subject has a lung cancer. Further provided herein are compositions, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are compositions, the subject has a pancreatic cancer. Further provided herein are compositions, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are compositions, wherein the subject has a metastatic cancer. Further provided herein are compositions, wherein the at least one nucleic acid encodes for two or more cancer-associated proteins, wherein the two or more cancer-associated proteins are selected from: (i) epidermal growth factor receptor (EGFR); (ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCND1); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (u) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (1) Melanoma-associated antigen recognized by T cells 1 (MART-1); and functional fragments thereof. Further provided herein are compositions, wherein the MAGE is MAGE-A1, MAGE-A3, MART-1/Melan-A, MAGE-A, MAGE-B, MAGE-C, MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Further provided herein are compositions, the cluster of differentiation family protein is CD5, CD19, CD20, CD22, CD23, CD25, CD27, CD30, CD33, CD36, CD46, CD52, CD79a, CD79b, CD123, or CD317. Further provided herein are compositions, the RNA polymerase complex region is downstream of a subgenomic promoter from an alphavirus. Further provided herein are compositions, wherein RNA polymerase complex region encodes for an RNA-dependent RNA polymerase. Further provided herein are compositions, the RNA-dependent RNA polymerase is Venezuelan equine encephalitis virus (VEEV) RNA polymerase. Further provided herein are compositions, wherein the cationic surface comprises a cationic lipid. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), 306Oi10, tetrakis(8-methylnonyl) 3,3',3",3'"-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9""'-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2, 1-diyl) (9Z,9'Z,9"Z,9"'Z,12Z,12'Z,12"Z,12"'Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein each nanoparticle further comprises a hydrophobic core. Further provided herein are compositions, wherein the hydrophobic core comprises an oil. Further provided herein are compositions, wherein the oil is in liquid phase. Further provided herein are compositions, wherein the oil comprises α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein each nanoparticle comprises a cationic lipid and an oil. Further provided herein are compositions, wherein each nanoparticle further comprises a surfactant. Further provided herein are compositions, wherein the surfactant is polysorbate, a phosphorous-terminated surfactant, a carboxylate-terminated surfactant, a sulfate-terminated surfactant, an amine-terminated surfactant, trioctylphosphine oxide (TOPO), or distearyl phosphatidic acid (DSPA). Further provided herein are compositions, wherein the composition is lyophilized. Further provided herein are compositions, wherein the composition is in a liquid, semi-liquid, solution, propellant, or powder dosage form. Further provided herein are compositions, wherein the composition is formulated as a suspension.

Provided herein are compositions, wherein the compositions comprise: at least one nucleic acid, wherein the at least one nucleic acid comprises a sequence encoding for: an antibody or a functional fragment thereof; and an RNA polymerase complex region; and a plurality of nanoparticles, wherein each nanoparticle comprises a cationic surface, and wherein the at least one nucleic acid is complexed to the cationic surface. Further provided herein are compositions, wherein the an antibody or a functional fragment thereof is a cancer therapeutic antibody. Further provided herein are compositions, wherein the antibody is a monoclonal antibody. Further provided herein are compositions, wherein the antibody, the antibody fragment, or the functional fragment thereof is a murine antibody, a camelid antibody, a humanized antibody, or a fully human antibody. Further provided herein are compositions, wherein the antibody is an immunoglobulin (Ig) molecule or a functional fragment thereof. Further provided herein are compositions, wherein the immunoglobulin molecule is an IgG, IgE, IgM, IgD, IgA, or an IgY isotype immunoglobulin molecule or a functional fragment thereof. Further provided herein are compositions, wherein the immunoglobulin molecule of the functional fragment comprises at least a fragment of an IgG1, an IgG2, an IgG3, an IgG4, an IgGA1, or an IgGA2 subclass immunoglobulin molecule. Further provided herein are compositions, wherein the antibody or the functional fragment thereof is recombinant, chimeric, or multivalent. Further provided herein are compositions, wherein the antibody or the functional fragment thereof is a bispecific antibody, a trispecific antibody, a multispecific antibody, or a functional fragment thereof. Further provided herein are compositions, wherein the antibody or the functional fragment is an antigen-binding fragment (Fab), and Fab2 a F(ab'), a $F(ab')_2$, an dAb, an Fe, a Fv, a disulfide linked Fv, a scFv, a tandem scFv, a free LC, a half antibody, a single domain antibody (dAb), a diabody, or a nanobody. Further provided herein are compositions, wherein the antibody or functional fragment thereof specifically binds to a cancer-associated protein or a microbial antigen. Further provided herein are compositions, wherein the antibody or functional fragment thereof is atezolizumab, avelumab, bevacizumab, cemiplimab, cetuximab, daratumumab, dinutuximab, durvalumab, elotuzumab, ipilimumab, isatuximab, mogamulizumab, necitumumab, nivolumab, obinutuzumab, ofatumumab, olaratumab, panitumumab, pembrolizumab, pertuzumab, ramucirumab, rituximab, or trastuzumab. Further provided herein are compositions, wherein the at least one nucleic acid is RNA or DNA. Further provided herein are compositions, wherein the plurality of cancer-associated proteins are expressed by one or more cancer cells of a subject. Further provided herein are compositions, wherein the subject has a solid tumor or a blood cancer. Further provided herein are compositions, wherein the solid tumor is a carcinoma, a melanoma, or a sarcoma. Further provided herein are compositions, wherein the blood cancer is lymphoma or leukemia. Further provided herein are compositions, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are compositions, wherein the subject has a lung cancer. Further provided herein are compositions, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are compositions, the subject has a pancreatic cancer. Further provided herein are compositions, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are compositions, wherein the subject has a metastatic cancer. Further provided herein are compositions, wherein the at least one nucleic acid encodes for two or more cancer-associated proteins, wherein the two or more cancer-associated proteins are selected from: (i) epidermal growth factor receptor (EGFR); (ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCND1); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (u) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (l) Melanoma-associated antigen recognized by T cells 1 (MART-1); and functional fragments thereof. Further provided herein are compositions, wherein the MAGE is MAGE-A1, MAGE-A3, MART-1/Melan-A, MAGE-A, MAGE-B, MAGE-C, MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Further provided herein are compositions, the cluster of differentiation family protein is CD5, CD19, CD20, CD22, CD23, CD25, CD27, CD30, CD33, CD36, CD46, CD52, CD79a, CD79b, CD123, or CD317. wherein the plurality of nucleic acids comprises sequence encoding for any one of: SEQ ID NOS: 3-70, 72-74, 77, 78, 87. Further provided herein are compositions, wherein the sequence comprises one of more of SEQ ID NOS: 1, 2, 71, 75, 76, 80-86, 88, 89. Further provided herein are compositions, the RNA polymerase complex region is downstream of a subgenomic promoter from an alphavirus. Further provided herein are compositions, wherein RNA polymerase complex region encodes for an RNA-dependent RNA polymerase. Further provided herein are compositions, wherein the RNA-dependent RNA polymerase is Venezuelan equine encephalitis virus (VEEV) RNA polymerase. Further provided herein are compositions, wherein the RNA polymerase complex region comprises a sequence of SEQ ID NO: 71. Further provided herein are compositions, wherein the cationic lipid is 1,2-dioleoyloxy-3 (trimethylammonium)propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis (2-hydroxydodecyl)amino)ethyl)(2-hydroxydodecyl)amino) ethyl)piperazin-1-yl)ethyl)azanediyl)bis(dodecan-2-ol) (C12-200), 306Oi10, tetrakis(8-methylnonyl) 3,3',3'',3'''-(((methylazanediyl)bis(propane-3,1 diyl))bis (azanetriyl)) tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9'',9''', 9'''',9'''''-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2,1-diyl) (9Z,9'Z,9''Z,9'''Z,12Z,12'Z,12''Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are compositions, wherein each lipid carrier further comprises a hydrophobic core. Further provided herein are compositions, wherein the hydrophobic core comprises an oil. Further provided herein are compositions, wherein the oil is in liquid phase. Further provided herein are compositions, wherein the oil comprises α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein each lipid carrier comprises a cationic lipid and an oil. Further provided herein are compositions, wherein the hydrophilic surfactant is polysorbate. Further provided herein are compositions, wherein the hydrophobic surfactant is a phosphorous-terminated surfactant, a carboxylate-terminated surfactant, a sulfate-terminated surfactant, an amine-terminated surfactant, trioctylphosphine oxide (TOPO), or distearyl phosphatidic acid (DSPA). Further provided herein are compositions, wherein the composition is lyophilized. Further provided herein are compositions, wherein the composition is in a liquid, semi-liquid, solution, propellant, or powder dosage form. Further provided herein are compositions, wherein the composition is formulated as a suspension. Further provided herein are compositions, wherein the compositions comprise: a plurality of nucleic acids, wherein the plurality of nucleic acids comprises sequence encoding separately for: an antibody or a functional fragment thereof; and an RNA polymerase complex region; and a plurality of nanoparticles, wherein each nanoparticle comprises a cationic surface, and wherein the at least one nucleic acid is complexed to the cationic surface.

Provided herein are compositions, wherein the compositions comprise: a plurality of nucleic acids, wherein the plurality of nucleic acids comprises sequence encoding separately for: an antibody or a functional fragment thereof; and an RNA polymerase complex region; and a plurality of nanoparticles, wherein each nanoparticle comprises a cationic surface, and wherein the at least one nucleic acid is complexed to the cationic surface. Further provided herein are compositions, wherein the an antibody or a functional fragment thereof is a cancer therapeutic antibody. Further provided herein are compositions, wherein the antibody is a monoclonal antibody. Further provided herein are compositions, wherein the antibody, the antibody fragment, or the functional fragment thereof is a murine antibody, a camelid antibody, a humanized antibody, or a fully human antibody. Further provided herein are compositions, wherein the antibody is an immunoglobulin (Ig) molecule or a functional fragment thereof. Further provided herein are compositions, wherein the immunoglobulin molecule is an IgG, IgE, IgM, IgD, IgA, or an IgY isotype immunoglobulin molecule or a functional fragment thereof. Further provided herein are compositions, wherein the immunoglobulin molecule of the functional fragment comprises at least a fragment of an IgG1, an IgG2, an IgG3, an IgG4, an IgGA1, or an IgGA2 subclass immunoglobulin molecule. Further provided herein are compositions, wherein the antibody or the functional fragment thereof is recombinant, chimeric, or multivalent. Further provided herein are compositions, wherein the antibody or the functional fragment thereof is a bispecific antibody, a trispecific antibody, a multispecific antibody, or a functional fragment thereof. Further provided herein are compositions, wherein the antibody or the functional fragment is an antigen-binding fragment (Fab), and Fab2 a F(ab'), a $F(ab')_2$, an dAb, an Fc, a Fv, a disulfide linked Fv, a scFv, a tandem scFv, a free LC, a half antibody, a single domain antibody (dAb), a diabody, or a nanobody. Further provided herein are compositions, wherein the antibody or functional fragment thereof specifically binds to a cancer-associated protein or a microbial antigen. Further provided herein are compositions, wherein the antibody or functional fragment thereof is atezolizumab, avelumab, bevacizumab, cemiplimab, cetuximab, daratumumab, dinutuximab, durvalumab, elotuzumab, ipilimumab, isatuximab, mogamulizumab, necitumumab, nivolumab, obinutuzumab, ofatumumab, olaratumab, panitumumab, pembrolizumab, pertuzumab, ramucirumab, rituximab, or trastuzumab. Further provided herein are compositions, wherein the at least one nucleic acid is RNA or DNA. Further provided herein are compositions, wherein the plurality of cancer-associated proteins are expressed by one or more cancer cells of a subject. Further provided herein are compositions, wherein the subject has a solid tumor or a blood cancer. Further provided herein are compositions, wherein the solid tumor is a carcinoma, a melanoma, or a sarcoma. Further provided herein are compositions, wherein the blood cancer is lymphoma or leukemia. Further provided herein are compositions, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are compositions, wherein the subject has a lung cancer. Further provided herein are compositions, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are compositions, the subject has a pancreatic cancer. Further provided herein are compositions, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are compositions, wherein the subject has a metastatic cancer. Further provided herein are compositions, wherein the at least one nucleic acid encodes for two or more cancer-associated proteins, wherein the two or more cancer-associated proteins are selected from: (i) epidermal growth factor receptor (EGFR); (ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCND1); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (u) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (1) Melanoma-associated antigen recognized by T cells 1 (MART-1); and functional fragments thereof. Further provided herein are compositions, wherein the MAGE is MAGE-A1, MAGE-A3, MART-1/Melan-A, MAGE-A, MAGE-B, MAGE-C, MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Further provided herein are compositions, the cluster of differentiation family protein is CD5, CD19, CD20, CD22, CD23, CD25, CD27, CD30, CD33, CD36, CD46, CD52, CD79a, CD79b, CD123, or CD317. wherein the plurality of nucleic acids comprises sequence encoding for any one of: SEQ ID NOS: 3-70, 72-74, 77, 78, 87. Further provided herein are compositions, wherein the sequence comprises one of more of SEQ ID NOS: 1, 2, 71, 75, 76, 80-86, 88, 89. Further provided herein are compositions, the RNA polymerase complex region is downstream of a subgenomic promoter from an alphavirus. Further provided herein are compositions, wherein RNA polymerase complex region encodes for an RNA-dependent RNA polymerase. Further provided herein are compositions, wherein the RNA-dependent RNA polymerase is Venezuelan equine encephalitis virus (VEEV) RNA polymerase. Further provided herein are compositions, wherein the RNA polymerase complex region comprises a sequence of SEQ ID NO: 71. Further provided herein are compositions, wherein the cationic lipid is 1,2-dioleoyloxy-3 (trimethylammonium) propane (DOTAP), 30-[N—(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy)propyl]N,N, Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl) azanediyl)bis(dodecan-2-ol) (C12-200), 306Oi10, tetrakis (8-methylnonyl) 3,3',3",3"'-(((methylazanediyl)bis (propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl) azanediyl)dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy) carbonyl)amino)-N,N-bis(2-hydroxyethyl)-N-methylethan-1-aminium bromide; cKK-E12, 3,6-bis(4-(bis(2-hydroxydodecyl)amino)butyl)piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9""'-((((benzene-1,3,5-tricarbonyl)yris (azanediyl)) tris (propane-3,1-diyl)) tris(azanetriyl)) hexanonanoate; Lipid H (SM-102), heptadecan-9-yl 8-((2-hydroxyethyl)(6-oxo-6-(undecyloxy)hexyl)amino) octanoate; OF-Deg-Lin, (((3,6-dioxopiperazine-2,5-diyl)bis (butane-4, 1-diyl))bis(azanetriyl))tetrakis(ethane-2,1-diyl) (9Z,9'Z,9"Z,9"'Z,12Z,12'Z,12"Z,12"'Z)-tetrakis (octadeca-9,12-dienoate); PEG2000-DMG, (R)-2,3-bis(myristoyloxy) propyl-1-(methoxy poly(ethylene glycol)2000) carbamate; TT3, or N1,N3,N5-tris(3-(didodecylamino)propyl)benzene-1,3,5-tricarboxamide. Further provided herein are compositions, wherein each lipid carrier further comprises a hydrophobic core. Further provided herein are compositions, wherein the hydrophobic core comprises an oil. Further provided herein are compositions, wherein the oil is in liquid phase. Further provided herein are compositions, wherein the oil comprises α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein each lipid carrier comprises a cationic lipid and an oil. Further provided herein are compositions, wherein the hydrophilic surfactant is polysorbate. Further provided herein are compositions, wherein the hydrophobic surfactant is a phosphorous-terminated surfactant, a carboxylate-terminated surfactant, a sulfate-terminated surfactant, an amine-terminated surfactant, trioctylphosphine oxide (TOPO), or distearyl phosphatidic acid (DSPA). Further provided herein are compositions, wherein the composition is lyophilized. Further provided herein are compositions, wherein the composition is in a liquid, semi-liquid, solution, propellant, or powder dosage form. Further provided herein are compositions, wherein the composition is formulated as a suspension. Further provided herein are compositions, wherein the compositions comprise: a plurality of nucleic acids, wherein the plurality of nucleic acids comprises sequence encoding separately for: an antibody or a functional fragment thereof; and an RNA polymerase complex region; and a plurality of nanoparticles, wherein each nanoparticle comprises a cationic surface, and wherein the at least one nucleic acid is complexed to the cationic surface.

Provided herein are pharmaceutical compositions comprising any one of the compositions provided herein; and a pharmaceutically acceptable excipient.

Provided herein are methods for modulating an immune response, wherein the methods comprise: administering to a subject having cancer the composition provided herein or a pharmaceutical composition provided herein.

Provided herein are methods for modulating an immune response, wherein the methods comprise: administering to a subject having a cancer, a composition, wherein the composition comprises: at least one nucleic acid, wherein the at least one nucleic acid comprises a sequence encoding for a plurality of cancer-associated proteins, wherein, prior to the administering, the plurality of cancer-associated proteins are increased in presence compared to non-cancer cells of the subject or comprise a sequence modification compared to non-cancer cells of the subject; and a plurality of nanoparticles, wherein each nanoparticle comprises a cationic surface, and wherein the at least one nucleic acid is complexed to the cationic surface. Further provided herein are methods, wherein the methods further comprise screening cancer cells of the subject for proteins or nucleic acids with increased presence or sequence modification compared to non-cancer cells. Further provided herein are methods, the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has a metastatic cancer. Further provided herein are methods, wherein at least one cancer-associated protein of the plurality of cancer-associated proteins is a protein expressed by a melanoma cell. Further provided herein are methods, wherein the plurality of cancer-associated proteins are selected from: (i) epidermal growth factor receptor (EGFR);

(ii) vascular endothelial growth factor (VEGF); (iii) Wilms tumor 1 (WT1); (iv) preferentially expressed antigen of melanoma (PRAME); (v) PR1; (vi) proteinase 3; (vii) elastase; (viii) cathepsin G; (ix) survivin; (x) New York esophagus 1 (NY-Eso-1); (xi) melanoma-associated antigen (MAGE); (xii) tyrosinase; (xiii) glycoprotein 100 (gp100); (xiv) carcinoembryonic antigen (CEA); (xv) mucin; (xvi) fibroblast growth factor (FGF); (xvii) programmed cell death protein (PD-1); (xviii) metastasis tumor antigen (MTA); (xix) human epidermal growth factor receptor 2 (Her2); (xx) Mammaglobin A (SCGB2A2); (xxi) alpha lactalbumin (LALBA); (xxii) cyclin D1 (CCND1); (xxiii) folate receptor 1 (FOLR1); (xxiv) telomerase (TERT); (xxv) RecQ protein-like (DNA helicase Q1-like) (RECQL); (xxvi) leptin receptor (LEPR); (xxvii) ERBB receptor feedback inhibitor 1(ERRFI1); (xxviii) lysosomal protein transmembrane 4 alpha (LAPTM4A); (xxix) Kirsten rat sarcoma virus (K-Ras); (xxx) S100 protein; (xxxi) a cluster of differentiation (CD) family protein; (xxxii) alphafetoprotein (AFP); (xxxiii) epithelial tumor antigen (ETA); (xxxiv) tumor protein p53; (xxxv) ephrin receptor; (xxxvi) transferrin receptor; (xxxvii) neoglycoprotein; (xxxviii) tumor necrosis factor (TNF)-alpha (a) receptor; (xxxvix) human papillomavirus-E6; (xl) human papillomavirus-E7; (xli) cytokeratin; (xlii) beta-catenin; (xliii) carboxypeptidase M; (xliv) EP4 receptor; (xlv) human milk fat glomeruli antigen; (xlvi) tumor necrosis factor (TNF)-beta (β) receptor; (xlvii) B7-1 protein; (xlviii) B7-2 protein; (xlix) TNF receptor-associated factor 2; (1) Melanoma-associated antigen recognized by T cells 1 (MART-1); and functional fragments thereof. Further provided herein are methods, wherein the MAGE is MAGE-A1, MAGE-A3, MART-1/Melan-A, MAGE-A, MAGE-B, MAGE-C, MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Further provided herein are methods, wherein the cluster of differentiation family protein is CD5, CD19, CD20, CD22, CD23, CD25, CD27, CD30, CD33, CD36, CD46, CD52, CD79a, CD79b, CD123, or CD317. Further provided herein are methods, wherein the plurality of nucleic acids comprises sequence encoding for any one of: SEQ ID NOS: 3-7, 72, 74, 77, 78, 87. Further provided herein are methods, wherein the sequences comprises one of more of SEQ ID NOS: 1, 2, 71, 75, 76, 80-86, 88, 89. Further provided herein are methods, wherein the at least one nucleic acid further comprises an RNA polymerase complex region. Further provided herein are methods, wherein the RNA polymerase complex region is downstream of a sub-genomic promoter from an alphavirus. Further provided herein are methods, wherein the RNA polymerase complex region encodes for an RNA-dependent RNA polymerase. Further provided herein are methods, wherein the RNA-dependent RNA polymerase is Venezuelan equine encephalitis virus (VEEV) RNA polymerase. Further provided herein are methods, wherein the cationic surface comprises a cationic lipid. Further provided herein are methods, wherein the cationic lipid is 1,2-dioleoyloxy-3 (trimethylammonium)propane (DOTAP), 3O-[N—(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3'',3'''-(((methylazanediyl)bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 3O-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9'',9''', 9'''',9'''''-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4, 1-diyl))bis(azanetriyl))tetrakis(ethane-2,1-diyl) (9Z,9'Z,9''Z,9'''Z,12Z,12'Z,12''Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein are methods, wherein each nanoparticle further comprises a hydrophobic core. Further provided herein are methods, wherein the hydrophobic core comprises an oil. Further provided herein are methods, wherein the oil is in liquid phase. Further provided herein are methods, wherein the oil comprises α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E. Further provided herein are methods, wherein the triglyceride is capric triglyceride, caprylic triglyceride, a caprylic and capric triglyceride, a triglyceride ester, or myristic acid triglycerin. Further provided herein are methods, wherein each nanoparticle comprises a cationic lipid and an oil. Further provided herein are methods, wherein each nanoparticle further comprises a surfactant. Further provided herein are methods, wherein the surfactant is polysorbate, a phosphorous-terminated surfactant, a carboxylate-terminated surfactant, a sulfate-terminated surfactant, an amine-terminated surfactant, trioctylphosphine oxide (TOPO), or distearyl phosphatidic acid (DSPA). Further provided herein are methods, wherein the administering is local administration or systemic administration. Further provided herein are methods, wherein the administering is via an intratumoral, subcutaneous, intradermal, intramuscular, inhalation, intravenous, intraperitoneal, intracranial, or intrathecal route. Further provided herein are methods, wherein the composition is administered with a cancer therapeutic antibody or the composition provided herein. Further provided herein are methods, wherein the administering results in a reduction of a tumor size or a reduction in a tumor volume in the subject. Further provided herein are methods, wherein the administering results in a reduction of a cancer recurrence. Further provided herein are methods, wherein the administering results in a reduction in tumor metastasis.

Provided herein is a method of prophylactically immunizing a subject for a cancer, the method comprising: administering to a subject the composition provided herein or the pharmaceutical composition provided herein, thereby immunizing the subject to a cancer. Further provided herein are methods, wherein the administering is via an intratumoral, subcutaneous, intradermal, intramuscular, inhalation, intravenous, intraperitoneal, intracranial, or intrathecal route. Further provided herein are methods, wherein the subject is at risk for developing a skin cancer. Further provided herein are methods, wherein the skin cancer is a basal cell cancer, a melanoma, a Merkel cell cancer, a squamous cell carcinoma, a cutaneous lymphoma, a Kaposi sarcoma, or a skin adnexal cancer.

Provided herein are methods for the treatment of a cancer in a subject, the methods comprising: administering to the subject a composition provided herein or a pharmaceutical composition provided herein, thereby treating the cancer in the subject. Further provided herein are methods, wherein the administering is via an intratumoral, subcutaneous, intradermal, intramuscular, inhalation, intravenous, intraperitoneal, intracranial, or intrathecal route. Further provided herein are methods, wherein the composition is administered with a cancer therapeutic antibody or the composition provided herein. Further provided herein are methods, wherein the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are methods, wherein the subject has a lung cancer. Further provided herein are methods, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are methods, the subject has a pancreatic cancer. Further provided herein are methods, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are methods, wherein the subject has a metastatic cancer. Further provided herein are methods, wherein the administering results in a reduction of a tumor size or a reduction in a tumor volume in the subject. Further provided herein are methods, wherein the administering results in a reduction of a cancer recurrence. Further provided herein are methods, wherein the administering results in a reduction in tumor metastasis.

Provided herein are methods for the personalized treatment of cancer in a subject, the methods comprising: (a) receiving the results of an assay that indicates that the subject has a tumor, wherein the tumor comprises a cancer-associated protein; (b) administering to the subject a composition provided herein, wherein the composition comprises at least one nucleic acid encoding for the cancer-associated protein in (a), thereby treating the cancer in the subject. Further provided herein are methods, wherein the administering is via an intratumoral, subcutaneous, intradermal, intramuscular, inhalation, intravenous, intraperitoneal, intracranial, or intrathecal route. Further provided herein are methods, wherein the composition is administered with a cancer therapeutic antibody or the composition provided herein. Further provided herein are methods, wherein the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are methods, wherein the subject has a lung cancer. Further provided herein are methods, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are methods, the subject has a pancreatic cancer. Further provided herein are methods, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are methods, wherein the subject has a metastatic cancer. Further provided herein are methods, wherein the administering results in a reduction of a tumor size or a reduction in a tumor volume in the subject. Further provided herein are methods, wherein the administering results in a reduction of a cancer recurrence. Further provided herein are methods, wherein the administering results in a reduction in tumor metastasis.

Provided herein are methods for the personalized treatment of cancer in a subject, the methods comprising: (a) receiving the results of an assay that indicates that the subject has a tumor, wherein the tumor comprises a cancer-associated protein; (b) administering to the subject a composition provided herein, wherein the composition comprises at least one nucleic acid encoding for an antibody that specifically binds to the cancer-associated protein in (a), thereby treating the cancer in the subject. Further provided herein are methods, wherein the administering is via an intratumoral, subcutaneous, intradermal, intramuscular, inhalation, intravenous, intraperitoneal, intracranial, or intrathecal route. Further provided herein are methods, wherein the composition is administered with at least one additional cancer therapeutic agent. Further provided herein are methods, wherein the subject has a solid tumor or a blood cancer. Further provided herein are methods, wherein the solid tumor is a carcinoma, a melanoma, or a sarcoma. Further provided herein are methods, wherein the blood cancer is lymphoma or leukemia. Further provided herein are methods, wherein the subject has a skin cancer. Further provided herein are compositions, wherein the skin cancer is a basal cell cancer, a melanoma, a Merkel cell cancer, a squamous cell carcinoma, a cutaneous lymphoma, a Kaposi sarcoma, or a skin adnexal cancer. Further provided herein are methods, wherein the subject has a lung cancer. Further provided herein are methods, wherein the lung cancer is a non-small cell lung cancer (NSCLC) or a small cell lung cancer (SCLC). Further provided herein are compositions, wherein the NSCLC is an adenocarcinoma, a squamous cell carcinoma, a large cell carcinoma, an adenosquamous carcinoma, or a sarcomatoid carcinoma. Further provided herein are methods, the subject has a pancreatic cancer. Further provided herein are methods, wherein the pancreatic cancer is a pancreatic adenocarcinoma, a pancreatic exocrine cancer, a pancreatic neuroendocrine cancer, an islet cell cancer, or a pancreatic endocrine cancer. Further provided herein are methods, wherein the subject has a metastatic cancer. Further provided herein are methods, wherein the administering results in a reduction of a tumor size or a reduction in a tumor volume in the subject. Further provided herein are methods, wherein the administering results in a reduction of a cancer recurrence. Further provided herein are methods, wherein the administering results in a reduction in tumor metastasis.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Techniques and Materials for the Production of Lipid Nanoparticles The following materials were used in the manufacturing of lipid-inorganic nanoparticles (i.e., lipid nanoparticles). The compositions, kits and methods described herein are not limited to the techniques or materials described herein.

Iron oxide nanoparticles at 25 mg Fe/ml in chloroform and of various average diameters (5, 10, 15, 20, 25 and 30 nm) were purchased from Ocean Nanotech (San Diego, CA, USA). Squalene and SPAN® 60 (sorbitan monostearate) were purchased from Millipore Sigma. TWEEN® 80 (polyethylene glycol sorbitan monooleate) and sodium citrate dihydrate were purchased from Fisher Chemical. The chloride salt of the cationic lipid 1,2-dioleoyl-3-trimethylammonium-propane (DOTAP chloride) was purchased from Corden Pharma. Ultrapure water (18.2 mega ohm-centimeter (MOhm-cm) resistivity) was obtained from a Milli-Q water purification system (Millipore Sigma).

The lipid carrier comprises squalene, sorbitan monostearate (e.g., SPAN® 60), polysorbate 80 (e.g., TWEEN® 80), DOTAP chloride, iron oxide nanoparticles and sodium citrate dihydrate. In general, to iron oxide nanoparticles with a number-weighted average diameter of 5 nm, chloroform was added. Chloroform was allowed to evaporate in a fume hood leaving behind a dry coating of iron oxide nanoparticles. To the iron oxide nanoparticles, SPAN® 60, squalene, and DOTAP chloride were added to prepare the "oil" phase.

The oil phase was sonicated 30 minutes in a water bath pre-heated to 60° C. Separately, in a 1 liter glass bottle, the "aqueous" phase was prepared by adding TWEEN® 80 to sodium citrate dihydrate solution prepared with Milli-Q water.

The aqueous phase was stirred for 30 minutes to allow complete dissolution of TWEEN® 80. After complete dissolution of TWEEN® 80, the aqueous phase was transferred to a beaker and incubated in a water bath pre-heated to 60° C. To the heated oil phase, the pre-heated aqueous phase was added.

The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi.

The fluid was passaged until the z-average hydrodynamic diameter, measured by dynamic light scattering (Malvern Zetasizer Nano S), was 59 nm with a 0.2 polydispersity index.

The microfluidized lipid carrier sample was terminally filtered with a 200 nm pore-size polyethersulfone (PES) syringe filter.

Example 2: Exemplary Techniques and Materials for Producing Lipid Nanoparticles The following materials were used in the manufacturing of lipid-inorganic nanoparticles (i.e., lipid nanoparticles). The compositions, kits and methods described herein are not limited to the techniques or materials describe herein.

Iron oxide nanoparticles at 25 mg Fe/ml in chloroform and of various average diameters (5, 10, 15, 20, 25 and 30 nm) were purchased from Ocean Nanotech (San Diego, CA). Squalene and SPAN® 60 (sorbitan monostearate) were purchased from Millipore Sigma. TWEEN® 80 (polyethylene glycol sorbitan monooleate) and sodium citrate dihydrate were purchased from Fisher Chemical. The chloride salt of the cationic lipid 1,2-dioleoyl-3-trimethylammonium-propane (DOTAP chloride) was purchased from Corden Pharma. Ultrapure water (18.2 MOhm-cm resistivity) was obtained from a Milli-Q water purification system (Millipore Sigma).

Lipid carriers were prepared which comprised 37.5 mg/ml squalene, 37 mg/ml SPAN® 60, 37 mg/ml TWEEN® 80, 30 mg/ml DOTAP chloride, 0.1 mg/ml 10 nm iron oxide nanoparticles and 10 mM sodium citrate dihydrate.

The lipid carriers were manufactured using the following procedures. In a 200 ml beaker, 0.4 ml of iron oxide nanoparticles at 25 mg Fe/ml in chloroform, with a number-weighted average diameter of 10 nm, were added.

Chloroform was allowed to evaporate in a fume hood leaving behind a dry coating of iron oxide nanoparticles. To the iron oxide nanoparticles, 3.7 grams of SPAN® 60, 3.75 grams of squalene, and 3 grams of DOTAP chloride were added to prepare the "oil" phase.

The oil phase was sonicated 30 minutes in a water bath pre-heated to 60° C. Separately, in a 1 liter glass bottle, the "aqueous" phase was prepared by adding 39 grams of TWEEN® 80 to 1,000 ml 10 mM sodium citrate dihydrate solution prepared with Milli-Q water.

The aqueous phase was stirred for 30 minutes to allow complete dissolution of TWEEN® 80. After complete dissolution of TWEEN® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 54 nm with a 0.2 polydispersity index. The microfluidized lipid carrier sample was terminally filtered with a 200 nm pore-size polyethersulfone (PES) syringe filter.

Example 3: Exemplary Techniques and Materials for Producing Nanoparticles Described Herein Lipid carriers were prepared which comprised 37.5 mg/ml squalene, 37 mg/ml SPAN® 60, 37 mg/ml TWEEN® 80, 30 mg/ml DOTAP chloride, 0.2 mg/ml 15 nm iron oxide nanoparticles, and 10 M sodium citrate dihydrate. The lipid carriers of Example 9 were manufactured using the following procedures.

In a 200 ml beaker, 0.8 ml of iron oxide nanoparticles at 25 mg Fe/ml in chloroform, with a number-weighted average diameter of 15 nm, was added. Chloroform was allowed to evaporate in a fume hood leaving behind a dry coating of iron oxide nanoparticles. To the iron oxide nanoparticles, 3.7 grams of SPAN® 60, 3.75 grams of squalene, and 3 grams of DOTAP chloride were added to prepare the "oil" phase.

The oil phase was sonicated 30 minutes in a water bath pre-heated to 60° C. Separately, in a 1 liter glass bottle, the "aqueous" phase was prepared by adding 39 grams of TWEEN® 80 to 1,000 ml of 10 mM sodium citrate dihydrate solution prepared with Milli-Q water. The aqueous phase was stirred for 30 minutes to allow complete dissolution of TWEEN® 80.

After complete dissolution of TWEEN® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi.

The fluid was passaged until the z-average hydrodynamic diameter, measured by dynamic light scattering (Malvern Zetasizer Nano S), was 52 nm with a 0.2 polydispersity index. The microfluidized lipid carrier sample was terminally filtered with a 200 nm pore-size polyethersulfone (PES) syringe filter.

Example 4: Composition for Use as a Cancer Vaccine Prepared Using the Construct of SEQ ID NO: 75 or SEQ ID NO: 76

Lipid carrier-RNA complexes are prepared and aliquoted for lyophilization. Samples are lyophilized and then collected and selected for reconstitution. All lyophilized cakes are then reconstituted in 0.7 ml milliQ® water. Table 4 discloses exemplary materials used in the preparation of lipid carrier-RNA complexes.

TABLE 4

| Conditions. | | |
|---|---|---|
| Name | Molecular weight | Concentration |
| lipid carrier | | 30 mg DOTAP/ml |
| repRNA comprising sequence set forth in SEQ ID NO: 1, SEQ ID NO: 2, SEQ ID NO: 75, or SEQ ID NO: 76 | | 1015 ng RNA/μl |

TABLE 4-continued

| Conditions. | | |
|---|---|---|
| Name | Molecular weight | Concentration |
| Sucrose | 342.3 | |
| D-Glucose | 180.16 | |
| D-Mannitol | 182.17 | |
| Maltose monohydrate | 360.31 | |
| Trehalose dihydrate | 378.33 | |
| Sodium citrate | | 1M |

Exemplary conditions for lyophilization are set forth as below in Tables 5-7.

TABLE 5

| Lyophilization Cycle # 1. | | |
|---|---|---|
| Time [hr] | T [C.] | P [mTorr] |
| 0 | 20 | 760000 |
| 1.5 | −50 | 760000 |
| 2 | −50 | 760000 |
| 2.1 | −50 | 50 |
| 2.5 | −30 | 50 |
| 20 | −30 | 50 |
| 20.5 | 25 | 50 |
| 22 | 25 | 50 |
| 22.1 | 25 | 760000 |

TABLE 6

| Lyophilization Cycle # 2. | | |
|---|---|---|
| Time [hr] | T [C.] | P [mTorr] |
| 0 | 20 | 760000 |
| 1.5 | −65 | 760000 |
| 2 | −65 | 760000 |
| 2.1 | −65 | 15 |
| 2.5 | −50 | 15 |
| 24 | −50 | 15 |
| 24.5 | 25 | 15 |
| 26 | 25 | 15 |
| 26.1 | 25 | 760000 |

TABLE 7

| Lyophilization Cycle # 3. | | |
|---|---|---|
| Time [hr] | T [C.] | P [mTorr] |
| 0 | 20 | 760000 |
| 1.5 | −65 | 760000 |
| 2 | −65 | 760000 |
| 2.1 | −65 | 15 |
| 2.5 | −50 | 15 |
| 26.5 | −50 | 15 |
| 26.6 | −30 | 15 |
| 46 | −30 | 15 |
| 48 | 25 | 15 |
| 48.1 | 25 | 760000 |

Preparation of diluents: The diluents comprising the sugar and citrate were prepared as outlined in Table 8. Each sugar was weighed out in a 50 ml RNase free conical tube. About 35-40 ml of nuclease free water was added to dissolve the sugar and slight heat and sonication was used, as needed. Pipette-in 0.5 ml of 1M Na-citrate, pH=6 solution. After all sugar has dissolved and solution is clear, Q.S. with nuclease free water to 50 ml mark in conical tube. Filter diluents with 0.22 μm STERIFLIP® and screw on cap aseptically to maintain sterility.

TABLE 8

| Preparation of diluents | | | | |
|---|---|---|---|---|
| Diluent | Composition ID | Total Volume [ml] | Actual mass [g] | Calculated conc [g/L] |
| 22% sucrose/10 mM citrate | 22% sucrose | 50.0 | 11.1 | 222.0 |
| 50% sucrose/10 mM citrate | 50% sucrose | 50.0 | 25.0 | 500.0 |
| 22% maltose/10 mM citrate | 22% maltose | 50.0 | 11.7 | 233.7 |
| 22% trehalose/10 mM citrate | 22% trehalose | 50.0 | 12.3 | 245.4 |
| 11% glucose/10 mM citrate | 11% glucose | 50.0 | 5.6 | 111.0 |
| 11% mannitol/10 mM citrate | 11% mannitol | 50.0 | 5.6 | 111.0 |

Preparation of pre-complex formulation: Lipid carrier "DS" is the bulk solution at 30 mg DOTAP/ml and refers to Fe-lipid carrier formulation, whose preparation is described in Example 2.

Lipid carrier "DS" (30 mg DOTAP/ml) 10-fold was diluted in each diluent to make 3 mg DOTAP/ml lipid carrier "DP", except in 50% sucrose composition lipid carrier 5-fold was diluted to make 2×6 mg DOTAP/ml lipid carrier "DP". The target RNA concentration in liquid formulation was 50 ng/μl, complexed with lipid carrier at N:P of 15. This simulates 25 μg RNA dose per vial. Table 9 discloses the preparation of pre-complex lipid carrier complex. The unused lipid carrier was stored at 2-8 degrees Celsius.

TABLE 9

| Pre-complex lipid carrier preparation. | | | |
|---|---|---|---|
| Composition ID | Lipid Carrier DS [μl] | Diluent [μl] | Total [μl] |
| 22% sucrose | 420 | 3780 | 4200 |
| 50% sucrose | 420 | 1680 | 2100 |
| 22% maltose | 420 | 3780 | 4200 |
| 22% trehalose | 420 | 3780 | 4200 |
| 11% glucose | 420 | 3780 | 4200 |
| 11% mannitol | 420 | 3780 | 4200 |
| Maltose monohydrate | Sigma | 360.31 | |
| Trehalose dihydrate | sigma | 378.33 | |
| Sodium citrate | Teknova | | 1M |

Table 10 discloses the preparation of pre-complex nanostructured lipid carrier (NLC) complex. The NLCs were used as control. The unused NLC was stored at 2-8 degrees Celsius for fresh complex controls.

TABLE 10

| Pre-complex NLC preparation. | | | |
|---|---|---|---|
| Composition ID | NLC [μl] | Diluent [μl] | Total [μl] |
| 22% sucrose | 420 | 3780 | 4200 |

The preparation of RNA pre-complex is disclosed in Table 11. The RNA stock was prepared. About 7.5 ml or 0.63 ml for 50% sucrose per aliquot were split and stored at −80 degrees Celsius.

TABLE 11

| Preparation of RNA pre-complex. | | | | |
|---|---|---|---|---|
| Composition ID | RNA Stock [μl] | 5 mM citrate [μl] | Total [μl] | Actual RNA concentration pre-complex [ng/μl] |
| all | 2141.4 | 19593.6 | 21735.0 | 107.3 |
| 50% sucrose | 356.9 | 1454.4 | 1811.3 | 221.0 |

The preparation of lipid carrier-RNA complex is disclosed in Table 11. The RNA stock was prepared. The volume of diluted RNA was (+5%) and diluted lipid carrier was (+5%) per complexing per lyophilization (lyo) cycle.

Complexes of lipid carrier+RNA or NLC+RNA were prepared by mixing 1:1 by volume each diluted formulation listed in the above described Table 10 and Table 11, with the corresponding "Composition ID" diluted RNA disclosed in Table 12. The complexes were equilibrated for 30 minutes at room temperature before subjecting to the lyophilization cycles or long-term storage conditions.

TABLE 12

| Preparation of lipid carrier-RNA pre-complex. | | | | | | |
|---|---|---|---|---|---|---|
| Composition ID | Diluted RNA | Diluted lipid carrier | Diluted NLC [μl] | Total [μl] | Final RNA conc. [ng/μl] | Final Sugar conc. [% w/v] |
| 22% sucrose | 1102.5 | 1102.5 | | 2205 | 50 | 10 |
| 50% sucrose | 551.25 | 551.25 | | 1102.5 | 100 | 20 |
| 22% maltose | 1102.5 | 1102.5 | | 2205 | 50 | 10 |
| 22% trehalose | 1102.5 | 1102.5 | | 2205 | 50 | 10 |
| 11% glucose | 1102.5 | 1102.5 | | 2205 | 50 | 5 |
| 11% mannitol | 1102.5 | 1102.5 | | 2205 | 50 | 5 |
| 22% sucrose | 1102.5 | | 1102.5 | 2205 | 50 | 10 |

The RNA is a construct having a nucleic acid sequence as set forth in either SEQ ID NO: 75 or SEQ ID NO: 76, each comprising a VEEV RNA sequence backbone and an RNA sequence encoding a cancer-associated protein antigen.

Example 5: Macrophage Immune Response

Various formulations of lipid carrier and repRNA were prepared and analyzed to assay innate immune response of the lipid carrier in macrophages. Protein expression and stimulation of TNF production in THP-1 macrophages was studied.

Initially, the THP-1 monocytes were differentiated into macrophages using phorbol 12-myristate 13-acetate (PMA). The cells were then transfected with various formulations with Nano Luciferase encoding replicon RNA (SEQ ID NO: 71). The cell culture media was then assessed for NanoLuc and TNF expression.

The formulations and their characteristics such as particle size and PDI that were used in this assay are described in Table 13. The concentration of repRNA encoding NanoLuc was 909 ng/μl and maintained at −80 degrees Celsius. MIGLYOL® 812 N, a triglyceride ester of saturated coconut/palm-kernel oil derived caprylic and capric fatty acids and plant derived glycerol was used in this assay.

TABLE 13

Formulations.

| Formulation | Particle size [diameter, nm] | PDI | Iron [mg Fe/ml] | Aluminum [mg Al/ml] | DOTAP [mg/ml] | Squalene [mg/ml] | MIGLYOL [mg/ml] | Solanesol [mg/ml] |
|---|---|---|---|---|---|---|---|---|
| Fe-lipid carrier | 59.3 | 0.23 | 0.19 | n/a | 27.9 | 39.4 | n/a | n/a |
| High Fe-lipid carrier | 57.5 | 0.24 | 0.85 | n/a | 29.1 | 40.5 | n/a | n/a |
| Fe-lipid carrier MIGLYOL | 48.7 | 0.2 | 0.18 | n/a | 28.3 | n/a | not measured | n/a |
| High Fe-lipid carrier MIGLYOL | 62.6 | 0.28 | 0.94 | n/a | 27.7 | n/a | not measured | n/a |
| Alum-lipid carrier | 64.5 | 0.25 | n/a | 0.88 | 27.4 | 41.2 | n/a | n/a |
| Fe-lipid carrier solanesol (SLN) | 86.1 | 0.26 | 0.16 | n/a | 26.2 | n/a | n/a | 36 |
| NLC | 50 | 0.26 | n/a | n/a | 26.7 | 34.1 | n/a | n/a |
| CNE | 105.4 | 0.06 | n/a | n/a | 4.4 | 47.4 | n/a | n/a |
| lipid carrier (w/o IO) | 54.2 | 0.22 | n/a | n/a | 19.3 | 32.6 | n/a | n/a |

Example 6: Fe-Lipid Carrier Formulation—NP-1 (Prepared at 100 ml Scale)

Figure 6:
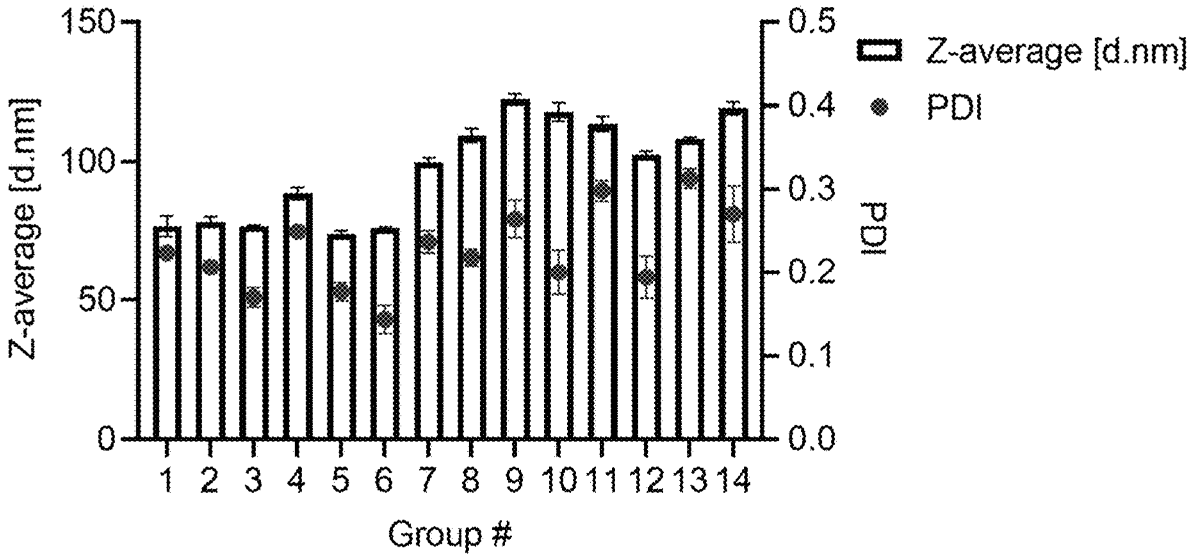
FIG. 6 is a bar chart with measurements of Z-average measurement and polydispersity index (PDI) on the Y-axis and group number on the X-axis for conditions 1 to 14.

Fe-lipid carrier formulation comprises 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 12 nm oleic acid-coated iron oxide nanoparticles (Imagion Biosystems, San Diego, CA, USA) and 10 mM sodium citrate dihydrate (Fisher Chemical). 1 ml of 20 mg Fe/ml 12 nm diameter oleic acid-coated iron oxide nanoparticles in chloroform (Imagion Biosystems, lot #95-127) were washed three times by magnetically separating in a 4:1 acetone: chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International, Radnor, PA, USA) and the resulting crude emulsion was processed by passaging through a M110P microfluidizer (Microfluidics, Westwood, MA, USA) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.25 polydispersity index (PDI) (FIG. 6). The microfluidized NP-1 formulation was terminally filtered with a 200 nm pore-size polyethersulfone (PES) filter and stored at 2 to 8 degrees C. Iron concentration was determined by inductively coupled plasma-optical emission spectrometry (ICP-OES). DOTAP and squalene concentration were measured by reverse phase high-performance liquid chromatography (RP-HPLC).

Example 7: High Fe-Lipid Carrier Formulation NP-2 (Prepared at 100 ml Scale)

High Fe-lipid carrier formulation comprises 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 1 mg Fe/ml 15 nm oleic acid-coated iron oxide nanoparticles (Imagion Biosystems) and 10 mM sodium citrate dihydrate (Fisher Chemical). 5 ml of 20 mg Fe/ml 15 nm diameter oleic acid-coated iron oxide nanoparticles in chloroform (Imagion Biosystems, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degree Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP and Squalene concentration were measured by RP-HPLC.

Example 8: Fe-Lipid Carrier Miglyol Formulation NP-3 (Prepared at 100 ml Scale)

The Fe-lipid carrier miglyol formulation comprises 37.5 mg/ml Miglyol 812 N (IOI Oleo GmbH), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 15 nm oleic acid-coated iron oxide nanoparticles (Imagion Biosystems) and 10 mM sodium citrate dihydrate (Fisher Chemical). 1 ml of 20 mg Fe/ml 15 nm diameter oleic acid-coated iron oxide nanoparticles in chloroform (Imagion Biosystems, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degree C. for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP concentration was measured by RP-HPLC.

Example 9: High Fe-Lipid Carrier Miglyol Formulation NP-4 (Prepared at 100 ml Scale)

High Fe-lipid carrier Miglyol formulation comprises 37.5 mg/ml Miglyol 812 N (IOI Oleo GmbH), 37 mg/ml SPAN® 60 (Millipore Sigma), 37 mg/ml TWEEN® 80 (Fisher Chemical), 30 mg/ml DOTAP chloride (LIPOID), 1 mg/ml 15 nm oleic acid-coated iron oxide nanoparticles (ImagionBio) and 10 mM sodium citrate dihydrate (Fisher Chemical). 5 ml of 20 mg Fe/ml 15 nm diameter oleic acid-coated iron oxide nanoparticles in chloroform (ImagionBio, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP concentration was measured by RP-HPLC.

Example 10: Alum-Lipid Carrier Formulation NP-5 (Prepared at 100 ml Scale)

Alum-lipid carrier formulation comprises 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 1 mg Al/ml TOPO-coated Alhydrogel® (aluminum oxyhydroxide) particles (Croda) and 10 mM sodium citrate. 10 ml of Alhydrogel was washed three times in methanol by centrifuging at 1000 rpm for 20 minutes. After the third wash, Alhydrogel was dispersed in 10 ml methanol and to this dispersion was added 1 ml of 250 mg/ml trioctylphosphine oxide (TOPO) and incubated overnight in a 37° C. orbital shaker. Excess TOPO was removed by additional methanol washes and then dispersed in 11 ml methanol. Methanol was allowed to evaporate overnight in the fume hood leaving behind a dry layer of TOPO-Alhydrogel. To this dry TOPO-Alhydrogel layer, 3.75 grams squalene, 3.7 grams SPAN® 60, and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Aluminum concentration was determined by ICP-OES. DOTAP and Squalene concentration were measured by RP-HPLC.

Example 11: Fe-Lipid Carrier Solanesol Formulation NP-6 (Prepared at 100 ml Scale)

Fe-lipid carrier solanesol formulation (NP-6) comprises 37.5 mg/ml Solanesol (Cayman chemicals), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml oleic acid-coated iron oxide nanoparticles (ImagionBio) and 10 mM sodium citrate. 1 ml of 20 mg Fe/ml 15 nm diameter oleic acid-coated iron oxide nanoparticles in chloroform (ImagionBio, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams solanesol, 3.7 grams SPAN® 60, and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber. The microfluidized formulation was terminally filtered with a 200 nm pore-size polyethersulfone (PES) filter and stored at 2 to 8 degrees C. Iron concentration was determined by ICP-OES. DOTAP and solanesol concentration were measured by RP-HPLC.

Example 12: NP-7 Formulation (Prepared at 100 ml Scale)

NP-7 formulation comprises 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 2.4 mg/ml Dynasan 114 (101 Oleo GmbH) and 10 mM sodium citrate. To a 200 ml beaker 3.75 grams squalene, 3.7 grams SPAN® 60, 0.24 grams Dynasan 114 and 3 grams DOTAP were added to produce the oil phase. The oil phase was sonicated for 45 minutes in a 65 degree C. water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. DOTAP and squalene concentration were measured by RP-HPLC.

Example 13: NP-8 Formulation (Prepared at 100 ml Scale)

The NP-8 formulation comprises 43 mg/ml squalene (SEPPIC), 5 mg/ml SPAN® 85 (Millipore Sigma), 5 mg/ml TWEEN® 80 (Fisher Chemical), 4 mg/ml DOTAP chloride (LIPOID) and 10 mM sodium citrate. To a 200 ml beaker 4.3 grams squalene, 0.5 grams SPAN® 85, and 0.4 grams DOTAP were added to produce the oil phase. The oil phase was sonicated for 45 minutes in a 65 degree C. water bath. Separately, the aqueous phase was prepared by dissolving 2.6 grams TWEEN® 80 in 500 ml of 10 mM sodium citrate buffer prepared in nuclease free water. 95 ml of the aqueous phase was transferred to a separate glass bottle and heated to 65 degrees Celsius for 30 minutes. The oil phase was mixed with the 95 ml of aqueous phase by adding the warm oil phase to the warm aqueous phase. The mixture was emulsified using a VWR® 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 100±10 nm with a 0.05-0.1 polydispersity index (PDI). The microfluidized formulation was terminally filtered with a 200 nm pore-size polyethersulfone (PES) filter and stored at 2 to 8 degrees C. DOTAP and Squalene concentration were measured by RP-HPLC.

Example 14: Lipid Nanoparticles and Cell-Based Assays for Evaluating Protein Production The treatment groups were prepared. Eight of those groups were NanoLuc repRNA groups, with 600 ng dose per well was prepared using the Fe-lipid carrier, High Fe-lipid carrier, Fe-lipid carrier miglyol, High Fe-lipid carrier miglyol, Alum-lipid carrier, Fe-lipid carrier solanesol (SLN), NLC, and CNE formulations. The untreated group did not have NanoLuc. The various formulations were prepared by diluting NanoLuc repRNA to 8 ng/μL in 2.2 mL of RNAse-free water. The lipid carrier formulations and RNA master mix was complexed by adding 250 μL of each diluted formulation with 250 μL of diluted RNA, and mixed by pipetting up and down.

Cell transfections were carried out by seeding $7\times10^5$ THP-1s per well in a 24-well plate. 80 micromolar (μM) PMA added to each well and incubated at 37 degrees Celsius. The next day, the PMA-containing media was removed and replaced with complete RPMI (cRPMI) medium for one hour before transfection. The samples were then serially diluted in Opti-MEM™ (Thermo Fisher Scientific, Waltham, MA USA) to make a 10-point 1.5-fold dilution series starting at 0.45 ng/μL. The culture media was then removed from the plates by pipetting. 450 μL of Opti-MEM™ and 150 μL of the complexed formulation were added to the plate in duplicate. The empty wells were given 450 μL of Opti-MEM™ only. After four hours, the samples were removed from the plate by pipetting and replaced with 500 μL of growth media. The plate was then incubated overnight at 37 degrees Celsius. The growth media was harvested the next day and stored at −80 degrees Celsius. Downstream assays were conducted and described below.

The luciferase assay was performed by first diluting the Nano-Glo® luciferase assay reagent 1:50 in buffer. 25 μL of supernatant was removed and mixed with 25 μL of Nano-Glo® reagent in a 96-well plate. This was incubated at room temperature for 3 minutes. The luminescence was read using a luminometer.

Next, an ELISA assay was performed to evaluate the TNF-alpha (a) protein levels in cell culture media using the human TNF-α DUOSET™ ELISA (R&D Systems) according to the manufacturer's protocol. The 96-well microplate was coated with anti-TNFα capture antibody. The plate was blocked and then media samples were added directly without dilution. After addition of the biotinylated detection antibody, SA-HRP, and substrate, the absorbance was read at 450 nm on a SPECTRAMAX® i3 (Molecular Devices) plate reader.

Figure 2A:
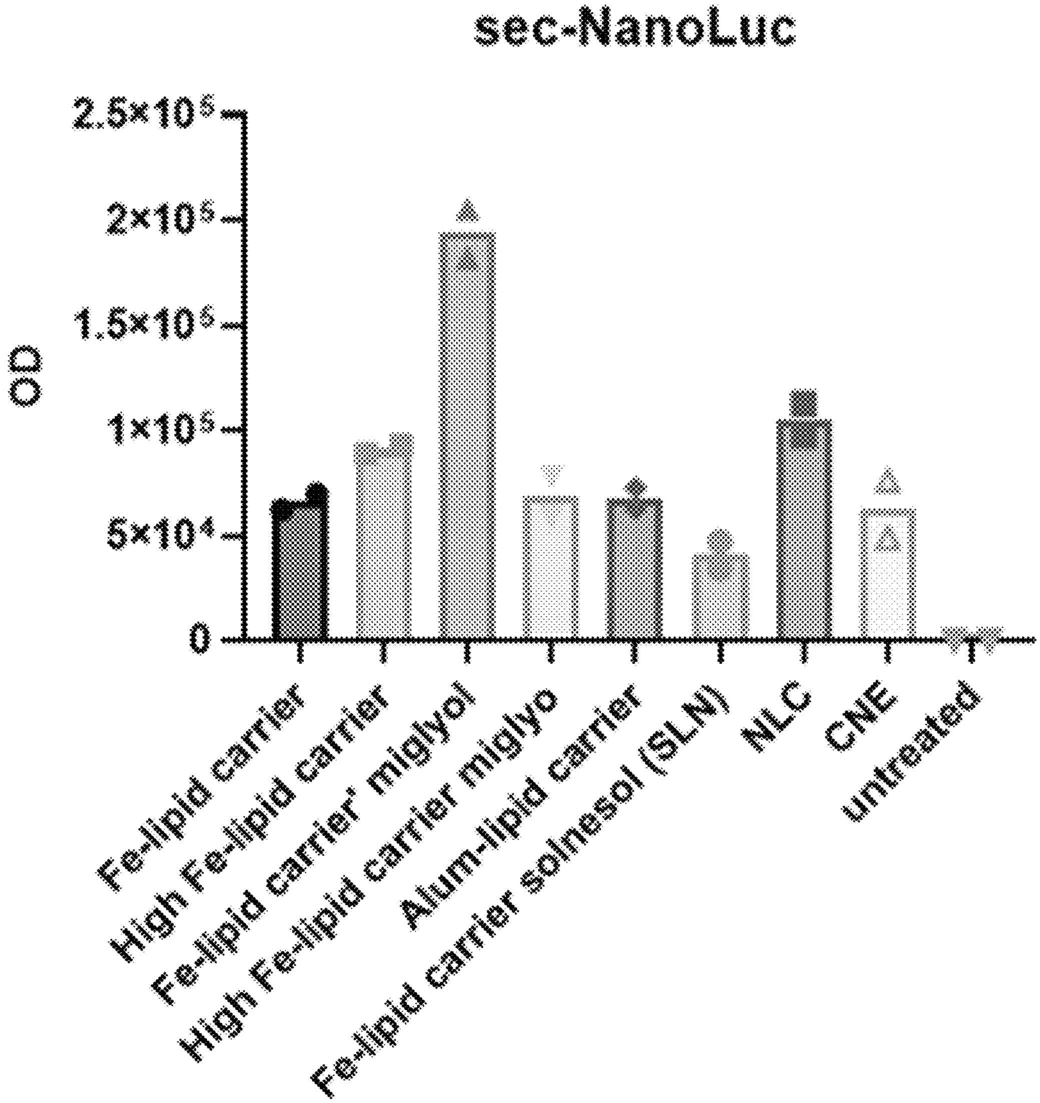
FIGS. 2A-2B show the increased protein production induced by the Miglyol lipid carrier formulation, NP-3.
Figure 2B:
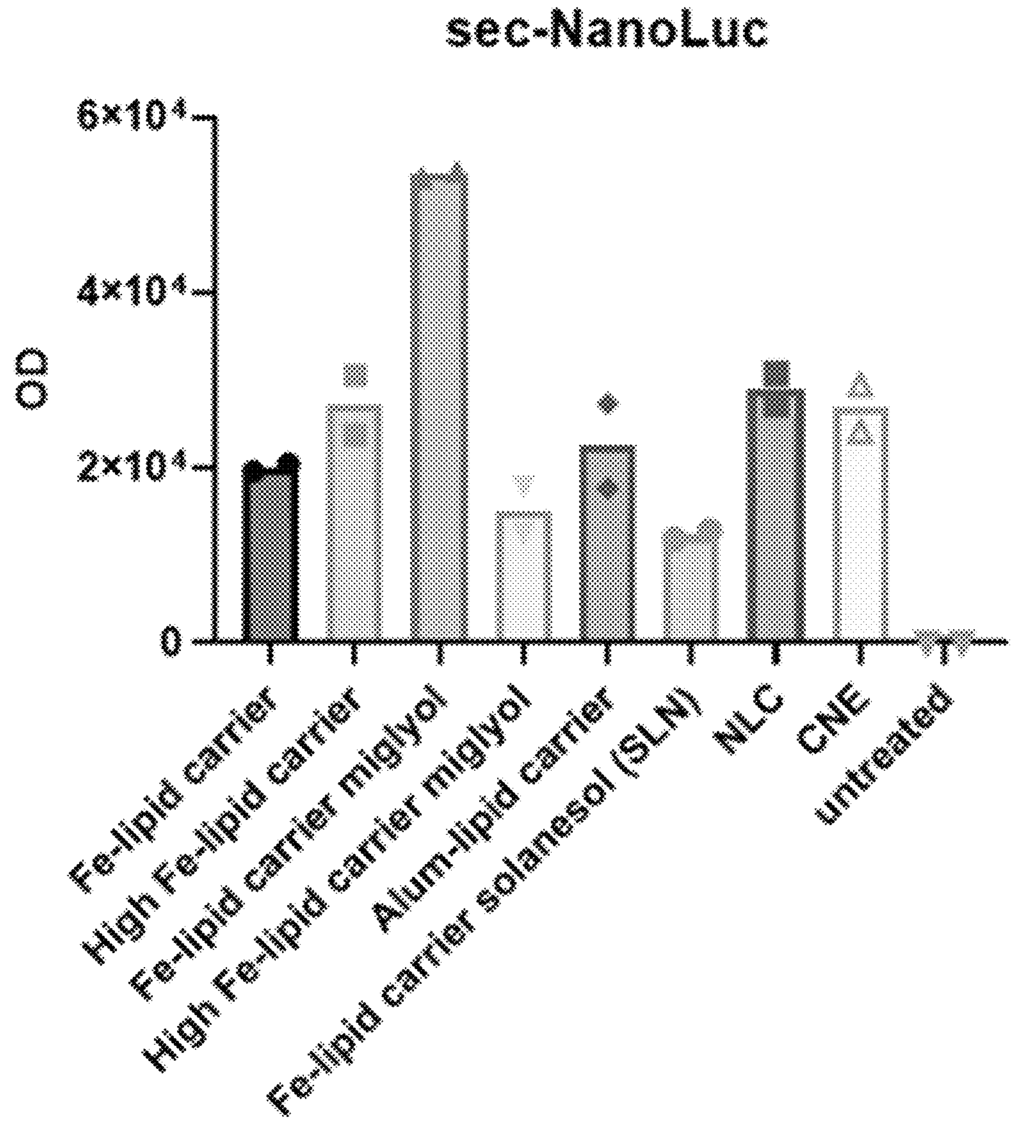
Figure 3A:
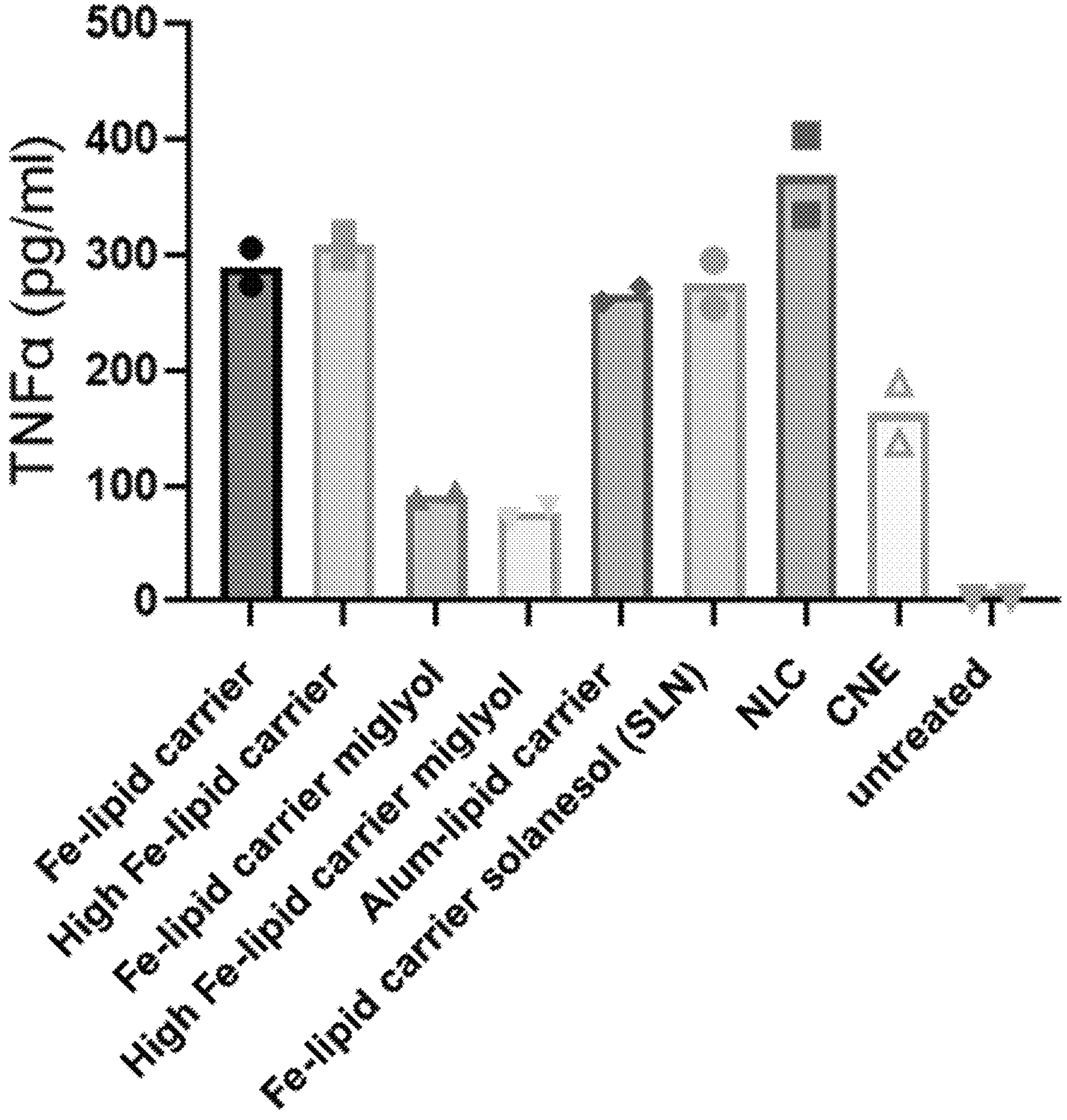
FIGS. 3A-3B show the decreased immune response induced by the Miglyol lipid carrier formulation, NP-3.
Figure 3B:
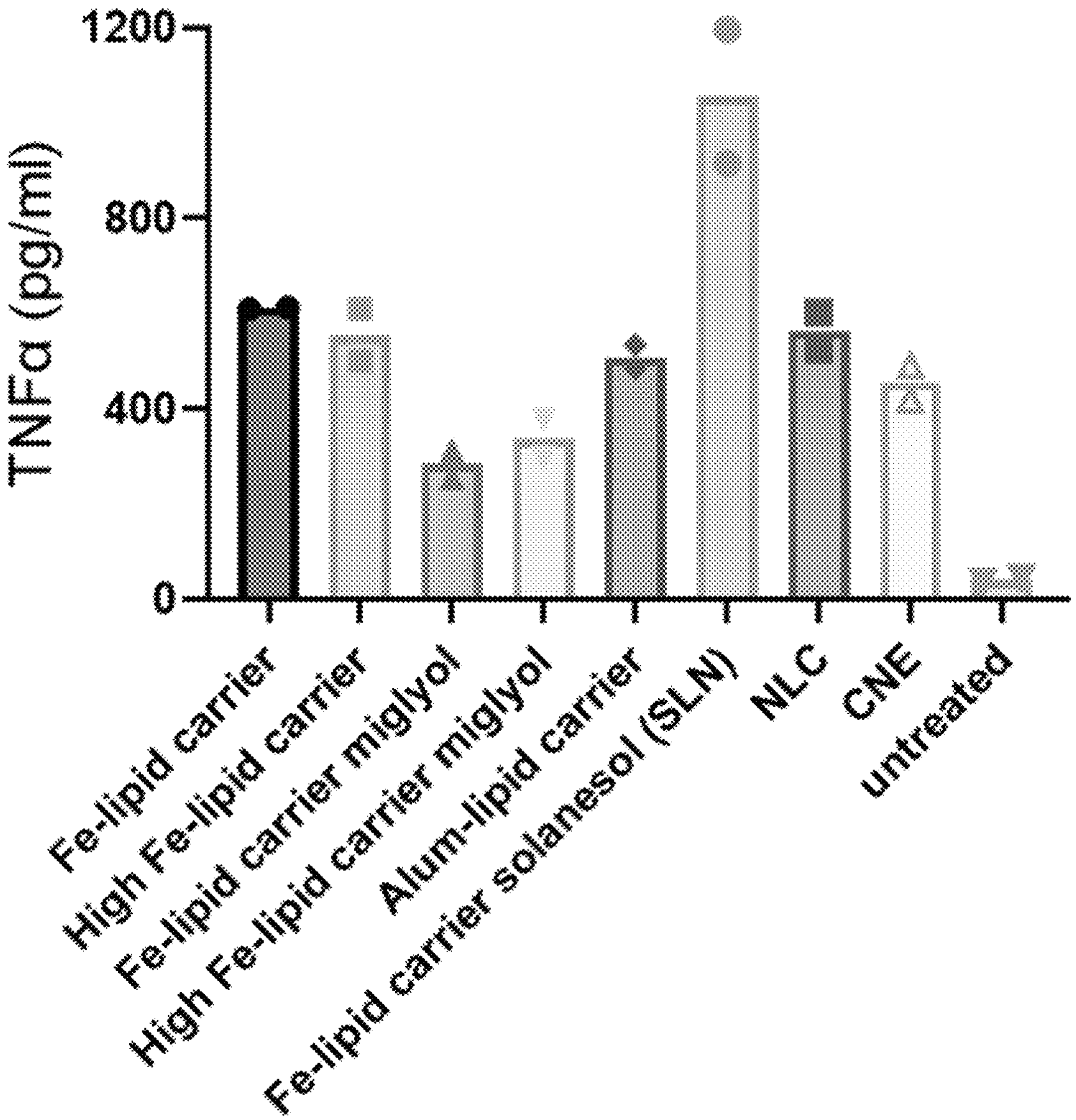

All studies in this example were done in duplicates. Results from the duplicates are presented as first experiment and second experiment respectively. The formulation comprising a lipid carrier and miglyol induced higher protein production off the replicon, as shown in the first experiment in FIG. 2A and in the second experiment in FIG. 2B. A reduced innate immune response was detected, as measured by TNF-α secretion (FIG. 3A-3B).

Figure 4A:
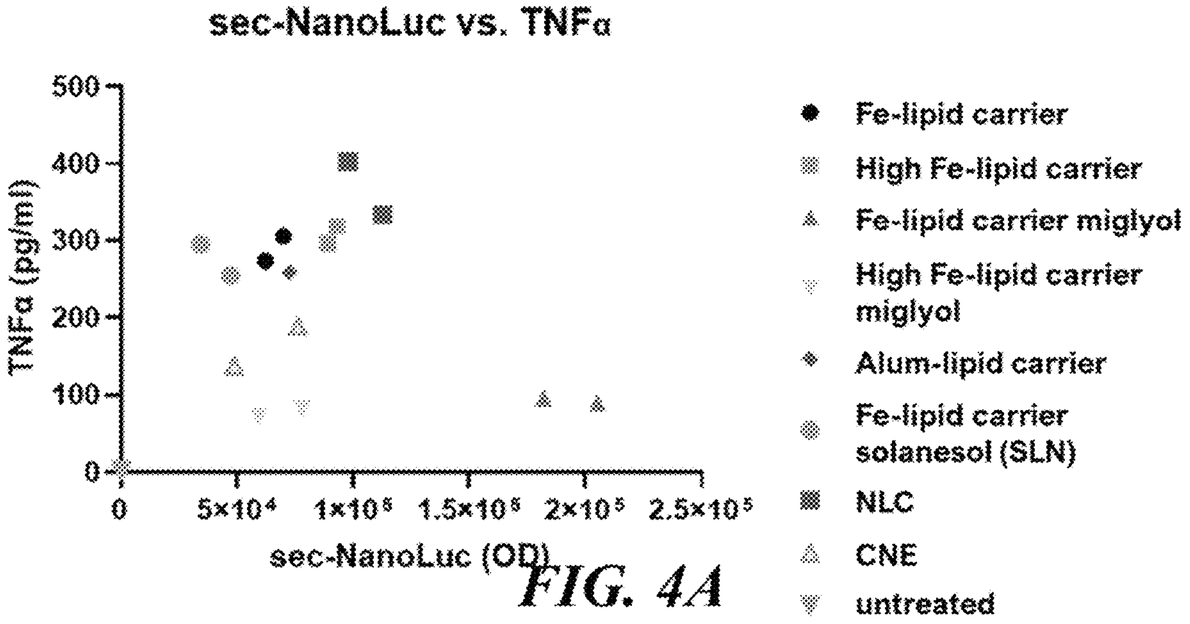
FIGS. 4A-4B show the correlation between enhanced protein production and low TNF (e.g., TNF alpha) stimulation observed with NP-3 as a result of the first and second assays.
Figure 4B:
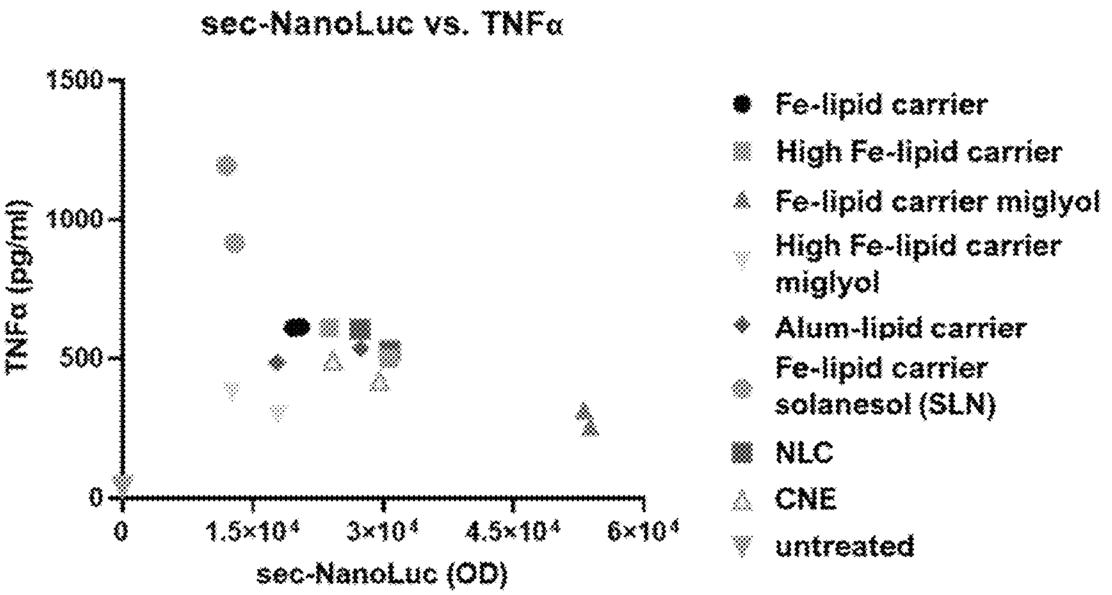
Figure 5A:
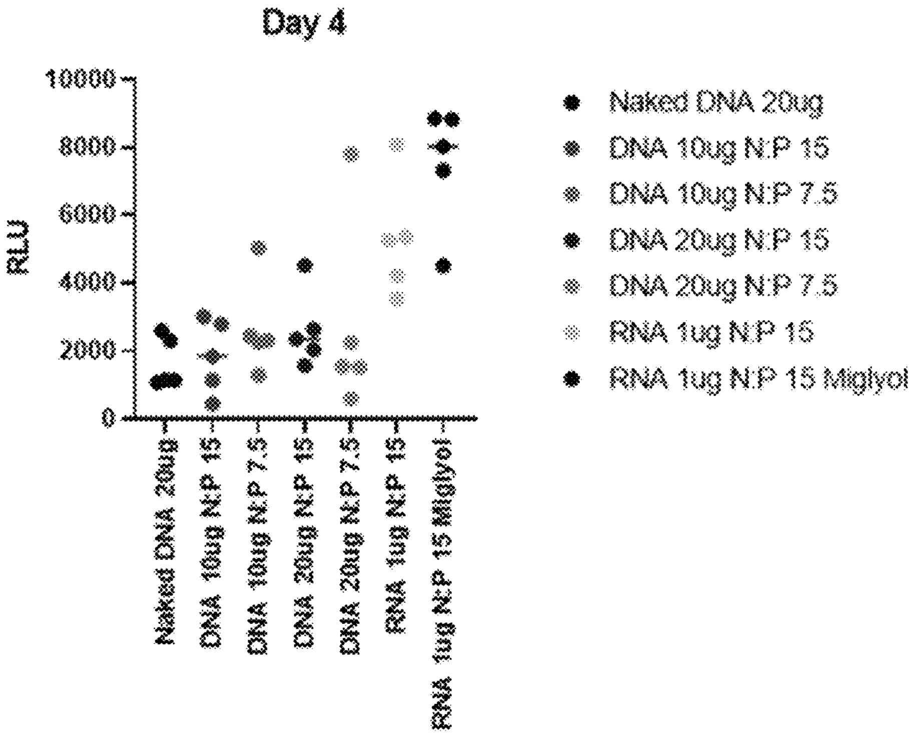
FIGS. 5A-5F show SEAP levels in BALB/c mice injected intramuscularly with various embodiments of lipid carrier formulations described herein.
Figure 5B:
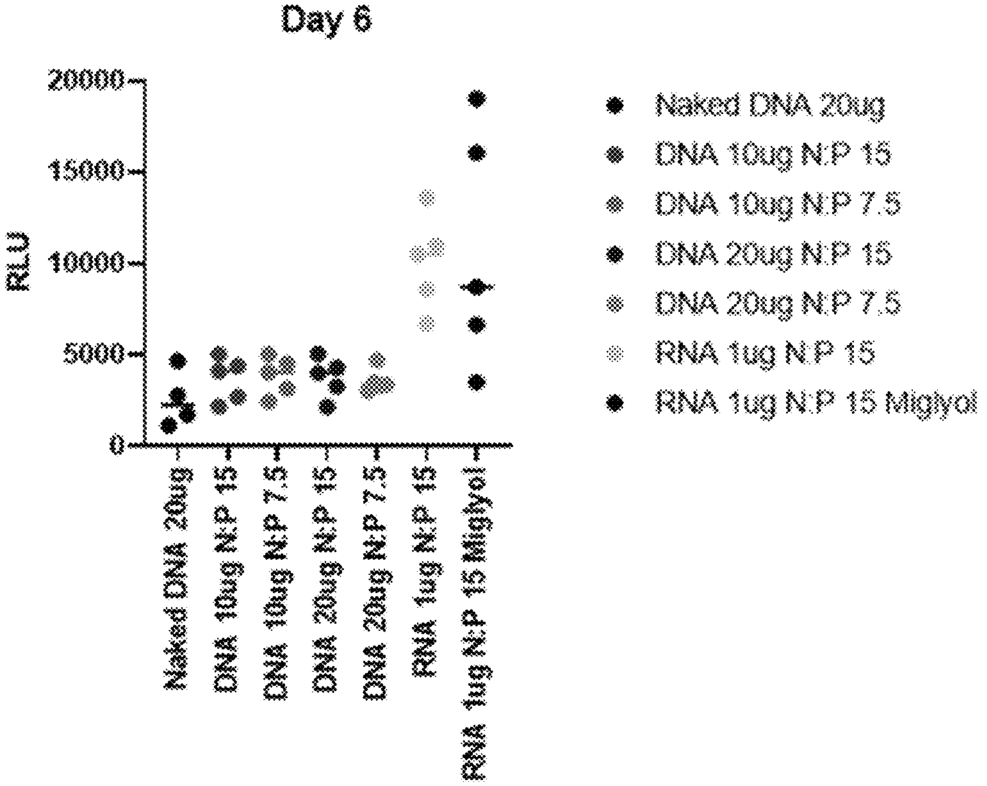
Figure 5C:
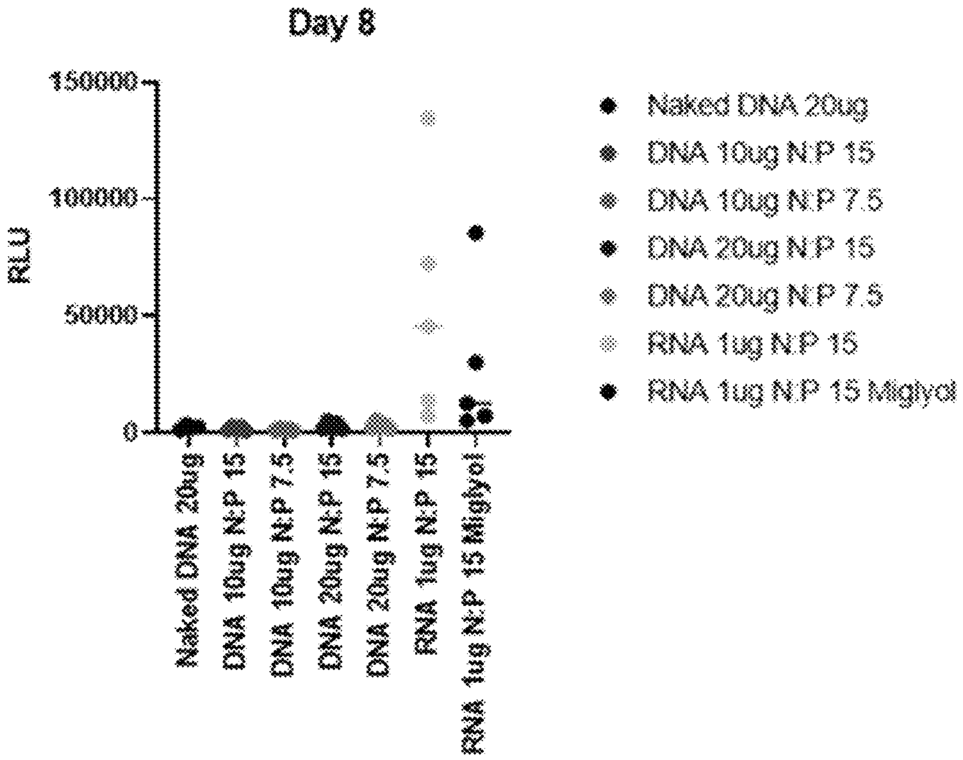
Figure 5D:
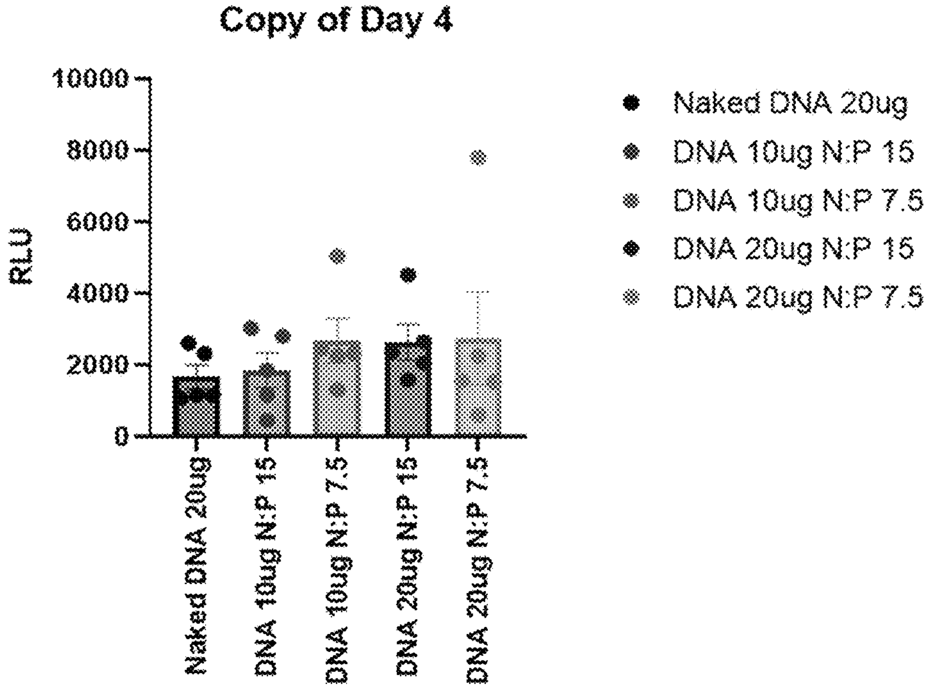
Figure 5E:
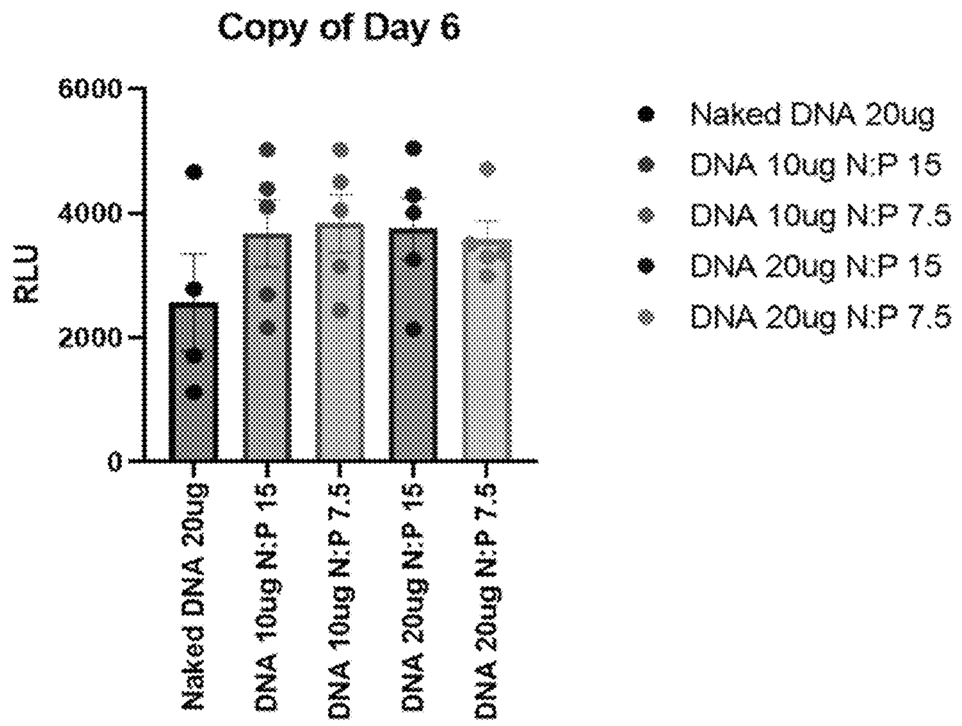
Figure 5F:
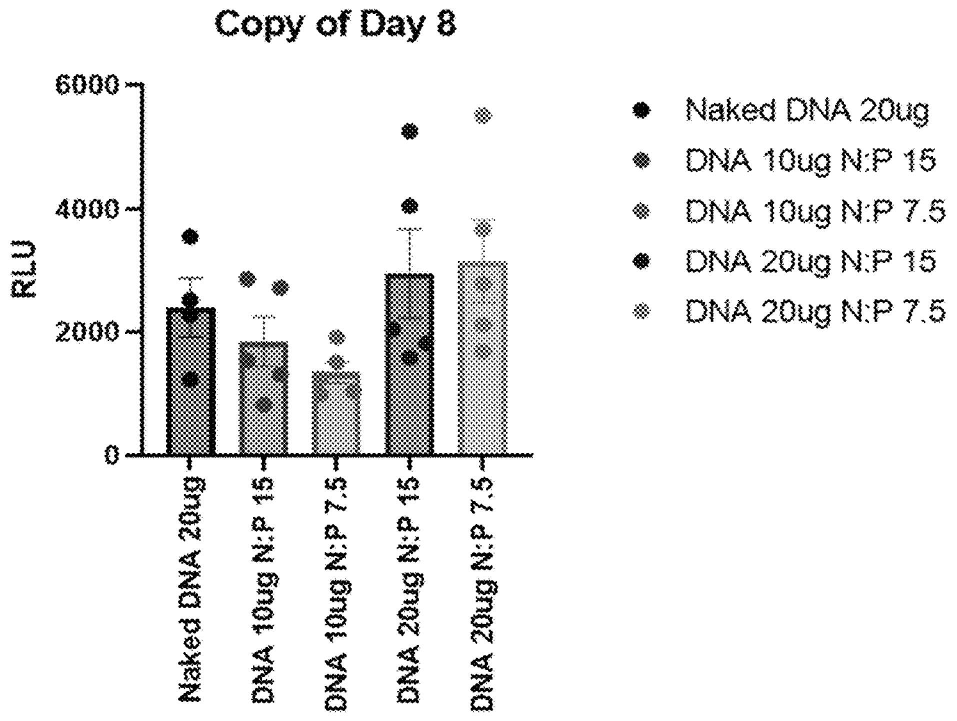

The correlation between enhanced protein production and low TNF-alpha stimulation was observed with the miglyol lipid carrier formulation, as shown in the first experiment in FIG. 4A and in the second experiment in FIG. 4B. The solanesol lipid carrier formulation induced slightly lower protein production, but a higher TNFα production (FIGS. 4A-4B). Correlation data from the first assay is shown in FIG. 4A are derived from the data represented in FIG. 2A and FIG. 3A. Correlation data from second assay is shown in FIG. 4B, which is derived from the data represented in FIG. 2B and FIG. 3B.

Example 15: Exemplary Techniques and Materials for Producing Nanoparticles Described Herein In a murine assay, C57BL/6 mice were inoculated as described in Table 6 below, after which secreted embryonic alkaline phosphatase (SEAP) levels were measured in serum. A summary of the materials used in the example is provided in Table 14.

TABLE 14

Materials.

| Description | Concentration | Temperature/Location |
|---|---|---|
| DNA encoding SEAP (DNA sequence as set forth in SEQ ID NO: 79) | 5 mg/mL | −20° C. |
| repRNA encoding SEAP | 2217 μg/mL | −80° C. |
| Lipid carrier formulation | 30 mg DOTAP/mL | 4° C. |

TABLE 15

Treatment Groups.

| Group | n | Formulation | DNA/RNA-SEAP | RNA dose [μg] | DNA dose [μg] | N:P | Injection Volume [μL] |
|---|---|---|---|---|---|---|---|
| 1 | 5 | Naked | DNA-SEAP | | 20 | n/a | 50 |
| 2 | 5 | Lipid carrier | DNA-SEAP | | 10 | 15 | 50 |
| 3 | 5 | Lipid carrier | DNA-SEAP | | 10 | 7.5 | |
| 4 | 5 | Lipid carrier | DNA-SEAP | | 20 | 15 | |
| 5 | 5 | Lipid carrier | DNA-SEAP | | 20 | 7.5 | |
| 6 | 5 | Lipid carrier | RNA-SEAP | 1 | | 15 | 50 |
| 7 | 5 | Miglyol + lipid carrier | RNA-SEAP | 1 | | 15 | 50 |

Seven different formulations were prepared and administered intramuscularly across the seven treatment groups (Groups 1-7). DNA-SEAP or RNA-SEAP was diluted according to the volumes set forth in Table 16 to prepare the formulations for Groups 1-7.

TABLE 16

Formulation Preparation; Dilution of RNA/DNA.

| Group | DNA- or RNA-SEAP | DNA or RNA [μL] | 40% sucrose [μL] | water [μL] | Total [μL] |
|---|---|---|---|---|---|
| 1 | DNA-SEAP | 40.0 | 125.0 | 85.0 | 250.0 |
| 2 | DNA-SEAP | 20.0 | 0.0 | 230.0 | 250.0 |
| 3 | DNA-SEAP | 20.0 | 0.0 | 230.0 | 250.0 |
| 4 | DNA-SEAP | 40.0 | 125.0 | 85.0 | 250.0 |
| 5 | DNA-SEAP | 40.0 | 0.0 | 210.0 | 250.0 |
| 6 | RNA-SEAP | 4.5 | 0.0 | 245.5 | 250.0 |
| 7 | RNA-SEAP | 4.5 | 0.0 | 245.5 | 250.0 |

The concentrations of diluted DNA or RNA prior to complexing with the lipid carrier was as follows (measured by NanoDrop spec): Groups 1, 4 and 5 contains about 820 μg/ml DNA; Groups 2 and 3 contained about 480 μg/ml DNA; and Groups 6 and 7 contained about 43 g/ml RNA.

Formulations for Groups 1-7 were diluted with 100 mM citrate as set forth in Table 17 below.

TABLE 17

Dilution of lipid carrier formulations.

| Group | Formulation | Lipid Carrier [μl] | 40% sucrose [μl] | 100 mM citrate [μl] | Water [μl] | Total [μl] |
|---|---|---|---|---|---|---|
| 1 | Naked | 0 | 0 | 30 | 270 | 300 |
| 2 | Lipid carrier | 120 | 150 | 30 | 0 | 300 |
| 3 | Lipid carrier | 60 | 150 | 30 | 60 | 300 |
| 4 | Lipid carrier | 240 | 0 | 30 | 30 | 300 |
| 5 | Lipid carrier | 120 | 150 | 30 | 0 | 300 |
| 6 | Lipid carrier | 12 | 150 | 30 | 108 | 300 |
| 7 | Miglyol + lipid carrier | 12 | 150 | 30 | 108 | 300 |

The above formulations were complexed by adding 250 μl diluted lipid carrier to 250 μl diluted DNA or RNA. The resulting complexed formulations were incubated on ice for at least 30 minutes. Table 18 sets forth the experiment schedule for the assay.

TABLE 18

| Experiment schedule. | | |
|---|---|---|
| Day | Procedure | Notes on Mice |
| 0 | All inoculations | None |
| 4 | Bleed | Group 4 had ruffled fur, one mouse emaciated (died during collection). Hydropaque placed in cage. |
| 6 | Bleed | None |
| 8 | Bleed | None |
| 11 | Bleed | None |
| 14 | Bleed | None |

Mice were bled at regular intervals and serum was prepared immediately and stored at −80 degrees Celsius until analyses for SEAP activity.

To evaluate SEAP levels in serum, all serum samples were thawed at the same time and SEAP detection was conducted. FIGS. 5A-5F illustrate the SEAP levels in BALB/c mice injected intramuscularly with varying iterations of lipid carrier-formulated DNA SEAP. Mice were bled at regular intervals, serum prepared and stored until analysis by SEAP assay. Data are displayed as mean and SE (n=5 per group).

As can be seen from FIGS. 5A-5F, lipid carrier formulations aid target protein production over delivery of DNA alone, particularly after day 6 following injection. Additionally, the data shows that inclusion of miglyol enhances protein production from an RNA replicon over lipid carrier formulations lacking miglyol.

Example 16: Self-Replicating mRNA Construct

A plasmid encoding a T7 promoter followed by the 5' and 3' UTRs and nonstructural genes of Venezuelan equine encephalitis virus (VEEV) strain TC-83 was generated using standard DNA synthesis and cloning methods. The VEEV replicon mRNA backbone is set forth in SEQ ID NO: 71.

Example 17: Additional Nanoparticle Formulations

Additional nanoparticle formulations are produced according to the following tables (Table 19 and Table 10). The mRNA comprises a sequence encoding the TRP-1 tumor associated antigen with a VEEV replicon mRNA backbone (SEQ ID NO: 71).

TABLE 19 mRNA Vaccine Formulation.
Dosage form: Solution for Injection

Composition:

| Each 0.5 ml Vial Contains: | Quantity | Concentration (mg/ml) |
|---|---|---|
| mRNA | 25 mcg | 0.05 |
| DOTAP | 0.75 mg | 1.5 |
| Iron Oxide Nanoparticles | 0.005 mg | 0.01 |
| Squalene | 0.94 mg | 1.88 |
| Sorbitan Monostearate | 0.93 mg | 1.86 |
| Polysorbate 80 | 0.93 mg | 1.86 |
| Sucrose IP | 50 mg | 100 |
| Citric Acid Monohydrate | 1.05 mg | 2.1 |
| Water for Injection | q.s. to 0.5 ml | |

TABLE 10

Lyophilized mRNA Vaccine Formulation.
Dosage form: Lyophilized powder

Composition:

| Each 5 dose vial contains: | Quantity | Concentration (mg/ml) | Approximate dry weight % |
|---|---|---|---|
| mRNA | 50 mcg | 0.02 | 0.02 |
| DOTAP | 1.5 mg | 0.6 | 0.57 |
| Squalene | 1.88 mg | 0.752 | 0.72 |
| Sorbitan Monostearate | 1.86 mg | 0.744 | 0.71 |
| Polysorbate 80 | 1.86 mg | 0.744 | 0.71 |
| Sucrose IP | 250 mg | 100 | 95.3 |
| Citric Acid Monohydrate | 5.25 mg | 2.1 | 2 |
| Water for Injection (for reconstitution) | 2.5 ml | | |

Example 18: TRP-1 Replicon Prevents B16F0 Tumor Growth

B16 subcutaneous melanoma mouse models were used in the assays provided herein. Upon subcutaneous injection, B16 animals will form a palpable tumor in approximately 5 to 10 days and grow to approximately a 1×1×1-cm tumor in approximately 14 to 21 days.

A lipid carrier and a TRP-1 RNA replicon were generated (SEQ ID NO: 76). The amino acid sequence of the TRP-1 is SEQ ID NO: 78.

Female C57BL/6 mice were immunized by intramuscular injection of repRNA-TRP1 at either a 0.2 mcg or 1 mcg dose, on either one or two occasions. Table 11 provides the assay conditions used.

TABLE 11

| Immunization groups and conditions. | | | | | | |
|---|---|---|---|---|---|---|
| Group | n | Immunization | Day 0 | Day 14 | Volume [μl] | Route |
| 1 | 5 | Lipid carrier + 0.2 μg TRP-1 repRNA | yes | yes | 50 | i.m. |
| 2 | 5 | Lipid carrier + 0.2 μg TRP-1 repRNA | — | yes | 50 | i.m. |
| 3 | 5 | Lipid carrier + 1 μg TRP-1 repRNA | yes | yes | 50 | i.m. |
| 4 | 5 | Lipid carrier + 1 μg TRP-1 repRNA | — | yes | 50 | i.m. |
| 5 | 5 | none | — | — | 50 | — |

Figure 7A:
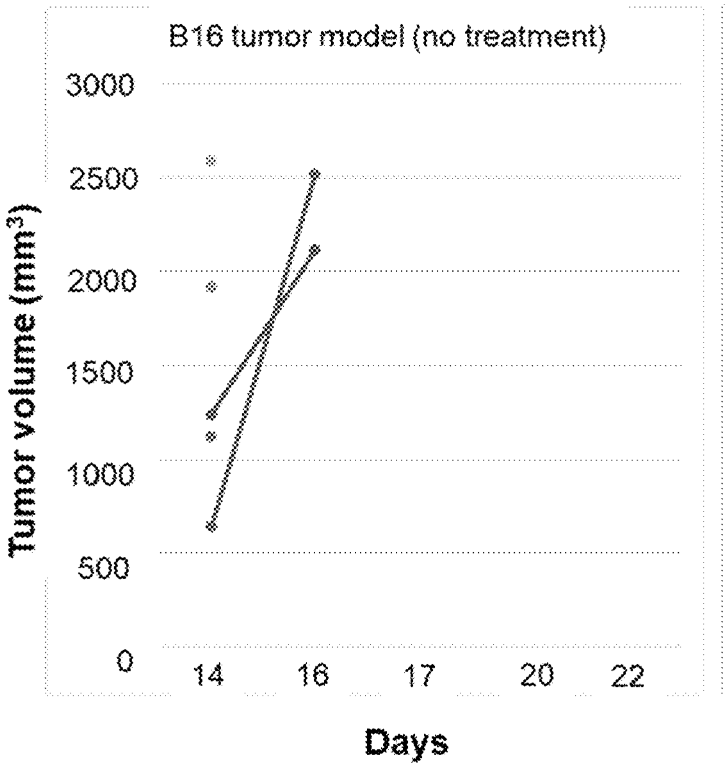
FIGS. 7A-7F show the effect of lipid carrier+TRP-1 replicon vaccine compositions on tumor volume in a B16 tumor model of melanoma.
Figure 7B:
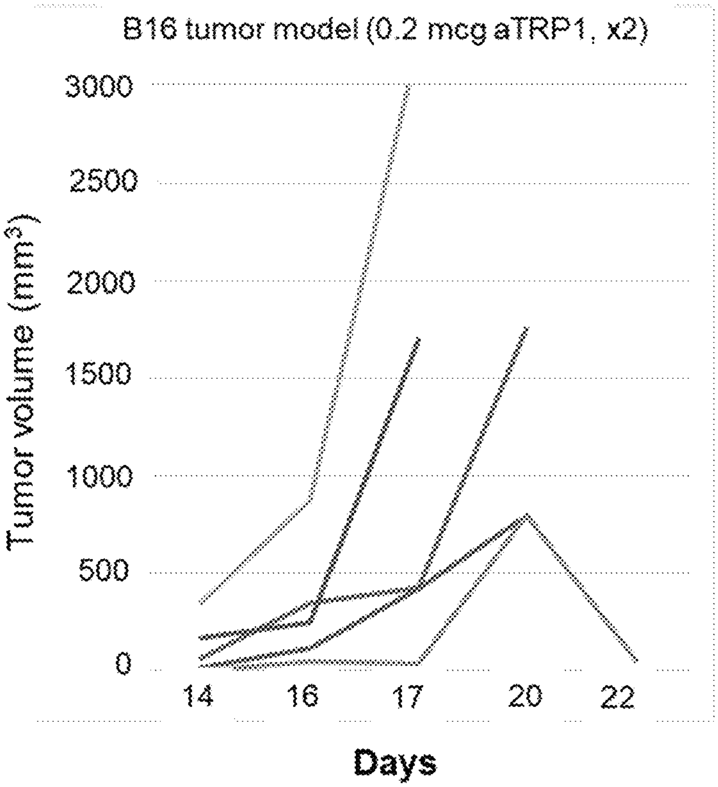
Figure 7C:
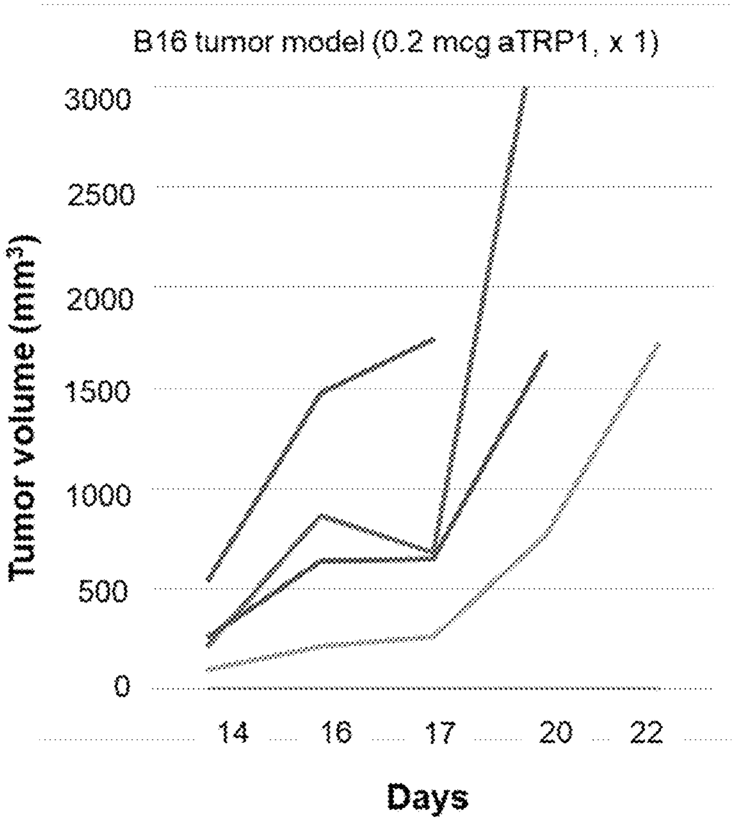
Figure 7D:
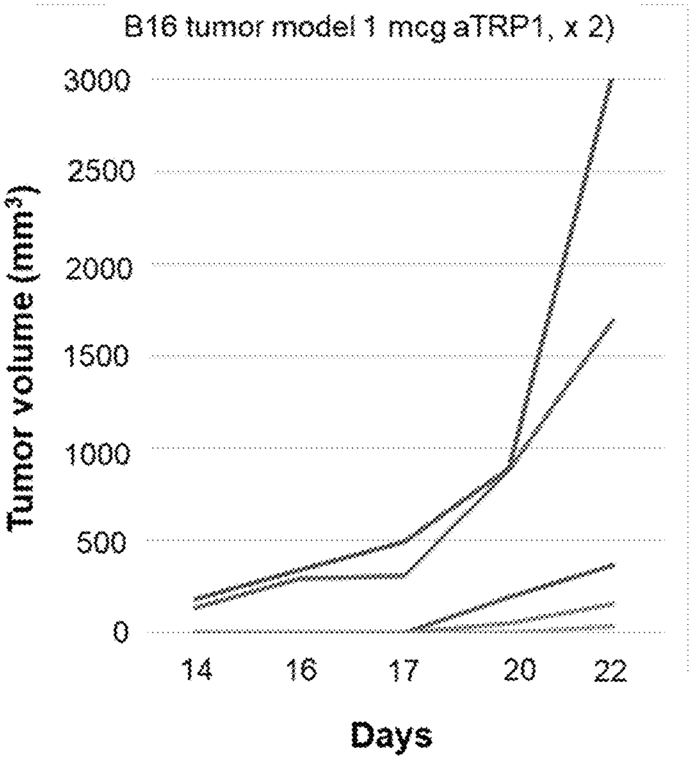
Figure 7E:
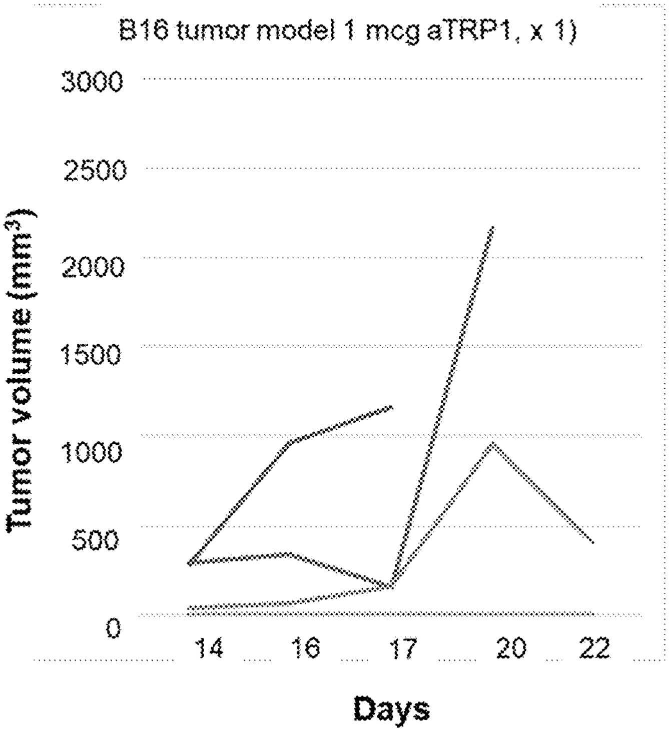
Figure 7F:
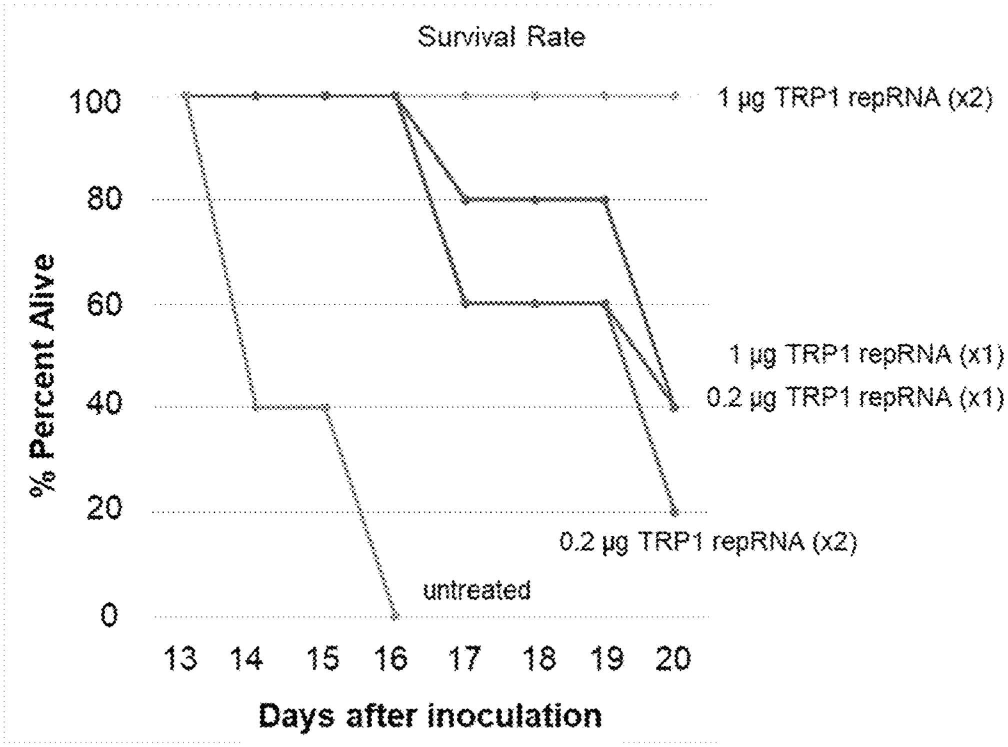

Blood was collected 2 weeks after completion of immunization regimen, serum prepared for each animal and antibodies binding TRP 1 assessed by ELISA. n=5 per group. Results are presented as tumor growth for each individual animal (FIGS. 7A-7E) and as survival (FIG. 7F). Immunization with TRP1-expressing replicon limits B16 outgrowth in a dose dependent manner.

Next, the therapeutic efficacy of TRP-1 repRNA vaccinations were investigated at various doses and treatment regimens as shown in Table 12.

TABLE 12

| Immunization groups and conditions. | | | | | | |
|---|---|---|---|---|---|---|
| | Group # | N | Lipid Carrier | Dose (RNA) | Regimen | Time/Tumor size |
| Arm 1 | 1 | 5 | NP-1 | 0 μg (control) | — | — |
| | 2 | 5 | NP-1 | 1 μg | Weekly | Pre-palpable (day 3) |
| | 3 | 5 | NP-1 | 5 μg | Weekly | Pre-palpable (day 3) |
| | 4 | 5 | NP-1 | 1 μg | Weekly | Palpable 3-4 mm (day 7-9) |
| | 5 | 5 | NP-1 | 5 μg | Weekly | Palpable 3-4 mm (day 7-9) |
| Arm 2 | 6 | 5 | NP-1 | 5 μg scrambled RNA (control) | Weekly | — |
| | 7 | 5 | NP-1 | 1 μg | Single | Pre-palpable (day 3) |
| | 8 | 5 | NP-1 | 5 μg | Single | Pre-palpable (day 3) |
| | 9 | 5 | NP-1 | 1 μg | Single | Palpable 3-4 mm (day 7-9) |
| | 10 | 5 | NP-1 | 5 μg | Single | Palpable 3-4 mm (day 7-9) |

Figure 8:
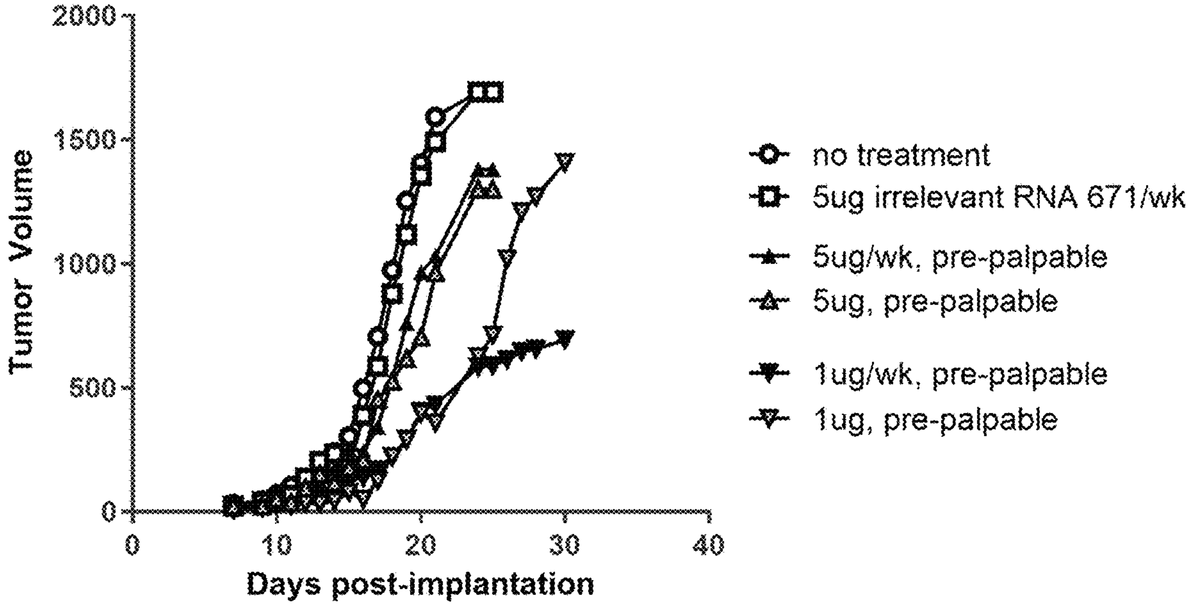
FIG. 8 shows mean B16 tumor volume over time in untreated and lipid carrier+repRNA-TRP-1 vaccinated mice. X-axis: days post-implantation, Y-axis: tumor volume ($mm^3$).
Figure 9:
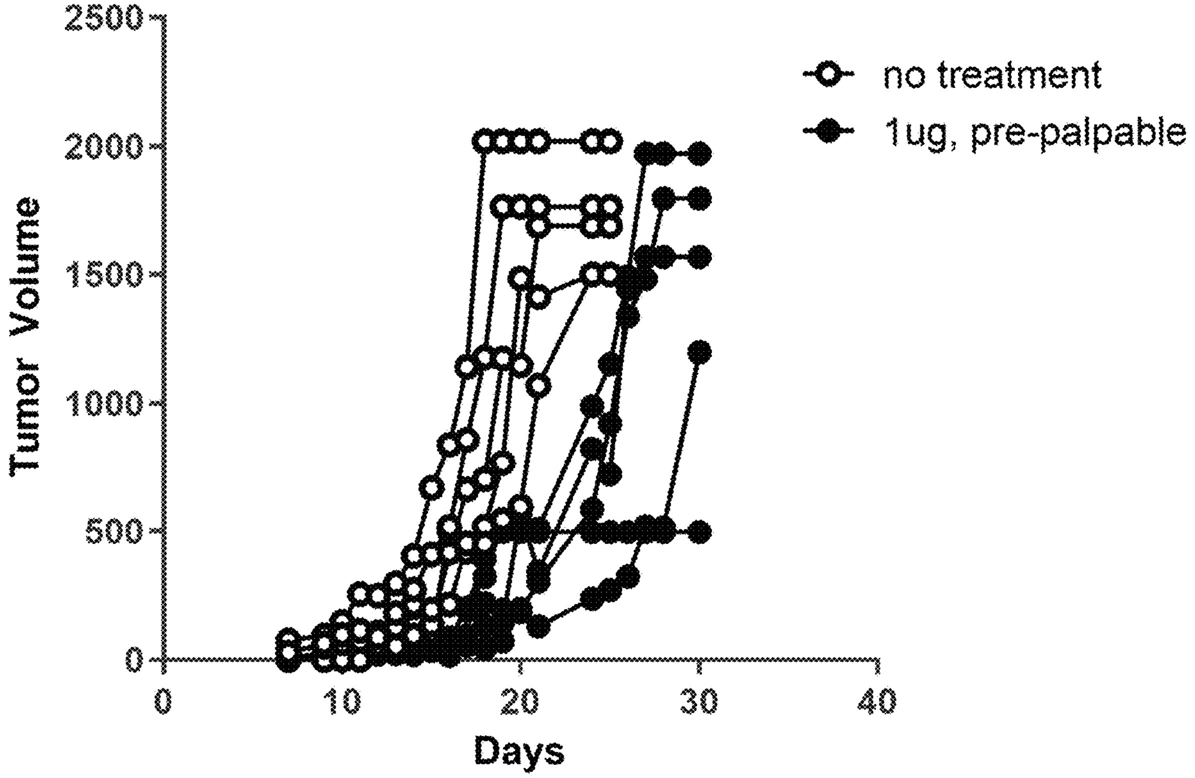
FIG. 9 shows individual tumor growth for control (scramble RNA) and animals that were prophylactically administered lipid carrier+1 μg TRP-1 repRNA vaccines prior to melanoma cell injection.

Female C57BL/6 mice were immunized by intramuscular injection of repRNA-TRP1 at either a 1 mcg or 5 mcg dose, beginning on day 3 (pre-palpable) or day 7 (post-palpable) after tumor cell implantation. Immunizations were repeated weekly thereafter. n=5 per group. Results are presented as mean tumor growth for each group (FIG. 8) and for each individual animal (FIG. 9). The results further confirm that immunization with TRP1-expressing replicon limits B 16 outgrowth.

Example 19: MAGE-A1 Replicon Induces Antigen-Specific T Cells

A lipid nanoparticle carrier and a MAGE-A1 RNA replicon were generated (SEQ ID NO: 75). The amino acid sequence of the MAGE-A1 is SEQ ID NO: 77.

Figure 10A:
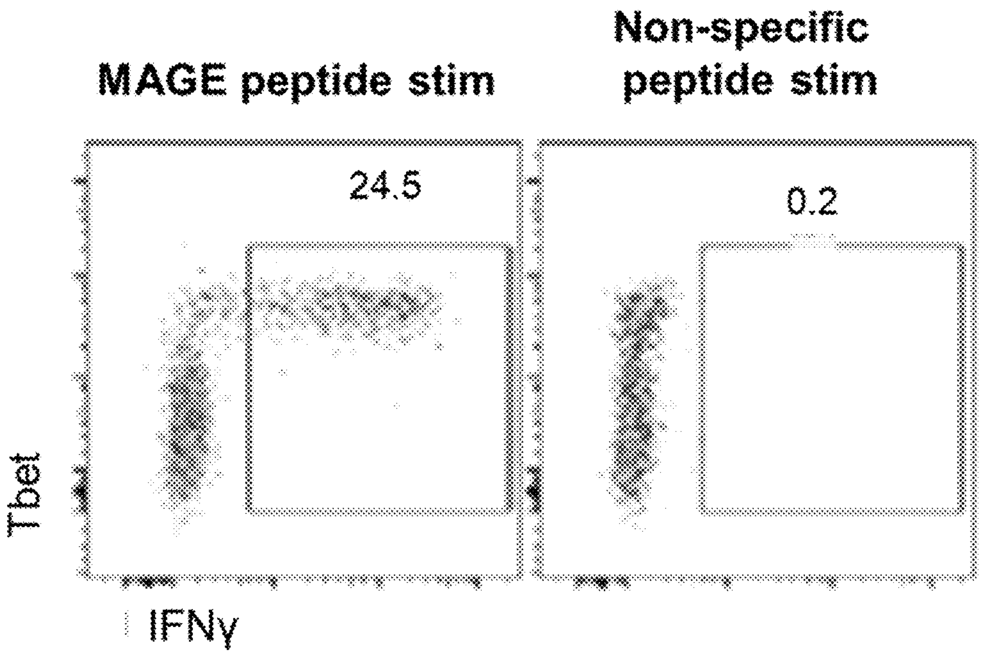
FIGS. 10A-10D show that immunization with MAGE-expressing replicon induces antigen-specific T cells.
Figure 10B:
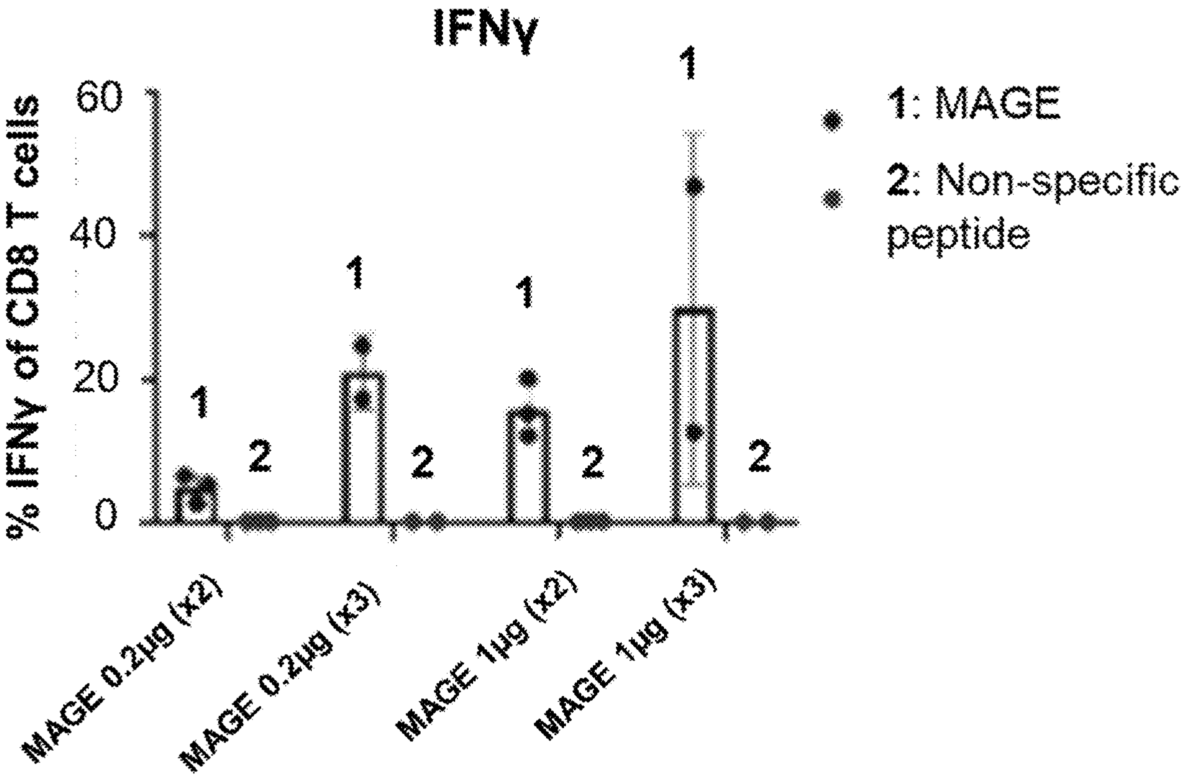
Figure 10C:
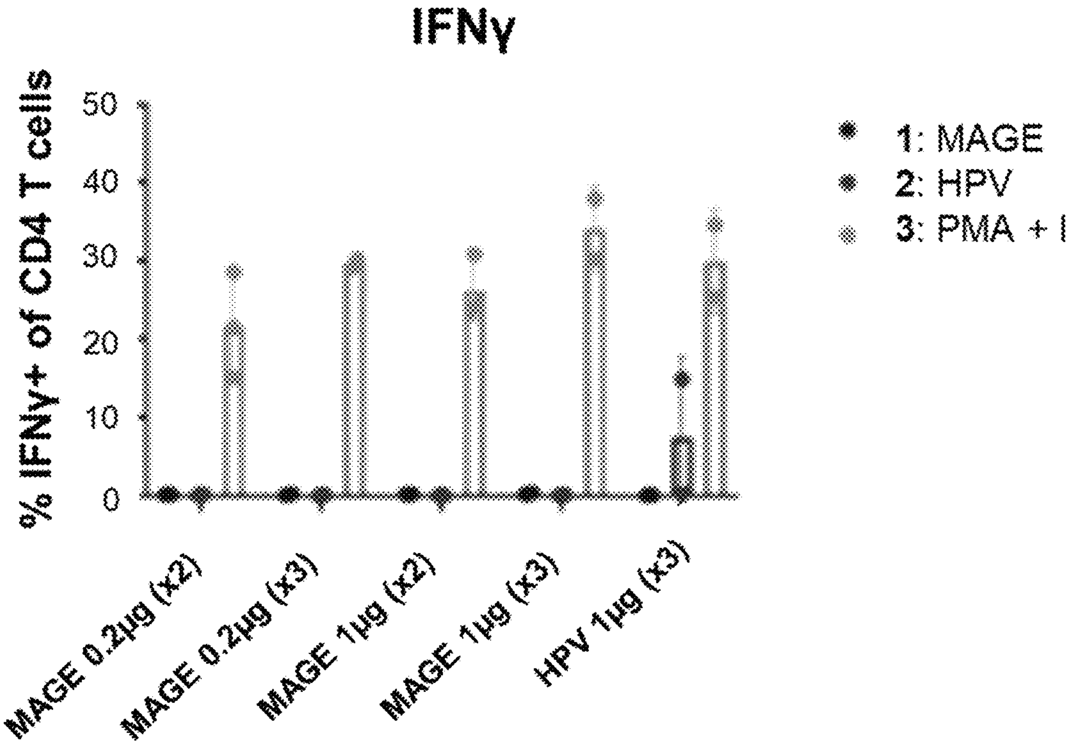
Figure 10D:
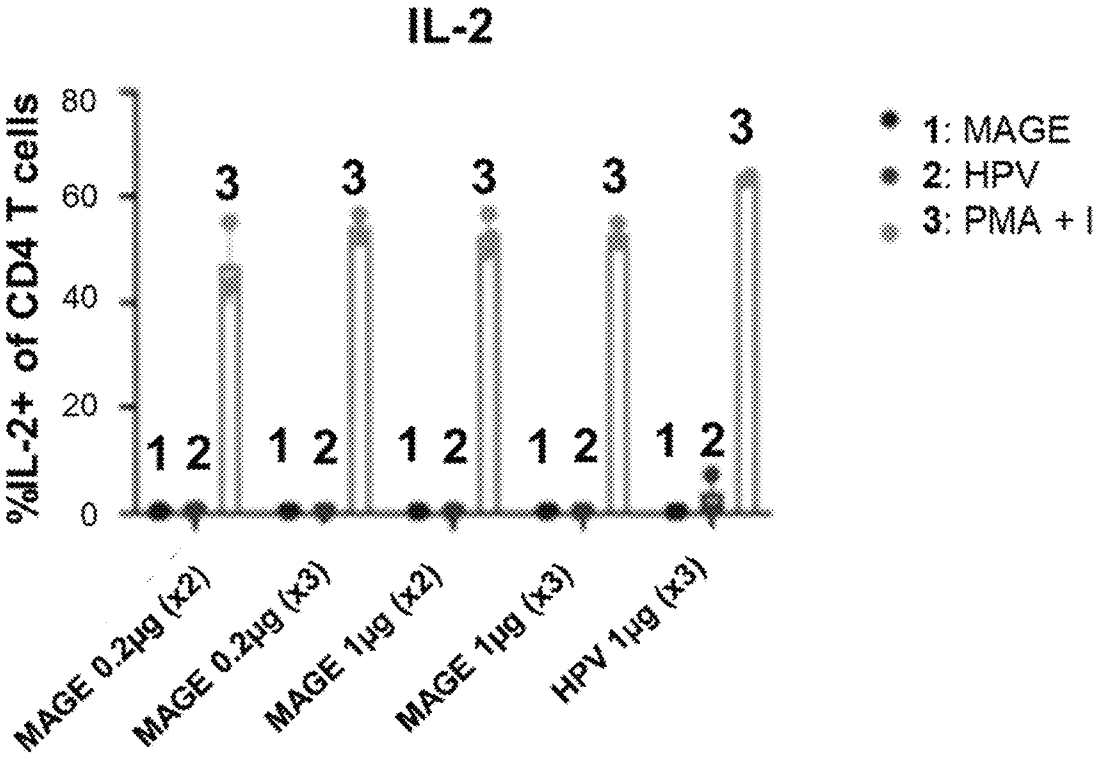

Female C57BL/6 mice were immunized by intramuscular injection of a repRNA-MAGE-A1 at either 0.2 or 1 mcg dose. Immunizations were performed on day 0, 14 and 80 (3×) or day 14 and 80 (2×), then spleens collected on day 91 and single cell suspensions prepared. Cells were then incubated with MAGE-A1 or a HPV E6 (non-specific) peptide pool, and subjected to flow cytometry. CD8 T cells expressing Tbet and producing IFN-gamma (γ) (FIGS. 10A-10B) and CD4 T cells producing IFNγ or IL-2 (FIGS. 10C-10D) are shown. Immunization with MAGE-expressing replicon induces antigen-specific T cells.

Example 20: TRP-1 and MAGE-A3 Combination Therapy Reduces Tumor Volume

A lipid nanoparticle carrier was combined with a MAGE-A3 RNA replicon and a TRP-1 RNA replicon. The amino acid sequence of the TRP-1 is SEQ ID NO: 78 The amino acid sequence of the MAGE-A3 is SEQ ID NO: 87.

B16 subcutaneous melanoma mouse models were used in the assays provided herein according to Example 17. The therapeutic efficacy of TRP-1 and MAGE-A3 repRNA vaccinations were investigated at various doses and treatment regimens as shown in Table 12.

Figure 11A:
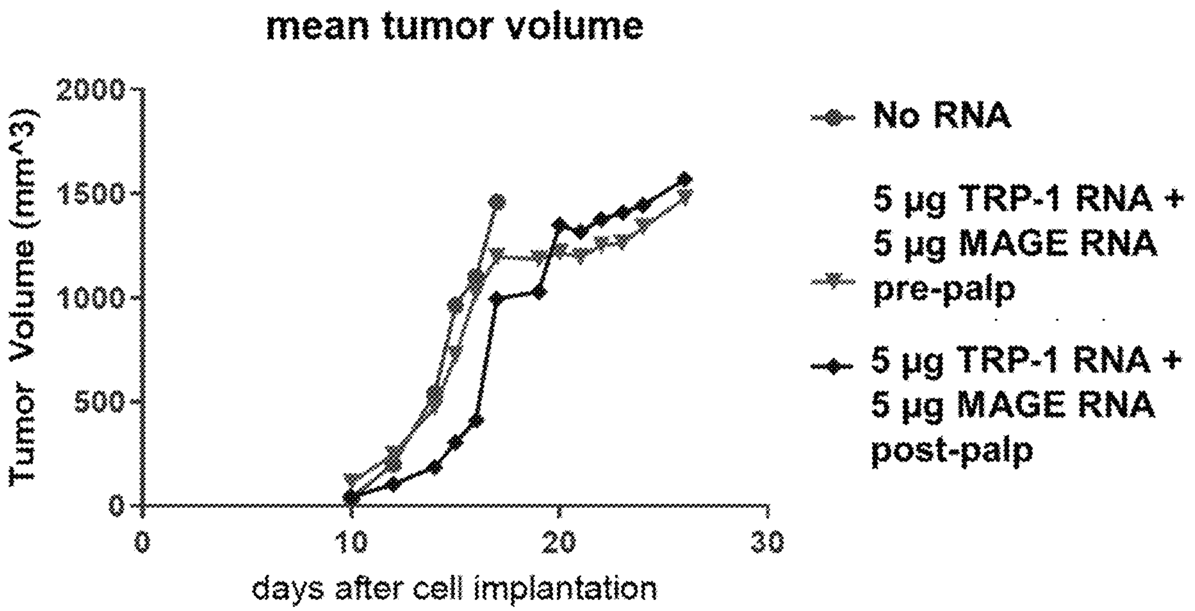
FIGS. 11A-11B show graphs of mean tumor volume and survival of animals immunized with replicons encoding for MAGE-A3 (SEQ ID NO: 87) and TRP1 encoding for (SEQ ID NO: 78).
Figure 11B:
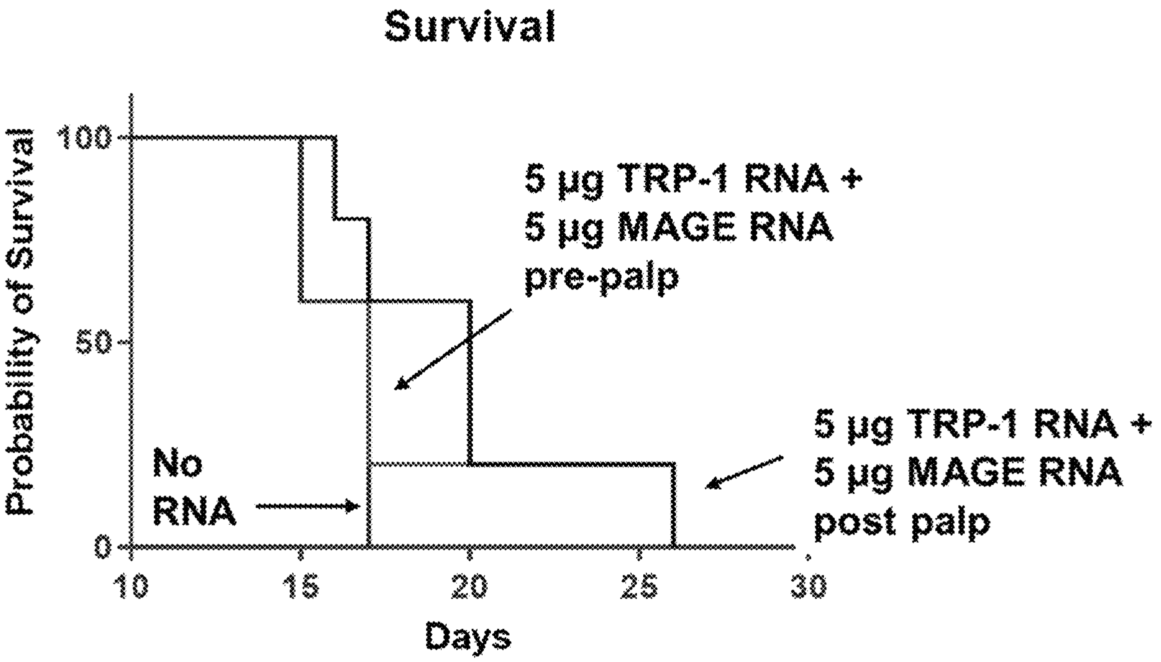

Tumor volume was quantified (FIG. 11A) for control, NP-1+TRP-1+MAGE-A3 pre-palpable animals, and NP-1+TRP-1+MAGE-A3. The probability of survival increased for animals treated with the lipid carrier and TRP-1 and MAGE-A3 encoding repRNAs relative to untreated animals (FIG. 11B).

Example 21: Self-Replicating RNA Prostein Construct

A lipid nanoparticle carrier was combined with a prostein-encoding RNA replicon. The RNA encoding for the prostein protein encodes for an amino acid sequence of SEQ ID NO: 90. The VEEV replicon mRNA backbone sequence is set forth in SEQ ID NO: 71.

SEQUENCES
(MAGE-A1 RNA Encoding Sequence)
SEQ ID NO: 1

```
augccgcuggagcagcgaucccaacauugcaaaccagaggaaggccucgaggcaagaggugaggcccuggggcucguc

ggagcucaggcaccggcaacggaggagcaagaagcggccucuagcagcuccacacucgucgaagugacacucggcgag

gucccccgcugcggaaucucccgauccuccgcaaagcccucaaggggcuuccucccuccccacuacuaugaacuauccg

uuguggagccaaagcuaugaggauuccucaaaccaagaggaggaaggccccuccacauucccggaccucgaaucugag

uuccaggcagcgcucagcaggaaaguggcggaacuuguacaguuuuuguugcuuaaauaccgggcucgggagccaguc

acgaaagccgagauguuaggcagcgugguggguaauuggcaguacuucuuccccgucaucuuuuccaaggcuuccucu

ucuuugcaacucguuuuuggcauagagcuuauggaaguagacccgacaggucaucuuuacauuuuugcaacgugucuc

ggccucaguuaugacgggcugcucggugacaaucaaauuaugccuaaggccggacugcuuaucaucgucuuggcuaua

auugcccgagagggcgacugugcucccgaagagaaaauaugggaggagcucuccgugcuggagguauuugagggaaga

gaagauagcauacugggagacccuaagaaauugcuuacacaacacuuuguacaagagaacuauuuggaguaucgacag

guccccggaucugacccagcauguuaugaguuccuguggggccaagggcacucguagagacgucauaugucaaggug

cugcaccacauggucaaaauaagcggcggcccccacauaagcuacccaccccuccaugaaugguuuugagggagggu
```

-continued gaagaa (TRP-1 RNA Encoding Sequence)
SEQ ID NO: 2
ccacgagagugugccaauauugaggcucugagacgugggguguguugcccagaccugcucccuuccucuggaccgggg acugacccuuguggcucaucaucaggaagaggcagguguguggcugugauugcagacucccgaccccacagccgccau uauccccacgaugguaaagaugaccgagaagccuggccucugagguucuuuaauagaacaugucagugcaaugauaau uucucaggacacaacugugggacuugccguccuggguggagaggagcugcaugcaaccagaaaauucucacagucagg agaaaucuucuagacuuaaguccagaagaaaagagccacuuugucagggccuuggauauggcgaagcgcacaacucac ccucaauuugucauugccacaaggagguuagaagacauacugggaccagauggcaacacaccacaauuugagaacauu uccguuuauaacuacuuuguuuggacacacuauuauucagucaaaaaaaccuuccucgggacaggacaggaaagcuuu ggggauguggauuucucucacgaaggacccgcuuuucucacauggcacagguaccaucugcugcagcuggagagagac augcaggagaugcugcaggagccuucuuucucccuuccuuacuggaauuuugcaacugggaaaaacgucugcgauguc ugcacugaugacuugaugggauccagaagcaacuucgauucuacucuuauaagccccaacucugucuuuucucaaugg agaguggucugugaauccuuggaagaguacgauacccugggaacacuuuguaacagcacugaggguggaccaaucagg agaaacccagcuggaaauguagggagaccagcagugcagcgucuuccugagccacaggaugucacucagugcuuggag guccguguauuugacacaccuccuuuuuauuccaauucuacagacaguuuucgaaauacaguggaagguuacagugcu cccacgggaaaauaugacccugcuguucgaagccuucacaaccuggcccaccucuuccugaauggaacgggaggacaa acccauuugucucccaaugauccuauuuuuguccuccugcacacuuucacugaugcggucuuugacgaauggcuaagg agguauaacgccgauauuucuaccuucccguuggaaaacgcaccuauuggacauaacaggcaauacaacauggugcca uucuggccuccaguuaccaacacagaaauguuuguuacugcuccagacaaucugggauauauguaugaaguucaaugg gggguugcuucuugucugauccguucuagaagcaccaagaaugaagccaaccagccucuccucacugaucacuaucaa cgcuaugcugaggacuaugaggagcucccgaauccuaaccacuccaugguc SEQ ID NOS: 3-47:
See Table 1

SEQ ID NOS: 48-70:
See Table 2

VEEV RNA Sequence
SEQ ID NO: 71:
AUAGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

-continued

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUCCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

-continued

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

-continued

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAG

VEEV RNA polymerase Amino Acid Sequence
(NCBI Accession: AXP98866.1)
SEQ ID NO: 72
RELPVLDSAAFNVECEKKYACNNEYWETEKENPIRLTEENVVNYITKLKGP VEEV RNA polymerase Amino Acid Sequence
(NCBI Accession: AXP98867.1)
SEQ ID NO: 73
TQMRELPVLDSAAENVECFKKYACNNEYWETFKENPIRLTE Polyprotein Amino Acid Sequence
[Venezuelan equine encephalitis virus]
(GenBank: ALE15116.1)
SEQ ID NO: 74:
MKAITARRILQGLGHYLKAEGKVECYRTLHPVPLYSSSVNRAFSSPKVAVEACNAMLKENFPTVASYCIIPEYDAYLD

MIDGASCCLDTASFCPAKLRSFPKKHSYLEPTIRSAVPSAIQNTLONVLAAATKRNCNVTQMRELPVLDSAAENVECF

KKYACNNEYWKTFKENPIRLTEENVINYITKLKGPKAAALYAKTHNLNMLQDIPMDRFVMDLKRDVKVTPGTKHTEER

PKVQVIQAADPLATAYLCGIHRELVRRLNAVLLPNIHTLEDMSAEDFDAIIAEHFQPGDCVLETDIASFDKSEDDAMA

LTAMMILEDLGVDAELLTLIEAAFGEISSIHLPTKTKFKFGAMMKSGMFLTLFVNTVINIVIASRVLRERLTGSPCAA

FIGDDNIVKGVKSDKLMADRCATWLNMEVKIIDAVVGEKAPYFCGGFILCDSVTGTACRVADPLKRLEKLGKPLAADD

EHDDDRRRALHEESTRWNRVGILPELCKAVESRYETVGTSVIVMAMATLASSVKSFSYLRGAPITLYG

Full-length VEEV + MAGE Antigen Encoding RNA Sequence
SEQ ID NO: 75
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccucccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaaagaauagcuaucaguccaggccuguaug ggaagccuucaggcuaugcugcuacgaugcaccgcgagggauucuugugcugcaaagugacagacacauugaacgggg agagggucucuuuucccgugugcacquaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca -continued uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauaggggguguauggcgugccaggaucaggcaagucuggcaucauuaaaagcgcagucaccaaaaaagauc uagugguggagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag gguggggugaagcaguugcaaauagauuacaaaggcaacgaaauaaugacggcagcugccucucaagggcugacccgua aaggugugguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu -continued uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuagguguggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuauuucuguggaggguuuauuuugugugacuccgugaccggcacag cgugccgugugggcagaccccccuaaaaaggcuguuuaagcuuggcaaaccucuggcagcagacgaugaacaugaugaug acaggagaagggcauugcaugaagagucaacacgcuggaaccgagugggguauucuuucagagcugugcaaggcaguag aaucaagguaugaaaccguaggaacuuccaucauaguuauggccaugacuacucuagcuagcaguguuaaaucauuca gcuaccugagagggggccccuauaacucucuacggcuaaccugaauggacuacgacauagucuaguccgccgccaccAU

GCCGCUGGAGCAGCGAUCCCAACAUUGCAAACCAGAGGAAGGCCUCGAGGCAAGAGGUGAGGCCCUGGGGCUCGUCGG

AGCUCAGGCACCGGCAACGGAGGAGCAAGAAGCGGCCUCUAGCAGCUCCACACUCGUCGAAGUGACACUCGGCGAGGU

CCCCGCUGCGGAAUCUCCCGAUCCUCCGCAAAGCCCUCAAGGGGCUUCCUCCCUCCCCACUACUAUGAACUAUCCGUU

GUGGAGCCAAAGCUAUGAGGAUUCCUCAAACCAAGAGGAGGAAGGCCCCUCCACAUUCCCGGACCUCGAAUCUGAGUU

CCAGGCAGCGCUCAGCAGGAAAGUGGCGGAACUUGUACAGUUUUUGUUGCUUAAAUACCGGGCUCGGGAGCCAGUCAC

GAAAGCCGAGAUGUUAGGCAGCGUGGUGGGUAAUUGGCAGUACUUCUUCCCCGUCAUCUUUUCCAAGGCUUCCUCUUC

UUUGCAACUCGUUUUUGGCAUAGAGCUUAUGGAAGUAGACCCGACAGGUCAUCUUUACAUUUUUGCAACGUGUCUCGG

-continued

CCUCAGUUAUGACGGGCUGCUCGGUGACAAUCAAAUUAUGCCUAAGGCCGGACUGCUUAUCAUCGUCUUGGCUAUAAU

UGCCCGAGAGGGCGACUGUGCUCCCGAAGAGAAAAUAUGGGAGGAGCUCUCCGUGCUGGAGGUAUUUGAGGGAAGAGA

AGAUAGCAUACUGGGAGACCCUAAGAAAUUGCUUACACAACACUUUGUACAAGAGAACUAUUUGGAGUAUCGACAGGU

CCCCGGAUCUGACCCAGCAUGUUAUGAGUUCCUGUGGGGGCCAAGGGCACUCGUAGAGACGUCAUAUGUCAAGGUGCU

GCACCACAUGGUCAAAAUAAGCGGCGGCCCCCACAUAAGCUACCCACCCCUCCAUGAAUGGGUUUUGAGGGAGGGUGA

AGAAugauaaccgcggugucaaaaaccgcguggacgugguuaacaucccugcugggaggaucagccguaauuauuaua auuggcuuggugcuggcuacuauuguggccauguacgugcugaccaaccagaaacauaauugaauacagcagcaauug aaucggauuuuguuuuuaauauuucaaaaaaaaaaaaaaaaaaaaaaaaaaaaaaaaaaaaaaaaaaaaaa Full-length VEEV + TRP-1 Antigen Encoding RNA Sequence
SEQ ID NO: 76
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacquagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacquaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucaugggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguggagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu -continued gucaugcagguacucucagagcgcucauagccauuauaagaccuaaaaaggcagugcucugcggggaucccaaacagu gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacgugugu ugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggguguguggcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca

-continued acccgccaggcguaaauagggugauuacaagagaggaguuugaggcguucguagcacaacaacaaugacgguuugaug
cgggugcauacaucuuuuccuccgacaccggucaagggcauuuacaacaaaaaucaguaaggcaaacggugcuauccg
aagugguguuggagaggaccgaauuggagauuucguaugccccgcgccucgaccaagaaaaagaagaauuacuacgca
agaaauuacaguuaaaucccacaccugcuaacagaagcagauaccaguccaggaagguggagaacaugaaagccauaa
cagcuagacguauucugcaaggccuagggcauuauuugaaggcagaaggaaaaguggagugcuaccgaacccugcauc
cuguuccuuuguauucaucuagugugaaccgugccuuuucaagccccaaggucgcaguggaagccuguaacgccaugu
ugaaagagaacuuuccgacuguggcuucuuacuguauuauuccagaguacgaugccuauuuggacaugguugacggag
cuucaugcugcuuagacacugccaguuuuugcccugcaaagcugcgcagcuuuccaaagaaacacuccuauuuggaac
ccacaauacgaucggcagugccuucagcgauccagaacacgcuccagaacguccuggcagcugccacaaaaagaaauu
gcaaugucacgcaaaugagagaauugcccguauuggauucggcggccuuuaauguggaaugcuucaagaaauaugcgu
guaauaaugaauauugggaaacguuuaaagaaaaccccaucaggcuuacugaagaaaacgugguaaauuacauuacca
aauuaaaaggaccaaaagcugcugcucuuuuugcgaagacacauaauuugaauauguugcaggacauaccaauggaca
gguuuguaauggacuuaaagagagacgugaaagugacuccaggaacaaaacauacugaagaacggcccaagguacagg
ugauccaggcugccgauccgcuagcaacagcguaucugugcggaauccaccgagagcugguuaggagauuaaaugcgg
uccugcuuccgaacauucauacacuguuugauaugucggcugaagacuuugacgcuauuauagccgagcacuuccagc
cuggggauuguguucuggaaacugacaucgcgucguuugauaaaagugaggacgacgccauggcucugaccgcguuaa
ugauucuggaagacuuagguguggacgcagagcuguugacgcugauugaggcggcuuucggcgaaauuucaucaauac
auuugcccacuaaaacuaaauuuaaauucggagccaugaugaaaucuggaauguuccucacacuguuugugaacacag
ucauuaacauuguaaucgcaagcagaguguugagagaacggcuaaccggaucaccaugugcagcauucauuggagaug
acaauaucgugaaaggagucaaaucggacaaauuaauggcagacaggugcgccaccugguugaauauggaagucaaga
uuauagaugcugugguggggcgagaaagcgccuuauuucuguggaggguuuauuuugugugacuccgugaccggcacag
cgugccguguggcagaccccccuaaaaaggcuguuuaagcuuggcaaaccucuggcagcagacgaugaacaugaugaug
acaggagaagggcauugcaugaagagucaacacgcuggaaccgaguggguauucuuucagagcugugcaaggcaguag
aaucaagguaugaaaccguaggaacuuccaucauaguuauggccaugacuacucuagcuagcaguguuaaaucauuca
gcuaccugagaggggccccuauaacucucuacggcuaaccugaauggacuacgacauagucuaguccgccgccaccAU
GAAAUCUUACAACGUCCUCCCCCUAGCCUAUAUCUCCCUUUUCCUGAUGCUGUUUUAUCAGGUUUGGGCUCAGUUUCC
ACGAGAGUGUGCCAAUAUUGAGGCUCUGAGACGUGGGGUGUGUUGCCCAGACCUGCUCCCUUCCUCUGGACCGGGGAC
UGACCCUUGUGGCUCAUCAUCAGGAAGAGGCAGGUGUGUGGCUGUGAUUGCAGACUCCCGACCCCACAGCCGCCAUUA
UCCCCACGAUGGUAAAGAUGACCGAGAAGCCUGGCCUCUGAGGUUCUUUAAUAGAACAUGUCAGUGCAAUGAUAAUUU
CUCAGGACACAACUGUGGGACUUGCCGUCCUGGGUGGAGAGGAGCUGCAUGCAACCAGAAAAUUCUCACAGUCAGGAG
AAAUCUUCUAGACUUAAGUCCAGAAGAAAAGAGCCACUUUGUCAGGGCCUUGGAUAUGGCGAAGCGCACAACUCACCC
UCAAUUUGUCAUUGCCACAAGGAGGUUAGAAGACAUACUGGGACCAGAUGGCAACACACCACAAUUUGAGAACAUUUC
CGUUUAUAACUACUUUGUUUGGACACACUAUUAUUCAGUCAAAAAAACCUUCCUCGGGACAGGACAGGAAAGCUUUGG
GGAUGUGGAUUUCUCUCACGAAGGACCCGCUUUUCUCACAUGGCACAGGUACCAUCUGCUGCAGCUGGAGAGAGACAU
GCAGGAGAUGCUGCAGGAGCCUUCUUUCUCCCUUCCUUACUGGAAUUUUGCAACUGGGAAAAACGUCUGCGAUGUCUG
CACUGAUGACUUGAUGGGAUCCAGAAGCAACUUCGAUUCUACUCUUAUAAGCCCCAACUCUGUCUUUUCUCAAUGGAG
AGUGGUCUGUGAAUCCUUGGAAGAGUACGAUACCCUGGGAACACUUUGUAACAGCACUGAGGGUGGACCAAUCAGGAG
AAACCCAGCUGGAAAUGUAGGGAGACCAGCAGUGCAGCGUCUUCCUGAGCCACAGGAUGUCACUCAGUGCUUGGAGGU
CCGUGUAUUUGACACACCUCCUUUUUAUUCCAAUUCUACAGACAGUUUUCGAAAUACAGUGGAAGGUUACAGUGCUCC
CACGGGAAAAUAUGACCCUGCUGUUCGAAGCCUUCACAACCUGGCCCACCUCUUCCUGAAUGGAACGGGAGGACAAAC -continued

CCAUUUGUCUCCCAAUGAUCCUAUUUUUGUCCUCCUGCACACUUUCACUGAUGCGGUCUUUGACGAAUGGCUAAGGAG

GUAUAACGCCGAUAUUUCUACCUUCCCGUUGGAAAACGCACCUAUUGGACAUAACAGGCAAUACAACAUGGUGCCAUU

CUGGCCUCCAGUUACCAACACAGAAAUGUUUGUUACUGCUCCAGACAAUCUGGGAUAUAUGUAUGAAGUUCAAUGGCC

AGGUCAGGAGUUUACUGUAUCUGAAAUCAUUACCAUUGCUGUAGUGGCUGCGUUGUUACUUGUAGCUGCCAUUUUCGG

GGUUGCUUCUUGUCUGAUCCGUUCUAGAAGCACCAAGAAUGAAGCCAACCAGCCUCUCCUCACUGAUCACUAUCAACG

CUAUGCUGAGGACUAUGAGGAGCUCCCGAAUCCUAACCACUCCAUGGUCugauaaccgcgguguc aaaaaccgcgugg acgugguuaacaucccugcugggaggaucagccguaauuauuauaaauuggcuuggugcuggcuacuauuguggccaug uacgugcugaccaaccagaaacauaaauugaauacagcagcaauuggcaagcugcuuacauagaacucgcggcgauugg aaaaaaaaaaaaaaaaaaaaaaaaaaaaaaaaaaaaa MAGE-A1 Amino Acid Sequence
SEQ ID NO: 77
MPLEQRSQHCKPEEGLEARGEALGLVGAQAPATEEQEAASSSSTLVEVTLGEVPAAESPDPPQSPQGASSLPTTMNYP

LWSQSYEDSSNQEEEGPSTFPDLESEFQAALSRKVAELVQFLLLKYRAREPVTKAEMLGSVVGNWQYFFPVIFSKASS

SLQLVFGIELMEVDPTGHLYIFATCLGLSYDGLLGDNQIMPKAGLLIIVLAIIAREGDCAPEEKIWEELSVLEVFEGR

EDSILGDPKKLLTQHFVQENYLEYRQVPGSDPACYEFLWGPRALVETSYVKVLHHMVKISGGPHISYPPLHEWVLREG

EE

TRP-1 Amino Acid Sequence
SEQ ID NO: 78
MKSYNVLPLAYISLFLMLFYQVWAQFPRECANIEALRRGVCCPDLLPSSGPGTDPCGSSSGRGRCVAVIADSRPHSRH

YPHDGKDDREAWPLRFFNRTCQCNDNFSGHNCGTCRPGWRGAACNQKILTVRRNLLDLSPEEKSHFVRALDMAKRTTH

PQFVIATRRLEDILGPDGNTPQFENISVYNYFVWTHYYSVKKTFLGTGQESFGDVDESHEGPAFLTWHRYHLLQLERD

MQEMLQEPSFSLPYWNFATGKNVCDVCTDDLMGSRSNEDSTLISPNSVFSQWRVVCESLEEYDTLGTLCNSTEGGPIR

RNPAGNVGRPAVQRLPEPQDVTQCLEVRVEDTPPFYSNSTDSFRNTVEGYSAPTGKYDPAVRSLHNLAHLFLNGTGGQ

THLSPNDPIFVLLHTFTDAVEDEWLRRYNADISTFPLENAPIGHNRQYNMVPFWPPVTNTEMFVTAPDNLGYMYEVQW

PGQEFTVSEIITIAVVAALLLVAAIFGVASCLIRSRSTKNEANQPLLTDHYQRYAEDYEELPNPNHSMV

DNA Sequence Encoding SEAP
SEQ ID NO: 79
tcgcgcgtttcggtgatgacggtgaaaacctctgacacatgcagctcccggagacggtcacagcttgtctgtaagcgg atgccgggagcagacaagcccgtcagggcgcgtcagcgggtgttggcgggtgtcggggctggcttaactatgcggcat cagagcagattgtactgagagtgcaccatatgcggtgtgaaataccgcacagatgcgtaaggagaaaataccgcatca gattggctattggccattgcatacgttgtatccatatcataatatgtacatttatattggctcatgtccaacattacc gccatgttgacattgattattgactagttattaatagtaatcaattacggggtcattagttcatagcccatatatgga gttccgcgttacataacttacggtaaatggcccgcctggctgaccgcccaacgacccccgcccattgacgtcaataat gacgtatgttcccatagtaacgccaatagggactttccattgacgtcaatgggtggagtatttacggtaaactgccca cttggcagtacatcaagtgtatcatatgccaagtacgccccctattgacgtcaatgacggtaaatggcccgcctggca ttatgcccagtacatgaccttatgggactttcctacttggcagtacatctacgtattagtcatcgctattaccatggt gatgcggttttggcagtacatcaatgggcgtggatagcggtttgactcacggggatttccaagtctccaccccattga cgtcaatgggagtttgttttggcaccaaaatcaacgggactttccaaaatgtcgtaacaactccgccccattgacgca aatgggcggtaggcgtgtacggtgggaggtctatataagcagagctcgtttagtgaaccgtcagatcgcctggagacg ccatccacgctgttttgacctccatagaagacaccgggaccgatccagcctccgcggccgggaacggtgcattggaac gcggattccccgtgccaagagtgacgtaagtaccgcctatagactctataggcacacccctttggctcttatgcatgc tatactgtttttggcttggggcctatacacccccgcttccttatgctataggtgatggtatagcttagcctataggtg tgggttattgaccattattgaccactcccctattggtgacgatactttccattactaatccataacatggctctttgc cacaactatctctattggctatatgccaatactctgtccttcagagactgacacggactctgtatttttacaggatgg -continued ggtcccatttattatttacaaattcacatatacaacaacgccgtcccccgtgcccgcagtttttattaaacatagcgt gggatctccacgcgaatctcgggtacgtgttccggacatgggctcttctccggtagcggcggagcttccacatccgag ccctggtcccatgcctccagcggctcatggtcgctcggcagctccttgctcctaacagtggaggccagacttaggcac agcacaatgcccaccaccaccagtgtgccgcacaaggccgtggcggtagggtatgtgtctgaaaatgagcgtggagat tgggctcgcacggctgacgcagatggaagacttaaggcagcggcagaagaagatgcaggcagctgagttgttgtattc tgataagagtcagaggtaactcccgttgcggtgctgttaacggtggagggcagtgtagtctgagcagtactcgttgct gccgcgcgcgccaccagacataatagctgacagactaacagactgttcctttccatgggtcttttctgcagtcaccgt cgtcgacaagcttcctgcatgctgctgctgctgctgctgctgggcctgaggctacagctctccctgggcatcatccca gttgaggaggagaacccggacttctggaaccgcgaggcagccgaggccctgggtgccgccaagaagctgcagcctgca cagacagccgccaagaacctcatcatcttcctgggcgatgggatgggggtgtctacggtgacagctgccaggatccta aaagggcagaagaaggacaaactggggcctgagataccccctggccatggaccgcttcccatatgtggctctgtccaag acatacaatgtagacaaacatgtgccagacagtggagccacagccacggcctacctgtgcggggtcaagggcaacttc cagaccattggcttgagtgcagccgcccgctttaaccagtgcaacacgacacgcggcaacgaggtcatctccgtgatg aatcgggccaagaaagcagggaagtcagtgggagtggtaaccaccacacgagtgcagcacgcctcgccagccggcacc tacgcccacacggtgaaccgcaactggtactcggacgccgacgtgcctgcctcggcccgccaggaggggtgccaggac atcgctacgcagctcatctccaacatggacattgacgtgatcctaggtggaggccgaaagtacatgtttcgcatggga accccagaccctgagtacccagatgactacagccaaggtgggaccaggctggacgggaagaatctggtgcaggaatgg ctggcgaagcgccagggtgcccggtatgtgtggaaccgcactgagctcatgcaggcttccctggacccgtctgtgacc catctcatgggtctctttgagcctggagacatgaaatacgagatccaccgagactccacactggacccctccctgatg gagatgacagaggctgccctgcgcctgctgagcaggaacccccgcggcttcttcctcttcgtggagggtggtcgcatc gaccatggtcatcatgaaagcagggcttaccgggcactgactgagacgatcatgttcgacgacgccattgagagggcg ggccagctcaccagcgaggaggacacgctgagcctcgtcactgccgaccactcccacgtcttctccttcggaggctac cccctgcgagggagctccatcttcgggctggcccctggcaaggcccgggacaggaaggcctacacggtcctcctatac ggaaacggtccaggctatgtgctcaaggacggcgcccggccggatgttaccgagagcgagagcgggagccccgagtat cggcagcagtcagcagtgcccctggacgaagagacccacgcaggcgaggacgtggcggtgttcgcgcgcggcccgcag gcgcacctggttcacggcgtgcaggagcagaccttcatagcgcacgtcatggccttcgccgcctgcctggagccctac accgcctgcgacctggcgcccccgccggcaccaccgacgccgcgcacccgggttaacccgtggtcagatccagatcc agatcacttctggctaataaaagatcagagctctagagatctgtgtgttggtttttgtggatctgctgtgccttcta gttgccagccatctgttgtttgcccctcccccgtgccttccttgaccctggaaggtgccactcccactgtcctttcct aataaaatgaggaaattgcatcgcattgtctgagtaggtgtcattctattctggggggtggggtggggcagcacagca agggggaggattgggaagacaatagcaggcatgctggggatgcggtgggctctatgggtacctctctctctctctctc tctctctctctctctctctctcggtacctctctctctctctctctctctctctctctctctctcggtaccag gtgctgaagaattgacccggttcctcctgggccagaaagaagcaggcacatccccttctctgtgacacaccctgtcca cgcccctggttcttagttccagccccactcataggacactcatagctcaggagggctccgccttcaatcccacccgct aaagtacttggagcggtctctccctccctcatcagcccaccaaaccaaacctagcctccaagagtgggaagaaattaa agcaagataggctattaagtgcagagggagagaaaatgcctccaacatgtgaggaagtaatgagagaaatcatagaat ttcttccgcttcctcgctcactgactcgctgcgctcggtcgttcggctgcggcgagcggtatcagctcactcaaaggc ggtaatacggttatccacagaatcaggggataacgcaggaaagaacatgtgagcaaaaggccagcaaaaggccaggaa ccgtaaaaaggccgcgttgctggcgtttttccataggctccgcccccctgacgagcatcacaaaaatcgacgctcaag tcagaggtggcgaaacccgacaggactataaagataccaggcgtttccccctggaagctccctcgtgcgctctcctgt -continued tccgaccctgccgcttaccggatacctgtccgcctttctcccttcgggaagcgtggcgctttctcaatgctcacgctg taggtatctcagttcggtgtaggtcgttcgctccaagctgggctgtgtgcacgaaccccccgttcagcccgaccgctg cgccttatccggtaactatcgtcttgagtccaacccggtaagacacgacttatcgccactggcagcagccactggtaa caggattagcagagcgaggtatgtaggcggtgctacagagttcttgaagtggtggcctaactacggctacactagaag gacagtatttggtatctgcgctctgctgaagccagttaccttcggaaaaagagttggtagctcttgatccggcaaaca aaccaccgctggtagcggtggtttttttgtttgcaagcagcagattacgcgcagaaaaaaaggatctcaagaagatcc tttgatcttttctacggggtctgacgctcagtggaacgaaaactcacgttaagggattttggtcatgagattatcaaa aaggatcttcacctagatccttttaaattaaaaatgaagttttaaatcaatctaaagtatatatgagtaaacttggtc tgacagttaccaatgcttaatcagtgaggcacctatctcagcgatctgtctatttcgttcatccatagttgcctgact ccggggggggggggcgctgaggtctgcctcgtgaagaaggtgttgctgactcataccaggcctgaatcgccccatcat ccagccagaaagtgagggagccacggttgatgagagctttgttgtaggtggaccagttggtgattttgaacttttgct ttgccacggaacggtctgcgttgtcgggaagatgcgtgatctgatccttcaactcagcaaaagttcgatttattcaac aaagccgccgtcccgtcaagtcagcgtaatgctctgccagtgttacaaccaattaaccaattctgattagaaaaactc atcgagcatcaaatgaaactgcaatttattcatatcaggattatcaataccatatttttgaaaaagccgtttctgtaa tgaaggagaaaactcaccgaggcagttccataggatggcaagatcctggtatcggtctgcgattccgactcgtccaac atcaatacaacctattaatttcccctcgtcaaaaataaggttatcaagtgagaaatcaccatgagtgacgactgaatc cggtgagaatggcaaaagcttatgcatttctttccagacttgttcaacaggccagccattacgctcgtcatcaaaatc actcgcatcaaccaaaccgttattcattcgtgattgcgcctgagcgagacgaaatacgcgatcgctgttaaaaggaca attacaaacaggaatcgaatgcaaccggcgcaggaacactgccagcgcatcaacaatattttcacctgaatcaggata ttcttctaatacctggaatgctgttttcccggggatcgcagtggtgagtaaccatgcatcatcaggagtacggataaa atgcttgatggtcggaagaggcataaattccgtcagccagtttagtctgaccatctcatctgtaacatcattggcaac gctacctttgccatgtttcagaaacaactctggcgcatcgggcttcccatacaatcgatagattgtcgcacctgattg cccgacattatcgcgagcccatttatacccatataaatcagcatccatgttggaatttaatcgcggcctcgagcaaga cgtttcccgttgaatatggctcataacaccccttgtattactgtttatgtaagcagacagttttattgttcatgatga tatatttttatcttgtgcaatgtaacatcagagattttgagacacaacgtggctttcccccccccccccattattgaag catttatcagggttattgtctcatgagcggatacatatttgaatgtatttagaaaaataaacaaataggggttccgcg cacatttccccgaaaagtgccacctgacgtctaagaaaccattattatcatgacattaacctataaaaataggcgtat cacgaggccctttcgtc Vector Backbone RNA Sequence 1
SEQ ID NO: 80
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacquagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug -continued ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucaugggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacgugucguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccgggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucaugguggugcgag -continued gggauauugccacggccaccgaaggagugauuauaaaugcugcuaacagcaaaggacaaccuggcggagggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugcggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuagcuuggcaaaccucuggcagcagacgaugaacaugaugaugaca -continued ggagaagggcauugcaugaagagucaacacgcuggaaccgaguggguauucuuucagagcugugcaaggcaguagaau caagguaugaaaccguaggaacuuccaucauaguuauggccaugacuacucuagcuagcaguguuaaaucauucagcu accugagaggggccccuauaacucucuacggcuaaccugaauggacuacgacauagucuaguccgccaagXugauaac cgcggugucaaaaaccgcguggacgugguuaacaucccugcugggaggaucagccguaauuauuauaauuggcuuggu gcuggcuacuauuguggccauguacgugcugaccaaccagaaacauaauugaauacagcagcaauuggcaagcugcuu acauagaacucgcggcgauuggcaugccgccuuaaaauuuuuauuuuauuuuuucuuuucuuuuccgaaucggauuuu guuuuuaauauuucaaaaaaaaaaaaaaaaaaaaaaaaaaaaaaaaaaaaaa Vector Backbone RNA Sequence 2
SEQ ID NO: 81
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacquagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu -continued gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggguguguggcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuccaccccgccaggcgugaauagggugga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug -continued cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugguggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuagcuuggcaaaccucuggcagcagacgaugaacaugaugaugaca ggagaagggcauugcaugaagagucaacacgcuggaaccgagugguauucuuucagagcugugcaaggcaguagaau caagguaugaaaccguaggaacuuccaucauaguuauggccaugacuacucuagcuagcaguguuaaaucauucagcu accugagaggggccccuauaacucucuacggcuaaccugaauggacuacgacauagucuaguccgccaag*X*ugauaac cgcggugucaaaaaccgcguggacgugguuaacaucccugcugggaggaucagccguaauuauuauaauuggcuuggu gcuggcuacuauuguggccauguacgugcugaccaaccagaaacauaauugaauacagcagcaauuggcaagcugcuu acauagaacucgcggcgauuggcaugccgccuuaaaauuuuuauuuuauuuuuucuuuucuuuuccgaaucggauuuu guuuuuaauauuucaaaaaaaaaaaaaaaaaaaaaaaaaaaaaaaaaaaaaaaaaaa Vector Backbone RNA Sequence 3
SEQ ID NO: 82
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacquagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug -continued ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucaugggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguga gcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucc gucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggguguguc g -continued gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauucccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaaccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuagguguggacgcagagcuguugacgcugauugaggcggcuuucggcgaaauuucaucaauac auuugcccacuaaaacuaaauuuaaauucggagccaugaugaaaucuggaauguucuccacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuagcuuggcaaaccucuggcagcagacgaugaacaugaugaugaca -continued ggagaagggcauugcaugaagagucaacacgcuggaaccgagugggguauucuuucagagcugugcaaggcaguagaau caagguaugaaaccguaggaacuuccaucauaguuauggccaugacuacucuagcuagcaguguuaaaucauucagcu accugagaggggccccuauaacucucuacggcuaaccugaauggacuacgacauagucuaguccgccaagXuaguaac cgcggugucaaaaaccgcguggacgugguuaacaucccugcugggaggaucagccguaauuauuauaaauuggcuuggu gcuggcuacuauuguggccauguacgugcugaccaaccagaaacauaauugaauacagcagcaauuggcaagcugcuu acauagaacucgcggcgauuggcaugccgccuuaaaauuuuuauuuuauuuuuucuuuucuuuuccgaaucggauuuu guuuuuaauauuucaaaaaaaaaaaaaaaaaaaaaaaaaaaaaaaaaaaaaaaaaaaaa Vector Backbone RNA Sequence 4
SEQ ID NO: 83 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauaggggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu -continued cucgccguugcacuaaaucugugacuucggucgucucaaccuuguuuuacgacaaaaaaaugagaacgacgaauccga
aagagacuaagauugugauugacacuaccggcaguaccaaaccuaagcaggacgaucucauucucacuuguuucagag
ggugggugaagcaguugcaaauagauuacaaaggcaacgaaauaaugacggcagcugccucucaagggcugacccgua
aagguguguaugccguucgguacaaggugaaugaaaauccucuguacgcacccaccucagaacaugugaacguccuac
ugacccgcacggaggaccgcaucguguggaaaacacuagccggcgacccauggauaaaaacacugacugccaaguacc
cugggaauuucacugccacgauagaggaguggcaagcagagcaugaugccaucaugaggcacaucuuggagagaccgg
acccuaccgacgucuuccagaauaaggcaaacguguguugggccaaggcuuuagugccggugcugaagaccgcuggca
uagacaugaccacugaacaauggaacacuguggauuauuuugaaacggacaaagcucacucagcagagauaguauuga
accaacuaugcgugagguucuuuggacucgaucuggacuccggucuauuuucugcacccacuguuccguuauccauua
ggaauaaucacugggauaacuccccgucgccuaacauguacgggcugaauaaagaagugguccgucagcucucucgca
gguacccacaacugccucgggcaguugccacuggaagagucuaugacaugaacacugguacacugcgcaauuaugauc
cgcgcauaaaccuaguaccuguaaacagaagacugccucaugcuuuaguccuccaccauaaugaacacccacagagug
acuuuucuucauucgucagcaaauugaagggcagaacuguccugguggucggggaaaaguuguccgucccaggcaaaa
ugguugacugguugucagaccggccugaggcuaccuucagagcucggcuggauuuaggcaucccaggugaugugccca
aauaugacauaauauuuguuaaugugaggaccccauauaaauaccaucacuaucagcagugugaagaccaugccauua
agcuuagcauguugaccaagaaagcuugucugcaucugaaucccggcggaaccugugucagcauagguuaugguuacg
cugacagggccagcgaaagcaucauuggugcuauagcgcggcaguucaaguuucccggguaugcaaaccgaaauccu
cacuugaagagacggaaguucuguuuguauucauugguacgaucgcaaggcccguacgcacaauccuuacaagcuuu
caucaaccuugaccaacauuuauacagguuccagacuccacgaagccggaugugcacccucauaucaugguggugcgag
gggauauugccacggccaccgaaggagugauuauaaaugcugcuaacagcaaaggacaaccuggcggaggggugugcg
gagcgcuguauaagaaauucccggaaagcuucgauuuacagccgaucgaaguaggaaaagcgcgacuggucaaaggug
cagcuaaacauaucauucaugccguaggaccaaacuucaacaaaguuucggagguugaaggugacaaacaguuggcag
aggcuuaugaguccaucgcuaagauugucaacgauaacaauuacaagucaguagcgauuccacuguuguccaccggca
ucuuuuccgggaacaaagaucgacuaacccaaucauugaaccauuugcugacagcuuuagacaccacugaugcagaug
uagccauauacugcagggacaagaaaugggaaaugacucucaaggaagcaguggcuaggagagaagcaguggaggaga
uaugcauauccgacgacucuucagugacagaaccugaugcagagcuggugagggugcauccgaagaguucuuuggcug
gaaggaagggcuacagcacaagcgauggcaaaacuuucucauauuuggaagggaccaaguuucaccaggcggccaagg
auauagcagaaauuaaugccauguggcccguugcaacggaggccaaugagcagguaugcauguauauccucggagaaa
gcaugagcaguauuaggucgaaaugccccgucgaagagucggaagccuccacaccaccuagcacgcugccuugcuugu
gcauccaugccaugacuccagaaagaguacagcgccuaaaagccucacguccagaacaaauuacugugugcucauccu
uuccauugccgaaguauagaaucacuggugugcagaagauccaaugcucccagccuauauuguucucaccgaaagugc
cugcguauauucauccaaggaaguaucucguggaaacaccaccgguagacgagacuccggagccaucggcagagaacc
aauccacagaggggacaccugaacaaccaccacuuauaaccgaggaugagaccaggacuagaacgccugagccgauca
ucaucgaagaggaagaagaggauagcauaaguuugcugucagauggcccgacccaccaggugcugcaagucgaggcag
acauucacgggccgcccucuguaucuagcucauccugguccauuccucaugcauccgacuuugauguggacaguuuau
ccauacuugacacccuggagggagcuagcgugaccagcggggcaacgucagccgagacuaacucuuacuucgcaaaga
guauggaguuucuggcgcgaccggugccugcgccucgaacaguauucaggaacccuccacaucccgcuccgcgcacaa
gaacaccgucacuugcacccagcagggccugcucgagaaccagccuaguuuccaccccgccaggcgugaauagggu ga
ucacuagagaggagcucgaggcgcuuaccccgucacgcacuccuagcaggucggucucgagaaccagccuggucucca
acccgccaggcguaaauagggugauuacaagagaggaguuugaggcguucguagcacaacaacaaugacgguuugaug -continued cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacucuauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcuguggugggcgagaaagcgccuuagcuuggcaaaccucuggcagcagacgaugaacaugaugaugaca ggagaagggcauugcaugaagagucaacacgcuggaaccgaguggguauucuuucagagcugugcaaggcaguagaau caagguaugaaaccguaggaacuuccaucauaguuauggccaugacuacucuagcuagcaguguuaaaucauucagcu accugagaggggccccuauaacucucuacggcuaaccugaauggacuacgacauagucuaguccgccaag*X*ugauaac cgcggugucaaaaaccgcguggacgugguuaacaucccugcugggaggaucagccguaauuauuauaauuggcuuggu gcuggcuacuauuguggccauguacgugcugaccaaccagaaacauaauugaauacagcagcaauuggcaagcugcuu acauagaacucgcggcgauuggcaugccgccuuaaaauuuuuauuuuauuuuuucuuuucuuuuccgaaucggauuuu guuuuuaauauuucaaaaaaaaaaaaaaaaaaaaaaaaaaaaaaaaaaaaaaaaaaaaaa Vector Backbone RNA Sequence 5
SEQ ID NO: 84
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacquagagggaugucccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaaagaauagcuaucaguccaggccuguaug ggaagccuucaggcuaugcugcuacgaugcaccgcgagggauucuugugcugcaaagugacagacacauugaacgggg -continued agagggucucuuuucccgugugcacguaugugccagcuacauugugugaccaaaugacuggcauacuggcaacagaug
ucagugcggacgacgcgcaaaaacugcugguugggcucaaccagcguauagucgucaacggucgcacccagagaaaca
ccaauaccaugaaaaauuaccuuuugcccguaguggcccaggcauuugcuaggugggcaaaggaauauaaggaagauc
aagaagaugaaaggccacuaggacuacgagauagacaguuagucauggggguguuguugggcuuuuagaaggcacaaga
uaacaucuauuuauaagcgcccggauacccaaaccaucaucaaagugaacagcgauuucccacucauucgugcugccca
ggauaggcaguaacacauuggagaucgggcugagaacaagaaucaggaaaauguuagaggagcacaaggagccgucac
cucucauuaccgccgaggacguacaagaagcuaagugcgcagccgaugaggcuaaggaggugcgugaagccgaggagu
ugcgcgcagcucuaccaccuuuggcagcugauguugaggagcccacucuggaggcagacgucgacuugauguuacaag
aggcuggggccggcucaguggagacaccucguggcuugauaaagguuaccagcuacgauggcgaggacaagaucggcu
cuuacgcugugcuuucuccgcaggcuguacucaagagugaaaaauuaucuugcauccacccucucgcugaacaaguca
uagugauaacacacucuggccgaaaagggcguuaugccguggaaccauaccaugguaaaguaguggugccagagggac
augcaauacccguccaggacuuucaagcucugagugaaagugccaccauuguguacaacgaacgugaguucguaaaca
gguaccugcaccauauugccacacauggaggagcgcugaacacugaugaagaauauuacaaaacugucaagcccagcg
agcacgacggcgaauaccuguacgacaucgacaggaaacagugcgucaagaaagaacuagucacugggcuagggcuca
caggcgagcugguggauccucccuuccaugaauucgccuacgagagucugagaacacgaccagccgcuccuuaccaag
uaccaaccauagggguguauggcgugccaggaucaggcaagucuggcaucauuaaaagcgcagucaccaaaaaagauc
uaguggugagcgccaagaaagaaaacugugcagaaauuauaagggacgucaagaaaaugaaagggcuggacgucaaug
ccagaacuguggacucagugcucuugaauggaugcaaacaccccguagagacccuguauauugacgaagcuuuugcuu
gucaugcagguacucucagagcgcucauagccauuauaagaccuaaaaaggcagugcucugcggggaucccaaacagu
gcgguuuuuuuaacaugaugugccugaaagugcauuuuaaccacgagauuugcacacaagucuucccacaaaagcaucu
cucgccguugcacuaaaucugugacuucggucgucucaaccuuguuuuacgacaaaaaaaugagaacgacgaauccga
aagagacuaagauugugauugacacuaccggcaguaccaaaccuaagcaggacgaucucauucucacuuguuucagag
ggugggugaagcaguugcaaauagauuacaaaggcaacgaaauaaugacggcagcugccucucaagggcugacccgua
aaggugugugaugccguucgguacaaggugaaugaaaauccucuguacgcacccaccucagaacaugugaacguccuac
ugacccgcacggaggaccgcaucguguggaaaacacuagccggcgacccauggauaaaaacacugacugccaaguacc
cugggaauuucacugccacgauagaggaguggcaagcagagcaugaugccaucaugaggcacaucuuggagagaccgg
acccuaccgacgucuuccagaauaaggcaaacgugugguugggccaaggcuuuagugccggugcugaagaccgcuggca
uagacaugaccacugaacaauggaacacuguggauuauuuugaaacggacaaagcucacucagcagagauaguauuga
accaacuaugcgugagguucuuuggacucgaucuggacuccggucuauuuucugcacccacuguuccguuauccauua
ggaauaaucacugggauaacuccccgucgccuaacauguacgggcugaauaaagaagugguccgucagcucucucgca
gguacccacaacugccucgggcaguugccacuggaagagucuaugacaugaacacugguacacugcgcaauuaugauc
cgcgcauaaaccuaguaccuguaaacagaagacugccucaugcuuuaguccuccaccauaaugaacacccacagagug
acuuuucuucauucgucagcaaauugaagggcagaacugcccugguggucggggaaaaguuguccgucccaggcaaaa
ugguugacugguugucagaccggccugaggcuaccuucagagcucggcuggauuuaggcaucccaggugaugugccca
aauaugacauaauauuuguuaaugugaggaccccauauaaauaccaucacuaucagcagugugaagaccaugccauua
agcuuagcauguugaccaagaaagcuugucugcaucugaaucccggcggaaccugugucagcauagguuaugguuacg
cugacagggccagcgaaagcaucauugguguuauagcgcggcaguucaaguuuucccggguaugcaaaccgaaauccu
cacuugaagagacggaaguucuguuuguauucauuggguacgaucgcaaggcccguacgcacaauccuuacaagcuuu
caucaaccuugaccaacauuuauacagguuccagacuccacgaagccggaugugcacccucauaucauguggugcgag
gggauauugccacggccaccgaaggagugauuauaaaugcugcuaacagcaaaggacaaccuggcggagggguguguug -continued gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugg acgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcuguggugggcgagaaagcgccuuauuucuguggaggguuuauuuugugugacuccgugaccggcacag cgugccguguggcagacccccuaaaaaggcuguuuaagcuuggcaaaccucuggcagcagacgaugaacaugaugaug -continued acaggagaagggcauugcaugaagagucaacacgcuggaaccgaguggguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgccaagXugau aaccgcggugucaaaaaccgcguggacgugguuaacaucccugcugggaggaucagccguaauuauuauaauuggcuu ggugcuggcuacuauuguggccauguacgugcugaccaaccagaaacauaauugaauacagcagcaauuggcaagcug cuuacauagaacucgcggcgauuggcaugccgccuuaaaauuuuuauuuuauuuuuucuuuucuuuucchaauchhau uuuhuuuuuaauauuucaaaaaaaaaaaaaaaaaaaaaaaaaaaaaaaaaaaaaaaaaaa Vector Backbone RNA Sequence 6
SEQ ID NO: 85
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu -continued gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aaggugugaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucguccagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucauguggugcgag gggauauugccacggccaccgaaggagugauuauaaaugcugcuaacagcaaaggacaaccuggcggaggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggug a ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug -continued cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuugcccugcaaagcugcgcagcuuuccaaaagaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccacc ugguggauuguguucuggaaacugacaucgcgucguuugauaaaagugaggacgacgccauggcucugaccgcguuaa ugauucuggaagacuuaggugguggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggcgagaaagcgccuuagcuuggcaaaccucuggcagcagacgaugaacaugaugaugaca ggagaagggcauugcaugaagagucaacacgcuggaaccgagugguauucuuucagagcugugcaaggcaguagaau caagguaugaaaccguaggaacuuccaucauaguuauggccaugacuacucuagcuagcaguguuaaaucauucagcu accugagaggggccccuauaacucucuacggcuaaccugaauggacuacgacauagucuaguccgccaag*AUG**UUUCU*

*GCUCACAACCAAACGCACU**AUG**UUUGUUUUCCUCGUGCUGCUCCCUUUGGUAAGUUCU*CAGUGUGUAAACCUGAGAAC

ACGAACCCAGUUGCCUCCAGCUUAUACCAACUCAUUUACUCGCGGAGUAUAUUAUCCCGAUAAGGUCUUUAGAAGUAG

CGUGUUGCACUCUACACAGGAUCUGUUCUUGCCCUUCUUUAGUAACGUUACCUGGUUUCAUGCAAUACAUGUGAGCGG

AACAAAUGGAACAAAAAGAUUUGACAAUCCAGUGCUUCCAUUUAAUGAUGGGGUUUACUUUGCCAGUAUCGAAAAGUC

AAACAUAAUCCGGGGGUGGAUCUUUGGAACCACUUUGGACUCUAAGACACAGUCUCUCCUCAUAGUAAACAACGCCAC

CAAUGUUGUCAUAAAAGUAUGCGAAUUUCAGUUUUGCAACGAUCCCUUUCUCGACGUGUAUUACCAUAAGAAUAAUAA

AUCCUGGAUGGAGUCUGGGGUUUAUAGUAGUGCUAAUAAUUGCACUUUCGAAUACGUGUCCCAACCAUUCCUCAUGGA

CCUUGAGGGCAAACAGGGGAAUUUUAAAAACUUGCGCGAAUUUGUCUUUAAGAAUAUCGACGGAUACUUUAAGAUCUA

UAGUAAACACACUCCUAUCAACCUCGUUCGGGAUCUUCCCCAAGGCUUUUCUGCUCUCGAACCCCUCGUAGACUUGCC

AAUUGGGAUAAAUAUCACUCGCUUUCAAACUUUGCUUGCCCUCCACAGGAGCUACCUGACACCCGGCGACUCUUCUUC

UGGUUUGACCGCCGGCGCCGCUGCCUAUUAUGUUGGUUACCUUCAGCCACGAACAUUCUUGCUCAAGUAUAACGAGAA

UGGCACCAUUACCGACGCCGUCGAUUGUGCAUUGGAUCCCUUGUCUGAAACAAAAUGUACCUUGAAGUCCUUUACCGU

AGAGAAAGGCAUAUACCAGACUUCCAACUUCCGAGUUCAGCCUACAGAAUCCAUCGUACGAUUUCCCAACAUCACAAA

CCUCUGCCCUUUCGGUGAAGUAUUUAAUGCUACACGCUUCGCUUCAGUCUAUGCCUGGAAUAGGAAGCGCAUAUCAAA

UUGCGUGGCCGAUUAUUCAGUCCUCUAUAAUAGCGCAUCCUUCAGUACUUUCAAGUGCUACGGCGUUUCCCCCACCAA

ACUCAAUGAUCUUUGCUUCACCAACGUCUAUGCUGACAGUUUUGUCAUACGAGGCGACGAAGUACGCCAGAUUGCCCC

CGGGCAGACAGGUAAUAUUGCUGAUUAUAAUUAUAAACUCCCAGAUGACUUUACUGGAUGCGUCAUAGCCUGGAAUUC

-continued

CAACAAUCUAGAUUCCAAGGUUGGUGGGAAUUAUAAUUACCGUUAUCGACUGUUCAGAAAGAGUAACUUGAAACCAUU

UGAGAGAGACAUAUCCACCGAGAUUUACCAGGCAGGCAGUAAGCCUUGUAACGGCGUUGAGGGAUUUAACUGCUAUUU

UCCUUUGCAAUCCUAUGGCUUUCAACCAACAAACGGGGUUGGCUAUCAACCCUAUCGAGUGGUUGUCCUCAGCUUUGA

ACUUUUGCACGCUCCCGCCACAGUCUGCGGACCAAAAAAGAGUACAAAUCUUGUCAAGAAUAAGUGCGUAAAUUUCAA

UUUCAAUGGCCUUACAGGAACAGGCGUGCUGACUGAGUCAAACAAGAAUUUCCUGCCAUUUCAGCAGUUUGGGCGGGA

UAUAGCAGACACAACUGACGCUGUACGCGAUCCUCAGACUUUGGAGAUCUUGGACAUCACUCCCUGUUCUUUCGGAGG

GGUAUCUGUCAUCACCCCCGGAACUAAUACAUCAAAUCAGGUCGCUGUGUUGUACCAAGGUGUCAACUGCACAGAAGU

CCCCGUUGCUAUACACGCAGACCAGCUCACCCCCACAUGGCGGGUGUACUCAACUGGCUCAAACGUAUUCCAGACCAG

AGCUGGGUGCUUGAUCGGUGCUGAACACGUGAACAAUAGCUAUGAAUGCGAUAUUCCCAUCGGUGCCGGGAUCUGCGC

UAGCUAUCAGACACAGACCAAUUCCCGCAGGCGGGCUCGCUCUGUAGCAUCCCAGUCUAUUAUUGCCUACACUAUGUC

AUUGGGCGCCGAGAAUAGCGUCGCAUAUUCAAAUAAUUCUAUUGCAAUACCCACCAACUUCACAAUCUCCGUAACUAC

AGAAAUACUUCCAGUUUCCAUGACAAAGACAUCAGUGGAUUGUACAAUGUAUAUAUGCGGAGAUUCCACAGAAUGUUC

AAAUUUGCUCUUGCAGUACGGCUCCUUCUGCACCCAGCUCAACAGGGCACUUACAGGUAUUGCUGUCGAACAGGACAA

GAACACACAAGAAGUCUUCGCCCAAGUCAAACAGAUAUACAAAACUCCUCCCAUAAAGGAUUUUGGCGGCUUCAACUU

UAGUCAGAUCCUCCCAGACCCUUCAAAACCAUCUAAACGAUCAUUUAUUGAAGAUCUGCUGUUCAACAAGGUCACUCU

UGCCGAUGCUGGAUUCAUUAAGCAAUACGGUGACUGCCUUGGUGAUAUUGCUGCCCGAGAUCUGAUCUGUGCCCAGAA

AUUCAACGGGCUCACUGUACUCCCUCCACUGCUCACAGACGAAAUGAUUGCACAGUACACAAGUGCCCUGUUGGCAGG

CACAAUCACUAGCGGCUGGACCUUUGGCGCAGGUGCAGCACUCCAAAUACCUUUUGCCAUGCAGAUGGCCUAUCGGUU

UAAUGGGAUAGGCGUGACUCAAAAUGUCCUCUACGAAAACCAAAAGUUGAUAGCUAACCAAUUCAAUUCAGCAAUCGG

GAAGAUACAGGAUUCACUGUCUAGUACUGCUAGUGCCCUUGGUAAGCUGCAGAACGUUGUCAACCAGAAUGCUCAAGC

UCUGAAUACAUUGGUUAAGCAGCUCUCUAGUAAUUUUGGGGCCAUCUCUUCAGUACUUAAUGAUAUUUUGAGCCGAUU

GGACCCACCUGAAGCUGAAGUACAGAUCGACAGGCUGAUAACAGGCCGGCUCCAAUCCCUCCAAACAUACGUGACACA

ACAACUCAUACGCGCAGCCGAAAUCCGAGCCAGCGCUAACCUGGCAGCUACCAAGAUGUCAGAAUGCGUUCUGGGCCA

GAGUAAACGCGUAGAUUUCUGCGGGAAAGGGUACCACCUGAUGUCCUUUCCACAAUCUGCACCUCACGGGGUCGUCUU

UUUGCAUGUAACAUACGUACCCGCACAAGAGAAGAAUUUUACUACCGCUCCUGCCAUCUGUCAUGACGGGAAAGCUCA

UUUUCCUCGCGAAGGUGUGUUUGUAUCUAAUGGUACACAUUGGUUUGUCACACAGCGGAAUUUCUAUGAACCCCAGAU

CAUUACAACUGACAACACUUUUGUUUCCGGGAAUUGUGACGUGGUCAUAGGAAUCGUAAAUAACACUGUAUAUGAUCC

CCUCCAACCAGAGCUGGACUCUUUUAAAGAAGAACUGGAUAAAUAUUUCAAGAACCACACAAGUCCCGACGUGGACCU

UGGGGACAUAAGUGGUAUUAACGCAUCUGUGGUUAACAUUCAAAAGGAAAUCGACAGACUCAACGAGGUGGCCAAAAA

CCUGAACGAAAGCUUGAUAGAUCUCCAGGAGUUGGGCAAGUAUGAACAGUACAUUAAAUGGCCAUGGUACAUAUGGCU

UGGCUUUAUCGCUGGCCUUAUCGCCAUCGUAAUGGUUACAAUCAUGCUGUGCUGCAUGACCUCCUGCUGUUCUUGUUU

GAAAGGGUGUUGUUCUUGUGGUAGUUGUUGCAAGUUUGACGAAGAUGAUUCCGAACCUGUUCUUAAGGGGGUAAAGCU

UCACUAUACAUGAuaaccgcggugucaaaaaccgcguggacgugguuaacaucccugcugggaggaucagccguaauu auuauaauuggcuuggugcuggcuacuauuguggccauguacgugcugaccaaccagaaacauaauugaauacagcag caauuggcaagcugcuuacauagaacucgcggcgauuggcaugccgccuuaaaauuuuuauuuuauuuuuucuuuucu uuuccgaaucggauuuuguuuuuaauauuucaaaaaaaaaaaaaaaaaaaaaaaaaaaaaaaaaaaaaaaaaaaaaaa Vector Backbone RNA Sequence 7
SEQ ID NO: 86
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc -continued cggacagauuguauaaguaugcaacuaagcugaagaaaaacuguaaggaaauaacugauaaggaauuggacaagaaaa
ugaaggagcuggccgccgucaugagcgacccugaccuggaaacugagacuaugugccuccacgacgacgagucguguc
gcuacgaagggcaagucgcuguuuaccaggauguauacgcgguugacggaccgacaagucucuaucaccaagccaaua
agggaguuagagucgccuacuggauaggcuuugacaccaccccuuuuauguuuaagaacuuggcuggagcauauccau
cauacucuaccaacugggccgacgaaaccguguuaacggcucguaacauaggccuaugcagcucugacguuauggagc
ggucacquagagggauguccauucuuagaaagaaguauuugaaaccauccaacaauguucuauucucuguuggcucga
ccaucuaccacgagaagagggacuuacugaggagcuggcaccugccgucuguauuucacuuacguggcaagcaaaauu
acacaugucggugugagacuauaguuaguugcgacggguacgucguuaaaagaauagcuaucaguccaggccuguaug
ggaagccuucaggcuaugcugcuacgaugcaccgcgagggauucuugugcugcaaagugacagacacauugaacgggg
agagggucucuuuucccgugugcacguaugugccagcuacauugugugaccaaaugacuggcauacuggcaacagaug
ucagugcggacgacgcgcaaaaacugcugguugggcucaaccagcguauagucgucaacggucgcacccagagaaaca
ccaauaccaugaaaaauuaccuuuugcccguaguggcccaggcauuugcuaggugggcaaaggaauauaaggaagauc
aagaagaugaaaggccacuaggacuacgagauagacaguuagucaugggguguuguugggcuuuuagaaggcacaaga
uaacaucuauuuauaagcgcccggauacccaaaccaucaucaaagugaacagcgauuuccacucauucgugcugccca
ggauaggcaguaacacauuggagaucgggcugagaacaagaaucaggaaaauguuagaggagcacaaggagccgucac
cucucauuaccgccgaggacguacaagaagcuaagugcgcagccgaugaggcuaaggaggugcgugaagccgaggagu
ugcgcgcagcucuaccaccuuuggcagcugauguugaggagcccacucuggaggcagacgucgacuugauguuacaag
aggcuggggccggcucaguggagacaccucguggcuugauaaagguuaccagcuacgauggcgaggacaagaucggcu
cuuacgcugugcuuucuccgcaggcuguacucaagagugaaaaauuaucuugcauccacccucucgcugaacaaguca
uagugauaacacacucuggccgaaaagggcguuaugccguggaaccauaccaugguaaaguaguggugccagagggac
augcaauacccguccaggacuuucaagcucugagugaaagugccaccauuguguacaacgaacgugaguucguaaaca
gguaccugcaccauauugccacacauggaggagcgcugaacacugaugaagaauauuacaaaacugucaagcccagcg
agcacgacggcgaauaccuguacgacaucgacaggaaacagugcgucaagaaagaacuagucacugggcuagggcuca
caggcgagcugguggauccucccuuccaugaauucgccuacgagagucugagaacacgaccagccgcuccuuaccaag
uaccaaccauagggguguauggcgugccaggaucaggcaagucuggcaucauuaaaagcgcagucaccaaaaaagauc
uaguggugagcgccaagaaagaaaacugugcagaaauuauaagggacgucaagaaaaugaaagggcuggacgucaaug
ccagaacuguggacucagugcucuugaauggaugcaaacaccccguagagacccuguauauugacgaagcuuuugcuu
gucaugcagguacucucagagcgcucauagccauuauaagaccuaaaaaggcagugcucugcggggaucccaaacagu
gcgguuuuuuaacaugaugugccugaaagugcauuuuaaccacgagauuugcacacaagucuuccacaaaagcaucu
cucgccguugcacuaaaucugugacuucggucgucucaaccuuguuuuacgacaaaaaaaugagaacgacgaauccga
aagagacuaagauugugauugacacuaccggcaguaccaaaccuaagcaggacgaucucauucucacuuguuucagag
ggugggugaagcaguugcaaauagauuacaaaggcaacgaaauaaugacggcagcugccucucaagggcugacccgua
aaggugugaugccguucgguacaaggugaaugaaaauccucuguacgcacccaccucagaacaugugaacguccuac
ugacccgcacggaggaccgcaucguguggaaaacacuagccggcgacccauggauaaaaacacugacugccaaguacc
cugggaauuucacugccacgauagaggaguggcaagcagagcaugaugccaucaugaggcacaucuuggagagaccgg
acccuaccgacgucuuccagaauaaggcaaacguguguugggccaaggcuuuagugccggugcugaagaccgcuggca
uagacaugaccacugaacaauggaacacuguggauuauuuugaaacggacaaagcucacucagcagagauaguauuga
accaacuaugcgugagguucuuuggacucgaucuggacuccggucuauuuucugcacccacuguuccguuauccauua
ggaauaaucacugggauaacuccccgucgccuaacauguacgggcugaauaaagaaguggucegucagcucucucgca
gguacccacaacugccucgggcaguugccacuggaagagucuaugacaugaacacugguacacugcgcaauuaugauc -continued cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucaugugguggcgag gggauauugccacggccaccgaaggagugauuauaaaugcugcuaacagcaaaggacaaccuggcggagggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg -continued ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcuguggugggcgagaaagcgccuuauuucuguggagguuuuauuuugugugacuccgugaccggcacag cgugccguguggcagaccccuaaaaaggcuguuuaagcuuggcaaaccucuggcagcagacgaugaacaugaugaug acaggagaagggcauugcaugaagagucaacacgcuggaaccgagugguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgccgccacc*X*u aaccgcggugucaaaaaccgcguggacgugguuaacaucccugcugggaggaucagccguaauuauuauaauuggcuu ggugcuggcuacuauuguggccauguacgugcugaccaaccagaaacauaauugaauacagcagcaauuggcaagcug cuuacauagaacucgcggcgauuggcaugccgccuuaaaauuuuuauuuuauuuuuucuuuucuuuuccgaaucggau uuuguuuuuaauauuucaaaaaaaaaaaaaaaaaaaaaaaaaaaaaaaaaaaaaaaaaaaaaa melanoma-associated antigen 3 (MAGE-A3) [*Homo sapiens*]
NCBI Reference Sequence: NP_005353.1
SEQ ID NO: 87
MPLEQRSQHCKPEEGLEARGEALGLVGAQAPATEEQEAASSSSTLVEVTLGEVPAAESPDPPQSPQGASSLPTTMNYP

LWSQSYEDSSNQEEEGPSTFPDLESEFQAALSRKVAELVHFLLLKYRAREPVTKAEMLGSVVGNWQYFFPVIFSKASS

SLQLVFGIELMEVDPIGHLYIFATCLGLSYDGLLGDNQIMPKAGLLIIVLAIIAREGDCAPEEKIWEELSVLEVFEGR

EDSILGDPKKLLTQHFVQENYLEYRQVPGSDPACYEFLWGPRALVETSYVKVLHHMVKISGGPHISYPPLHEWVLREG

EE

RNA encoding for MAGE-A3
SEQ ID NO: 88
Augccgcuggagcagcgaucccaacauugcaaaccagaggaaggccucgaggcaagaggugaggcccuggggcucguc ggagcucaggcaccggcaacggaggagcaagaagcggccucuagcagcucccacacucgucgaagugacacucggcgag guccccgcugcggaaucucccgauccuccgcaaagcccucaaggggcuuccucccucccccacuacuaugaacuauccg uuguggagccaaagcuaugaggauuccucaaaccaagaggaggaaggccccuccacauucccggaccucgaaucugag uuccaggcagcgcucagcaggaaaguggcggaacuuguacaguuuuuguugcuuaaaauaccgggcucgggagccaguc ucuuugcaacucguuuuuggcauagagcuuauggaaguagacccgacaggucaucuuuacauuuuugcaacgugucuc ggccucaguuaugacgggcugcucggugacaaucaaauuaugccuaaggccggacugcuuaucaucgucuuggcuaua auugcccgagagggcgacugugcucccgaagagaaaauaugggaggagcucuccgugcuggagguauuugagggaaga gaagauagcauacugggagacccuaagaaauugcuuacacaacacuuuguacaagagaacuauuuggaguaucgacag guccccggaucugacccagcauguuaugaguuccugugggggccaagggcacucguagagacgucauaugucaaggug cugcaccacaauggucaaaauaagcggcggcccccacauaagcuacccaccccuccaugaaugggguuuugagggagggu gaagaa Full length VEEV + RNA encoding for MAGE-A3
Sequence 89 has been formatted to indicate
the MAGE-A3 encoding sequence (bold).
SEQ ID NO: 89
auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacquaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggaucccucccuuccaugaauucgccuacgagagucugagaacacgaccagccgcuccuuaccaag uaccaaccauaggggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacucccccgucgccuaacauguacgggcugaauaaagaagugguccgucagcucucucgca -continued gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggcgag gggauauugccacggccaccgaaggagugauuauaaaugcugcuaacagcaaaggacaaccuggcggaggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca -continued gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcuguggugggcgagaaagcgccuuauuucuguggaggguuuauuuugugugacuccgugaccggcacag cgugccguguggcagaccccccuaaaaaggcuguuuaagcuuggcaaaccucuggcagcagacgaugaacaugaugaug acaggagaagggcauugcaugaagagucaacacgcuggaaccgaguggguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgcCGCCACCau gccgcuggagcagcgaucccaacauugcaaaccagaggaaggccucgaggcaagaggugaggcccuggggcucgucgg agcucaggcaccggcaacggaggagcaagaagcggccucuagcagcucccacacucgucgaagugacacucggcgaggu ccccgcuggggaaucucccgauccucccgcaaagcccucaaggggcuuccuccccucccccacuacuaugaacuaucguu guggagccaaagcuaugaggauuccucaaaccaagaggaggaaggccccuccacauucccggaccucgaaucugaguu ccaggcagcgcucagcaggaaaguggcggaacuuguacaguuuuuguugcuuaaaauaccgggcucgggagccagucac gaaagccgagauguuaggcagcgugguggguaauuggcaguacuucuuccccgucaucuuuuccaaggcuucccucuuc uuugcaacucguuuuuggcauagagcuuauggaaguagacccgacaggucaucuuuacauuuuugcaacgugucucgg ccucaguuaugacgggcugcucggugacaaucaaauuaugccuaaggccggacugcuuaucaucgucuuggcuauaau ugcccgagagggcgacugugcucccgaagagaaaauaugggaggagcucuccgugcuggagguauuugagggaagaga agauagcauacugggagacccuaagaaauugcuuacacaacacuuuguacaagagaacuauuuggaguaucgacaggu ccccggaucugacccagcauguuaugaguuccugugggggccaagggcacucguagagacgucauaugucaaggugcu gcaccacauggucaaaauaagcggcggcccccacauaagcuacccaccccuccaugaauggguuugagggaggguga agaaUGAuaaccgcggugucaaaaaccgcguggacgugguuaacaucccugcugggaggaucagccguaauuauuaua auuggcuuggugcuggcuacuauuguggccauguacgugcugaccaaccagaaacauaauugaauacagcagcaauug aaucggauuuuguuuuuaauauuucaaaaaaaaaaaaaaaaaaaaaaaaaaaaaaaaaaaaaaaaaaaaaaa Prostein [*Homo sapiens*] AAK54386.1 prostein
[*Homo sapiens*]
SEQ ID NO: 90
MVQRLWVSRLLRHRKAQLLLVNLLTFGLEVCLAAGITYVPPLLLEVGVEEKFMTMVLGIGPVLGLVCVPLLGSASDHW

RGRYGRRRPFIWALSLGILLSLFLIPRAGWLAGLLCPDPRPLELALLILGVGLLDFCGQVCFTPLEALLSDLERDPDH

CRQAYSVYAFMISLGGCLGYLLPAIDWDTSALAPYLGTQEECLFGLLTLIFLTCVAATLLVAEEAALGPTEPAEGLSA

PSLSPHCCPCRARLAFRNLGALLPRLHQLCCRMPRTLRRLFVAELCSWMALMTFTLFYTDFVGEGLYQGVPRAEPGTE

ARRHYDEGVRMGSLGLFLQCAISLVFSLVMDRLVQRFGTRAVYLASVAAFPVAAGATCLSHSVAVVTASAALTGFTES

ALQILPYTLASLYHREKQVELPKYRGDTGGASSEDSLMTSFLPGPKPGAPFPNGHVGAGGSGLLPPPPALCGASACDV

SVRVVVGEPTEARVVPGRGICLDLAILDSAFLLSQVAPSLFMGSIVQLSQSVTAYMVSAAGLGLVAIYFATQVVEDKS

DLAKYSA

SEQUENCE LISTING

Sequence total quantity: 94
SEQ ID NO: 1 moltype = RNA length = 942
FEATURE Location/Qualifiers
source 1..942
mol_type = other RNA
organism = synthetic construct
SEQUENCE: 1
atgccgctgg agcagcgatc ccaacattgc aaaccagagg aaggcctcga ggcaagaggt 60
gaggccctgg ggctcgtcgg agctcaggca ccggcaacgg aggagcaaga agcggcctct 120
agcagctcca cactcgtcga agtgacactc ggcgaggtcc ccgctgcgga atctcccgat 180
cctccgcaaa gccctcaagg ggcttcctcc ctccccacta ctatgaacta tccgttgtgg 240
agccaaagct atgaggattc ctcaaaccaa gaggaggaag gcccctccac attcccggac 300
ctcgaatctg agttccaggc agcgctcagc aggaaagtgg cggaacttgt acagtttttg 360
ttgcttaaat accgggctcg ggagccagtc acgaaagccg agatgttagg cagcgtggtg 420
ggtaattggc agtacttctt ccccgtcatc ttttccaagg cttcctcttc tttgcaactc 480
gtttttggca tagagcttat ggaagtagac ccgacaggtc atctttacat ttttgcaacg 540
tgtctcggcc tcagttatga cgggctgctc ggtgacaatc aaattatgcc taaggccgga 600
ctgcttatca tcgtcttggc tataattgcc cgagagggcg actgtgctcc cgaagagaaa 660
atatgggagg agctctccgt gctggaggta tttgagggaa gagaagatag catactggga 720
gaccctaaga aattgcttac acaacacttt gtacaagaga actatttgga gtatcgacag 780
gtccccggat ctgacccagc atgttatgag ttcctgtggg ggccaagggc actcgtagag 840
acgtcatatg tcaaggtgct gcaccacatg gtcaaaataa gcggcggccc ccacataagc 900
tacccacccc tccatgaatg ggttttgagg gagggtgaag aa 942

SEQ ID NO: 2 moltype = RNA length = 1611
FEATURE Location/Qualifiers
source 1..1611
mol_type = other RNA
organism = synthetic construct
SEQUENCE: 2
atgaaatctt acaacgtcct ccccctagcc tatatctccc ttttcctgat gctgttttat 60
caggtttggg ctcagtttcc acgagagtgt gccaatattg aggctctgag acgtggggtg 120
tgttgcccag acctgctccc ttcctctgga ccggggactg acccttgtgg ctcatcatca 180
ggaagaggca ggtgtgtggc tgtgattgca gactcccgac cccacagccg ccattatccc 240
cacgatggta aagatgaccg agaagcctgg cctctgaggt tctttaatag aacatgtcag 300
tgcaatgata atttctcagg acacaactgt gggacttgcc gtcctgggtg gagaggagct 360
gcatgcaacc agaaaattct cacagtcagg agaaatcttc tagacttaag tccagaagaa 420
aagagccact ttgtcagggc cttggatatg gcgaagcgca caactcaccc tcaatttgtc 480
attgccacaa ggaggttaga agacatactg ggaccagatg gcaacacacc acaatttgag 540
aacatttccg tttataacta ctttgtttgg acacactatt attcagtcaa aaaaaccttc 600
ctcgggacag gacaggaaag ctttggggat gtggatttct ctcacgaagg acccgctttt 660
ctcacatggc acaggtacca tctgctgcag ctggagagag acatgcagga gatgctgcag 720
gagccttctt tctcccttcc ttactggaat tttgcaactg ggaaaaacgt ctgcgatgtc 780
tgcactgatg acttgatggg atccagaagc aacttcgatt ctactcttat aagccccaac 840
tctgtctttt ctcaatggag agtggtctgt gaatccttgg aagagtacga taccctggga 900
acactttgta acagcactga gggtggacca atcaggagaa acccagctgg aaatgtaggg 960
agaccagcag tgcagcgtct tcctgagcca caggatgtca ctcagtgctt ggaggtccgt 1020
gtatttgaca cacctccttt ttattccaat tctacagaca gttttcgaaa tacagtggaa 1080
ggttacagtg ctcccacggg aaaatatgac cctgctgttc gaagccttca caacctggcc 1140
cacctcttcc tgaatggaac gggaggacaa acccatttgt ctcccaatga tcctattttt 1200
gtcctcctgc acactttcac tgatgcggtc tttgacgaat ggctaaggag gtataacgcc 1260
gatatttcta ccttcccgtt ggaaaacgca cctattggac ataacaggca atacaacatg 1320
gtgccattct ggcctccagt taccaacaca gaaatgtttg ttactgctcc agacaatctg 1380
ggatatatgt atgaagttca atggccaggt caggagttta ctgtatctga aatcattacc 1440
attgctgtag tggctgcgtt gttacttgta gctgccattt tcggggttgc ttcttgtctg 1500
atccgttcta gaagcaccaa gaatgaagcc aaccagcctc tcctcactga tcactatcaa 1560
cgctatgctg aggactatga ggagctcccg aatcctaacc actccatggt c 1611

SEQ ID NO: 3 moltype = AA length = 9
FEATURE Location/Qualifiers
source 1..9
mol_type = protein
organism = Homo sapiens
SEQUENCE: 3
KCDICTDEY 9

SEQ ID NO: 4 moltype = AA length = 9
FEATURE Location/Qualifiers
source 1..9
mol_type = protein
organism = Homo sapiens
SEQUENCE: 4
YMDGTMSQV 9

SEQ ID NO: 5 moltype = AA length = 9
FEATURE Location/Qualifiers
source 1..9
mol_type = protein

```
                        organism = Homo sapiens
SEQUENCE: 5
MLLAYLYQL                                                        9

SEQ ID NO: 6            moltype = AA  length = 9
FEATURE                 Location/Qualifiers
source                  1..9
                        mol_type = protein
                        organism = Homo sapiens
SEQUENCE: 6
AFLPWHRLF                                                        9

SEQ ID NO: 7            moltype = AA  length = 9
FEATURE                 Location/Qualifiers
source                  1..9
                        mol_type = protein
                        organism = Homo sapiens
SEQUENCE: 7
SEIWRDIDF                                                        9

SEQ ID NO: 8            moltype = AA  length = 9
FEATURE                 Location/Qualifiers
source                  1..9
                        mol_type = protein
                        organism = Homo sapiens
SEQUENCE: 8
YLEPGPVTA                                                        9

SEQ ID NO: 9            moltype = AA  length = 9
FEATURE                 Location/Qualifiers
source                  1..9
                        mol_type = protein
                        organism = Homo sapiens
SEQUENCE: 9
KTWGQUWQV                                                        9

SEQ ID NO: 10           moltype = AA  length = 9
FEATURE                 Location/Qualifiers
source                  1..9
                        mol_type = protein
                        organism = Homo sapiens
SEQUENCE: 10
ITDQVPFSV                                                        9

SEQ ID NO: 11           moltype = AA  length = 10
FEATURE                 Location/Qualifiers
source                  1..10
                        mol_type = protein
                        organism = Homo sapiens
SEQUENCE: 11
VLYRYGSFSV                                                       10

SEQ ID NO: 12           moltype = AA  length = 10
FEATURE                 Location/Qualifiers
source                  1..10
                        mol_type = protein
                        organism = Homo sapiens
SEQUENCE: 12
LLDGTATLRL                                                       10

SEQ ID NO: 13           moltype = AA  length = 9
FEATURE                 Location/Qualifiers
source                  1..9
                        mol_type = protein
                        organism = Homo sapiens
SEQUENCE: 13
ALLAVGATK                                                        9

SEQ ID NO: 14           moltype = AA  length = 9
FEATURE                 Location/Qualifiers
source                  1..9
                        mol_type = protein
                        organism = Homo sapiens
SEQUENCE: 14
MLGTHTMEV                                                        9

SEQ ID NO: 15           moltype = AA  length = 9
FEATURE                 Location/Qualifiers
source                  1..9
```

```
                        mol_type = protein
                        organism = Homo sapiens
SEQUENCE: 15
LIYRRRLMK                                                            9

SEQ ID NO: 16           moltype = AA  length = 9
FEATURE                 Location/Qualifiers
source                  1..9
                        mol_type = protein
                        organism = Homo sapiens
SEQUENCE: 16
ALNFPGSQK                                                            9

SEQ ID NO: 17           moltype = AA  length = 9
FEATURE                 Location/Qualifiers
source                  1..9
                        mol_type = protein
                        organism = Homo sapiens
SEQUENCE: 17
AAGIGILTV                                                            9

SEQ ID NO: 18           moltype = AA  length = 9
FEATURE                 Location/Qualifiers
source                  1..9
                        mol_type = protein
                        organism = Homo sapiens
SEQUENCE: 18
ILTVILGVL                                                            9

SEQ ID NO: 19           moltype = AA  length = 9
FEATURE                 Location/Qualifiers
source                  1..9
                        mol_type = protein
                        organism = Homo sapiens
SEQUENCE: 19
MSLQRQFLR                                                            9

SEQ ID NO: 20           moltype = AA  length = 9
FEATURE                 Location/Qualifiers
source                  1..9
                        mol_type = protein
                        organism = Homo sapiens
SEQUENCE: 20
SVYDFFVWL                                                            9

SEQ ID NO: 21           moltype = AA  length = 9
FEATURE                 Location/Qualifiers
source                  1..9
                        mol_type = protein
                        organism = Homo sapiens
SEQUENCE: 21
LLGPGRPYR                                                            9

SEQ ID NO: 22           moltype = AA  length = 9
FEATURE                 Location/Qualifiers
source                  1..9
                        mol_type = protein
                        organism = Homo sapiens
SEQUENCE: 22
YLSGANLNL                                                            9

SEQ ID NO: 23           moltype = AA  length = 9
FEATURE                 Location/Qualifiers
source                  1..9
                        mol_type = protein
                        organism = Homo sapiens
SEQUENCE: 23
KIFGSLAFL                                                            9

SEQ ID NO: 24           moltype = AA  length = 10
FEATURE                 Location/Qualifiers
source                  1..10
                        mol_type = protein
                        organism = Homo sapiens
SEQUENCE: 24
VMAGVGSPYV                                                           10

SEQ ID NO: 25           moltype = AA  length = 9
FEATURE                 Location/Qualifiers
```

```
source                  1..9
                        mol_type = protein
                        organism = Homo sapiens
SEQUENCE: 25
IISAVVGIL                                                    9

SEQ ID NO: 26           moltype = AA  length = 9
FEATURE                 Location/Qualifiers
source                  1..9
                        mol_type = protein
                        organism = Homo sapiens
SEQUENCE: 26
LLHETDSAV                                                    9

SEQ ID NO: 27           moltype = AA  length = 9
FEATURE                 Location/Qualifiers
source                  1..9
                        mol_type = protein
                        organism = Homo sapiens
SEQUENCE: 27
ALFDIESKV                                                    9

SEQ ID NO: 28           moltype = AA  length = 9
FEATURE                 Location/Qualifiers
source                  1..9
                        mol_type = protein
                        organism = Homo sapiens
SEQUENCE: 28
EADPTGHSY                                                    9

SEQ ID NO: 29           moltype = AA  length = 9
FEATURE                 Location/Qualifiers
source                  1..9
                        mol_type = protein
                        organism = Homo sapiens
SEQUENCE: 29
SLFRAVITK                                                    9

SEQ ID NO: 30           moltype = AA  length = 9
FEATURE                 Location/Qualifiers
source                  1..9
                        mol_type = protein
                        organism = Homo sapiens
SEQUENCE: 30
SAYGEPRKL                                                    9

SEQ ID NO: 31           moltype = AA  length = 9
FEATURE                 Location/Qualifiers
source                  1..9
                        mol_type = protein
                        organism = Homo sapiens
SEQUENCE: 31
KMVELVHFL                                                    9

SEQ ID NO: 32           moltype = AA  length = 10
FEATURE                 Location/Qualifiers
source                  1..10
                        mol_type = protein
                        organism = Homo sapiens
SEQUENCE: 32
YLOLVFGIEV                                                   10

SEQ ID NO: 33           moltype = AA  length = 9
FEATURE                 Location/Qualifiers
source                  1..9
                        mol_type = protein
                        organism = Homo sapiens
SEQUENCE: 33
EVDPIGHLY                                                    9

SEQ ID NO: 34           moltype = AA  length = 9
FEATURE                 Location/Qualifiers
source                  1..9
                        mol_type = protein
                        organism = Homo sapiens
SEQUENCE: 34
FLWGPRALV                                                    9

SEQ ID NO: 35           moltype = AA  length = 10
```

```
FEATURE                 Location/Qualifiers
source                  1..10
                        mol_type = protein
                        organism = Homo sapiens
SEQUENCE: 35
MEVDPIGHLY                                                     10

SEQ ID NO: 36           moltype = AA  length = 9
FEATURE                 Location/Qualifiers
source                  1..9
                        mol_type = protein
                        organism = Homo sapiens
SEQUENCE: 36
AARAVFLAL                                                      9

SEQ ID NO: 37           moltype = AA  length = 8
FEATURE                 Location/Qualifiers
source                  1..8
                        mol_type = protein
                        organism = Homo sapiens
SEQUENCE: 37
YRPRPRRY                                                       8

SEQ ID NO: 38           moltype = AA  length = 9
FEATURE                 Location/Qualifiers
source                  1..9
                        mol_type = protein
                        organism = Homo sapiens
SEQUENCE: 38
VLPDVFIRC                                                      9

SEQ ID NO: 39           moltype = AA  length = 9
FEATURE                 Location/Qualifiers
source                  1..9
                        mol_type = protein
                        organism = Homo sapiens
SEQUENCE: 39
QLSLLMWIT                                                      9

SEQ ID NO: 40           moltype = AA  length = 9
FEATURE                 Location/Qualifiers
source                  1..9
                        mol_type = protein
                        organism = Homo sapiens
SEQUENCE: 40
SLLMWITQC                                                      9

SEQ ID NO: 41           moltype = AA  length = 10
FEATURE                 Location/Qualifiers
source                  1..10
                        mol_type = protein
                        organism = Homo sapiens
SEQUENCE: 41
ASGPGGGAPR                                                     10

SEQ ID NO: 42           moltype = AA  length = 10
FEATURE                 Location/Qualifiers
source                  1..10
                        mol_type = protein
                        organism = Homo sapiens
SEQUENCE: 42
QDLTMKYQIF                                                     10

SEQ ID NO: 43           moltype = AA  length = 10
FEATURE                 Location/Qualifiers
source                  1..10
                        mol_type = protein
                        organism = Homo sapiens
VARIANT                 1
                        note = E or absent
SEQUENCE: 43
XAYGLDFYIL                                                     10

SEQ ID NO: 44           moltype = AA  length = 9
FEATURE                 Location/Qualifiers
source                  1..9
                        mol_type = protein
                        organism = Homo sapiens
SEQUENCE: 44
```

```
SYLDSGIHF                                                   9

SEQ ID NO: 45          moltype = AA  length = 9
FEATURE                Location/Qualifiers
source                 1..9
                       mol_type = protein
                       organism = Homo sapiens
SEQUENCE: 45
ETVSEQSNV                                                   9

SEQ ID NO: 46          moltype = AA  length = 9
FEATURE                Location/Qualifiers
source                 1..9
                       mol_type = protein
                       organism = Homo sapiens
SEQUENCE: 46
FPSDSWCYF                                                   9

SEQ ID NO: 47          moltype = AA  length = 9
FEATURE                Location/Qualifiers
source                 1..9
                       mol_type = protein
                       organism = Homo sapiens
SEQUENCE: 47
EEKLIVVLF                                                   9

SEQ ID NO: 48          moltype = AA  length = 448
FEATURE                Location/Qualifiers
source                 1..448
                       mol_type = protein
                       organism = synthetic construct
SEQUENCE: 48
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                  448

SEQ ID NO: 49          moltype = AA  length = 450
FEATURE                Location/Qualifiers
source                 1..450
                       mol_type = protein
                       organism = synthetic construct
SEQUENCE: 49
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                450

SEQ ID NO: 50          moltype = AA  length = 453
FEATURE                Location/Qualifiers
source                 1..453
                       mol_type = protein
                       organism = synthetic construct
SEQUENCE: 50
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                            453

SEQ ID NO: 51          moltype = AA  length = 444
FEATURE                Location/Qualifiers
source                 1..444
                       mol_type = protein
                       organism = synthetic construct
SEQUENCE: 51
EVQLLESGGV LVQPGGSLRL SCAASGFTFS NFGMTWVRQA PGKGLEWVSG ISGGGRDTYF  60
ADSVKGRFTI SRDNSKNTLY LQMNSLKGED TAVYYCVKWG NIYFDYWGQG TLVTVSSAST  120
```

```
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 52          moltype = AA  length = 449
FEATURE                Location/Qualifiers
source                 1..449
                       mol_type = protein
                       organism = synthetic construct
SEQUENCE: 52
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 53          moltype = AA  length = 452
FEATURE                Location/Qualifiers
source                 1..452
                       mol_type = protein
                       organism = synthetic construct
SEQUENCE: 53
EVQLLESGGG LVQPGGSLRL SCAVSGFTFN SFAMSWVRQA PGKGLEWVSA ISGSGGGTYY  60
ADSVKGRFTI SRDNSKNTLY LQMNSLRAED TAVYFCAKDK ILWFGEPVFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 54          moltype = AA  length = 443
FEATURE                Location/Qualifiers
source                 1..443
                       mol_type = protein
                       organism = synthetic construct
SEQUENCE: 54
EVQLLQSGPE LEKPGASVMI SCKASGSSFT GYNMNWVRQN IGKSLEWIGA IDPYYGGTSY  60
NQKFKGRATL TVDKSSSTAY MHLKSLTSED SAVYYCVSGM EYWGQGTSVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKR VEPKSCDKTH TCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PGK                                         443

SEQ ID NO: 55          moltype = AA  length = 451
FEATURE                Location/Qualifiers
source                 1..451
                       mol_type = protein
                       organism = synthetic construct
SEQUENCE: 55
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 56          moltype = AA  length = 449
FEATURE                Location/Qualifiers
source                 1..449
                       mol_type = protein
                       organism = synthetic construct
SEQUENCE: 56
EVQLVESGGG LVQPGGSLRL SCAASGFDFS RYWMSWVRQA PGKGLEWIGE INPDSSTINY  60
APSLKDKFII SRDNAKNSLY LQMNSLRAED TAVYYCARPD GNYWYFDVWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
```

```
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 57          moltype = AA  length = 448
FEATURE                Location/Qualifiers
source                 1..448
                       mol_type = protein
                       organism = synthetic construct
SEQUENCE: 57
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 58          moltype = AA  length = 450
FEATURE                Location/Qualifiers
source                 1..450
                       mol_type = protein
                       organism = synthetic construct
SEQUENCE: 58
QVQLVQSGAE VAKPGTSVKL SCKASGYTFT DYWMQWVKQR PGQGLEWIGT IYPGDGDTGY  60
AQKFQGKATL TADKSSKTVY MHLSSLASED SAVYYCARGD YYGSNSLDYW GQGTSVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 59          moltype = AA  length = 449
FEATURE                Location/Qualifiers
source                 1..449
                       mol_type = protein
                       organism = synthetic construct
SEQUENCE: 59
EVQLVESGGD LVQPGRSLRL SCAASGFIFS NYGMSWVRQA PGKGLEWVAT ISSASTYSYY  60
PDSVKGRFTI SRDNAKNSLY LQMNSLRVED TALYYCGRHS DGNFAFGYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 60          moltype = AA  length = 451
FEATURE                Location/Qualifiers
source                 1..451
                       mol_type = protein
                       organism = synthetic construct
SEQUENCE: 60
QVQLQESGPG LVKPSQTLSL TCTVSGGSIS SGDYYWSWIR QPPGKGLEWI GYIYYSGSTD  60
YNPSLKSRVT MSVDTSKNQF SLKVNSVTAA DTAVYYCARV SIFGVGTFDY WGQGTLVTVS  120
SASTKGPSVL PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 61          moltype = AA  length = 440
FEATURE                Location/Qualifiers
source                 1..440
                       mol_type = protein
                       organism = synthetic construct
SEQUENCE: 61
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 62          moltype = AA  length = 449
```

```
FEATURE                 Location/Qualifiers
source                  1..449
                        mol_type = protein
                        organism = synthetic construct
SEQUENCE: 62
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 63           moltype = AA  length = 222
FEATURE                 Location/Qualifiers
source                  1..222
                        mol_type = protein
                        organism = synthetic construct
SEQUENCE: 63
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SSASTKGPSV FPLAPGSSKS TSGTAALGCL VKDYFPEPVT VSWNSGALTS GVHTFPAVLQ  180
SSGLYSLSSV VTVPSSSLGT QTYICNVNHK PSNTKVDKKV EP                     222

SEQ ID NO: 64           moltype = AA  length = 456
FEATURE                 Location/Qualifiers
source                  1..456
                        mol_type = protein
                        organism = synthetic construct
SEQUENCE: 64
QLQLQESGPG LVKPSETLSL TCTVSGGSIN SSSYYWGWLR QSPGKGLEWI GSFFYTGSTY  60
YNPSLRSRLT ISVDTSKNQF SLMLSSVTAA DTAVYYCARQ STYYYGSGNY YGWFDRWDQG  120
TLVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKRVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLTCLVK GFYPSDIAVE WESNGQPENN YKTTPPVLDS DGSFFLYSKL  420
TVDKSRWQQG NVFSCSVMHE ALHNHYTQKS LSLSPG                            456

SEQ ID NO: 65           moltype = AA  length = 220
FEATURE                 Location/Qualifiers
source                  1..220
                        mol_type = protein
                        organism = synthetic construct
SEQUENCE: 65
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK                        220

SEQ ID NO: 66           moltype = AA  length = 446
FEATURE                 Location/Qualifiers
source                  1..446
                        mol_type = protein
                        organism = synthetic construct
SEQUENCE: 66
VQLVQSGVEV KKPGASVKVS CKASGYTFTN YYMYWVRQAP GQGLEWMGGI NPSNGGTNFN  60
EKFKNRVTLT TDSSTTTAYM ELKSLQFDDT AVYYCARRDY RFDMGFDYWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 67           moltype = AA  length = 226
FEATURE                 Location/Qualifiers
source                  1..226
                        mol_type = protein
                        organism = synthetic construct
SEQUENCE: 67
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTH                 226

SEQ ID NO: 68           moltype = AA  length = 446
FEATURE                 Location/Qualifiers
```

```
source                1..446
                      mol_type = protein
                      organism = synthetic construct
SEQUENCE: 68
EVQLVQSGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVT DAFDIWGQGT MVTVSSASTK  120
GPSVLPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 69         moltype = AA  length = 451
FEATURE               Location/Qualifiers
source                1..451
                      mol_type = protein
                      organism = synthetic construct
SEQUENCE: 69
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                               451

SEQ ID NO: 70         moltype = AA  length = 449
FEATURE               Location/Qualifiers
source                1..449
                      mol_type = protein
                      organism = synthetic construct
SEQUENCE: 70
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 71         moltype = RNA  length = 7561
FEATURE               Location/Qualifiers
source                1..7561
                      mol_type = genomic RNA
                      organism = Venezuelan equine encephalitis virus
SEQUENCE: 71
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
```

```
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
```

```
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
g                                                                  7561
```

```
SEQ ID NO: 72           moltype = AA  length = 51
FEATURE                 Location/Qualifiers
source                  1..51
                        mol_type = protein
                        organism = Venezuelan equine encephalitis virus
SEQUENCE: 72
RELPVLDSAA FNVECFKKYA CNNEYWETFK ENPIRLTEEN VVNYITKLKG P           51
```

```
SEQ ID NO: 73           moltype = AA  length = 41
FEATURE                 Location/Qualifiers
source                  1..41
                        mol_type = protein
                        organism = Venezuelan equine encephalitis virus
SEQUENCE: 73
TQMRELPVLD SAAFNVECFK KYACNNEYWE TFKENPIRLT E                     41
```

```
SEQ ID NO: 74           moltype = AA  length = 536
FEATURE                 Location/Qualifiers
source                  1..536
                        mol_type = protein
                        organism = Venezuelan equine encephalitis virus
SEQUENCE: 74
MKAITARRIL QGLGHYLKAE GKVECYRTLH PVPLYSSSVN RAFSSPKVAV EACNAMLKEN  60
FPTVASYCII PEYDAYLDMI DGASCCLDTA SFCPAKLRSF PKKHSYLEPT IRSAVPSAIQ  120
NTLQNVLAAA TKRNCNVTQM RELPVLDSAA FNVECFKKYA CNNEYWKTFK ENPIRLTEEN  180
VINYITKLKG PKAAALYAKT HNLNMLQDIP MDRFVMDLKR DVKVTPGTKH TEERPKVQVI  240
QAADPLATAY LCGIHRELVR RLNAVLLPNI HTLFDMSAED FDAIIAEHFQ PGDCVLETDI  300
ASFDKSEDDA MALTAMMILE DLGVDAELLT LIEAAFGEIS SIHLPTKTKF KFGAMMKSGM  360
FLTLFVNTVI NIVIASRVLR ERLTGSPCAA FIGDDNIVKG VKSDKLMADR CATWLNMEVK  420
IIDAVVGEKA PYFCGGFILC DSVTGTACRV ADPLKRLFKL GKPLAADDEH DDDRRRALHE  480
ESTRWNRVGI LPELCKAVES RYETVGTSVI VMAMATLASS VKSFSYLRGA PITLYG      536
```

```
SEQ ID NO: 75           moltype = RNA  length = 8806
FEATURE                 Location/Qualifiers
source                  1..8806
                        mol_type = other RNA
                        organism = synthetic construct
SEQUENCE: 75
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
```

-continued

```
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccatagggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggga tattgccacg gccaccgaag  4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
```

```
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgccg ctggagcagc gatcccaaca ttgcaaacca gaggaaggcc tcgaggcaag  7620
aggtgaggcc ctggggctcg tcggagctca ggcaccggca acggaggagc aagaagcggc  7680
ctctagcagc tccacactcg tcgaagtgac actcggcgag gtccccgctg cggaatctcc  7740
cgatcctccg caaagccctc aaggggcttc ctccctcccc actactatga actatccgtt  7800
gtggagccaa agctatgagg attcctcaaa ccaagaggag gaaggcccct ccacattccc  7860
ggacctcgaa tctgagttcc aggcagcgct cagcaggaaa gtggcggaac ttgtacagtt  7920
tttgttgctt aaataccggg ctcgggagcc agtcacgaaa gccgagatgt taggcagcgt  7980
ggtgggtaat tggcagtact tcttccccgt catcttttcc aaggcttcct cttctttgca  8040
actcgttttt ggcatagagc ttatggaagt agacccgaca ggtcatcttt acatttttgc  8100
aacgtgtctc ggcctcagtt atgacgggct gctcggtgac aatcaaatta tgcctaaggc  8160
cggactgctt atcatcgtct tggctataat tgcccgagag ggcgactgtg ctcccgaaga  8220
gaaaatatgg gaggagctct ccgtgctgga ggtatttgag ggaagagaag atagcatact  8280
gggagaccct aagaaattgc ttacacaaca ctttgtacaa gagaactatt tggagtatcg  8340
acaggtcccc ggatctgacc cagcatgtta tgagttcctg tgggggccaa gggcactcgt  8400
agagacgtca tatgtcaagg tgctgcacca catggtcaaa ataagcggcg gcccccacat  8460
aagctaccca cccctccatg aatgggtttt gagggagggt gaagaatgat aaccgcggtg  8520
tcaaaaaccg cgtggacgtg gttaacatcc ctgctgggag gatcagccgt aattattata  8580
attggcttgg tgctggctac tattgtggcc atgtacgtgc tgaccaacca gaaacataat  8640
tgaatacagc agcaattggc aagctgctta catagaactc gcggcgattg gcatgccgcc  8700
ttaaaatttt tattttattt tttcttttct tttccgaatc ggattttgtt tttaatattt  8760
caaaaaaaaa aaaaaaaaaa aaaaaaaaaa aaaaaaaaaa aaaaaa                 8806

SEQ ID NO: 76           moltype = RNA  length = 9475
FEATURE                 Location/Qualifiers
source                  1..9475
                        mol_type = other RNA
                        organism = synthetic construct
SEQUENCE: 76
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
```

```
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agtttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
```

```
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgaaa tcttacaacg tcctcccccct agcctatatc tccctttcc tgatgctgtt  7620
ttatcaggtt tgggctcagt ttccacgaga gtgtgccaat attgaggctc tgagacgtgg  7680
ggtgtgttgc ccagacctgc tcccttcctc tggaccgggg actgaccctt gtggctcatc  7740
atcaggaaga ggcaggtgtg tggctgtgat tgcagactcc cgaccccaca gccgccatta  7800
tccccacgat ggtaaagatg accgagaagc ctggcctctg aggttcttta atagaacatg  7860
tcagtgcaat gataatttct caggacacaa ctgtgggact tgccgtcctg ggtggagagg  7920
agctgcatgc aaccagaaaa ttctcacagt caggagaaat cttctagact taagtccaga  7980
agaaaagagc cactttgtca gggccttgga tatggcgaag cgcacaactc accctcaatt  8040
tgtcattgcc acaaggaggt tagaagacat actgggacca gatggcaaca caccacaatt  8100
tgagaacatt tccgtttata actactttgt ttggacacac tattattcag tcaaaaaaac  8160
cttcctcggg acaggacagg aaagctttgg ggatgtggat ttctctcacg aaggacccgc  8220
ttttctcaca tggcacaggt accatctgct gcagctggag agagacatgc aggagatgct  8280
gcaggagcct tctttctccc ttccttactg gaattttgca actgggaaaa acgtctgcga  8340
tgtctgcact gatgacttga tgggatccag aagcaacttc gattctactc ttataagccc  8400
caactctgtc ttttctcaat ggagagtggt ctgtgaatcc ttggaagagt acgataccct  8460
gggaacactt tgtaacagca ctgagggtgg accaatcagg agaaacccag ctggaaatgt  8520
agggagacca gcagtgcagc gtcttcctga gccacaggat gtcactcagt gcttggaggt  8580
ccgtgtattt gacacacctc ctttttattc caattctaca gacagttttc gaaatacagt  8640
ggaaggttac agtgctccca cgggaaaata tgaccctgct gttcgaagcc ttcacaacct  8700
ggcccacctc ttcctgaatg gaacgggagg acaaacccat ttgtctccca atgatcctat  8760
ttttgtcctc ctgcacactt tcactgatgc ggtctttgac gaatggctaa ggaggtataa  8820
cgccgatatt tctaccttcc cgttggaaaa cgcacctatt ggacataaca ggcaatacaa  8880
catggtgcca ttctggcctc cagttaccaa cacagaaatg tttgttactg ctccagacaa  8940
tctgggatat atgtatgaag ttcaatggcc aggtcaggag tttactgtat ctgaaatcat  9000
taccattgct gtagtggctg cgttgttact tgtagctgcc attttcgggg ttgcttcttg  9060
tctgatccgt tctagaagca ccaagaatga agccaaccag cctctcctca ctgatcacta  9120
tcaacgctat gctgaggact atgaggagct cccgaatcct aaccactcca tggtctgata  9180
accgcggtgt caaaaaccgc gtggacgtgg ttaacatccc tgctgggagg atcagccgta  9240
attattataa ttggcttggt gctggctact attgtggcca tgtacgtgct gaccaaccag  9300
aaacataatt gaatacagca gcaattggca agctgcttac atagaactcg cggcgattgg  9360
catgccgcct taaaattttt attttatttt ttcttttctt ttccgaatcg gattttgttt  9420
ttaatatttc aaaaaaaaaa aaaaaaaaaa aaaaaaaaaa aaaaaaaaaa aaaaa       9475
```

```
SEQ ID NO: 77          moltype = AA  length = 314
FEATURE                Location/Qualifiers
source                 1..314
                       mol_type = protein
                       organism = synthetic construct
SEQUENCE: 77
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAELVQFL  120
LLKYRAREPV TKAEMLGSVV GNWQYFFPVI FSKASSSLQL VFGIELMEVD PTGHLYIFAT  180
CLGLSYDGLL GDNQIMPKAG LLIIVLAIIA REGDCAPEEK IWEELSVLEV FEGREDSILG  240
DPKKLLTQHF VQENYLEYRQ VPGSDPACYE FLWGPRALVE TSYVKVLHHM VKISGGPHIS  300
YPPLHEWVLR EGEE                                                  314
```

```
SEQ ID NO: 78          moltype = AA  length = 537
FEATURE                Location/Qualifiers
source                 1..537
                       mol_type = protein
                       organism = synthetic construct
SEQUENCE: 78
MKSYNVLPLA YISLFLMLFY QVWAQFPREC ANIEALRRGV CCPDLLPSSG PGTDPCGSSS  60
GRGRCVAVIA DSRPHSRHYP HDGKDDREAW PLRFFNRTCQ CNDNFSGHNC GTCRPGWRGA  120
ACNQKILTVR RNLLDLSPEE KSHFVRALDM AKRTTHPQFV IATRRLEDIL GPDGNTPQFE  180
NISVYNYFVW THYYSVKKTF LGTGQESFGD VDFSHEGPAF LTWHRYHLLQ LERDMQEMLQ  240
EPSFSLPYWN FATGKNVCDV CTDDLMGSRS NFDSTLISPN SVFSQWRVVC ESLEEYDTLG  300
TLCNSTEGGP IRRNPAGNVG RPAVQRLPEP QDVTQCLEVR VFDTPPFYSN STDSFRNTVE  360
```

-continued

```
GYSAPTGKYD PAVRSLHNLA HLFLNGTGGQ THLSPNDPIF VLLHTFTDAV FDEWLRRYNA  420
DISTFPLENA PIGHNRQYNM VPFWPPVTNT EMFVTAPDNL GYMYEVQWPG QEFTVSEIIT  480
IAVVAALLLV AAIFGVASCL IRSRSTKNEA NQPLLTDHYQ RYAEDYEELP NPNHSMV     537

SEQ ID NO: 79          moltype = DNA  length = 6569
FEATURE                Location/Qualifiers
source                 1..6569
                       mol_type = other DNA
                       organism = synthetic construct
SEQUENCE: 79
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctccg cggccgggaa cggtgcattg gaacgcggat  1020
tccccgtgcc aagagtgacg taagtaccgc ctatagactc tataggcaca cccctttggc  1080
tcttatgcat gctatactgt ttttggcttg gggcctatac acccccgctt ccttatgcta  1140
taggtgatgg tatagcttag cctataggtg tgggttattg accattattg accactcccc  1200
tattggtgac gatactttcc attactaatc cataacatgg ctctttgcca caactatctc  1260
tattggctat atgccaatac tctgtccttc agagactgac acggactctg tatttttaca  1320
ggatggggtc ccatttatta tttacaaatt cacatataca acaacgccgt cccccgtgcc  1380
cgcagttttt attaaacata gcgtgggatc tccacgcgaa tctcgggtac gtgttccgga  1440
catgggctct tctccggtag cggcggagct tccacatccg agccctggtc ccatgcctcc  1500
agcggctcat ggtcgctcgg cagctccttg ctcctaacag tggaggccag acttaggcac  1560
agcacaatgc ccaccaccac cagtgtgccg cacaaggccg tggcggtagg gtatgtgtct  1620
gaaaatgagc gtggagattg ggctcgcacg gctgacgcag atggaagact taaggcagcg  1680
gcagaagaag atgcaggcag ctgagttgtt gtattctgat aagagtcaga ggtaactccc  1740
gttgcggtgc tgttaacggt ggagggcagt gtagtctgag cagtactcgt tgctgccgcg  1800
cgcgccacca gacataatag ctgacagact aacagactgt tcctttccat gggtcttttc  1860
tgcagtcacc gtcgtcgaca agcttcctgc atgctgctgc tgctgctgct gctgggcctg  1920
aggctacagc tctccctggg catcatccca gttgaggagg agaacccgga cttctggaac  1980
cgcgaggcag ccgaggccct gggtgccgcc aagaagctgc agcctgcaca gacagccgcc  2040
aagaacctca tcatcttcct gggcgatggg atgggggtgt ctacggtgac agctgccagg  2100
atcctaaaag ggcagaagaa ggacaaactg gggcctgaga tacccctggc catggaccgc  2160
ttcccatatg tggctctgtc caagacatac aatgtagaca aacatgtgcc agacagtgga  2220
gccacagcca cggcctacct gtgcggggtc aagggcaact tccagaccat tggcttgagt  2280
gcagccgccc gctttaacca gtgcaacacg acacgcggca acgaggtcat ctccgtgatg  2340
aatcgggcca agaaagcagg gaagtcagtg ggagtggtaa ccaccacacg agtgcagcac  2400
gcctcgccag ccggcaccta cgcccacacg gtgaaccgca actggtactc ggacgccgac  2460
gtgcctgcct cggcccgcca ggaggggtgc caggacatcg ctacgcagct catctccaac  2520
atggacattg acgtgatcct aggtggaggc cgaaagtaca tgtttcgcat gggaacccca  2580
gaccctgagt acccagatga ctacagccaa ggtgggacca ggctggacgg gaagaatctg  2640
gtgcaggaat ggctggcgaa gcgccagggt gcccggtatg tgtggaaccg cactgagctc  2700
atgcaggctt ccctggaccc gtctgtgacc catctcatgg gtctctttga gcctggagac  2760
atgaaatacg agatccaccg agactccaca ctggacccct ccctgatgga gatgacagag  2820
gctgccctgc gcctgctgag caggaacccc cgcggcttct tcctcttcgt ggagggtggt  2880
cgcatcgacc atggtcatca tgaaagcagg gcttaccggg cactgactga gacgatcatg  2940
ttcgacgacg ccattgagag ggcgggccag ctcaccagcg aggaggacac gctgagcctc  3000
gtcactgccg accactccca cgtcttctcc ttcggaggct acccccctgcg agggagctcc  3060
atcttcgggc tggcccctgg caaggcccgg gacaggaagg cctacacggt cctcctatac  3120
ggaaacggtc caggctatgt gctcaaggac ggcgcccggc cggatgttac cgagagcgag  3180
agcgggagcc ccgagtatcg gcagcagtca gcagtgcccc tggacgaaga gacccacgca  3240
ggcgaggacg tggcggtgtt cgcgcgcggc ccgcaggcgc acctggttca cggcgtgcag  3300
gagcagacct tcatagcgca cgtcatggcc ttcgccgcct gcctggagcc ctacaccgcc  3360
tgcgacctgg cgccccccgc cggcaccacc gacgccgcgc acccgggtta acccgtggtc  3420
agatccagat ccagatcact tctggctaat aaaagatcag agctctagag atctgtgtgt  3480
tggttttttg tggatctgct gtgccttcta gttgccagcc atctgttgtt tgcccctccc  3540
ccgtgccttc cttgaccctg gaaggtgcca ctcccactgt cctttcctaa taaaatgagg  3600
aaattgcatc gcattgtctg agtaggtgtc attctattct ggggggtggg gtggggcagc  3660
acagcaaggg ggaggattgg gaagacaata gcaggcatgc tggggatgcg gtgggctcta  3720
tgggtacctc tctctctctc tctctctctc tctctctctc tctctctcgg tacctctctc  3780
tctctctctc tctctctctc tctctctctc tctcggtacc aggtgctgaa gaattgaccc  3840
ggttcctcct gggccagaaa gaagcaggca catccccttc tctgtgacac accctgtcca  3900
cgcccctggt tcttagttcc agccccactc ataggacact catagctcag gagggctccg  3960
ccttcaatcc cacccgctaa agtacttgga gcggtctctc cctccctcat cagcccacca  4020
aaccaaacct agcctccaag agtgggaaga aattaaagca agataggcta ttaagtgcag  4080
agggagagaa aatgcctcca acatgtgagg aagtaatgag agaaatcata gaatttcttc  4140
```

```
cgcttcctcg ctcactgact cgctgcgctc ggtcgttcgg ctgcggcgag cggtatcagc  4200
tcactcaaag gcggtaatac ggttatccac agaatcaggg gataacgcag gaaagaacat  4260
gtgagcaaaa ggccagcaaa aggccaggaa ccgtaaaaag gccgcgttgc tggcgttttt  4320
ccataggctc cgcccccctg acgagcatca caaaaatcga cgctcaagtc agaggtggcg  4380
aaacccgaca ggactataaa gataccaggc gtttccccct ggaagctccc tcgtgcgctc  4440
tcctgttccg accctgccgc ttaccggata cctgtccgcc tttctccctt cgggaagcgt  4500
ggcgctttct caatgctcac gctgtaggta tctcagttcg gtgtaggtcg ttcgctccaa  4560
gctgggctgt gtgcacgaac cccccgttca gcccgaccgc tgcgccttat ccggtaacta  4620
tcgtcttgag tccaacccgg taagacacga cttatcgcca ctggcagcag ccactggtaa  4680
caggattagc agagcgaggt atgtaggcgg tgctacagag ttcttgaagt ggtggcctaa  4740
ctacggctac actagaagga cagtatttgg tatctgcgct ctgctgaagc cagttacctt  4800
cggaaaaaga gttggtagct cttgatccgg caaacaaacc accgctggta gcggtggttt  4860
ttttgtttgc aagcagcaga ttacgcgcag aaaaaaagga tctcaagaag atcctttgat  4920
cttttctacg gggtctgacg ctcagtggaa cgaaaactca cgttaaggga ttttggtcat  4980
gagattatca aaaaggatct tcacctagat ccttttaaat taaaaatgaa gttttaaatc  5040
aatctaaagt atatatgagt aaacttggtc tgacagttac caatgcttaa tcagtgaggc  5100
acctatctca gcgatctgtc tatttcgttc atccatagtt gcctgactcc gggggggggg  5160
ggcgctgagg tctgcctcgt gaagaaggtg ttgctgactc ataccaggcc tgaatcgccc  5220
catcatccag ccagaaagtg agggagccac ggttgatgag agctttgttg taggtggacc  5280
agttggtgat tttgaacttt tgctttgcca cggaacggtc tgcgttgtcg ggaagatgcg  5340
tgatctgatc cttcaactca gcaaaagttc gatttattca acaaagccgc cgtcccgtca  5400
agtcagcgta atgctctgcc agtgttacaa ccaattaacc aattctgatt agaaaaactc  5460
atcgagcatc aaatgaaact gcaatttatt catatcagga ttatcaatac catatttttg  5520
aaaaagccgt ttctgtaatg aaggagaaaa ctcaccgagg cagttccata ggatggcaag  5580
atcctggtat cggtctgcga ttccgactcg tccaacatca atacaaccta ttaatttccc  5640
ctcgtcaaaa ataaggttat caagtgagaa atcaccatga gtgacgactg aatccggtga  5700
gaatggcaaa agcttatgca tttctttcca gacttgttca acaggccagc cattacgctc  5760
gtcatcaaaa tcactcgcat caaccaaacc gttattcatt cgtgattgcg cctgagcgag  5820
acgaaatacg cgatcgctgt taaaaggaca attacaaaca ggaatcgaat gcaaccggcg  5880
caggaacact gccagcgcat caacaatatt ttcacctgaa tcaggatatt cttctaatac  5940
ctggaatgct gttttcccgg ggatcgcagt ggtgagtaac catgcatcat caggagtacg  6000
gataaaatgc ttgatggtcg gaagaggcat aaattccgtc agccagttta gtctgaccat  6060
ctcatctgta acatcattgg caacgctacc tttgccatgt ttcagaaaca actctggcgc  6120
atcgggcttc ccatacaatc gatagattgt cgcacctgat tgcccgacat tatcgcgagc  6180
ccatttatac ccatataaat cagcatccat gttggaattt aatcgcggcc tcgagcaaga  6240
cgtttcccgt tgaatatggc tcataacacc ccttgtatta ctgtttatgt aagcagacag  6300
ttttattgtt catgatgata tatttttatc ttgtgcaatg taacatcaga gattttgaga  6360
cacaacgtgg ctttcccccc cccccatta ttgaagcatt tatcagggtt attgtctcat  6420
gagcggatac atatttgaat gtatttagaa aaataaacaa ataggggttc cgcgcacatt  6480
tccccgaaaa gtgccacctg acgtctaaga aaccattatt atcatgacat taacctataa  6540
aaataggcgt atcacgaggc cctttcgtc                                    6569

SEQ ID NO: 80          moltype = RNA  length = 7862
FEATURE                Location/Qualifiers
source                 1..7862
                       mol_type = other RNA
                       organism = synthetic construct
misc_difference        7562
                       note = a, c, g, or u
SEQUENCE: 80
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
```

```
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
```

```
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttatttttc ttttcttttc cgaatcggat  7800
tttgttttta atatttcaaa aaaaaaaaaa aaaaaaaaaa aaaaaaaaaa aaaaaaaaaa  7860
aa                                                                7862

SEQ ID NO: 81          moltype = RNA  length = 7862
FEATURE                Location/Qualifiers
source                 1..7862
                       mol_type = other RNA
                       organism = synthetic construct
misc_difference        7562
                       note = a, c, g, or u
SEQUENCE: 81
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
```

aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agtttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500

```
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttatttttc ttttctttc cgaatcggat  7800
tttgttttta atatttcaaa aaaaaaaaaa aaaaaaaaaa aaaaaaaaaa aaaaaaaaaa  7860
aa                                                                7862

SEQ ID NO: 82          moltype = RNA  length = 7862
FEATURE                Location/Qualifiers
source                 1..7862
                       mol_type = other RNA
                       organism = synthetic construct
misc_difference        7562
                       note = a, c, g, or u
SEQUENCE: 82
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catagggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
```

```
tgaatcccgg cggaacctgt gtcagcatag gttatggtta cgctgacagg gccagcgaaa  3840
gcatcattgg tgctatagcg cggcagttca agtttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntagtaacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttatttttttc ttttcttttc cgaatcggat  7800
tttgttttta atatttcaaa aaaaaaaaaa aaaaaaaaaa aaaaaaaaaa aaaaaaaaaa  7860
aa                                                                 7862
```

```
SEQ ID NO: 83          moltype = RNA  length = 7862
FEATURE                Location/Qualifiers
source                 1..7862
                       mol_type = other RNA
                       organism = synthetic construct
misc_difference        7562
                       note = a, c, g, or u
SEQUENCE: 83
ataggcggcg catgagagaa gcccagacca attacctacc caaaatggag aaagttcacg  60
```

```
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
```

```
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862
```

```
SEQ ID NO: 84          moltype = RNA  length = 7862
FEATURE                Location/Qualifiers
source                 1..7862
                       mol_type = other RNA
                       organism = synthetic construct
misc_difference        7562
                       note = a, c, g, or u
SEQUENCE: 84
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
```

-continued

```
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
```

```
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862

SEQ ID NO: 85           moltype = RNA  length = 11701
FEATURE                 Location/Qualifiers
source                  1..11701
                        mol_type = other RNA
                        organism = synthetic construct
SEQUENCE: 85
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
```

gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agtttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggagggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgtttctg ctcacaacca aacgcactat gtttgttttc ctcgtgctgc tccctttggt 7620
aagttctcag tgtgtaaacc tgagaacacg aacccagttg cctccagctt ataccaactc 7680
atttactcgc ggagtatatt atcccgataa ggtctttaga agtagcgtgt tgcactctac 7740
acaggatctg ttcttgccct tctttagtaa cgttacctgg tttcatgcaa tacatgtgag 7800
cggaacaaat ggaacaaaaa gatttgacaa tccagtgctt ccatttaatg atggggttta 7860
ctttgccagt atcgaaaagt caaacataat ccgggggtgg atctttggaa ccactttgga 7920
ctctaagaca cagtctctcc tcatagtaaa caacgccacc aatgttgtca taaaagtatg 7980
cgaatttcag ttttgcaacg atccctttct cgacgtgtat taccataaga ataataaatc 8040
ctggatggag tctggggttt atagtagtgc taataattgc actttcgaat acgtgtccca 8100
accattcctc atggaccttg agggcaaaca ggggaatttt aaaaacttgc gcgaatttgt 8160
ctttaagaat atcgacggat actttaagat ctatagtaaa cacactccta tcaacctcgt 8220
tcgggatctt ccccaaggct tttctgctct cgaacccctc gtagacttgc caattgggat 8280
aaatatcact cgctttcaaa ctttgcttgc cctccacagg agctacctga cacccggcga 8340
ctcttcttct ggtttgaccg ccggcgccgc tgcctattat gttggttacc ttcagccacg 8400
aacattcttg ctcaagtata acgagaatgg caccattacc gacgccgtcg attgtgcatt 8460
ggatcccttg tctgaaacaa aatgtacctt gaagtccttt accgtagaga aaggcatata 8520
ccagacttcc aacttccgag ttcagcctac agaatccatc gtacgatttc ccaacatcac 8580
aaacctctgc cctttcggtg aagtatttaa tgctacacgc ttcgcttcag tctatgcctg 8640
gaataggaag cgcatatcaa attgcgtggc cgattattca gtcctctata atagcgcatc 8700
cttcagtact ttcaagtgct acggcgtttc cccccaccaaa ctcaatgatc tttgcttcac 8760
caacgtctat gctgacagtt ttgtcatacg aggcgacgaa gtacgccaga ttgcccccgg 8820
gcagacaggt aatattgctg attataatta taaactccca gatgacttta ctggatgcgt 8880
catagcctgg aattccaaca atctagattc caaggttggt gggaattata attaccgtta 8940
tcgactgttc agaaagagta acttgaaacc atttgagaga gacatatcca ccgagattta 9000
ccaggcaggc agtaagcctt gtaacggcgt tgagggattt aactgctatt ttcctttgca 9060
atcctatggc tttcaaccaa caaacggggt tggctatcaa ccctatcgag tggttgtcct 9120
cagctttgaa cttttgcacg ctcccgccac agtctgcgga ccaaaaaaga gtacaaatct 9180
tgtcaagaat aagtgcgtaa atttcaattt caatggcctt acaggaacag gcgtgctgac 9240
tgagtcaaac aagaatttcc tgccatttca gcagtttggg cgggatatag cagacacaac 9300
tgacgctgta cgcgatcctc agactttgga gatcttggac atcactccct gttctttcgg 9360
aggggtatct gtcatcaccc ccggaactaa tacatcaaat caggtcgctg tgttgtacca 9420
aggtgtcaac tgcacagaag tccccgttgc tatacacgca gaccagctca cccccacatg 9480
gcgggtgtac tcaactggct caaacgtatt ccagaccaga gctgggtgct tgatcggtgc 9540
tgaacacgtg aacaatagct atgaatgcga tattcccatc ggtgccggga tctgcgctag 9600
ctatcagaca cagaccaatt cccgcaggcg ggctcgctct gtagcatccc agtctattat 9660
tgcctacact atgtcattgg gcgccgagaa tagcgtcgca tattcaaata attctattgc 9720
aatacccacc aacttcacaa tctccgtaac tacagaaata cttccagttt ccatgacaaa 9780
gacatcagtg gattgtacaa tgtatatatg cggagattcc acagaatgtt caaatttgct 9840
cttgcagtac ggctccttct gcacccagct caacagggca cttacaggta ttgctgtcga 9900
acaggacaag aacacacaag aagtcttcgc ccaagtcaaa cagatataca aaactcctcc 9960
cataaaggat tttggcggct tcaactttag tcagatcctc ccagaccctt caaaaccatc 10020
taaacgatca tttattgaag atctgctgtt caacaaggtc actcttgccg atgctggatt 10080
cattaagcaa tacggtgact gccttggtga tattgctgcc cgagatctga tctgtgccca 10140
gaaattcaac gggctcactg tactccctcc actgctcaca gacgaaatga ttgcacagta 10200
cacaagtgcc ctgttggcag gcacaatcac tagcggctgg acctttggcg caggtgcagc 10260
actccaaata ccttttgcca tgcagatggc ctatcggttt aatgggatag gcgtgactca 10320
aaatgtcctc tacgaaaacc aaaagttgat agctaaccaa ttcaattcag caatcgggaa 10380
gatacaggat tcactgtcta gtactgctag tgcccttggt aagctgcaga acgttgtcaa 10440
ccagaatgct caagctctga atacattggt taagcagctc tctagtaatt ttggggccat 10500
ctcttcagta cttaatgata ttttgagccg attggaccca cctgaagctg aagtacagat 10560
cgacaggctg ataacaggcc ggctccaatc cctccaaaca tacgtgacac aacaactcat 10620
acgcgcagcc gaaatccgag ccagcgctaa cctggcagct accaagatgt cagaatgcgt 10680
tctgggccag agtaaacgcg tagatttctg cgggaaaggg taccacctga tgtcctttcc 10740
acaatctgca cctcacgggg tcgtcttttt gcatgtaaca tacgtacccg cacaagagaa 10800
gaattttact accgctcctg ccatctgtca tgacgggaaa gctcattttc ctcgcgaagg 10860
tgtgtttgta tctaatggta cacattggtt tgtcacacag cggaatttct atgaacccca 10920
gatcattaca actgacaaca cttttgtttc cgggaattgt gacgtggtca taggaatcgt 10980
aaataacact gtatatgatc ccctccaacc agagctggac tcttttaaag aagaactgga 11040
taaatatttc aagaaccaca caagtcccga cgtggacctt ggggacataa gtggtattaa 11100
cgcatctgtg gttaacattc aaaaggaaat cgacagactc aacgaggtgg ccaaaaacct 11160
gaacgaaagc ttgatagatc tccaggagtt gggcaagtat gaacagtaca ttaaatggcc 11220
atggtacata tggcttggct ttatcgctgg ccttatcgcc atcgtaatgg ttacaatcat 11280
gctgtgctgc atgacctcct gctgttcttg tttgaaaggg tgttgttctt gtggtagttg 11340
ttgcaagttt gacgaagatg attccgaacc tgttcttaag gggtaaagc ttcactatac 11400
atgataaccg cggtgtcaaa aaccgcgtgg acgtggttaa catccctgct gggaggatca 11460
gccgtaatta ttataattgg cttggtgctg gctactattg tggccatgta cgtgctgacc 11520
aaccagaaac ataattgaat acagcagcaa ttggcaagct gcttacatag aactcgcggc 11580
gattggcatg ccgccttaaa atttttattt tatttttct tttcttttcc gaatcggatt 11640
ttgtttttaa tatttcaaaa aaaaaaaaaa aaaaaaaaaa aaaaaaaaaa aaaaaaaaaa 11700

```
a                                                                    11701

SEQ ID NO: 86             moltype = RNA  length = 7862
FEATURE                   Location/Qualifiers
source                    1..7862
                          mol_type = other RNA
                          organism = synthetic construct
misc_difference           7565
                          note = a, c, g, or u
SEQUENCE: 86
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
```

```
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccntaacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862
```

```
SEQ ID NO: 87          moltype = AA  length = 314
FEATURE                Location/Qualifiers
source                 1..314
                       mol_type = protein
                       organism = Homo sapiens
SEQUENCE: 87
MPLEQRSQHC KPEEGLEARG EALGLVGAQA PATEEQEAAS SSSTLVEVTL GEVPAAESPD  60
PPQSPQGASS LPTTMNYPLW SQSYEDSSNQ EEEGPSTFPD LESEFQAALS RKVAELVHFL  120
LLKYRAREPV TKAEMLGSVV GNWQYFFPVI FSKASSSLQL VFGIELMEVD PIGHLYIFAT  180
CLGLSYDGLL GDNQIMPKAG LLIIVLAIIA REGDCAPEEK IWEELSVLEV FEGREDSILG  240
DPKKLLTQHF VQENYLEYRQ VPGSDPACYE FLWGPRALVE TSYVKVLHHM VKISGGPHIS  300
YPPLHEWVLR EGEE                                                   314

SEQ ID NO: 88          moltype = RNA  length = 942
FEATURE                Location/Qualifiers
```

```
source                  1..942
                        mol_type = genomic RNA
                        organism = Homo sapiens
SEQUENCE: 88
atgccgctgg agcagcgatc ccaacattgc aaaccagagg aaggcctcga ggcaagaggt  60
gaggccctgg ggctcgtcgg agctcaggca ccggcaacgg aggagcaaga agcggcctct  120
agcagctcca cactcgtcga agtgacactc ggcgaggtcc ccgctgcgga atctcccgat  180
cctccgcaaa gccctcaagg ggcttcctcc ctccccacta ctatgaacta tccgttgtgg  240
agccaaagct atgaggattc ctcaaaccaa gaggaggaag gcccctccac attcccggac  300
ctcgaatctg agttccaggc agcgctcagc aggaaagtgg cggaacttgt acagtttttg  360
ttgcttaaat accgggctcg ggagccagtc acgaaagccg agatgttagg cagcgtggtg  420
ggtaattggc agtacttctt ccccgtcatc ttttccaagg cttcctcttc tttgcaactc  480
gtttttggca tagagcttat ggaagtagac ccgacaggtc atctttacat tttgcaacg  540
tgtctcggcc tcagttatga cggctgctc ggtgacaatc aaattatgcc taaggccgga  600
ctgcttatca tcgtcttggc tataattgcc cgagagggcg actgtgctcc cgaagagaaa  660
atatgggagg agctctccgt gctggaggta tttgagggaa gagaagatag catactggga  720
gaccctaaga aattgcttac acaacacttt gtacaagaga actatttgga gtatcgacag  780
gtccccggat ctgacccagc atgttatgag ttcctgtggg ggccaagggc actcgtagag  840
acgtcatatg tcaaggtgct gcaccacatg gtcaaaataa gcggcggccc ccacataagc  900
tacccacccc tccatgaatg ggttttgagg gagggtgaag aa                    942

SEQ ID NO: 89           moltype = RNA  length = 8806
FEATURE                 Location/Qualifiers
source                  1..8806
                        mol_type = other RNA
                        organism = synthetic construct
SEQUENCE: 89
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
```

```
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgccg ctggagcagc gatcccaaca ttgcaaacca gaggaaggcc tcgaggcaag  7620
aggtgaggcc ctggggctcg tcggagctca ggcaccggca acggaggagc aagaagcggc  7680
ctctagcagc tccacactcg tcgaagtgac actcggcgag gtccccgctg cggaatctcc  7740
cgatcctccg caaagccctc aaggggcttc ctccctcccc actactatga actatccgtt  7800
gtggagccaa agctatgagg attcctcaaa ccaagaggag gaaggcccct ccacattccc  7860
```

-continued

```
ggacctcgaa tctgagttcc aggcagcgct cagcaggaaa gtggcggaac ttgtacagtt  7920
tttgttgctt aaataccggg ctcgggagcc agtcacgaaa gccgagatgt taggcagcgt  7980
ggtgggtaat tggcagtact tcttccccgt catcttttcc aaggcttcct cttctttgca  8040
actcgttttt ggcatagagc ttatggaagt agacccgaca ggtcatcttt acatttttgc  8100
aacgtgtctc ggcctcagtt atgacgggct gctcggtgac aatcaaatta tgcctaaggc  8160
cggactgctt atcatcgtct tggctataat tgcccgagag ggcgactgtg ctcccgaaga  8220
gaaaatatgg gaggagctct ccgtgctgga ggtatttgag ggaagagaag atagcatact  8280
gggagaccct aagaaattgc ttacacaaca ctttgtacaa gagaactatt tggagtatcg  8340
acaggtcccc ggatctgacc cagcatgtta tgagttcctg tgggggccaa gggcactcgt  8400
agagacgtca tatgtcaagg tgctgcacca catggtcaaa ataagcggcg gcccccacat  8460
aagctaccca cccctccatg aatgggtttt gagggagggt gaagaatgat aaccgcggtg  8520
tcaaaaaccg cgtggacgtg gttaacatcc ctgctgggag gatcagccgt aattattata  8580
attggcttgg tgctggctac tattgtggcc atgtacgtgc tgaccaacca gaaacataat  8640
tgaatacagc agcaattggc aagctgctta catagaactc gcggcgattg gcatgccgcc  8700
ttaaaatttt tattttattt tttcttttct tttccgaatc ggattttgtt tttaatattt  8760
caaaaaaaaa aaaaaaaaaa aaaaaaaaaa aaaaaaaaaa aaaaaa                8806

SEQ ID NO: 90           moltype = AA  length = 553
FEATURE                 Location/Qualifiers
source                  1..553
                        mol_type = protein
                        organism = Homo sapiens
SEQUENCE: 90
MVQRLWVSRL LRHRKAQLLL VNLLTFGLEV CLAAGITYVP PLLLEVGVEE KFMTMVLGIG  60
PVLGLVCVPL LGSASDHWRG RYGRRRPFIW ALSLGILLSL FLIPRAGWLA GLLCPDPRPL  120
ELALLILGVG LLDFCGQVCF TPLEALLSDL FRDPDHCRQA YSVYAFMISL GGCLGYLLPA  180
IDWDTSALAP YLGTQEECLF GLLTLIFLTC VAATLLVAEE AALGPTEPAE GLSAPSLSPH  240
CCPCRARLAF RNLGALLPRL HQLCCRMPRT LRRLFVAELC SWMALMTFTL FYTDFVGEGL  300
YQGVPRAEPG TEARRHYDEG VRMGSLGLFL QCAISLVFSL VMDRLVQRFG TRAVYLASVA  360
AFPVAAGATC LSHSVAVVTA SAALTGFTFS ALQILPYTLA SLYHREKQVF LPKYRGDTGG  420
ASSEDSLMTS FLPGPKPGAP FPNGHVGAGG SGLLPPPPAL CGASACDVSV RVVVGEPTEA  480
RVVPGRGICL DLAILDSAFL LSQVAPSLFM GSIVQLSQSV TAYMVSAAGL GLVAIYFATQ  540
VVFDKSDLAK YSA                                                    553

SEQ ID NO: 91           moltype = AA  length = 9
FEATURE                 Location/Qualifiers
source                  1..9
                        mol_type = protein
                        organism = Homo sapiens
SEQUENCE: 91
AAGIGILTV                                                         9

SEQ ID NO: 92           moltype = AA  length = 9
FEATURE                 Location/Qualifiers
source                  1..9
                        mol_type = protein
                        organism = Homo sapiens
SEQUENCE: 92
SYLDSGIHS                                                         9

SEQ ID NO: 93           moltype = AA  length = 9
FEATURE                 Location/Qualifiers
source                  1..9
                        mol_type = protein
                        organism = Homo sapiens
SEQUENCE: 93
ETVSEESNV                                                         9

SEQ ID NO: 94           moltype = AA  length = 9
FEATURE                 Location/Qualifiers
source                  1..9
                        mol_type = protein
                        organism = Homo sapiens
SEQUENCE: 94
EEKLSVVLF                                                         9
```

What is claimed is:

1. A composition comprising:

lipid nanoparticles, wherein the lipid nanoparticles are characterized as having a z-average diameter particle size measurement of about 20 nm to about 60 nm when measured using dynamic light scattering, and wherein the lipid nanoparticles comprise:

a cationic lipid;

a hydrophilic surfactant; and a hydrophobic surfactant; and at least one nucleic acid, wherein the at least one nucleic acid comprises:

a sequence encoding for an RNA-dependent polymerase; and a sequence encoding for a transmembrane-binding domain, an outer cell membrane-contacting domain, and an inner cell membrane-contacting domain of a prostein protein.

2. The composition of claim 1, wherein the prostein protein comprises an amino acid sequence that is at least 80% identical to SEQ ID NO: 90.

3. The composition of claim 1, wherein the prostein protein comprises an amino acid sequence of SEQ ID NO: 90.

4. The composition of claim 1, wherein the prostein protein is expressed by a solid cancer cell.

5. The composition of claim 4, wherein the solid cancer cell comprises a melanoma cancer cell, a prostate cancer cell, a colon cancer cell, an ovarian cancer cell, a breast cancer cell, or a pancreatic cancer cell.

6. The composition of claim 1, wherein the at least one nucleic acid is in complex with the lipid nanoparticles to form nucleic acid-lipid nanoparticle complexes.

7. The composition of claim 1, wherein the RNA-dependent polymerase is a Venezuelan equine encephalitis virus (VEEV) RNA polymerase.

8. The composition of claim 1, wherein the sequence encoding for the RNA-dependent polymerase comprises SEQ ID NO: 71.

9. The composition of claim 1, wherein the lipid nanoparticles comprise a hydrophobic core.

10. The composition of claim 9, wherein lipids present in the hydrophobic core are in liquid phase at 25 degrees Celsius.

11. The composition of claim 9, wherein the hydrophobic core comprises liquid oil.

12. The composition of claim 11, wherein the liquid oil is a-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E.

13. The composition of claim 12, wherein the triglyceride is capric triglyceride, caprylic triglyceride, a caprylic and capric triglyceride, a triglyceride ester, or myristic acid triglycerin.

14. The composition of claim 1, wherein the cationic lipid is 1,2-dioleoyloxy-3 (trimethylammonium) propane, 3β-[N—(N',N'-dimethylaminoethane) carbamoyl] cholesterol, dimethyldioctadecylammonium, 1,2-dimyristoyl 3-trimethylammoniumpropane, dipalmitoyl (C 16:0) trimethyl ammonium propane, distearoyltrimethylammonium propane, N-[1-(2,3-dioleyloxy) propyl]N,N,Ntrimethylammonium, chloride, N,N-dioleoyl-N,N-dimethylammonium chloride, 1,2-dioleoyl-sn-glycero-3-ethylphosphocholine, 1,2-dioleoyl-3-dimethylammonium-propane, 3β-[N—(N', N'-dimethylaminoethane) carbamoyl] cholesterol, 1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol), tetrakis (8-methylnonyl) 3,3',3",3'"-(((methylazanediyl)bis(propane-3,1 diyl))bis (azanetriyl)) tetrapropionate, decyl (2-(dioctylammonio)ethyl)phosphate, ethyl 5,5-di((Z)-heptadec-8-en-1-yl)-1-(3-(pyrrolidin-1-yl) propyl)-2,5-dihydro-1H-imidazole-2-carboxylate, ((4-hydroxybutyl)azanediyl)bis(hexane-6,1-diyl)bis(2-hexyldecanoate), 2-[(polyethylene glycol)-2000]-N,N-ditetradecylacetamide, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol, bis(2-(dodecyldisulfanyl) ethyl) 3,3'-((3-methyl-9-oxo-10-oxa-13,14-dithia-3,6-diazahexacosy 1)azanediyl)dipropionate, 2-(((((3 S, 8 S,9S, 1 OR, 13R, 14S, 17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis (2-hydroxyethyl)-N-methylethan-1-aminium bromide, 3,6-bis(4-(bis(2-hydroxydodecyl)amino)butyl)piperazine-2,5-dione, 3β-[N—(N',N'-dimethylaminoethane)-carbamoyl] cholesterol, (6Z,9Z,28Z,31Z)-heptatriaconta-6,9,28,31-tetraen-19-yl 4-(dimethylamino)butanoate, 1,2-dioleoyl-sn-glycero-3-phosphoethanolamine, 2,3-dioleyloxy-N-[2-(sperminecarboxamido)ethyl]-N,N-dimethyl-1-propanaminium trifluoroacetate, 1,2-distearoyl-sn-glycero-3-phosphocholine, ethylphosphatidylcholine, hexa (octan-3-yl) 9, 9',9",9'", 9"", 9'""-((((benzene-1,3,5-tricarbonyl)yris (azanediyl))tris (propane-3,1-diyl))tris (azanetriyl)) hexanonanoate, heptadecan-9-yl 8-((2-hydroxyethyl)(6-oxo-6-(undecyloxy)hexyl)amino) octanoate, (((3,6-dioxopiperazine-2,5-diyl)bis(butane-4, 1-diyl))bis (azanetriyl))tetrakis(ethane-2,1-diyl) (9Z,9'Z,9"Z,9'"Z, 12Z, 12'Z, 12"Z, 12'"Z)-tetrakis (octadeca-9,12-dienoate), or N1,N3,N5-tris(3-(didodecylamino)propyl)benzene-1,3,5-tricarboxamide.

15. The composition of claim 1, wherein the lipid nanoparticles comprise an inorganic particle.

16. The composition of claim 15, wherein the inorganic particle is within a hydrophobic core of the lipid nanoparticles.

17. The composition of claim 15, wherein the inorganic particle comprises a metal.

18. The composition of claim 17, wherein the metal comprises a metal salt, a metal oxide, a metal hydroxide, or a metal phosphate.

19. The composition of claim 18, wherein the metal oxide comprises aluminum oxide, aluminum oxyhydroxide, iron oxide, titanium dioxide, or silicon dioxide.

20. The composition of claim 1, wherein the hydrophobic surfactant is sorbitan monolaurate, sorbitan monopalmitate, sorbitan monostearate, sorbitan monooleate, or sorbitan trioleate.

21. The composition of claim 1, wherein the hydrophilic surfactant is a polysorbate.

22. The composition of claim 9, wherein the hydrophobic core comprises squalene, wherein the hydrophilic surfactant is polysorbate 80, wherein the hydrophobic surfactant is sorbitan monolaurate, wherein the cationic lipid is 1,2-dioleoyloxy-3 (trimethylammonium) propane, and optionally further comprising sodium citrate.

23. The composition of claim 22, wherein the hydrophobic core further comprises oleic acid-coated iron oxide nanoparticles.

24. The composition of claim 1, wherein the at least one nucleic acid comprises DNA or RNA.

25. The composition of claim 24, wherein the RNA comprises mRNA.

26. A pharmaceutical composition comprising the composition of claim 1, and a pharmaceutically acceptable excipient.

* * * * *